(12) United States Patent
Priepke et al.

(10) Patent No.: US 8,759,537 B2
(45) Date of Patent: Jun. 24, 2014

(54) 3H-IMIDAZO [4, 5-C] PYRIDINE-6-CARBOXAMIDES AS ANTI-INFLAMMATORY AGENTS

(75) Inventors: Henning Priepke, Warthausen (DE); Henri Doods, Warthausen (DE); Raimund Kuelzer, Mittelbiberach (DE); Roland Pfau, Biberach (DE); Dirk Stenkamp, Biberach (DE); Benjamin Pelcman, Stockholm (SE); Robert Roenn, Uppsala (SE)

(73) Assignee: Boehringer Ingelheim International GmbH, Ingelhein am Rhein (DE)

( * ) Notice: Subject to any disclaimer, the term of this patent is extended or adjusted under 35 U.S.C. 154(b) by 0 days.

(21) Appl. No.: 13/211,470

(22) Filed: Aug. 17, 2011

(65) Prior Publication Data
US 2012/0214786 A1    Aug. 23, 2012

(30) Foreign Application Priority Data
Aug. 20, 2010  (EP) ................................. 10173501

(51) Int. Cl.
| | | |
|---|---|---|
| A61K 31/427 | (2006.01) | |
| A61K 31/428 | (2006.01) | |
| A61K 31/422 | (2006.01) | |
| A61K 31/4439 | (2006.01) | |
| C07D 401/12 | (2006.01) | |
| C07D 403/12 | (2006.01) | |
| C07D 413/12 | (2006.01) | |
| C07D 235/30 | (2006.01) | |
| C07D 417/12 | (2006.01) | |

(52) U.S. Cl.
USPC ............. 548/307.4; 546/273.4; 548/159; 548/181; 548/248; 514/338; 514/365; 514/367; 514/378; 514/388

(58) Field of Classification Search
USPC .................................................. 548/307.4
See application file for complete search history.

(56) References Cited

U.S. PATENT DOCUMENTS

| | | |
|---|---|---|
| 6,608,084 B1 | 8/2003 | Bourzat et al. |
| 8,466,186 B2 | 6/2013 | Priepke et al. |
| 2004/0198768 A1 | 10/2004 | Park Choo et al. |
| 2006/0287344 A1 | 12/2006 | Albers et al. |
| 2007/0060598 A1 | 3/2007 | Albers et al. |
| 2007/0173488 A1 | 7/2007 | Bounaud et al. |
| 2010/0004301 A1 | 1/2010 | Pelcman et al. |
| 2010/0256188 A1 | 10/2010 | Pfau et al. |
| 2011/0275656 A1 | 11/2011 | Pfau et al. |
| 2011/0312935 A1 | 12/2011 | Pfau et al. |
| 2012/0115902 A1 | 5/2012 | Pfau et al. |
| 2012/0122930 A1 | 5/2012 | Pfau et al. |
| 2012/0149676 A1 | 6/2012 | Priepke et al. |
| 2012/0196897 A1* | 8/2012 | Pfau et al. ................ 514/322 |
| 2012/0208839 A1 | 8/2012 | Priepke et al. |
| 2012/0309738 A1 | 12/2012 | Priepke et al. |
| 2012/0309755 A1 | 12/2012 | Priepke et al. |

FOREIGN PATENT DOCUMENTS

| | | |
|---|---|---|
| EP | 0034743 A1 | 9/1981 |
| EP | 0295656 A1 | 12/1988 |
| EP | 0419210 A1 | 3/1991 |
| EP | 1069124 A1 | 1/2001 |
| FR | 2851563 A1 | 8/2004 |
| FR | 2852957 A1 | 10/2004 |
| WO | 0015612 A1 | 3/2000 |
| WO | 0049005 A1 | 8/2000 |
| WO | 0061580 A1 | 10/2000 |
| WO | 0068213 A1 | 11/2000 |
| WO | 0125238 A2 | 4/2001 |
| WO | 03053939 A1 | 7/2003 |
| WO | 03074515 A1 | 9/2003 |
| WO | 03082272 A1 | 10/2003 |
| WO | 2004005323 A2 | 1/2004 |
| WO | 2004035740 A2 | 4/2004 |
| WO | 2004072068 A1 | 8/2004 |
| WO | 2004085425 A1 | 10/2004 |
| WO | 2004089951 A1 | 10/2004 |

(Continued)

OTHER PUBLICATIONS

R.D. Carpenter et al., Carbodiimide-based benzinidazole library method, Journal of Combinatorial Chemistry, Oct. 27, 2006, pp. 907-914, vol. 8, No. 6.
International Search Report Form PCT/ISA/210 and Written Opinion Form PCT/ISA/237 for corresponding PCT/EP2011/064258; date of mailing: Oct. 10, 2011.
D.J. Gale et al., The Amidomethylation of Some N,N-Dialkylanilines; Aust.J. Chem.; pp. 2447-2458; vol. 28; 1975.

(Continued)

*Primary Examiner* — Laura L. Stockton
(74) *Attorney, Agent, or Firm* — Michael P. Morris; Philip I. Datlow

(57) ABSTRACT

This invention relates to compounds of formula I

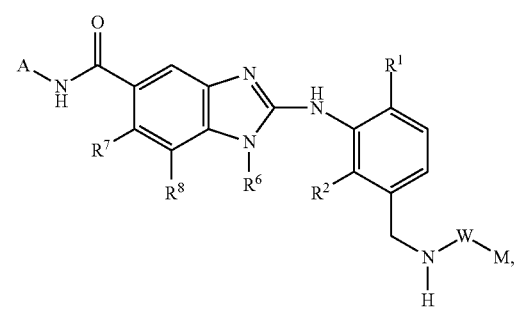

their use as inhibitors of the microsomal prostaglandin $E_2$ synthase-1 (mPGES-1), pharmaceutical compositions containing them, and their use as medicaments for the treatment and/or prevention of inflammatory diseases and associated conditions. A, M, W, $R^1$, $R^2$, $R^6$, $R^7$, $R^8$ have meanings given in the description.

27 Claims, No Drawings

(56) References Cited

FOREIGN PATENT DOCUMENTS

| WO | 2005044793 A2 | 5/2005 |
|----|---------------|--------|
| WO | 2005070906 A1 | 8/2005 |
| WO | 2005070920 A1 | 8/2005 |
| WO | 2005123674 A1 | 12/2005 |
| WO | 2006077366 A1 | 7/2006 |
| WO | 2006090167 A2 | 8/2006 |
| WO | 2007095124 A2 | 8/2007 |
| WO | 2007127382 A1 | 11/2007 |
| WO | 2008009924 A2 | 1/2008 |
| WO | 2008035956 A1 | 3/2008 |
| WO | 2008071944 A1 | 6/2008 |
| WO | 2008129276 A1 | 10/2008 |
| WO | 2010034796 A1 | 4/2010 |
| WO | 2010034797 A1 | 4/2010 |
| WO | 2010034798 A1 | 4/2010 |
| WO | 2010034799 A1 | 4/2010 |
| WO | 2010100249 A1 | 9/2010 |

OTHER PUBLICATIONS

Cancer [online], [retrieved on Jul. 6, 2007]. Retrieved from the internet, URL http://en.wikipedia.orglwikilCancer.
Cancer [online], [retrieved on Jul. 6, 2007]. Retrieved from the internet, URL http://www.nlm.nih.gov/medlineplus/cancer.html>.
Golub et al., Science (1999), vol. 286, 531-537.
Lala et al., Cancer and Metastasis reviews (1998), 17 (1), 91-106.
Silverman et al., The Organic Chemistry of Drug Design and Drug Action, Chapter 2: Drug Discovery, Design, and Development, Academic Press, p. 5-51, 1992.
Samuelsson et al., Pharmacology Review, vol. 59, No. 3, pp. 207-224, 2007.

\* cited by examiner

3H-IMIDAZO [4, 5-C] PYRIDINE-6-CARBOXAMIDES AS ANTI-INFLAMMATORY AGENTS

FIELD OF THE INVENTION

This invention relates to novel compounds, which are inhibitors of the microsomal prostaglandin $E_2$ synthase-1 (mPGES-1), pharmaceutical compositions containing them, and their use as medicaments for the treatment and/or prevention of inflammatory diseases and associated conditions such as inflammatory/nociceptive pain.

BACKGROUND OF THE INVENTION

There are many acute and chronic diseases/disorders that are inflammatory in their nature including but not limited to rheumatoid diseases e.g. rheumatoid arthritis, osteoarthritis, diseases of the visceral system e.g. inflammatory bowel syndrome, autoimmune diseases, e.g. lupus erythematodes, lung diseases like asthma and COPD. Current treatment with non-steroidal anti-inflammatory drugs (NSAIDs) and cyclooxygenase (COX)-2 inhibitors are efficacious, but show a prevalence for gastrointestinal and cardiovascular side effects. There is a high need for new treatment options showing equivalent efficacy with an improved side effect profile.

mPGES inhibitors may show such an improved side effect profile because they block the generation of $PGE_2$ in a more specific manner as described below.

NSAIDs and COX-2 inhibitors reduce inflammation and pain through inhibition of one or both isoformes of COX enzymes. The cyclooxygenase (COX) enzyme exists in two forms, one that is constitutively expressed in many cells and tissues (COX-1), and one that in most cells and tissues is induced by pro-inflammatory stimuli, such as cytokines, during an inflammatory response (COX-2). COXs metabolise arachidonic acid to the unstable intermediate prostaglandin $H_2$ ($PGH_2$). $PGH_2$ is further metabolized to other prostaglandins including $PGE_2$, $PGF_{2\alpha}$, $PGD_2$, prostacyclin and thromboxane $A_2$. These arachidonic acid metabolites are known to have pronounced physiological and pathophysiological activity including pro-inflammatory effects. $PGE_2$ in particular is known to be a strong pro-inflammatory mediator, and is also known to induce fever, inflammation and pain. Consequently, numerous drugs were developed with a view to inhibiting the formation of $PGE_2$, including "NSAIDs" (non-steroidal antiinflammatory drugs) and "coxibs" (selective COX-2 inhibitors). These drugs act predominantly by inhibition of COX-1 and/or COX-2, thereby reducing the formation of $PGE_2$.

However, the inhibition of COXs has the disadvantage that it results in the reduction of the formation of all metabolites downstream of $PGH_2$, some of which are known to have beneficial properties. In view of this, drugs which act by inhibition of COXs are therefore known/suspected to cause adverse biological effects.

For example, the non-selective inhibition of COXs by NSAIDs may give rise to gastrointestinal side-effects and affect platelet and renal function. Even the selective inhibition of COX-2 by coxibs, whilst reducing such gastrointestinal side-effects, is believed to give rise to cardiovascular problems.

An alternative treatment of inflammatory diseases that does not give rise to the above-mentioned side effects would thus be of real benefit in the clinic. In particular, a drug that preferably inhibits the transformation of $PGH_2$ to the pro-inflammatory mediator $PGE_2$ selectively might be expected to reduce the inflammatory response in the absence of a corresponding reduction of the formation of other, beneficial arachidonic acid metabolites. Such inhibition would accordingly be expected to alleviate the undesirable side-effects mentioned above.

$PGH_2$ may be transformed to $PGE_2$ by prostaglandin E synthases (PGES). Two microsomal prostaglandin E synthases (mPGES-1 and mPGES-2), and one cytosolic prostaglandin E synthase (cPGES) have been described. mPGES-1 is proposed to be closely linked to COX-2 and both enzyme's are upregulated during e.g. inflammation. Thus agents that are capable of inhibiting the action of mPGES-1 and thereby reducing the formation of $PGE_2$ are likely to be of benefit for the treatment of inflammation and more general acute and chronic pain conditions Benzimidazole and imidazopyridine derivatives with mPGES-1 inhibitory activity are disclosed in WO 2010/034796, WO 2010/034797, WO 2010/034798, WO 2010/034799. PCT/EP2010/052799 describes a broad class of different 2-arylamino benzimidazoles in which the aryl group bears a particular side chain.

DETAILED DESCRIPTION OF THE INVENTION

The present invention is a selection from the general formula of PCT/EP2010/052799 providing compounds that unexpectedly show improved activity in a cell based pharmacological assay.

Compounds with a similar affinity for the mPGES-1 enzyme as measured in the enzyme assay may have different potencies in the cell-based assay.

Data from a cell based pharmacological assay when compared with data from an enzyme assay are considered to allow for a better predictability and estimation of therapeutic effective concentrations/doses. Compounds of the present invention show high potency in both assays. Consequently, they are likely to be more suitable for the in-vivo use.

The present invention provides a compound of formula I,

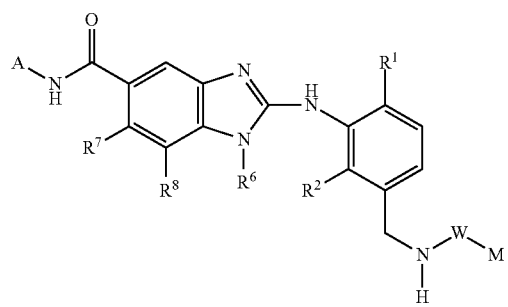

in which
$R^1$ and $R^2$ independently represent halo, —$C_{1-3}$alkyl, which latter alkyl group is optionally substituted by one or more fluorine atoms;
W represents —C(O)—, —C(O)O—, which groups are bound to the nitrogen of the —NH— moiety via the carbon atom;
M represents
—$C_{1-6}$alkyl, —$C_{3-7}$cycloalkyl, both of which groups are optionally substituted by one or more groups selected from —F, —OH, —CN, —$NH_2$, —NH($C_{1-2}$alkyl), —N($C_{1-2}$alkyl)$_2$, —$OC_{1-3}$alkyl, —$C_{1-5}$alkyl, —$C_{3-4}$cycloalkyl, in which latter three groups the alkyl or cycloalkyl groups are optionally substituted by one or more fluorine atoms;

or
oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —$C_{1-3}$ alkyl, which latter alkyl group is optionally substituted by one or more fluorine atoms;
or
phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —$C_{1-3}$alkyl, which latter alkyl group is optionally further substituted by one or more fluorine atoms;

$R^8$ represents —H, halogen, —$C_{1-3}$alkyl, which latter alkyl group is optionally substituted by one or more fluorine atoms;

$R^6$ represents —H, —$C_{1-5}$alkyl, —$C_{3-5}$cycloalkyl-$C_{0-2}$alkyl, in which latter three groups the alkyl or cycloalkyl fragments are optionally substituted by one or more fluorine atoms;

$R^7$ represents halo, $C_{1-5}$alkyl-O—, $C_{3-7}$cycloalkyl-$C_{0-2}$alkyl-O—, 4-7-membered heterocycloalkyl-$C_{0-2}$alkyl-O—, in which latter three groups the alkyl, cycloalkyl or heterocycloalkyl fragments are optionally substituted by one or more substituents selected from —F and —$OC_{1-3}$alkyl which latter alkyl group is optionally further substituted by one or more fluorine atoms;

A represents $C_{1-8}$ alkyl-, phenyl-, indanyl-, naphthyl-, 1,2,3,4-tetrahydronaphthyl-, pyridyl-, thienyl-, benzothienyl-, pyrrolyl-, indolyl-pyrazolyl-, thiazolyl-, benzothiazolyl-, oxazolyl-, benzoxazolyl-, isoxazolyl-, benzisoxazolyl-, phenyl-$C_{1-3}$alkyl-, thienyl-$C_{1-3}$alkyl-, pyridyl-$C_{1-3}$alkyl-, $C_{3-7}$cycloalkyl-$C_{0-3}$alkyl-, oxetanyl-$C_{0-3}$alkyl-, tetrahydrofuranyl-$C_{0-3}$alkyl, tetrahydropyranyl-$C_{0-3}$alkyl, in which groups the alkyl-, cycloalkyl- and heterocycloalkyl fragments are optionally substituted by one or more substituents selected from $R^{9a}$ and the aryl and heteroaryl fragments are optionally substituted by one or more substituents selected from $R^{9b}$;

each $R^{9a}$ independently represents —F, —Cl, —$C_{1-3}$alkyl which is optionally substituted by one or more substituents selected from —F, —$OC_{1-3}$ alkyl;

each $R^{9b}$ represents independently -halo, —CN; —$C_{1-3}$ alkyl which is optionally substituted by one or more fluorine atoms;

or a salt thereof, particularly a physiologically acceptable salt thereof.

In second embodiment, in the general formula I, A, M, W, $R^1$, $R^2$, $R^6$, $R^7$ have the same meaning as defined in any of the preceding embodiments, and
$R^8$ represents —H or fluoro.

In another embodiment, in the general formula I, A, M, W, $R^1$, $R^2$, $R^7$, $R^8$ have the same meaning as defined in any of the preceding embodiments, and
$R^6$ represents —H, —$CH_3$, cyclopropyl.

In another embodiment, in the general formula I, A, M, W, $R^6$, $R^7$, $R^8$ have the same meaning as defined in any of the preceding embodiments, and
$R^1$ and $R^2$ independently represent chloro, fluoro, —$CH_3$, —$CH_2F$, —$CF_3$.

In another embodiment, in the general formula I, A, M, W, $R^1$, $R^2$, $R^6$, $R^8$ have the same meaning as defined in any of the preceding embodiments, and
$R^7$ represents fluoro, —$OCHF_2$, —$OCH_2CH_2F$, —$OCH_2CHF_2$, —$OCH_2CF_3$, —O-tetrahydrofuran-3-yl, —O—$CH_2$-cyclopropyl.

In another embodiment, in the general formula I, M, W, $R^1$, $R^2$, $R^6$, $R^7$, $R^8$ have the same meaning as defined in any of the preceding embodiments, and A represents $C_{1-4}$ alkyl-, $C_{3-7}$cycloalkyl-$C_{0-2}$alkyl-, tetrahydrofuranyl-methyl-, phenyl-$C_{1-2}$ alkyl-, pyridyl-methyl-, phenyl-, indanyl-, pyridyl-, thienyl-, thiazolyl-, benzothiazolyl-, in which groups the alkyl-, cycloalkyl- and heterocycloalkyl-fragments are optionally substituted by one or more substituents selected from —F, —$CH_3$, —$CH_2F$, —$CF_3$, and the aryl and heteroaryl fragments are optionally substituted by —F, —Cl, —Br, —CN, —$CH_3$, $CH_2F$, $CHF_2$, —$CF_3$.

In another embodiment, in the general formula I, A, W, $R^1$, $R^2$, $R^6$, $R^7$, $R^8$ have the same meaning as defined in any of the preceding embodiments, and M represents
—$C_{1-4}$ alkyl, —$C_{3-5}$ cycloalkyl, both of which groups are optionally substituted by one or more groups selected from —F, —OH, —CN, —$NH_2$, —$OCH_3$, —$CH_3$, —$CH_2F$, —$CHF_2$, —$CF_3$, cyclopropyl;
or
oxetanyl-, tetrahydrofuranyl-, azetidinyl- or pyrrolidinyl-, all of which groups are optionally substituted by one or more substituents selected from —F, —$CH_3$, —$CH_2F$, —$CF_3$;
or
phenyl-, indanyl-, thienyl-, pyrrolyl-, pyrazolyl-, imidazolyl-, thiazolyl-, or isoxazolyl-, all of which groups are optionally substituted by one or more substituents selected from —F, —Cl, —$CH_3$, —$CH_2F$, —$CHF_2$, —$CF_3$.

Another embodiment of the present invention comprises compounds of formula Ia

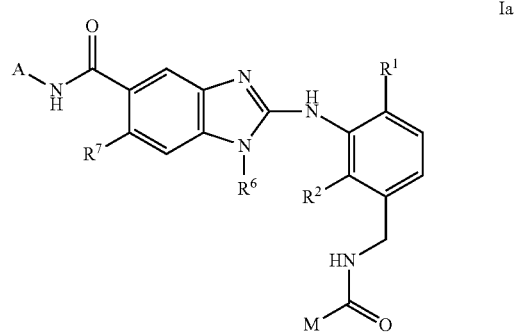

in which
A, M, $R^1$, $R^2$, $R^6$, $R^7$ have the same meaning as defined in any of the preceding embodiments.

A further embodiment of the present invention comprises compounds of formula Ia

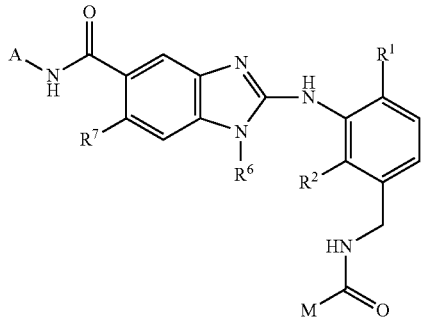

in which
M represents
methyl, ethyl, propyl, i-propyl, n-butyl, s-butyl, t-butyl, —CH$_2$-cyclopropyl, cyclopropyl, cyclobutyl, cyclopentyl, all of which groups are optionally substituted by one or more groups selected from —F, —OH, —CN, —NH$_2$, —OCH$_3$, —CH$_3$, —CF$_3$;
or is selected from the following groups

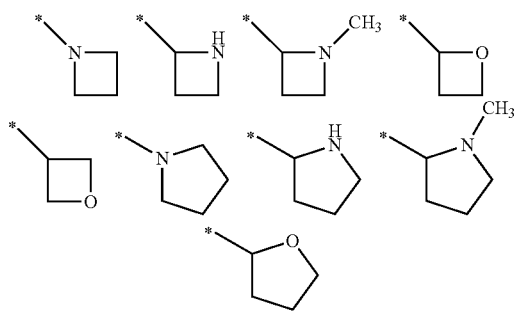

which latter nine groups are optionally substituted by one or more substituents selected from —F, —CH$_3$, —CF$_3$;
or is selected from the following groups

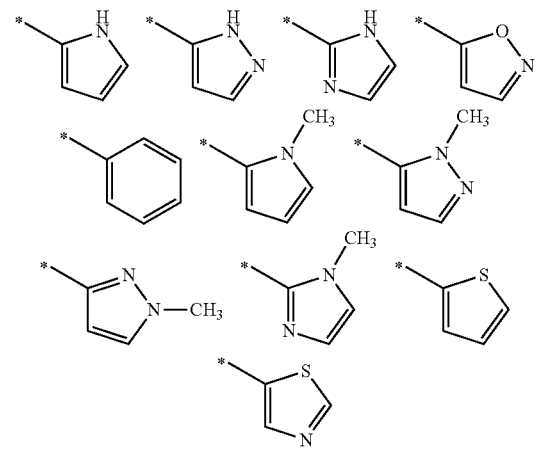

which latter eleven groups are optionally substituted by one or more substituents selected from —F, —Cl, —CH$_3$, —CF$_3$;

and
A, R$^1$, R$^2$, R$^6$, R$^7$ have the same meaning as defined in any of the preceding embodiments.

A further embodiment of the present invention comprises compounds of formula Ia in which A represents methyl, ethyl, propyl, i-propyl, n-butyl, s-butyl, t-butyl, which latter seven groups are optionally substituted by one or more fluorine atoms,
or cyclopropyl, cyclobutyl, cyclopentyl, cyclohexyl, which latter four groups are optionally substituted by one or more substituents selected from —F, —CH$_3$, —CHF$_2$, —CF$_3$;
or is selected from the following groups:

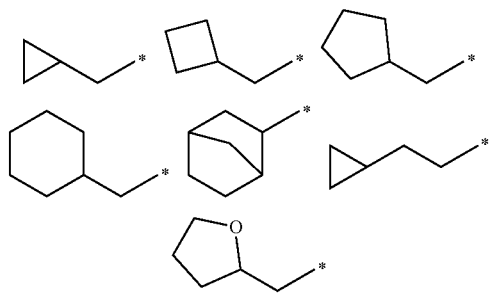

which latter seven groups are optionally substituted by one or more substituents selected from —F, —CH$_3$, —CHF$_2$, —CF$_3$;
or is selected from the following groups:

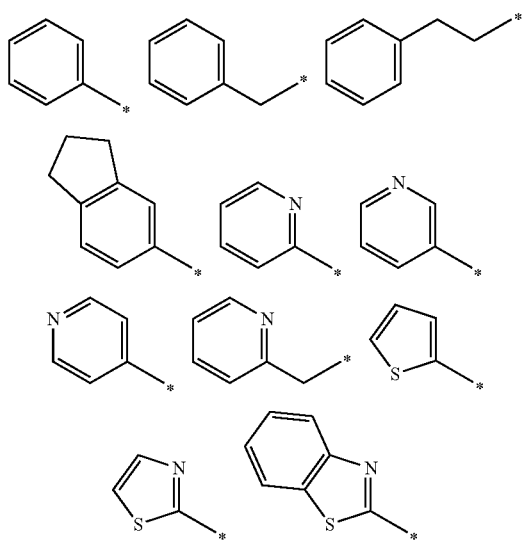

in which latter eleven groups the aryl and heteroaryl fragments are optionally substituted by one or more substituents selected from —F, —Cl, —Br, —CN, —CH$_3$, —CF$_3$;
and
M, R$^1$, R$^2$, R$^6$, R$^7$ have the same meaning as defined in any of the preceding embodiments.

A further embodiment of the present invention comprises compounds of formula Ib

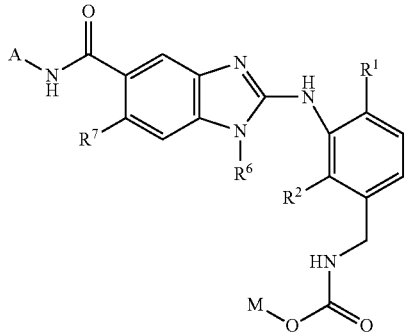

in which
M is tert-butyl;
and
A, R¹, R², R⁶, R⁷ have the same meaning as defined in any of the preceding embodiments.

A further embodiment of the present invention comprises compounds of formula Ia or Ib

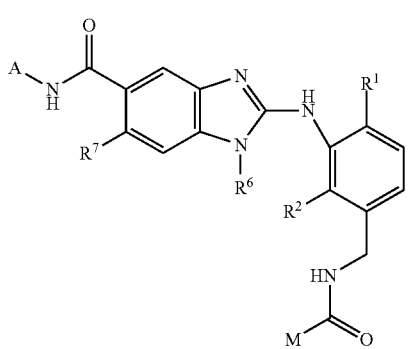

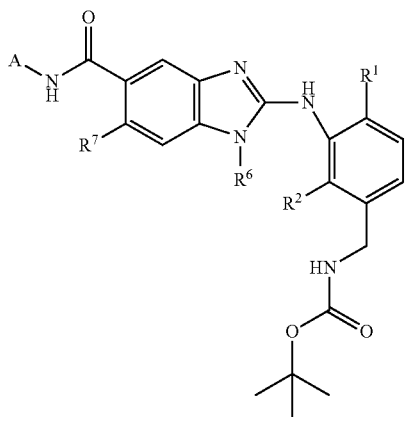

in which
R¹ and R² independently represent chloro, fluoro, —CH₃, —CH₂F, —CHF₂, —CF₃;
R⁶ represents —H, —CH₃, cyclopropyl;
R⁷ represents fluoro, —OCHF₂, —OCH₂CH₂F, —OCH₂CHF₂, —OCH₂CF₃, tetrahydrofuran-3-yl-O—, —O—CH₂-cyclopropyl;

A represents methyl, ethyl, propyl, i-propyl, n-butyl, s-butyl, t-butyl, which latter seven groups are optionally substituted by one or more fluorine atoms,
or cyclopropyl, cyclobutyl, cyclopentyl, cyclohexyl, which latter four groups are optionally substituted by one or more substituents selected from —F, —CH₃, —CHF₂, —CF₃;
or is selected from the following groups:

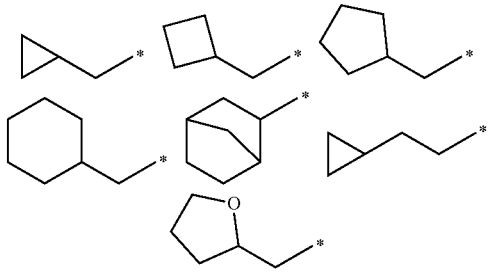

which latter seven groups are optionally substituted by one or more substituents selected from —F, —CH₃, —CHF₂, —CF₃;
or is selected from the following groups:

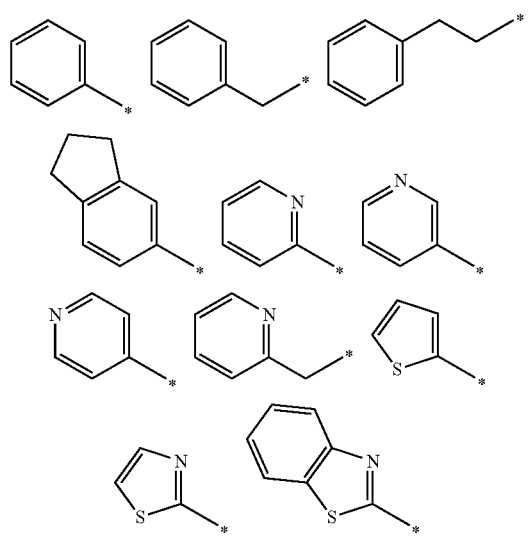

in which latter eleven groups the aryl and heteroaryl fragments are optionally substituted by one or more substituents selected from —F, —Cl, —Br, —CN, —CH₃, —CF₃;
M represents
methyl, ethyl, propyl, i-propyl, n-butyl, s-butyl, t-butyl, cyclopropyl, —CH₂-cyclopropyl, cyclobutyl, cyclopentyl, all of which groups are optionally substituted by one or more groups selected from —F, —OH, —CN, —NH₂, —OCH₃, —CH₃, —CF₃;
or is selected from the following groups

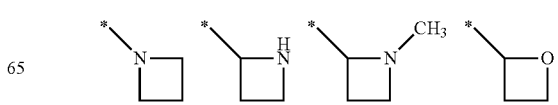

-continued

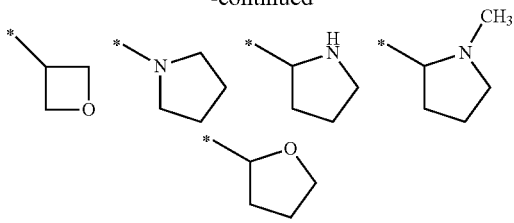

which latter nine groups are optionally substituted by one or more substituents selected from —F, —CH$_3$, —CF$_3$; or is selected from the following groups

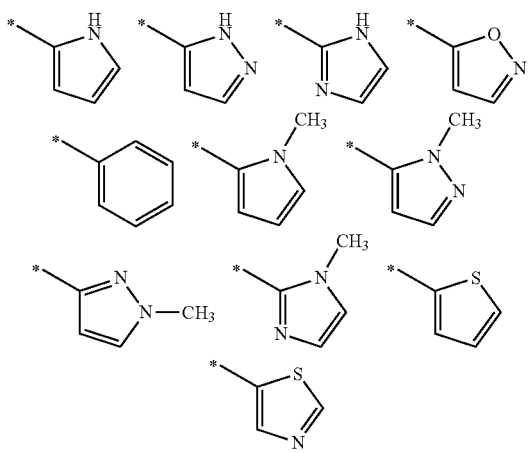

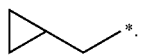

which latter eleven groups are optionally substituted by one or more substituents selected from —F, —Cl, —CH$_3$, —CF$_3$;

or salts thereof, particularly physiologically acceptable salts thereof.

TERMS AND DEFINITIONS USED

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, C$_{1-6}$-alkyl means an alkyl group or radical having 1 to 6 carbon atoms. In general, for groups comprising two or more subgroups, the last named subgroup is the radical attachment point, for example, the substituent "aryl-C$_{1-3}$-alkyl-" means an aryl group which is bound to a C$_{1-3}$-alkyl- group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined, for example a cyclopropylmethyl- group would be represented by the following drawing:

Stereochemistry/Solvates/Hydrates:

Unless specifically indicated, throughout the specification and the appended claims, a given chemical formula or name shall encompass tautomers (e.g. 1H-benzimidazole may be considered to be identical to a corresponding compound containing a 3H-benzimidazole) and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods.

Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term halogen generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Cycloalkyl:

The term "$C_{3-n}$-cycloalkyl", wherein n is an integer >3, either alone or in combination with another radical denotes a cyclic, saturated, hydrocarbon radical with 3 to n C atoms. For example the term $C_{3-7}$-cycloalkyl includes cyclopropyl, cyclobutyl, cyclopentyl, cyclohexyl and cycloheptyl.

The term "cycloalkyl" also includes bi-, tri- or tetra-cyclic ring structures consisting only of carbon and containing between one and four rings wherein such rings may be attached together in a pendent manner or may be fused. The term "cycloalkyl" additionally encompasses spiro systems, and bridged systems. The cyclic hydrocarbon radical may also be fused to an phenyl ring.

Thus, the term "cycloalkyl" includes the following exemplary structures which are not depicted as radicals as each form may be attached through a covalent bond to any atom of the cyclalkyl ring fragment as long as appropriate valencies are maintained:

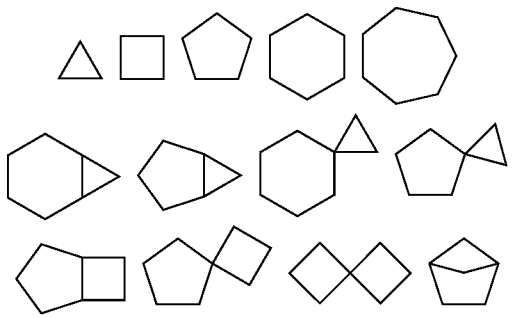
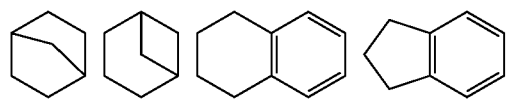

Heterocycloalkyl:

The term "$C_{3-n}$-heterocycloalkyl", wherein n is an integer >3, either alone or in combination with another radical denotes a cyclic non-aromatic mono-, bi-, tri- or spirocyclic radical with 3 to n ring atoms wherein at least one ring atom is selected from N, O or S and wherein n is the upper limit of ring atoms. The cyclic hydrocarbon radical may also be fused to an phenyl ring. Substituents on heterocycloalkyl groups may, where appropriate, be located on any atom in the ring system including a heteroatom.

The point of attachment of heterocycloalkyl radicals may be via any atom in the non-aromatic ring system including (where appropriate) a heteroatom (such as a nitrogen atom) and also including an atom on any fused non-aromatic carbocyclic ring fragment that may be present as part of the ring system.

Thus, the term "heterocycloalkyl" includes the following exemplary structures which are not depicted as radicals as each form may be attached through a covalent bond to any atom as long as appropriate valencies are maintained:

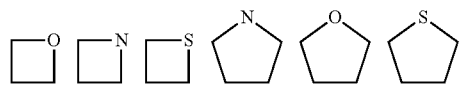
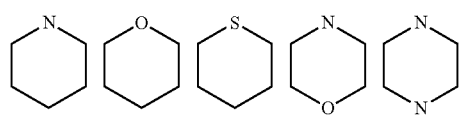
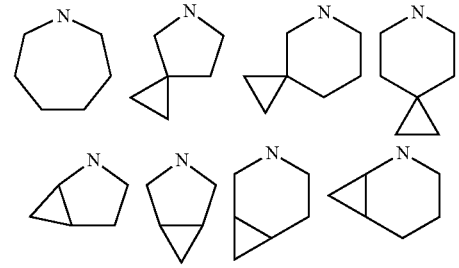

Methods of Preparation

Compounds of the present invention can be prepared in accordance with techniques that are well known to those skilled in the art, for example as described hereinafter and in the experimental section or in analogy to methods described in WO2010/034796 and WO2010/034797. According to a further aspect of the invention there is provided a process for the preparation of a compound of formula I, which process can be performed for example according to the following schemes A-C.

Scheme A (all variable groups are as defined in claim 1):

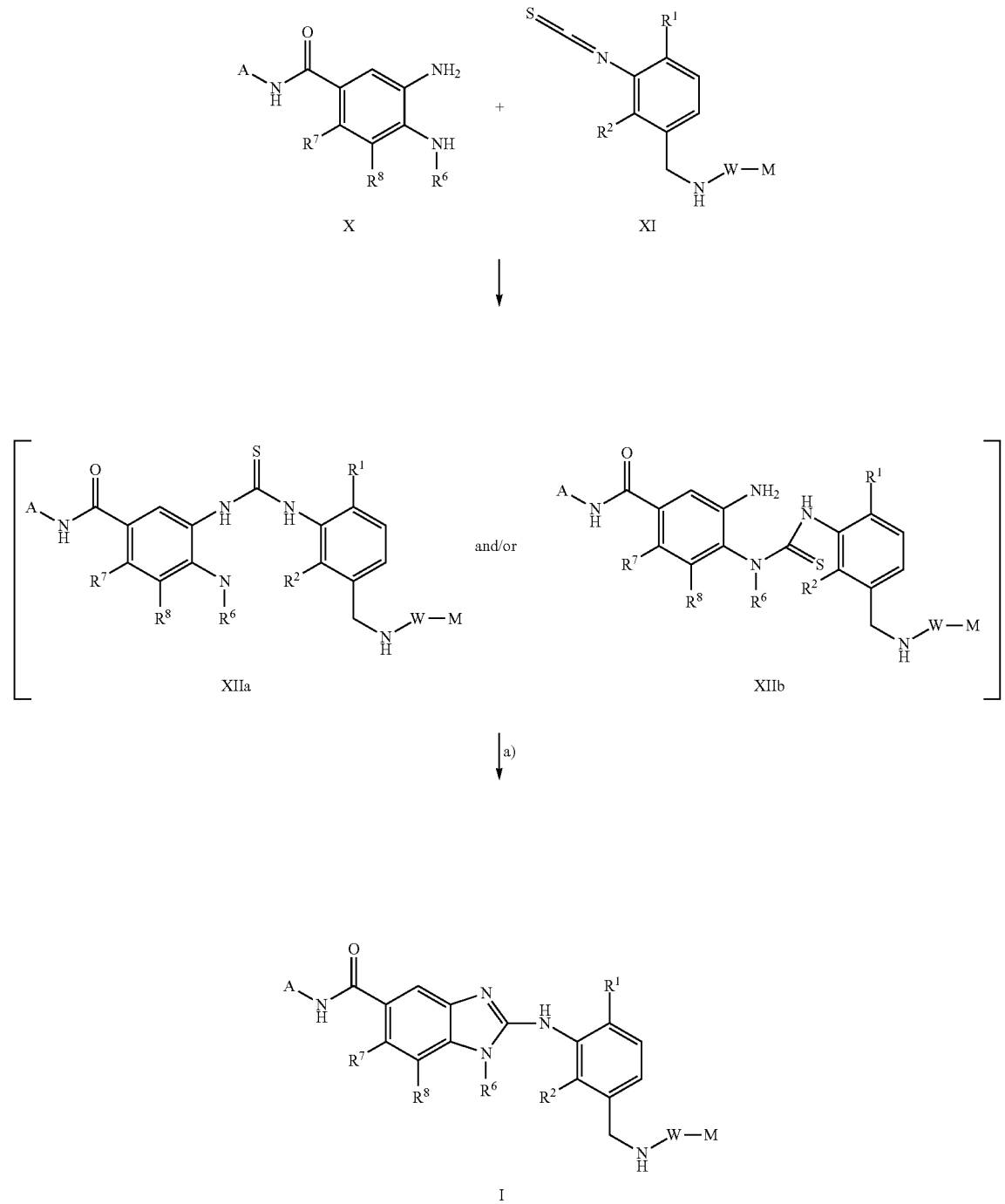

The reaction between phenylenediamine X and the thioisocyanate XI (Step a) can be performed under standard conditions known to those skilled in the art—for example in analogy to the process described in WO2010/034796—in presence of a suitable solvent such as diethyl ether (Et$_2$O), dimethylformamide (DMF), dichloromethane (DCM), acetonitrile (MeCN) and/or tetrahydrofuran (THF). The reaction is preferably performed in the presence of a suitable reagent which enhances the cyclisation step as for instance CH$_3$—I or a carbodiimide based compound such as N,N'-dicyclohexylcarbodiimide (DCC), 1-ethyl-3-(3-dimethylaminopropyl)carbodiimide (EDCI, or its salt, e.g. hydrochloride) or N,N'-diisopropylcarbodiimide (DIC). The reaction may proceed at any suitable temperature between 0° C. to 200° C., preferably between room temperature and 100° C. Step a can be performed in a step-wise reaction under isolation of the thiourea intermediates XIIa and/or XIIb or in a one-pot procedure.

Alternatively the compounds of formula I can be synthesized according to scheme B.

Scheme B (all variable groups are as defined in claim 1 and PG$^{acid}$ is a protecting group of a carboxylic acid function):

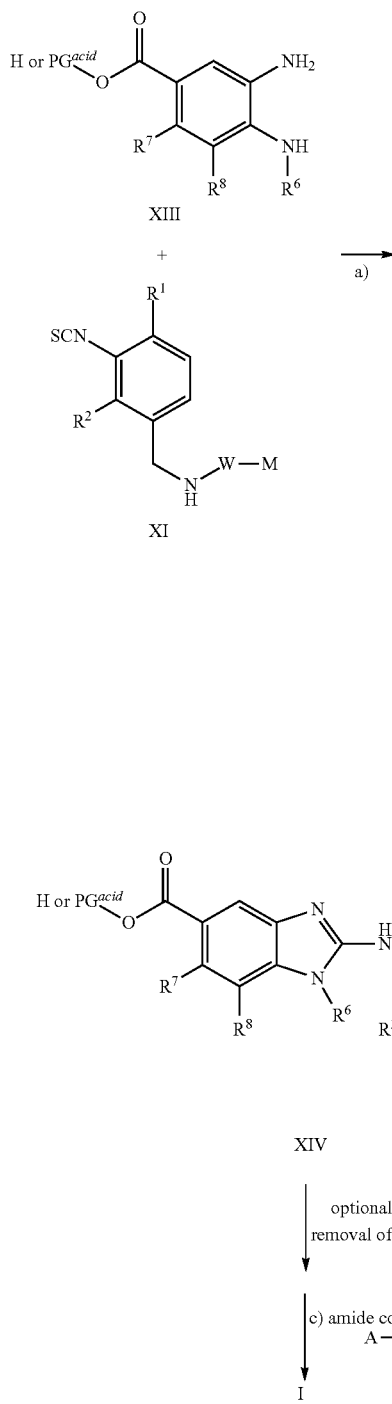

The protecting group PG$^{acid}$ is a literature known protecting group of a carboxylic acid, well known to those skilled in the art as for example described in "*Protective Groups in Organic Synthesis*", 3$^{rd}$ edition, T. W. Greene & P. G. M. Wutz, Wiley-Interscience (1999), for example a C$_{1-5}$-alkyl-, allyl- or a benzyl-group.

Step a) can be performed as described in scheme A, but may also be performed in the presence of an additive (such as 2,2,2-trifluoro-N,O-bis-(trimethylsilyl)-acetamide) when an unprotected carboxylic acid moiety is present in XIII.

Step b) can be performed under known saponification conditions, for example with aqueous LiOH, NaOH or KOH in ethanol (EtOH), methanol (MeOH), DMF, MeCN, THF or dioxane or with Pd/C in MeOH.

The amide formation in step c) can be performed with an additional in-situ activating agent like 1-propylphosphonic acid cyclic anhydride (PPA), O-(benzotriazol-1-yl)-N,N,N', N'-tetramethyl-uronium tetrafluoroborate (TBTU), O-(benzotriazol-1-yl)-N,N,N',N'-tetramethyl-uronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonylditriazole (CDT), 1-chloro-2-methyl-propenyl-dimethylamine, oxalyl chloride or other activating agents of the state of the art.

The coupling reaction is preferably performed in the presence of a base such as NaOH, KOH, NaHCO$_3$, triethylamine (TEA), N-ethyldiisopropylamine (DIPEA), pyridine, N,N,-dimethylaminopyridine (DMAP) or other appropriate bases of the state of the art and for example described in Houben-Weyl, "Methods in Organic Synthesis", Vol. E22a, p 425ff. The coupling reactions are performed in an appropriate solvent for example DCM, dioxane, THF, MeCN, DMF, dimethylacetamide (DMA), N-methylpyrrolidone (NMP) or in mixtures of the above mentioned solvents at any suitable temperature between 0° C. to 100° C.

When PG$^{acid}$ is a methyl or ethyl group the conversion of XIV to I can also be carried out in a one-pot procedure for example with trimethylaluminium or triethylaluminium in hexane, dioxane, THF at 20-80° C.

Alternatively the compounds of formula I can be synthesized according to scheme C.

Scheme C (all variable groups are as defined in claim 1 and PG$^{amino}$ is a protecting group of the benzylic amino group):

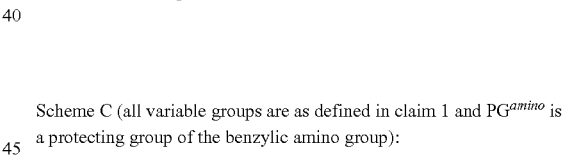

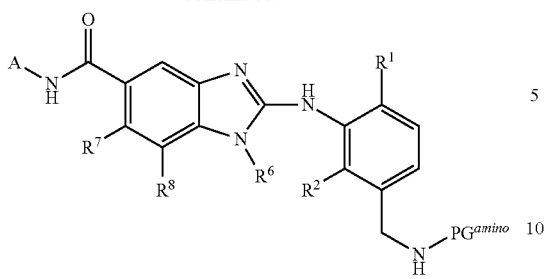

XVI

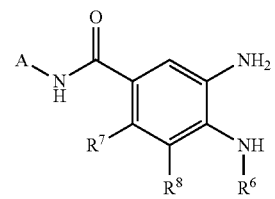

X d) removal of PG$^{amino}$ e) amide coupling with
HO—W—M or
Cl—W—M

I

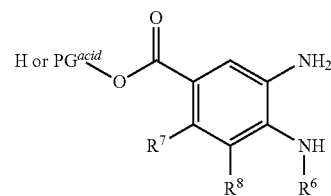

XIII

The protecting group PG$^{amino}$ in XV is a literature known protecting group of an amino group well known to those skilled in the art as for example described in "Protective Groups in Organic Synthesis", 3$^{rd}$ edition, T. W. Greene & P. G. M. Wutz, Wiley-Interscience (1999), for example a tert-butoxycarbonyl-, benzyloxycarbonyl-, ethoxycarbonyl-, methoxycarbonyl-, allyloxycarbonyl- or trifluormethylcarbonyl group.

Step a) can be performed as described in Scheme 1.

Step d) PG$^{amino}$ in XVI can be removed in accordance with techniques that are well known to those skilled in the art and which are exemplified hereinafter. For example XVI can be deprotected using an appropriate agent (depending on the protecting group) such as for example trifluoro acetic acid, HCl or H$_2$SO$_4$ solutions, KOH; Ba(OH)$_2$, Pd on carbon (Pd/C), trimethylsilyl iodide or other conditions as described in "Protective Groups in Organic Synthesis", 3$^{rd}$ edition, T. W. Greene & P. G. M. Wutz, Wiley-Interscience (1999). Appropriate co-solvent for this step is for example DCM, THF, MeCN, DMF, DMA, NMP or mixtures of the above mentioned solvents at any suitable temperature between 0° C. to 100° C.

The amide formation in step e) can be performed with the acids HO—W-M and an additional in-situ activating agent like PPA, TBTU, HBTU, HATU, DCC, EDCI, CD, CTI, 1-chloro-2-methyl-propenyl-dimethylamine, oxalyl chloride or other activating agents of the state of the art in analogy to Scheme B, step c; or directly with the corresponding acid chloride Cl—W-M under analogous conditions without an additional in situ activating agent.

The coupling reaction is preferably performed in the presence of a base such as NaOH, KOH, NaHCO$_3$, TEA, DIPEA, pyridine, DMAP or other appropriate bases of the state of the art and for example described in described in Houben-Weyl, "Methods in Organic Synthesis", Vol. E22a, p 425ff. The coupling reactions are performed in an appropriate solvent for example DCM, dioxane, THF, MeCN, DMF, DMA, NMP or in mixtures of the above mentioned solvents.

The synthesis of building blocks X and XIII wherein A, R$^6$-R$^8$ have the meaning as defined in claim 1 and PG$^{acid}$ is a literature known carboxylic acid protecting group as described above, can be performed in analogy to literature procedures which are well known to those skilled in the art, as for example in analogy to methods described in WO2010/034796 and WO2010/034797.

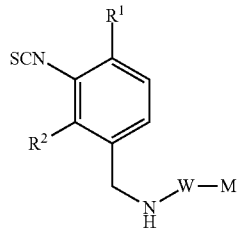

XI

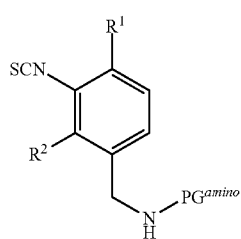

XV

The synthesis of the building blocks XI and XV—wherein all variable groups are as defined in claim 1 and PG$^{amino}$ is a protecting group of the benzylic amino group—is employing standard reaction conditions according to scheme D known to those skilled in the art which are exemplified in the experimental part in detail.

Scheme D (all variable groups are as defined in claim 1 and PG$^{amino}$ is a protecting group of the benzylic amino group):

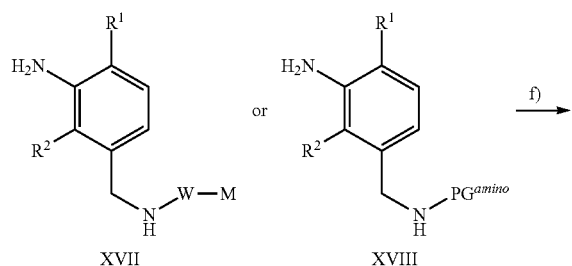

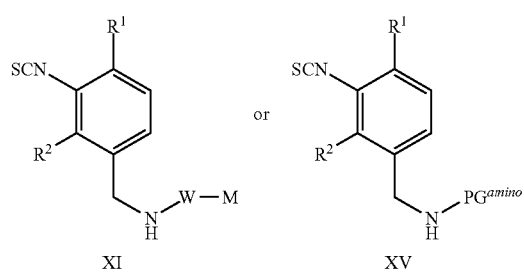

Step f) can be performed according to standard literature procedures for example with reagents such as 1,1'-thiocarbonyldi-2-pyridone, O,O'-di-2-pyridylthiocarbonate, 1,1'-thiocarbonyldiimidazole or with thiophosgene in a solvent as for example DCM, dioxane or DMF at temperatures between 0-150° C. and optionally under addition of a base like DMAP or TEA.

The building blocks XVII and XVIII can be prepared according to scheme E:

The amide formation in step g) can be performed in analogy to step c) or step e) to synthesize compound XVII or by using common reagents for amino group protection for example di-tert-butyl-dicarbonate, methyl-, ethyl-, benzyl or allyl-chloroformate under standard reaction conditions as described in "Protective Groups in Organic Synthesis", 3rd edition, T. W. Greene & P. G. M. Wutz, Wiley-Interscience (1999) to synthesize compounds XVIII.

The nitro group in precursor XVIIa or XVIIIa can be reduced to the amino group in step h) under literature known reduction conditions for example via hydrogenation (preferably at 1-5 bar) in presence of Pd/C or RaNi in MeOH, EtOH or THF optionally under acidic conditions in presence of HCl, or by using $SnCl_2$/HCl, $Na_2S_2O_4$, Zn/HCl, Fe/HCl, Fe-powder/aqueous $NH_4Cl$ solution or according to procedures described in the literature for example R. Larock, Comprehensive Organic Transformations, VCH Verlagsgemeinschaft, Weinheim (1989). Appropriate solvent for this step is for example DCM, THF, MeCN, DMF, DMA, NMP, EtOH, MeOH or mixtures of the above mentioned solvents at any suitable temperature between 0° C. to 100° C.

The building blocks XIX and XX can be prepared according to scheme F-G:

Scheme E (all variable groups are as defined in claim 1 and PG$^{amino}$ is a protecting group of the benzylic amino group):

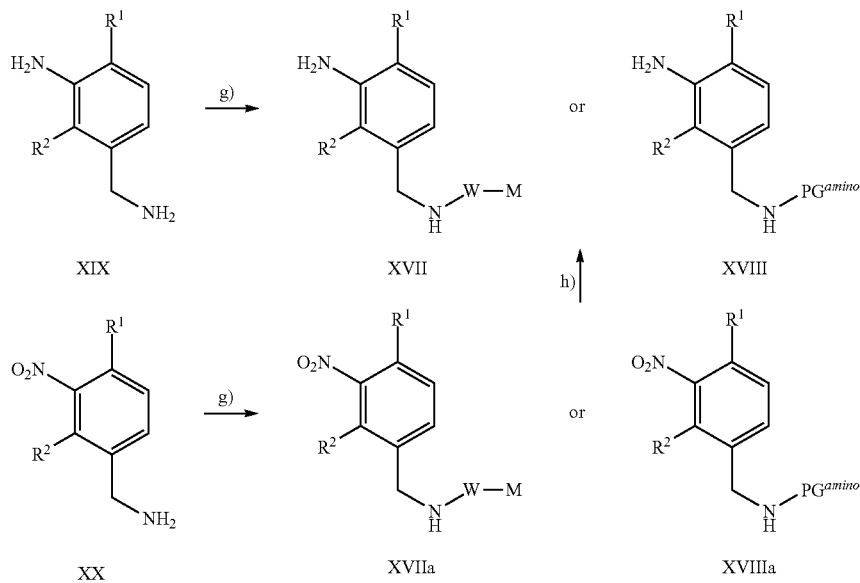

Scheme F (all variable groups are as defined in claim 1):

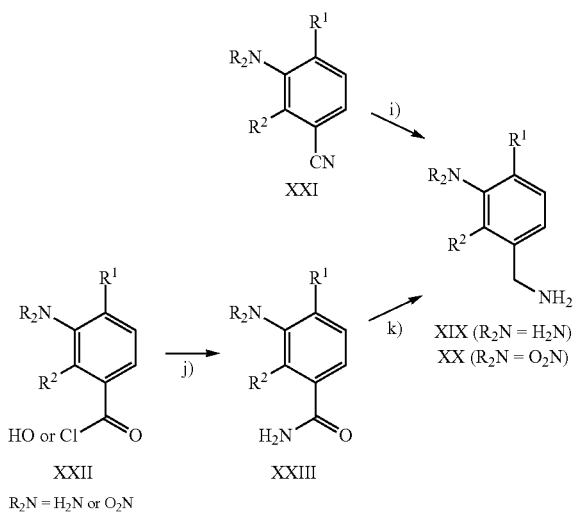

Step i) can be performed via hydrogenation (1-5 bar) with a catalyst like Pd/C, PtO$_2$ or RaNi in a suitable solvent like MeOH or EtOH optionally using HCl or NH$_3$ as additive at temperatures between 0-60° C. or via reduction with LiAlH$_4$ or BH$_3$-containing reagents under literature-known conditions.

Step j) can be performed under the amide coupling conditions described for step e) and using NH$_3$ as coupling partner, for example 1-chloro-2-methyl-propenyl-dimethylamine in THF can be used as activating agent.

Step k) can be performed using LiAlH$_4$ or BH$_3$-containing reagents under literature known conditions as for example compiled in R. C. Larock, Comprehensive Organic Transformations, VCH, 1989, p. 432-433, preferably with LiAlH$_4$ in THF at 0-80° C.

Alternatively compounds XIX and XX can be prepared according to scheme G

Scheme G (all variable groups are as defined in claim 1):

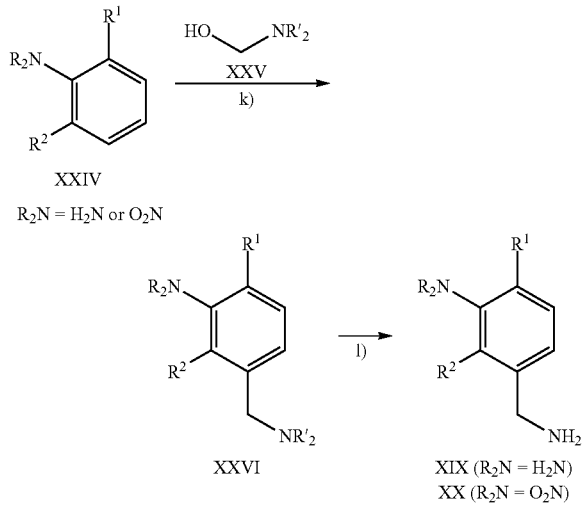

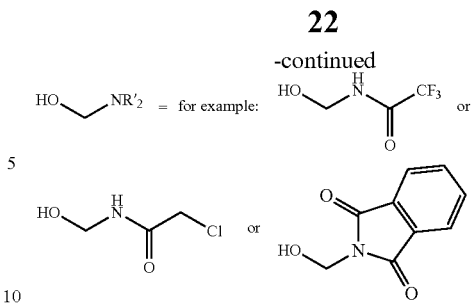

Step k) can be performed mixing XXIV with reagent XXV in concentrated H$_2$SO$_4$ or F$_3$C—SO$_3$H at temperatures between 0-150° C., preferably between 20-80° C.

Step l) can be performed using literature known deprotection procedures for the corresponding nitrogen protecting groups for example treatment of the phthalimide with hydrazine or cleavage of the amide bond using bases like NaOH in MeOH or EtOH at temperatures between 20-80° C. or under acidic conditions using aqueous HCl solution or HCl in dioxane at temperatures between 20-80° C.

Alternatively compounds XIX and XX can be prepared according to scheme H

Scheme H (all variable groups are as defined in claim 1):

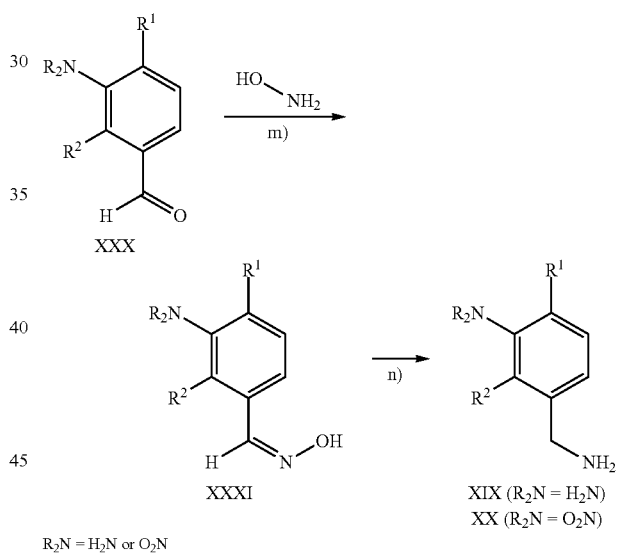

Step m) can be performed mixing XXX with HO—NH$_2$ in an appropriate solvent for example MeCN, DCM, THF, optionally using HCl as additive at temperatures between 0-60° C.

Step n) can be performed applying literature known reduction conditions for example via hydrogenation preferably at 1-5 bar H$_2$ pressure in presence of Pd/C or RaNi in MeOH, EtOH or THF optionally using HCl or HOAc as catalyst, or by using SnCl$_2$/HCl, Zn/HCl, Fe/HCl, Fe-powder/aqueous NH$_4$Cl solution or according to procedures described in the literature for example R. Larock, *Comprehensive Organic Transformations*, VCH Verlagsgemeinschaft, Weinheim (1989).

Therefore, a further aspect of the present invention is a process for preparing compounds of formula I comprising the following steps:

(1) reacting a compound of formula XIX

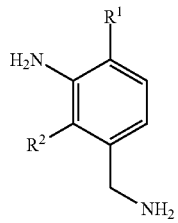

XIX in which
R¹ and R² independently represent halo, —$C_{1-3}$alkyl, which latter alkyl group is optionally substituted by one or more fluorine atoms;
with an acid chloride of formula Cl—W-M
in which
W represents —C(O)—, —C(O)O—, which groups are bound to the nitrogen of the —NH— moiety via the carbon atom;
M represents
—$C_{1-6}$alkyl, —$C_{3-7}$cycloalkyl, both of which groups are optionally substituted by one or more groups selected from —F, —OH, —CN, —$NH_2$, —$NH(C_{1-2}$alkyl), —$N(C_{1-2}$alkyl$)_2$, —$OC_{1-3}$alkyl, —$C_{1-3}$alkyl, —$C_{3-4}$cycloalkyl, in which latter three groups the alkyl or cycloalkyl groups are optionally substituted by one or more fluorine atoms;
or
oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —$C_{1-3}$ alkyl, which latter alkyl group is optionally substituted by one or more fluorine atoms;
or
phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —$C_{1-3}$alkyl, which latter alkyl group is optionally further substituted by one or more fluorine atoms;
or
with an acid of formula HO—W-M in the presence of a in situ activating agent selected from the group of 1-propylphosphonic acid cyclic anhydride (PPA), O-(benzotriazol-1-yl)-N,N,N',N'-tetramethyl-uronium tetrafluoroborate (TBTU), O-(benzotriazol-1-yl)-N,N,N',N'-tetramethyluronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonylditriazole (CDT), 1-chloro-2-methyl-propenyl-dimethylamine and oxalyl chloride;
and
in the presence of a base selected from the group of NaOH, KOH, $NaHCO_3$, triethylamine (TEA), N-ethyldiisopropylamine (DIPEA), pyridine, N,N,-dimethylaminopyridine (DMAP) in a solvent selected from the group of dichloromethane, dioxane, THF, MeCN, dimethylformamide, dimethylacetamide (DMA), N-methylpyrrolidone (NMP) or in mixtures thereof; at a temperature between 0° C. to 100° C. to obtain a compound of formula XVII

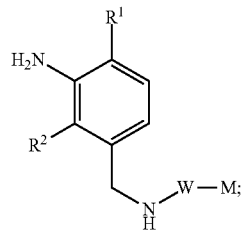

XVII (2) reacting the compound of formula XVII
with a reagent selected from the group of 1,1'-thiocarbonyldi-2-pyridone, O,O'-di-2-pyridylthiocarbonate, 1,1'-thiocarbonyldiimidazole and thiophosgene
in a solvent selected from the group of dichloromethane, dioxane and DMF
at temperatures between 0-150° C. and optionally in the presence of a base which is preferably DMAP or TEA
to obtain a compound of formula XI

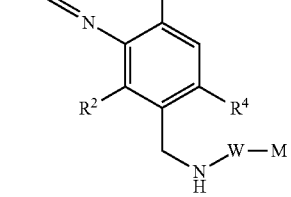

XI (3) reacting the compound of formula XI
with a compound of formula XIII

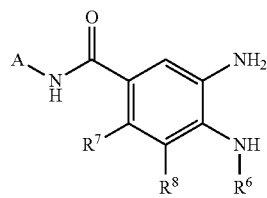

X in the presence of a reagent selected from the group of $CH_3$—I, N,N'-dicyclohexylcarbodiimide (DCC), 1-ethyl-3-(3-dimethylaminopropyl)carbodiimide (EDCI, or its hydrochloride) and N,N'-diisopropylcarbodiimide (DIC);
in a solvent selected from the group of diethyl ether ($Et_2O$), dimethylformamide (DMF), dichloromethane (DCM), acetonitrile (MeCN) and tetrahydrofuran (THF) preferably at a temperature between 0° C. and 100° C.

An alternative process for preparing compounds of formula I comprises the following steps:

(1) reacting a compound of formula XX

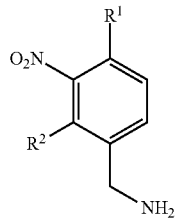

XX in which
R$^1$ and R$^2$ independently represent halo, —C$_{1-3}$alkyl, which latter alkyl group is optionally substituted by one or more fluorine atoms;
with an acid chloride of formula Cl—W-M
in which
W represents —C(O)—, —C(O)O—, which groups are bound to the nitrogen of the —NH— moiety via the carbon atom;
M represents
—C$_{1-6}$alkyl, —C$_{3-7}$cycloalkyl, both of which groups are optionally substituted by one or more groups selected from —F, —OH, —CN, —NH$_2$, —NH(C$_{1-2}$alkyl), —N(C$_{1-2}$alkyl)$_2$, —OC$_{1-3}$alkyl, —C$_{1-5}$alkyl, —C$_{3-4}$cycloalkyl, in which latter three groups the alkyl or cycloalkyl groups are optionally substituted by one or more fluorine atoms;
or
oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —C$_{1-3}$ alkyl, which latter alkyl group is optionally substituted by one or more fluorine atoms;
or
phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —C$_{1-3}$alkyl, which latter alkyl group is optionally further substituted by one or more fluorine atoms.
or
with an acid of formula HO—W-M in the presence of a in situ activating agent selected from the group of 1-propylphosphonic acid cyclic anhydride (PPA), O-(benzotriazol-1-yl)-N,N,N',N'-tetramethyl-uronium tetrafluoroborate (TBTU), O-(benzotriazol-1-yl)-N,N,N',N'-tetramethyluronium hexafluorophosphate (HBTU), O-(7-azabenzotriazol-1-yl)-N,N,N',N'-tetramethyluronium-hexafluorophosphate (HATU), DCC, EDCI, carbonyldiimidazole (CDI), carbonylditriazole (CDT), 1-chloro-2-methyl-propenyl-dimethylamine and oxalyl chloride;
and
in the presence of a base selected from the group of NaOH, KOH, NaHCO$_3$, triethylamine (TEA), N-ethyldiisopropylamine (DIPEA), pyridine, N,N,-dimethylaminopyridine (DMAP) in a solvent selected from the group of dichloromethane, dioxane, THF, MeCN, dimethylformamide, dimethylacetamide (DMA), N-methylpyrrolidone (NMP) or in mixtures thereof;
at a temperature between 0° C. to 100° C.

to obtain a compound of formula XVIIa

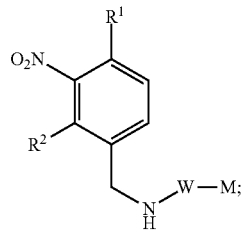

XVIIa (2) converting the compound of formula XVIIa into a compound of formula XVII

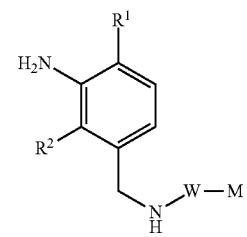

XVII by catalytic hydrogenation (preferably at 1-5 bar) in presence of Pd/C or RaNi in MeOH, EtOH or THF, optionally under acidic conditions in presence of HCl,
or
by reduction with a reagent selected from the group of SnCl$_2$/HCl, Na$_2$S$_2$O$_4$, Zn/HCl, Fe/HCl, Fe-powder/aqueous NH$_4$Cl solution in a solvent selected from the group of DCM, THF, MeCN, DMF, DMA, NMP, EtOH, MeOH or mixtures thereof at a temperature between 0° C. to 100° C.;

(3) reacting the compound of formula XVII
with a reagent selected from the group of 1,1'-thiocarbonyldi-2-pyridone, O,O'-di-2-pyridylthiocarbonate, 1,1'-thiocarbonyldiimidazole and thiophosgene
in a solvent selected from the group of dichloromethane, dioxane and DMF at temperatures between 0-150° C. and optionally in the presence of a base which is preferably DMAP or TEA
to obtain a compound of formula XI

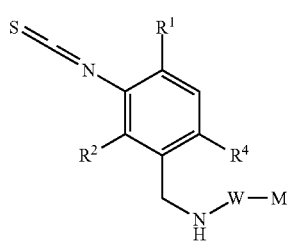

XI (4) reacting the compound of formula XI
with a compound of formula XIII

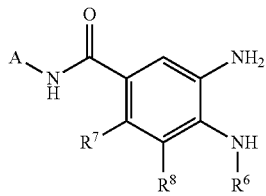

in the presence of a reagent selected from the group of CH$_3$—I, N,N'-dicyclohexylcarbodiimide (DCC), 1-ethyl-3-(3-dimethylaminopropyl)carbodiimide (EDCI, or its hydrochloride) and N,N'-diisopropylcarbodiimide (DIC);

in a solvent selected from the group of diethyl ether (Et$_2$O), dimethylformamide (DMF), dichloromethane (DCM), acetonitrile (MeCN) and tetrahydrofuran (THF) preferably at a temperature between 0° C. and 100° C.

A further aspect of the present invention is the intermediates of the formulae XI, XVII, XIX and XX

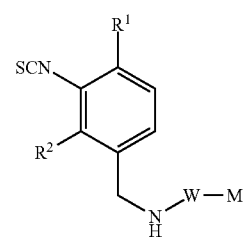

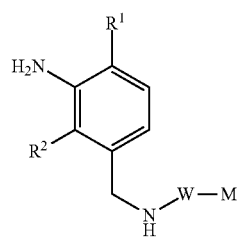

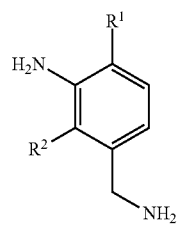

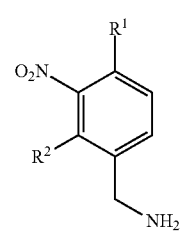

in which

R$^1$ and R$^2$ independently represent halo, —C$_{1-3}$alkyl, which latter alkyl group is optionally substituted by one or more fluorine atoms;

W represents —C(O)—, —C(O)O—, which groups are bound to the nitrogen of the —NH— moiety via the carbon atom;

M represents

—C$_{1-6}$alkyl, —C$_{3-7}$cycloalkyl, both of which groups are optionally substituted by one or more groups selected from —F, —OH, —CN, —NH$_2$, —NH(C$_{1-2}$alkyl), —N(C$_{1-2}$alkyl)$_2$, —OC$_{1-3}$alkyl, —C$_{1-5}$alkyl, —C$_{3-4}$cycloalkyl, in which latter three groups the alkyl or cycloalkyl groups are optionally substituted by one or more fluorine atoms;

or oxetanyl-, tetrahydrofuranyl-, tetrahydropyranyl-, azetidinyl-, pyrrolidinyl-, piperidinyl-, all of which groups are optionally substituted by one or more substituents selected from fluoro, —CN, —C$_{1-3}$ alkyl, which latter alkyl group is optionally substituted by one or more fluorine atoms;

or phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —C$_{1-3}$alkyl, which latter alkyl group is optionally further substituted by one or more fluorine atoms.

A second embodiment comprises as preferred intermediates compounds of formulae XIb, XIc, XVIIb, XVIIc, XIX and XX

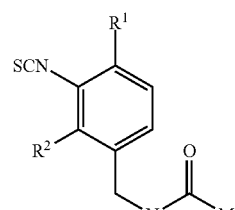

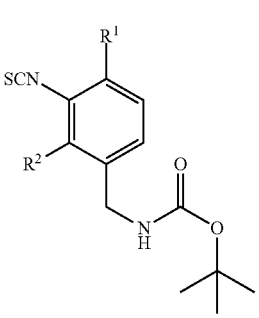

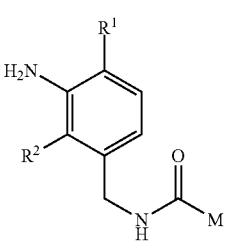

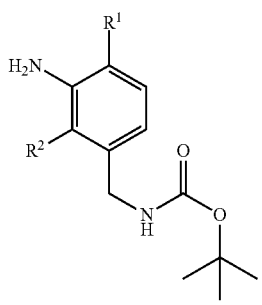

XVIIc

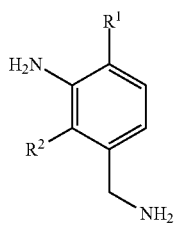

XIX

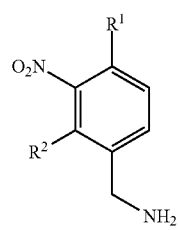

XX in which

R¹ and R² independently represent -chloro, fluoro or —CH₃;

M represents methyl, ethyl, propyl, i-propyl, n-butyl, s-butyl, t-butyl, cyclopropyl, —CH₂-cyclopropyl, cyclobutyl, cyclopentyl, all of which groups are optionally substituted by one or more groups selected from —F, —OH, —CN, —NH₂, —OCH₃, —CH₃,

—CF₃, or is selected from the following groups

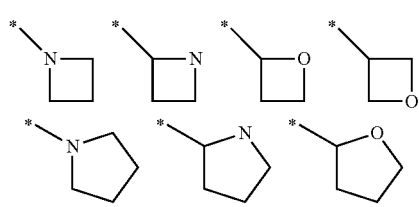

all of which groups are optionally substituted by one or more substituents selected from —F, —CH₃, or —CF₃;

or is selected from the following groups

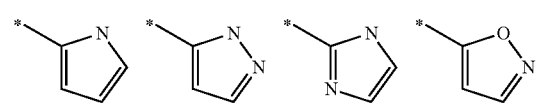

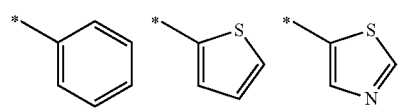

all of which groups are optionally substituted by one or more substituents selected from —F, —Cl, —CH₃, or —CF₃.

A further embodiment comprises, as more preferred intermediates, compounds of formulae XIb, XIc, XVIIb, XVIIc, XIX and XX, namely

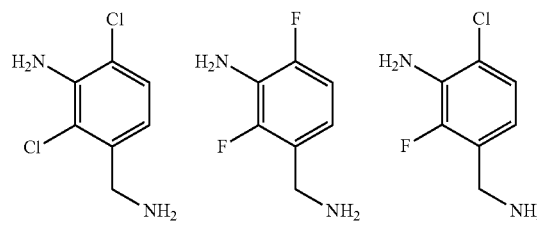

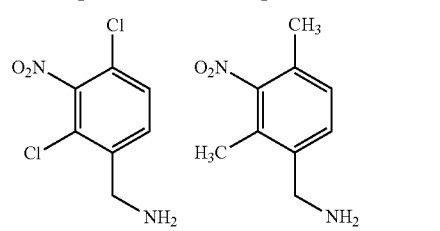

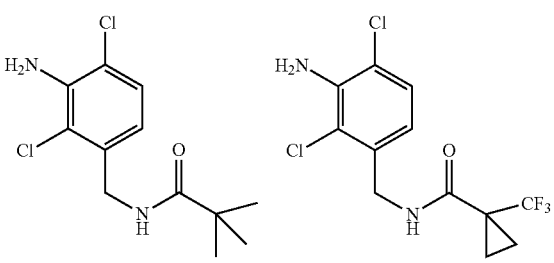

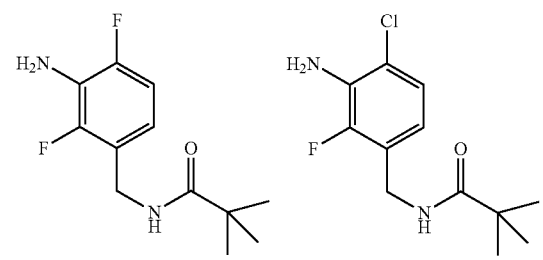

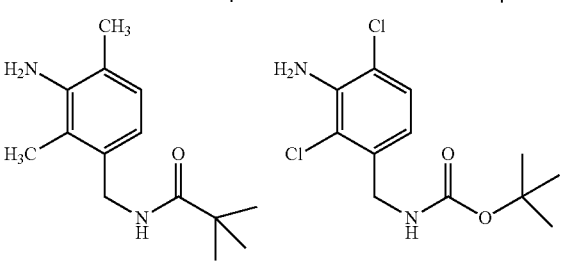

-continued

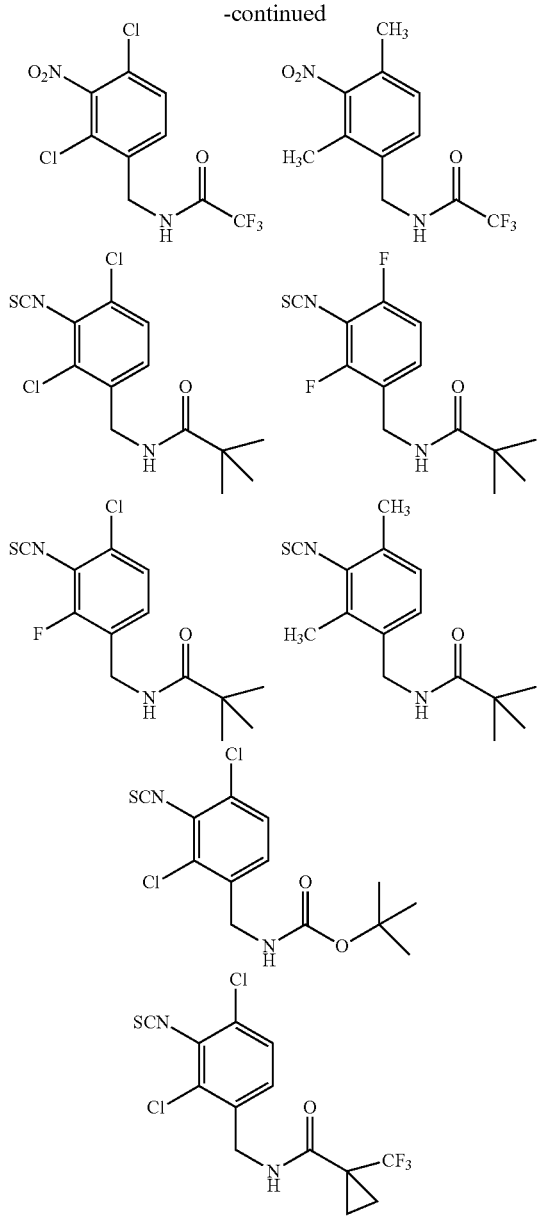

Biological Assays mPGES Protein Production

Microsomes from Rosetta *E. coli* bacteria expressing recombinant human mPGES-1 can be derived as described below:

Inoculate 5 ml LB with Ampicilin (50 μg/ml) and Chloramphenicol (34 μg/ml) with bacteria from freeze culture. Incubate 8 h at 37° C. with 200 rpm. Thereafter, inoculate 500-1000 ml LB containing Amp and Chloro with the 5 ml on culture and grow to OD640 of 0.8-1.0. Chill the culture to +4° C. before induction. Induce the culture with IPTG at a final concentration of 400 μM. Express the protein at room temp 18-23° C. with 200 rpm shaking over night.

The following steps can be performed on the following day:

1. Spin down the cells in 250 ml centrifuge flasks for 15 min at 7000 rpm (Beckmann Coulte Avanti J-E centrifuge)
2. Dissolve the pellet from 250 ml culture in 12.5 ml homogenization buffer
3. (15 mM Tris-HCL pH8, 1 mM EDTA pH8, 0.25 mM Sucrose, 2.5 mM GSH, 1 Tablet Protease inhibitor per 50 ml buffer)
4. Disintegrate the cells by sonication, 5×10 seconds at 48% amplitude of a 750 W sonifier
5. Add 2.5 ml $MgCl_2$ (100 mM) and DNase 12.5 μl (0.8 mg/ml) and incubate on ice for 30 min
6. Spin down the bacteria debris and save the supernatant, 7000 rpm for 15 min
7. Isolate the protein containing membranes in the supernatant by ultracentrifugation 120000×g for 2 hour at 4° C. (Sorvall T880 rotor).
8. Discard the supernatant and dissolve the pellet in 20 mM Potassium phosphate buffer pH7.4 ($KH_2PO_4$ and $K_2HPO_4$) buffer by sonication (5×10 s, 30% of a 50 W sonifier) and aliquot the enzyme and store aliquots at −80° C.

Before each experiment is performed an aliquot of the enzyme is thawed and it can then be dissolved in 0.1 M Potassium phosphate buffer pH7.4 ($KH_2PO_4$ and $K_2HPO_4$) buffer containing 2.5 mM GSH.

mPGES-1 Enzyme Assay

The aim of this assay is to determine the affinity of a test compound for the mPGES-1 enzyme.

47 μl of recombinant human mPGES-1 (~0.5 μg protein/well) containing microsomal suspension in a buffer containing GSH, (2.5 mmol/L L-Glutathione reduced, dissolved in 0.1 mol/L Phosphat Buffer pH 7.4) is dispensed in a 384-well plate and thereafter 1 μl of the test compound(s) is/are added and incubated for 25 minutes at room temperature. The enzyme reaction is started by the addition of 2 ul PGH2 (final conc. 2 μM) dissolved in water-free Diglyme. After 60 seconds the reaction is terminated by addition of a stop solution containing $FeCl_2$ (10 μL 0.074 mol/l $FeCl_2$). The samples are diluted between 1:25 in PBS (Phosphate Buffered Saline). 10 μl of the diluted samples are transferred to 384-well low volume plate. In order to quantify the amount of $PGE_2$ that has been formed, a homogenous time resolved fluorescent (HTRF) detecting of $PGE_2$ has been performed using a commercially available kit from Cisbio according to the manufactures recommendation. This HTRF-based assay has been described in detail (see: Goedken et al., J Biomol Screen, 2008, 13(7), 619-625). Briefly, the diluted samples are mixed with 5 μl $PGE_2$-d2 conjungate and 5 μl anti-$PGE_2$ cryptate conjungate. After an incubation period of the plates over night, the fluorescence is measured by the use of an appropriate microplate reader.

The fluorescence of Europium cryptate (maxex=307 nm, maxem=620 nm) and d2-$PGE_2$ (maxex=620 nm, maxem=665 nm) are measured.

The extent of the specific HTRF is measured as a ratio of the emission intensity at 665 nm vs. that at 620 nm at an excitation puts of 320 nm. The quantification plate contains also wells with different concentrations of $PGE_2$ as calibration curve for the calculation of the $PGE_2$ concentrations from the HTRF ratio values.

From all mPGES enzyme assay the background is subtracted and the $IC_{50}$ is calculated over a nonlinear regression with conventional software.

TABLE A mPGES-1 inhibitory effect (IC$_{50}$ values in nM) of compounds in the enzyme assay

| example | IC50 [nM] |
|---|---|
| 1 | 2 |
| 2 | 2 |
| 3 | 4 |
| 4 | 4 |
| 5 | 2 |
| 6 | 2 |
| 7 | 2 |
| 8 | 3 |
| 9 | 4 |
| 10 | 7 |
| 11 | 4 |
| 12 | 4 |
| 13 | 3 |
| 14 | 1 |
| 15 | 3 |
| 16 | 5 |
| 17 | 1 |
| 18 | 1 |
| 19 | 1 |
| 20 | 3 |
| 21 | 3 |
| 22 | 2 |
| 23 | 1 |
| 24 | 3 |
| 25 | 2 |
| 26 | 2 |
| 27 | 4 |
| 28 | 3 |
| 29 | 4 |
| 30 | 4 |
| 31 | 3 |
| 32 | 3 |
| 33 | 4 |
| 34 | 4 |
| 35 | 4 |
| 36 | 4 |
| 37 | 5 |
| 38 | 3 |
| 39 | 4 |
| 40 | 4 |
| 41 | 4 |
| 42 | 4 |
| 43 | 4 |
| 44 | 3 |
| 45 | 4 |
| 46 | 3 |
| 47 | 3 |
| 48 | 3 |
| 49 | 4 |
| 50 | 4 |
| 51 | 3 |
| 52 | 4 |
| 53 | 4 |
| 54 | 3 |
| 55 | 4 |
| 56 | 4 |
| 57 | 4 |
| 58 | 3 |
| 59 | 4 |
| 60 | 3 |
| 61 | 4 |
| 62 | 2 |
| 63 | 3 |
| 64 | 2 |
| 65 | 4 |
| 66 | 4 |
| 67 | 2 |
| 68 | 2 |
| 69 | 2 |
| 70 | 4 |
| 71 | 2 |
| 72 | 1 |
| 73 | 2 |
| 74 | 9 |
| 75 | 2 |
| 76 | 3 |
| 77 | 2 |
| 78 | 2 |
| 79 | 2 |
| 80 | 1 |
| 81 | 3 |
| 82 | 1 |
| 85 | 1 |
| 177 | 1 |
| 178 | 1 |
| 179 | 1 |
| 180 | 2 |

A549 Cell-Based Assay

Although the enzymatic assay is a high throughput assay the disadvantage is that it uses a recombinant protein which is not in its natural environment. Accordingly a cellular assay was established in which a cell line of human origin (A549) expressing the mPGES-1 protein was used. In addition in order to mimic the situation in humans in which compounds can be bound to plasma proteins 50% human serum is added in the assay. By having the combination of testing mPGES-1 in a cellular environment and the presence of 50% human serum this assay has a higher relevance to judge the therapeutic potential of a mPGES-inhibitor than the pure enzyme assay.

A549 cells (ATCC: CCL-185) are grown to about 90% confluence in F-12K Nutrient Mixture (Kaighn's Mod. Gibco) containing 10% FBS in a humified incubator at 37° C. and 5% $CO_2$. Cells were detached using Trypsin-EDTA. A549 cells were seeded in a 384-well collagene plate at a density of 7000 cells/well (50 µl) in F-12 medium containing 1% Penicillin-Streptomycin and 50% human serum. The cells were allowed to attach for 3-4 h. After that the cells were incubated for 20-24 h in F-12k medium supplemented with 50% human serum, 1% Penicillin-Streptomycin and containing IL-1β at a final concentration of 5 ng/ml as well as 10 nM arachidonic acid in the presence of a vehicle or a test compound. The total volume is 100 µl.

Concentrations of $PGE_2$ in the cell free medium (10 µl) were measured using a commercially available HTRF kit from Cisbio (as described above). The $PGE_2$ formation in the absence of test compound was taken as 100%.

IC$_{50}$ values were derived from at 6-8 point titrations using conventional software.

The compounds listed in table B are efficacious to block the generation of $PGE_2$. Compounds of formula I may therefore be expected to have therapeutic potential to treat inflammatory diseases and associated conditions such as inflammatory/nociceptive pain.

TABLE B mPGES-1 inhibitory effect (IC$_{50}$ values in nM) of compounds in the cell assay

| example | IC50 [nM] |
|---|---|
| 1 | <1 |
| 2 | 3 |
| 3 | 1 |

TABLE B-continued mPGES-1 inhibitory effect (IC$_{50}$ values in nM) of compounds in the cell assay

| example | IC50 [nM] |
|---|---|
| 4 | 2 |
| 5 | <1 |
| 6 | 2 |
| 7 | 1 |
| 8 | <1 |
| 9 | 79 |
| 10 | 4 |
| 11 | 4 |
| 12 | 7 |
| 13 | 28 |
| 14 | 5 |
| 15 | 11 |
| 16 | 106 |
| 17 | 1 |
| 18 | 4 |
| 19 | 2 |
| 20 | 14 |
| 21 | 36 |
| 22 | 1 |
| 23 | <1 |
| 25 | 9 |
| 26 | 11 |
| 27 | 124 |
| 28 | 1 |
| 29 | <1 |
| 30 | <1 |
| 31 | 1 |
| 32 | 1 |
| 33 | <1 |
| 34 | 1 |
| 35 | <1 |
| 36 | <1 |
| 37 | 9 |
| 38 | <1 |
| 39 | <1 |
| 40 | <1 |
| 41 | 1 |
| 42 | <1 |
| 43 | 4 |
| 44 | 1 |
| 45 | <1 |
| 46 | 1 |
| 47 | <1 |
| 48 | 1 |
| 49 | 1 |
| 50 | 1 |
| 51 | <1 |
| 52 | <1 |
| 53 | 1 |
| 54 | <1 |
| 55 | <1 |
| 56 | 3 |
| 57 | <1 |
| 58 | 2 |
| 59 | <1 |
| 60 | <1 |
| 61 | <1 |
| 62 | 1 |
| 63 | 1 |
| 64 | <1 |
| 65 | 6 |
| 66 | <1 |
| 67 | 1 |
| 68 | 1 |
| 69 | 3 |
| 70 | 16 |
| 71 | 16 |
| 72 | 9 |
| 73 | 1 |
| 74 | 1 |
| 75 | <1 |
| 76 | 2 |
| 77 | 12 |
| 78 | 8 |
| 79 | 1 |
| 80 | 7 |
| 81 | 50 |
| 82 | 43 |
| 84 | <1 |
| 85 | 4 |
| 86 | <1 |
| 87 | 221 |
| 88 | 68 |
| 90 | 36 |
| 91 | 10 |
| 92 | 9 |
| 93 | 66 |
| 95 | 13 |
| 96 | 14 |
| 98 | 2 |
| 100 | 52 |
| 101 | 11 |
| 102 | 15 |
| 103 | 18 |
| 107 | 106 |
| 108 | 59 |
| 109 | 57 |
| 110 | 8 |
| 111 | 7 |
| 112 | 19 |
| 113 | 25 |
| 115 | 300 |
| 16 | 3 |
| 17 | 20 |
| 18 | 11 |
| 20 | 9 |
| 21 | 119 |
| 22 | 4 |
| 23 | 3 |
| 24 | 28 |
| 25 | 220 |
| 126 | 72 |
| 127 | 85 |
| 128 | 26 |
| 130 | 3 |
| 131 | 1 |
| 132 | 2 |
| 133 | 1 |
| 134 | 8 |
| 135 | <1 |
| 136 | 17 |
| 137 | 4 |
| 138 | 49 |
| 139 | 27 |
| 141 | <1 |
| 142 | 2.5 |
| 144 | 2 |
| 145 | 7 |
| 146 | 2 |
| 147 | 4 |
| 148 | 2 |
| 149 | 1 |
| 150 | 1 |
| 151 | 1 |
| 152 | <1 |
| 153 | 3 |
| 154 | 36 |
| 155 | 2 |
| 156 | 10 |
| 158 | <1 |
| 159 | 1 |
| 160 | <1 |
| 161 | 2 |
| 162 | <1 |
| 163 | 5 |
| 164 | 15 |
| 165 | <1 |
| 166 | 7 |

TABLE B-continued mPGES-1 inhibitory effect (IC$_{50}$ values in nM) of compounds in the cell assay

| example | IC50 [nM] |
|---------|-----------|
| 167 | 6 |
| 168 | <1 |
| 169 | 1 |
| 170 | <1 |
| 171 | 4 |
| 172 | 2 |
| 174 | <1 |
| 176 | <1 |
| 177 | <1 |
| 178 | <1 |
| 179 | <1 |
| 180 | 93 |

TABLE C

Comparison of enzym and cell IC50 (nM) of selected benzimidazoles

| Structure | Enzym IC50 | Cell IC50 |
|-----------|------------|-----------|
| [structure 1] | 2 | <1 |
| [structure 2, of PCT/EP2010/052799] | 3 | 10 |
| [structure 3] | 2 | <1 |

TABLE C-continued

Comparison of enzym and cell IC50 (nM) of selected benzimidazoles

| Structure | Enzym IC50 | Cell IC50 |
|---|---|---|
| [structure with F$_3$C-cyclohexyl-NH-C(O)-benzimidazole, F$_2$HC-O, N-CH$_3$, NH-(4-Cl-phenyl)-CH$_2$-NH-C(O)-C(CH$_3$)$_3$] of PCT/EP2010/052799 | 3 | 17 |
| [structure with cyclopropyl-CH$_2$-NH-C(O)-benzimidazole, F$_2$HC-O, N-CH$_3$, NH-(2,6-dichlorophenyl)-CH$_2$-NH-C(O)-C(CH$_3$)$_3$] | 4 | 1 |
| [structure with cyclopropyl-CH$_2$-NH-C(O)-benzimidazole, F$_2$HC-O, N-CH$_3$, NH-(4-Cl-phenyl)-CH$_2$-NH-C(O)-C(CH$_3$)$_3$] of PCT/EP2010/052799 | 2 | >200 |

Tables A, B and C demonstrate that compounds with a similar affinity for the mPGES-1 enzyme as measured in the enzyme assay may have different potencies in the cell based assay.

Data from a cell based pharmacological assay when compared with data from an enzyme assay are considered to allow for a better predictability and estimation of therapeutic effective concentrations/doses. Compounds of the present invention show high potency in both assays. Consequently, they are likely to be more suitable for the in-vivo use.

Method of Treatment

The present invention relates to compounds of formula I which are useful in the prevention and/or treatment of a disease and/or condition in which the inhibition of prostaglandin E synthases, in particular that of the microsomal prostaglandin $E_2$ synthase-1 (mPGES-1) is of therapeutic benefit, including but not limited to the treatment and/or prevention of inflammatory diseases and/or associated conditions.

The term "inflammation" will be understood to include any inflammatory disease, disorder or condition per se, any condition that has an inflammatory component associated with it, and/or any condition characterised by inflammation as a symptom, including inter alia acute, chronic, ulcerative, specific, allergic and necrotic inflammation, and other forms of inflammation known to those skilled in the art. The term thus also includes, for the purposes of this invention, inflammatory pain, pain generally and/or fever.

Where a condition has an inflammatory component associated with it, or a condition characterised by inflammation as a symptom, the skilled person will appreciate that compounds of the invention may be useful in the treatment of the inflammatory symptoms and/or the inflammation associated with the condition.

Compounds of the invention may also have effects that are not linked to inflammatory mechanisms, such as in the reduction of bone loss in a subject. Such conditions include osteoporosis, osteoarthritis, Paget's disease and/or periodontal diseases.

A further aspect of the present invention relates to a compound of formula I as a medicament. Another aspect of the present invention is the use of compounds of formula I for the treatment and/or prevention of a disease and/or condition in which the inhibition of the mPGES-1 is of therapeutic benefit.

A further aspect of the present invention is the use of a compound of formula I for the treatment and/or prevention of inflammatory diseases and/or associated conditions.

The present invention also relates to the use of compounds of formula I for the treatment and/or prevention of the following diseases and conditions:

1. Rheumatic diseases or autoimmune diseases or muscoskeletal diseases: all forms of rheumatic diseases including e.g. soft tissue rheumatism, rheumatoid arthritis, polymyalgia rheumatica, reactive arthritis, tenosynovitis, gout or metabolic arthritis, bursitis, tendonitis, juvenile arthritis, spondyloarthropathies like e.g. spondylitis, ankylosing spondylitis, psoriatric arthropathy; sarcoidosis, fibromyalgia, myositis, polymyositis, osteoarthritis, traumatic arthritis, collagenoses of any origin e.g. systemic lupus erythematosus, scleroderma, dermatomyositis, Still's Disease, Sjögren syndrome, Felty syndrome; rheumatic fever and rheumatic heart disease, diseases of blood vessels like vasculitis, polyarthritis nodosa, Behcet's syndrome, giant cell arthritis, Wegener's granulomatosis, Henoch-Schönlein purpura; psoriatic arthritis, fungal arthritis, in particular including pain associated with any of the aforementioned conditions;
2. Headaches such as migraines with and without aura, tension-type headaches, cluster headaches and headaches with different origins;
3. Sympathetically maintained pain like complex regional pain syndrome Type I and II;
4. Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;
5. Cancer pain induced by or associated with tumors such as bone tumors, lymphatic leukemia; Hodgkin's disease, malignant lymphoma; lymphogranulomatoses; lymphosarcoma; solid malignant tumors; extensive metastases;
6. Visceral disorders such as chronic pelvic pain, pancreatitis, peptic ulcer, interstitial cystitis, cystitis, renal colic, angina, dysmenorrhoea, menstruation, gynaecological pain, irritable bowel disease (IBS), inflammatory bowel disease, Crohn's disease and ulcerative colitis, nephritis, prostatitis, vulvodynia, non-ulcer dyspepsia, non-cardiac chest pain, myocardial ischemia;
7. Inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;
8. Neurological diseases such as cerebral oedema and angioedema, cerebral dementia like e.g. Parkinson's and Alzheimers disease, senile dementia; multiple sclerosis, epilepsy, drug resistant epilepsy, stroke, myasthenia gravis, brain and meningeal infections like encephalomyelitis, meningitis, including HIV as well as schizophrenia, delusional disorders, autism, affective disorders and tic disorders;
9. Work-related diseases like pneumoconiosis, including aluminosis, anthracosis, asbestosis, chalicosis, ptilosis, siderosis, silicosis, tabacosis and byssinosis;
10. Lung diseases such as asthma including allergic asthma (atopic or non-atopic) as well as exercise-induced bronchoconstriction, occupational asthma, viral- or bacterial exacerbation of asthma, other non-allergic asthmas and "wheezy-infant syndrome", Chronic obstructive pulmonary disease (COPD) including emphysema, adult respiratory distress syndrome, bronchitis, pneumonia, adult respiratory distress syndrome (ARDS), pigeon fancier's disease, farmers lung;
11. Skin diseases such as psoriasis and eczema, dermatitis, sunburn, burns as well as aprains and strains and tissue trauma;
12. Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepathic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including *Chlamydia*-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;
13. Diabetes-associated symptoms such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion);
14. Benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; adenomatous polyps, including familial adenomatous polyposis (FAP) as well preventing polyps from forming in patients at risk of FAP.
15. Various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching.

Preferred according to the present invention is the use of a compound of formula I for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula I to a human being.

Dosage

The dose range of the compounds of formula I applicable per day is usually from 0.01 to 5000 mg, preferably from 1 to 2000 mg, more preferably from 5 to 500 mg, most preferably 10 to 250 mg. Each dosage unit may conveniently contain from 2 to 500 mg, preferably 5 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Formulations

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
  non-steroidal antiinflammatory drugs (NSAIDs) including COX-2 inhibitors;
  opiate receptor agonists;
  Cannabionoid agonists or inhibitors of the endocannabinoid pathway
  Sodium channel blockers;
  N-type calcium channel blockers;
  serotonergic and noradrenergic modulators;
  corticosteroids;
  histamine H1 receptor antagonists;
  histamine H2 receptor antagonists;
  proton pump inhibitors;
  leukotriene antagonists and 5-lipoxygenase inhibitors;
  local anesthetics;
  VR1 agonists and antagonists;
  Nicotinic acetylcholine receptor agonists;
  P2X3 receptor antagonists;
  NGF agonists and antagonists or anti-NGF antibodies;
  NK1 and NK2 antagonists;
  Bradykinin B1 antagonists
  CCR2 antagonists
  iNOS or nNOS or eNOS inhibitors
  NMDA antagonist;
  potassium channel modulators;
  GABA modulators;
  serotonergic and noradrenergic modulators;
  anti-migraine drugs;
  neuropathic pain drugs such as pregabaline or duloxetine.

Said list is not considered to have a limiting character.

In the following representative examples of such treatment options shall be given.

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs including but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like.

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Proton pump inhibitors: omeprazole, pantoprazole and esomeprazole and the like;

Leukotriene antagonists and 5-lipoxygenase inhibitors: zafirlukast, mon-telukast, pranlukast and zileuton and the like;

Local anesthetics such as ambroxol, lidocaine and the like;

Potassium channel modulators: like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

EXPERIMENTAL SECTION

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

AcOH acetic acid
aq aqueous
BSTFA N,O-bis(trimethylsilyl)trifluoroacetamide
Boc tert-butoxycarbonyl
Boc$_2$O di-tert-butyl-dicarbonate
CDT carbonylditriazole
CE chromatography equipment
CH cyclohexane
conc concentrated
DCM dichloromethane
DIC N,N-diisopropylcarbodiimide
DIPEA N-ethyldiisopropylamine
DMAP N,N-dimethylaminopyridine
DMSO dimethylsulphoxide
DMF N,N-dimethylformamide
EDC 1-(3-dimethylaminopropyl)-3-ethylcarbodiimide hydrochloride
EtOAc ethyl acetate
Et$_2$O diethyl ether
EtOH ethanol
HBTU O-(benzotriazol-1-yl)-N,N,N',N'-tetramethyluronium hexafluorophosphate
HPLC high performance liquid chromatography
i-PrOH isopropanol
KHMDS Potassium hexamethyldisilazane
MeCN acetonitrile
MeOH methanol
MS mass spectrometry
MTBE methyl-tert-butyl ether
PE petrol ether
PPA 1-propylphosphonic-acid cyclic anhydride
Pd/C 10% Palladium on carbon
RP reversed phase
rt room temperature
R$_f$ retention factor
R$_t$ retention time
sat saturated
TBTU O-(benzotriazol-1-yl)-N,N,N',N'-tetramethyluronium tetrafluoroborate
TCDI thiocarbonyl diimidazole
TEA triethylamine
THF tetrahydrofuran
TFA trifluoroacetic acid
TLC thin layer chromatography Analytical Methods All compounds specified in the examples below gave the correct mass spectra matching the theoretical isotope pattern. For practical reasons, only one of the major isotope peaks is given as representative data for the mass spectrum.

The TLC data is obtained by using the following tlc plates
a) Silica gel plates 60 F254 Merck No 1.05714.0001 abbreviated in the experimental part as "silica gel"
b) Reversed phase plates: RP-8 F 254s Merck No: 1.15684.0001 abbreviated in the experimental part as "RP-8".
c) Aluminiumoxide plates 60 F254 Merck 1.05713.0001 abbreviated in the experimental part as "Alox"

The R$_f$ values given are determined without chamber saturation.

Flash chromatography purifications are performed using silica gel from Millipore (MATREX™, 35 bis 70 µm) or Alox (E. Merck, Darmstadt, Aluminiumoxid 90 standardisiert, 63 bis 200 µm, Artikel-Nr: 1.01097.9050).

The HPLC/MS data, where specified, are obtained under the following conditions:

CE1:
Agilent HP 1200 with binary pump, Agilent MS 6140, HiPALS1367C
The diode array detection is measured in a wavelength range of 190-400 nm.
Range of mass-spectrometric detection: m/z 100 to m/z 1000.

CE 2:
Waters SQD MS, Acquity HPLC.
The diode array detection is measured in a wavelength range from 210-500 nm
Range of mass-spectrometric detection: m/z 120 to m/z 820

CE 3:
Agilent LC/MSD SL 61956B; Agilent 1100; quarternary. pump.

The diode array detection is measured in a wavelength range from 190-400 nm

Range of mass-spectrometric detection: m/z 100 to m/z 1000

CE 4:

Agilent HP 100 with binary pump, Waters ZQ2000,

The diode array detection is measured in a wavelength of 210-500 nm.

Range of mass-spectrometric detection: m/z 120 to m/z 820.

CE 5:

Acquity HPLC, Waters SQD MS,

The diode array detection is measured in a wavelength of 210-500 nm.

Range of mass-spectrometric detection: m/z 120 to m/z 820.

The following methods are used (if not stated otherwise the column temperature is 25° C.):

Method A (CE 2):

Stationary phase (column temperature: constant at 60° C.): Sunfire C18, 2.5. μm, 2.1×50 mm Mobile phase: E1: water with 0.1% HCOOH, E2: MeCN with 0.1% HCOOH Eluent gradient:

| time in min | % E1 | % E2 | flow rate in mL/min |
|---|---|---|---|
| 0.0 | 95 | 5 | 1.5 |
| 1.20 | 70 | 30 | 1.5 |
| 2.40 | 0 | 100 | 1.5 |
| 2.60 | 0 | 100 | 1.5 |
| 2.70 | 95 | 5 | 1.5 |

Method B (CE1):

Stationary phase: Zorbax Stable Bond C18, 1.8 μm, 3.0×30 mm

Mobile phase: E1: water with 0.15% HCOOH, E2: MeCN

Eluent gradient:

| time in min | % E1 | % E2 | flow rate in mL/min |
|---|---|---|---|
| 0.00 | 95 | 5 | 1.6 |
| 1.00 | 10 | 90 | 1.6 |
| 2.50 | 10 | 90 | 1.6 |
| 2.75 | 95 | 5 | 1.6 |

Method C(CE1):

Stationary phase: As described in method B.

Eluent gradient:

| time in min | % E1 | % E2 | flow rate in mL/min |
|---|---|---|---|
| 0.00 | 95 | 5 | 1.6 |
| 2.25 | 10 | 90 | 1.6 |
| 2.50 | 10 | 90 | 1.6 |
| 2.75 | 95 | 5 | 1.6 |

Method D (CE 4):

Stationary phase (column temperature: constant at 40° C.): XBridge C18, 3.5 μm, 4.6×50 mm Mobile phase: E1: water with 0.032% NH$_4$OH, E2: MeOH Eluent gradient:

| time in min | % E1 | % E2 | flow rate in mL/min |
|---|---|---|---|
| 0.00 | 95 | 5 | 1.5 |
| 2.00 | 0 | 100 | 1.5 |

Method E (CE1):

Stationary phase (column temperature: constant at 40° C.): Waters XBridge C18, 2.5 μm, 3.0×30 mm Mobile phase: E1: water with 0.15% HCOOH, E2: MeCN Eluent gradient:

| time in min | % E1 | % E2 | flow rate in mL/min |
|---|---|---|---|
| 0.00 | 95 | 5 | 1.6 |
| 2.25 | 10 | 90 | 1.6 |
| 2.50 | 10 | 90 | 1.6 |
| 2.75 | 95 | 5 | 1.6 |

Method F (CE 3):

Stationary phase (column temperature: constant at 40° C.): Zorbax Stable bond C18, 5 μm, 30×100 mm; Mobile phase: E1: water with 0.15% HCOOH, E2: MeCN Eluent gradient:

| time in min | % E1 | % E2 | flow rate in mL/min |
|---|---|---|---|
| 0.00 | 95 | 5 | 50 |
| 2.00 | 95 | 5 | 50 |
| 11.00 | 10 | 90 | 50 |
| 12.00 | 10 | 90 | 50 |
| 13.00 | 90 | 10 | 50 |

Method G (CE 3):

Stationary phase: Zorbax Stable Bond C18, 3.5 μm, 4.6×75 mm

Mobile phase: E1: water with 0.15% HCOOH, E2: MeCN

Eluent gradient:

| time in min | % E1 | % E2 | flow rate in mL/min |
|---|---|---|---|
| 0.00 | 95 | 5 | 1.6 |
| 2.00 | 10 | 90 | 1.6 |
| 5.00 | 10 | 90 | 1.6 |
| 5.50 | 95 | 5 | 1.6 |

Method H (CE 5)

Stationary phase (column temperature: constant at 60° C.): XBridge C18, 1.7 μm, 2.1×50 mm Mobile phase: E1: water with 0.1% NH$_4$OH, E2: MeCN Eluent gradient:

| time in min | % E1 | % E2 | flow rate in mL/min |
|---|---|---|---|
| 0.0 | 95 | 5 | 1.5 |
| 0.70 | 0 | 100 | 1.5 |
| 0.80 | 0 | 100 | 1.5 |
| 0.81 | 95 | 5 | 1.5 |
| 1.90 | 95 | 5 | 0.2 |

| time in min | % E1 | % E2 | flow rate in mL/min |
|---|---|---|---|
| 2.00 | 0 | 100 | 0.2 |
| 3.00 | 0 | 5 | 0.2 |

Method I (CE 4):

Stationary phase (column temperature: constant at 60° C.): Sunfire C18, 3.5. μm, 4.6×50 mm Mobile phase: E1: water with 0.1% TFA, E2: MeCN with 0.1% TFA Eluent gradient:

| time in min | % E1 | % E2 | flow rate in mL/min |
|---|---|---|---|
| 0.0 | 95 | 5 | 1.5 |
| 2.00 | 0 | 100 | 1.5 |
| 2.50 | 0 | 100 | 1.5 |
| 2.60 | 95 | 5 | 1.5 |

Synthesis of Building Blocks of the 2,3,4-Trisubstituted Benzylamine-Type

Building Block A

N-(2,4-Dichloro-3-isothiocyanato-benzyl)-2,2-dimethyl-propionamide water. The filtrate is cooled to rt, concentrated and slowly acidified with 6 M aq. HCl solution. The mixture is cooled in an ice bath, filtered and the filtercake is washed with cold water and dried to give the sub-title compound.

Yield: 11.6 g (78%). $R_f$=0.1 (silica gel, DCM:EtOH 9:1). MS m/z: 248 [M+H]$^+$.

(b) 3-Amino-2,4-dichloro-benzoic acid

3-Acetylamino-2,4-dichloro-benzoic acid (21.0 g, 84.6 mmol) is stirred in 6 M aq. HCl-solution (120 mL) and acetic acid (250 mL) at reflux for 24 h. The reaction mixture is cooled, concentrated, diluted with water and concentrated again. The residue is diluted with water, stirred under cooling and filtered. The filtercake is washed and dried to give the sub-title compound.

Yield: 16.8 g (96%). MS m/z: 204 [M−H]$^−$. HPLC-method C: $R_t$=1.46 min.

(c) 3-Amino-2,4-dichloro-benzamide (1-Chloro-2-methyl-propenyl)-dimethyl-amine (16.1 mL, 116 mmol) is added to 3-amino-2,4-dichloro-benzoic acid (20.0 g, 97.1 mmol) in THF (320 mL). After 4 h at rt the mixture is added dropwise to conc. NH$_3$ (320 mL) and stirred at rt overnight. The reaction mixture is concentrated, cooled and filtered. The filtercake is dried to give the sub-title compound.

Yield: 17.4 g (87%). MS m/z: 205 [M+H]$^+$. HPLC-method C: $R_t$=1.19 min.

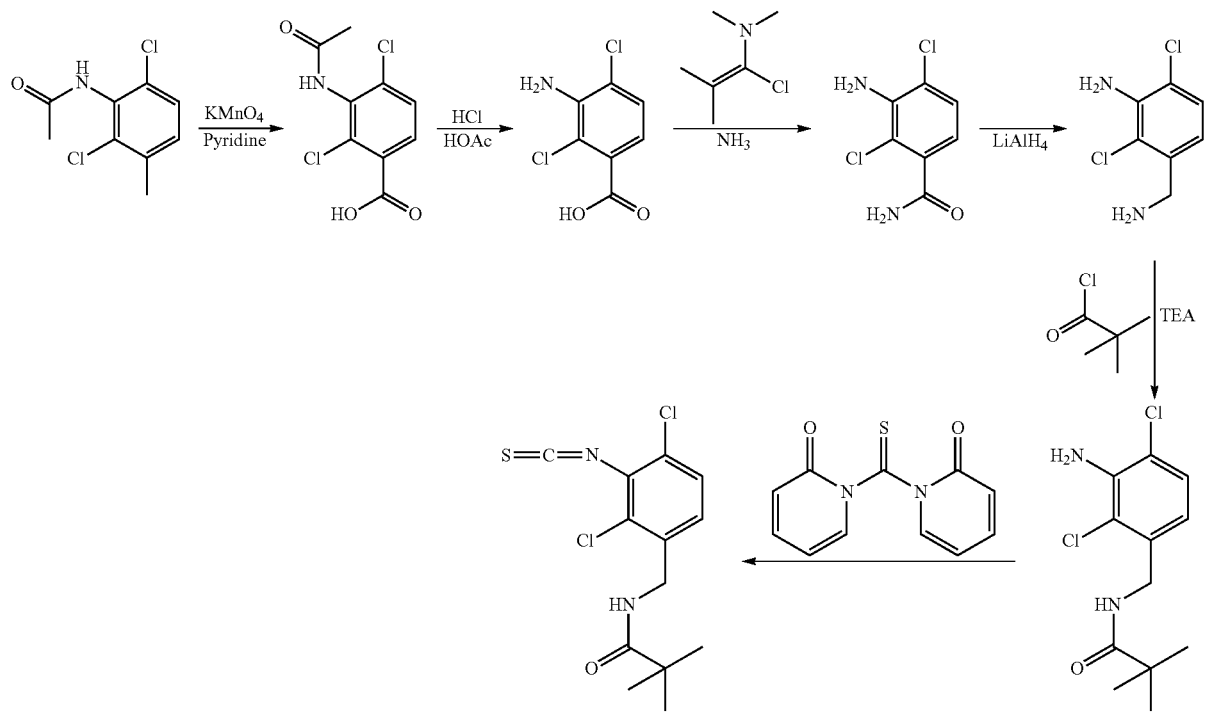

(a) 3-Acetylamino-2,4-dichloro-benzoic acid

Water (110 mL) is added to N-(2,6-dichloro-3-methylphenyl)-acetamide (13 g, 59 mmol) in pyridine (30 mL). The mixture is heated to 70° C. and KMnO$_4$ (47 g, 298 mmol) is cautiously added portionwise. After 6 h at reflux the reaction mixture is filtered through a pad of celite and washed with hot (d) 3-Amino-2,4-dichloro-benzylamine 3-Amino-2,4-dichloro-benzamide (2.00 g, 9.8 mmol) in THF (45 mL) is added dropwise to LiAlH$_4$ (1 M in THF, 24.4 mL) in THF (45 mL). The reaction mixture is stirred for 1 h at rt and 10 h at reflux. Excess LiAlH$_4$ is destroyed under cooling as described by L. F. Fieser & M. Fieser Vol 1, p 584 Wiley 1967. After 30 min the mixture is filtered and the filtrate is concentrated to give the sub-title compound.

Yield: 1.85 g (99%). $R_f$=0.12 (silica gel, DCM:EtOH 95:5). MS m/z: 191 [M+H]$^+$.

(e) N-(3-Amino-2,4-dichloro-benzyl)-2,2-dimethyl-propionamide

3-Amino-2,4-dichloro-benzylamine (2.28 g, 11.9 mmol) is added to a mixture of 2,2-dimethylpropionic acid chloride (1.47 mL, 11.9 mmol) and TEA (4.14 mL, 29.8 mmol) in THF (90 mL) and it is stirred for 3 h. The reaction mixture is concentrated, diluted with EtOAc, washed with 5% aq. NaHCO$_3$ solution and water, dried with Na$_2$SO$_4$ filtered and concentrated to give the sub-title compound.

Yield: 3.1 g (94%). $R_f$=0.61 (silica gel, DCM:EtOH 95:5).

(f) N-(2,4-Dichloro-3-isothiocyanato-benzyl)-2,2-dimethyl-propionamide 1,1'-Thiocarbonyldi-2-pyridone (4.87 g, 21 mmol) is added to a mixture of N-(3-amino-2,4-dichloro-benzyl)-2,2-dimethyl-propionamide (5.50 g, 20 mmol) and dioxane (200 mL) and stirred at rt for 2 h and at reflux for 8 h. The mixture is concentrated, diluted with DCM and filtered over silica gel. The filtrate is concentrated to give the sub-title compound.

Yield: 6.00 g (95%). HPLC-method B: $R_t$=1.58 min. MS m/z: 318 [M+H]$^+$.

Alternatively, building block A can also be prepared according to the following scheme:

mixture is stirred at 75° C. overnight, poured into ice water and stirred for 1 h. The precipitate is collected by filtration and dried. Yield 0.32 g (15%). MS [M–H]$^-$=315, HPLC-method B: $R_t$=1.43 min.

(h) 3-Nitro-2,4-dichloro-benzylamine

A mixture of N-(3-nitro-2,4-dichloro-benzyl)-2,2,2-trifluoroacetamide (0.66 g, impure, content ~50%), 4M NaOH-solution (1.3 mL, 5.2 mmol) and MeOH (15 mL) is refluxed for 4 h. Then the mixture is concentrated, diluted with water, acidified with 4M HCl, filtered, 4M NaOH-solution is added and it is extracted with EtOAc. The organic phase is dried with Na$_2$SO$_4$, filtered and concentrated. Yield 0.17 g MS m/z: 221 [M+H]$^+$. HPLC-method B: $R_t$=1.02 min.

(i) N-(3-Nitro-2,4-dichloro-benzyl)-2,2-dimethyl-propionamide 2,2-Dimethyl-propionic acid chloride (0.124 mL, 1.01 mmol) is added to a mixture of 3-nitro-2,4-dichloro-benzylamine (0.28 g, 1.01 mmol) and TEA (0.35 mL, 2.52 mmol) in THF (10 mL) and it is stirred overnight. The reaction mixture is concentrated, diluted with EtOAc, washed successively with 5% aq. NaHCO$_3$ solution and brine, dried with Na$_2$SO$_4$ filtered and concentrated.

Yield: 0.29 g. MS m/z: 306 [M+H]$^+$. HPLC-method B: $R_t$=1.42 min.

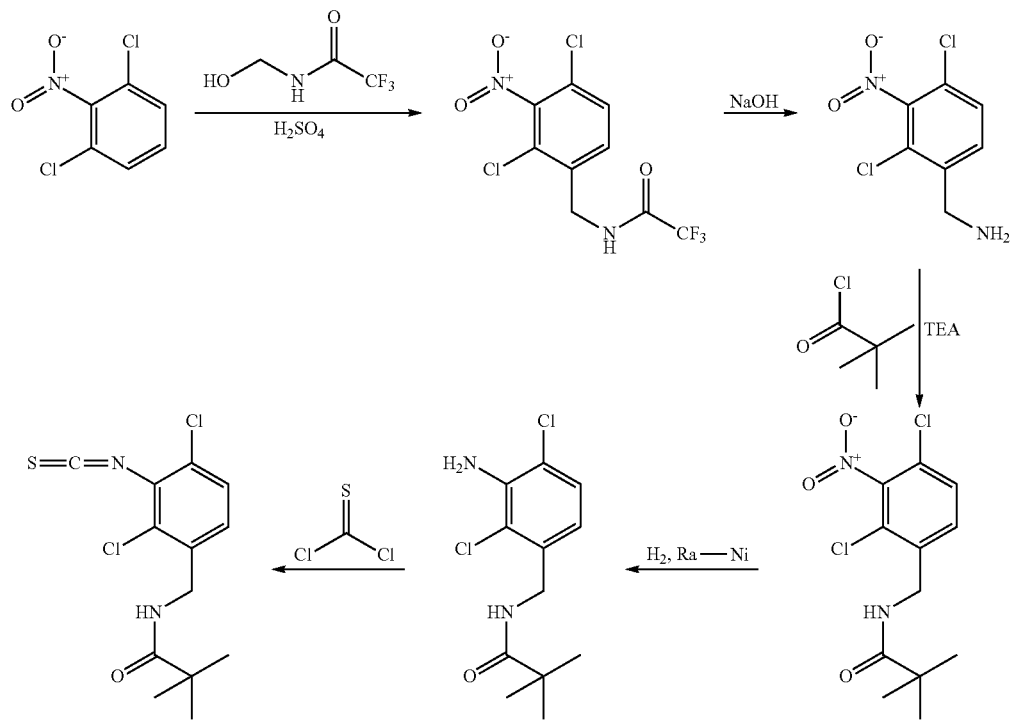

(g) N-(3-Nitro-2,4-dichloro-benzyl)-2,2,2-trifluoro-acetamide (g) N-(3-Amino-2,4-dichloro-benzyl)-2,2-dimethyl-propionamide N-(Hydroxymethyl)trifluoroacetamide (6.6 mmol; 0.946 g) is added to a mixture of 2,6-dichloro-nitrobenzene (0.899 mL; 6.6 mmol) and conc. H$_2$SO$_4$ (15 mL) at 75° C. The A mixture of 3-nitro-2,4-dichloro-benzylamine (290 mg, 0.95 mmol), RaNi (50 mg) and THF (15 mL) is stirred for 7 h under a hydrogen atmosphere (50 psi). The catalyst is removed by filtration and the filtrate is concentrated.

Yield: 0.26 g. MS m/z: 276 [M+H]⁺. HPLC-method B: $R_t$=1.32 min.

(h) N-(2,4-Dichloro-3-isothiocyanato-benzyl)-2,2-dimethyl-propionamide

A mixture of N-(3-amino-2,4-dichloro-benzyl)-2,2-dimethyl-propionamide (0.95 g, 3.4 mmol) in 4.0 mL dioxane is added to thiophosgene (0.45 mL, 5.8 mmol) in 2.5 mL water. The mixture is stirred overnight, extracted with DCM and the organic phase is washed with 5% aq NaHCO₃ solution and water and dried with Na₂SO₄. After filtration and concentration, the crude product is diluted with DCM, filtered through a pad of silica gel and concentrated.

Building Block B (2,4-Dichloro-3-isothiocyanato-benzyl)-carbamic acid tert-butyl ester

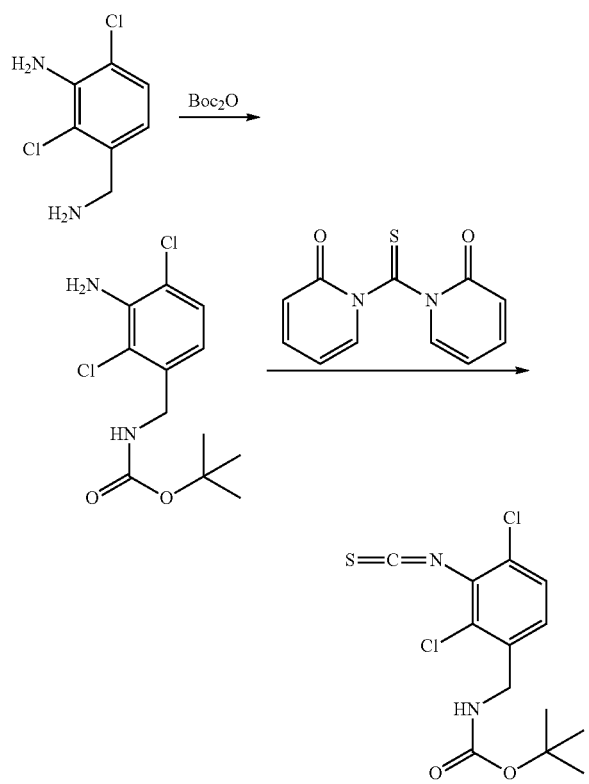

(a) (3-Amino-2,4-dichloro-benzyl)-carbamic acid tert-butyl ester

Boc₂O (1.48 g, 6.68 mmol) in 3.3 mL DCM is added at 0° C. to a mixture of 3-amino-2,4-dichloro-benzylamine (1.16 g, 6.07 mmol), 6.7 mL DCM and 12.1 mL 1 N NaOH-solution. The mixture is stirred vigourously for 2 d and diluted with 5% aq NH₃-solution. The organic phase is separated and the aq. phase is washed 2× with DCM. The combined organic phase is washed with brine, dried with Na₂SO₄, filtered and concentrated to give the sub-title compound.

Yield: 1.71 g (97%). $R_f$=0.65 (silica gel, DCM:EtOH 95:5). MS m/z: 291 [M+H]⁺.

(b) (2,4-Dichloro-3-isothiocyanato-benzyl)-carbamic acid tert-butyl ester 1,1'-Thiocarbonyldi-2-pyridone (0.42 g, 1.8 mmol) is added to a mixture of (3-amino-2,4-dichloro-benzyl)-carbamic acid tert-butyl ester (0.50 g, 1.7 mmol) and dioxane (25 mL) and stirred at rt for 2 h and at reflux for 2 d. The mixture is concentrated, diluted with DCM and filtered over silica gel. The filtrate is concentrated to give the title compound.

Yield: 0.49 g (86%). $R_f$=0.83 (silica gel, DCM:EtOH 95:5).

Building Block C

N-(2,4-Difluoro-3-isothiocyanato-benzyl)-2,2-dimethyl-propionamide

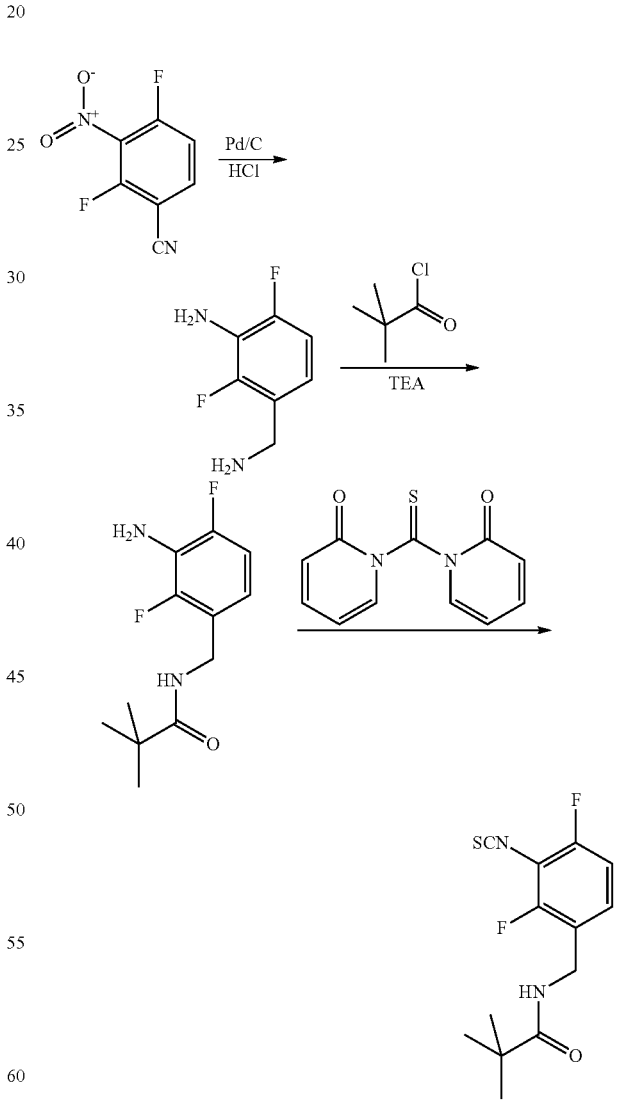

(a) 3-Aminomethyl-2,6-difluoro-aniline

A mixture of 3-nitro-2,4-difluoro-benzonitrile (500 mg, 2.72 mmol), Pd/C (200 mg), conc. HCl (1.50 mL, 18.0 mmol)

and MeOH (25 mL) is stirred at rt overnight under a hydrogen atmosphere (3.2 bar). The catalyst is removed by filtration, the filtrate is concentrated and evaporated twice from EtOH to give the sub-title compound as HCl salt.

Yield: 580 mg. MS m/z: 159 [M+H]$^+$.

(b) N-(3-Amino-2,4-difluoro-benzyl)-2,2-dimethyl-propionamide

TEA (400 µL, 2.86 mmol) followed by pivaloyl chloride (60 µL, 0.52 mmol) are added to 3-aminomethyl-2,6-difluoro-aniline (120 mg as HCl salt) in THF (10 mL) and stirred at rt overnight. The reaction mixture is diluted with EtOAc and sat. NaHCO$_3$-solution, the organic layer is washed with water and brine, dried and concentrated to give the sub-title compound.

Yield: 110 mg. HPLC-method B: R$_t$=1.19 min. MS m/z: 243 [M+H]$^+$. R$_f$=0.45 (silica gel, DCM:EtOH 95:5).

(c) N-(2,4-Difluoro-3-isothiocyanato-benzyl)-2,2-dimethyl-propionamide

A mixture of N-(3-amino-2,4-difluoro-benzyl)-2,2-dimethyl-propionamide (570 mg, 2.35 mmol), 1,1'-thiocarbonyldi-2(1H)-pyridone (550 mg, 2.35 mmol) and dioxane (20 mL) is stirred at reflux overnight. The reaction mixture is concentrated, diluted with DCM, filtered through a pad of silica gel and the filtrate is concentrated to give the title compound.

Yield: 440 mg (65%). R$_f$=0.80 (silica gel, DCM:EtOH 95:5).

Building Block D

N-(4-Chloro-fluoro-3-isothiocyanato-benzyl)-2,2-dimethyl-propionamide

(a) N-(6-Chloro-2-fluoro-3-methyl-phenyl)-acetamide

Acetylchloride (2.56 mL, 36.0 mmol) is added to a mixture of 6-chloro-2-fluoro-3-methyl-aniline (5.00 g, 31.3 mmol) and toluene (200 mL), additional toluene (50 mL) is added and the mixture is heated to reflux for 3 h. Then it is cooled with an ice bath and the formed precipitate is filtered off, washed with cold toluene and dried.

Yield: 4.75 g (75%). HPLC-method B: R$_t$=1.12 min. MS m/z: 202 [M+H]$^+$.

(b) 3-Acetylamino-4-chloro-2-fluoro-benzoic acid

The sub-title compound is prepared from N-(6-chloro-2-fluoro-3-methyl-phenyl)-acetamide and KMnO$_4$ in pyridine in analogy to step Aa.

Yield: 49%. R$_f$=0.2 (silica gel, DCM/EtOH 4:1). HPLC R$_f$=0.93 min (method B). MS m/z: 232 [M+H]$^+$.

(c) 3-Amino-4-chloro-2-fluoro-benzoic acid

The sub-title compound is prepared from 3-acetylamino-4-chloro-2-fluoro-benzoic acid and 6 M HCl-solution in analogy to step Ab.

Yield: 96%. HPLC R$_t$=1.10 min (method B). MS m/z: 190 [M+H]$^+$.

(d) 3-Amino-4-chloro-2-fluoro-benzamide

The sub-title compound is prepared from 3-amino-4-chloro-2-fluoro-benzoic acid, (1-chloro-2-methyl-propenyl)-dimethyl-amine and conc. NH$_3$ in analogy to step Ac.

Yield: 69%. R$_f$=0.3 (silica gel, PE:EtOAc 4:6). HPLC-method B: R$_t$=0.97 min. MS m/z: 189 [M+H]$^+$.

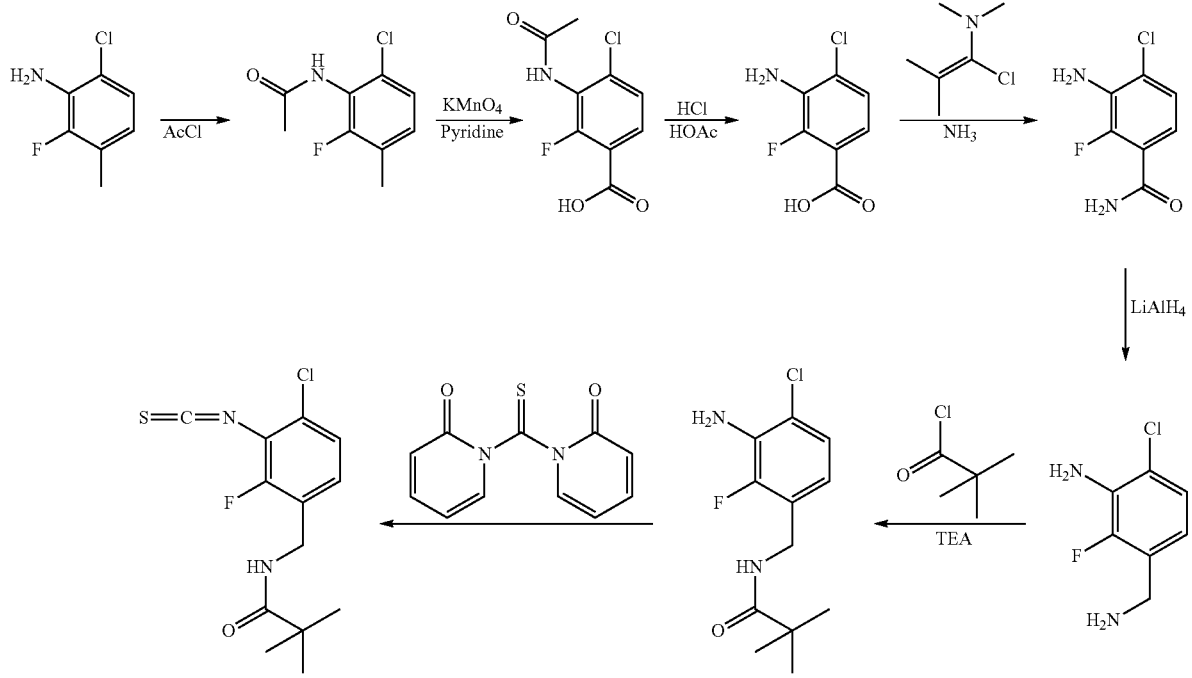

(e) 3-Amino-4-chloro-2-fluoro-benzylamine

The crude sub-title compound is prepared from 3-amino-4-chloro-2-fluoro-benzamide and LiAlH$_4$ in analogy to step Ad.

HPLC-method B: R$_t$=0.37 min. MS m/z: 175 [M+H]$^+$.

(f) N-(3-Amino-4-chloro-2-fluoro-benzyl)-2,2-dimethyl-propionamide

The sub-title compound is prepared from crude 3-amino-4-chloro-2-fluoro-benzylamine, 2,2-dimethyl-propionic acid chloride and TEA in analogy to example Ae.

Yield: 36% (side product in 29%: N-(3-Amino-4-chloro-benzyl)-2,2-dimethyl-propionamide).

R$_f$=0.6 (silica gel, PE:EtOAc 6:4). HPLC-method B: R$_t$=1.27 min. MS m/z: 259 [M+H]$^+$.

(g) N-(4-Chloro-2-fluoro-3-isothiocyanato-benzyl)-2,2-dimethyl-propionamide

The title compound is prepared from N-(3-amino-4-chloro-2-fluoro-benzyl)-2,2-dimethyl-propionamide, 1,1'-thiocarbonyldi-2-pyridone in analogy to step Af.

Yield: 65%. R$_f$=0.9 (silica gel, DCM:EtOH 95:5).

Building Block E

N-(2,4-Dimethyl-3-isothiocyanato-benzyl)-2,2-dimethyl-propionamide

(a) N-(3-Nitro-2,4-dimethyl-benzyl)-2,2,2-trifluoro-acetamide

N-(Hydroxymethyl)trifluoroacetamide (6.6 mmol; 0.946 g) is added to a mixture of 2,6-dimethyl-nitrobenzene (0.899 mL; 6.6 mmol) and conc. H$_2$SO$_4$ (15 mL). The mixture is stirred at rt overnight, poured into ice water and stirred for 2 h. The precipitate is collected by filtration and dried. Yield 1.5 g (84%). MS [M−H]$^−$=275, TLC: R$_f$=0.67 (silica gel, DCM:EtOH 95:5)).

(b) 3-Nitro-2,4-dimethyl-benzylamine

A mixture of N-(3-nitro-2,4-dimethyl-benzyl)-2,2,2-trifluoroacetamide (1.53 g, 5.54 mmol), 4M NaOH-solution (6.9 mL, 28 mmol) and MeOH (30 mL) is refluxed for 2 h. Then the mixture is concentrated, diluted with water and extracted with EtOAc. The organic phase is dried with Na$_2$SO$_4$, filtered and concentrated.

MS m/z: 181 [M+H]$^+$. HPLC-method C: R$_t$=1.13 min.

(c) N-(3-Nitro-2,4-dimethyl-benzyl)-2,2-dimethyl-propionamide

3-Nitro-2,4-dimethyl-benzylamine (1.40 g, crude) is added to a mixture of 2,2-dimethyl-propionic acid chloride (0.682 mL, 5.5 mmol) and TEA (1.92 mL, 13.8 mmol) in THF (30 mL) and it is stirred overnight. The reaction mixture is concentrated, diluted with EtOAc, washed successively with 2 M aq. HCl-solution, 5% aq. NaHCO$_3$ solution and water, dried with Na$_2$SO$_4$ filtered and concentrated.

Yield: 1.41 g. MS m/z: 265 [M+H]$^+$. HPLC-method B: R$_t$=1.37 min.

(d) N-(3-Amino-2,4-dimethyl-benzyl)-2,2-dimethyl-propionamide

A mixture of N-(3-nitro-2,4-dimethyl-benzyl)-2,2-dimethyl-propionamide (500 mg, 1.89 mmol), Pd/C (50 mg) and MeOH (20 mL) is stirred for 9 h under a hydrogen atmosphere (50 psi). The catalyst is removed by filtration and the filtrate is concentrated.

Yield: 0.42 g. MS m/z: 235 [M+H]$^+$. HPLC-method B: R$_t$=1.32 min.

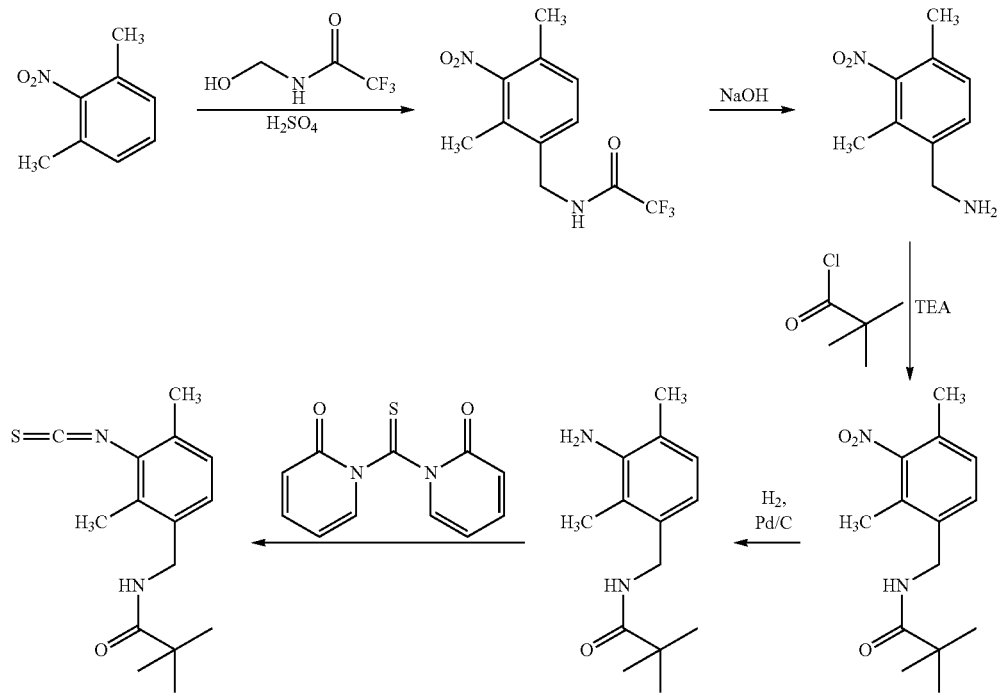

(e) N-(2,4-Dimethyl-3-isothiocyanato-benzyl)-2,2-dimethyl-propionamide

The title compound is prepared from N-(3-amino-2,4-dimethyl-benzyl)-2,2-dimethyl-propionamide, 1,1'-thiocarbonyldi-2-pyridone in analogy to step Af.

Yield: 65%. $R_f$=0.81 (silica gel, DCM:EtOH 95:5).

Building Block F

Dichloro-3-isothiocyanato-benzyl)-1-trifluoromethyl-cyclopropane carboxamide

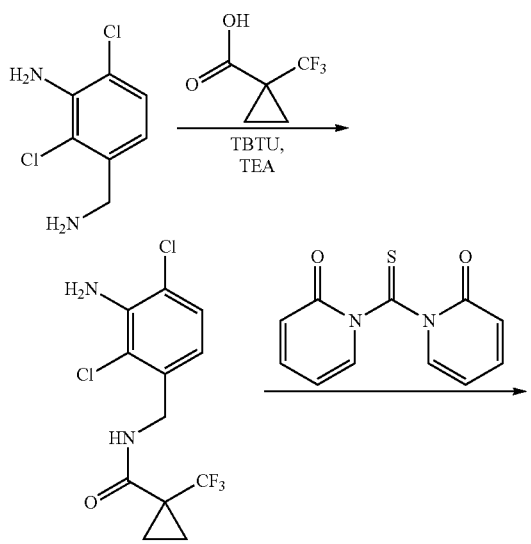

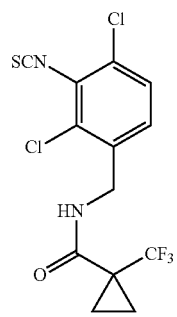

(a) N-(2,4-Dichloro-3-amino-benzyl)-1-trifluoromethyl-cyclopropane carboxamide

The sub-title compound is prepared from 3-amino-2,4-dichloro-benzylamine (0.310 g, 1.01 mmol), 1-trifluoromethyl-cyclopropane carboxylic acid (0.17 g, 1.1 mmol), TBTU (0.39 g, 1.2 mmol) and TEA (0.71 mL) in DMF in analogy to step 1 d.

Yield: 289 mg (83%). MS m/z: 327 [M+H]$^+$.

(b) N-(2,4-Dichloro-3-isothiocyanato-benzyl)-1-trifluoromethyl-cyclopropane carboxamide The title compound is prepared from N-(2,4-dichloro-3-amino-benzyl)-1-trifluoromethyl-cyclopropane carboxamide (150 mg, 0.45 mmol) and 1,1'-thiocarbonyldi-2-pyridone (89 mg, 0.38 mmol) in analogy to step Af.

Yield: 92 mg (crude).

Example 1

N-(trans-4-Trifluoromethyl-cyclohex-1-yl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide

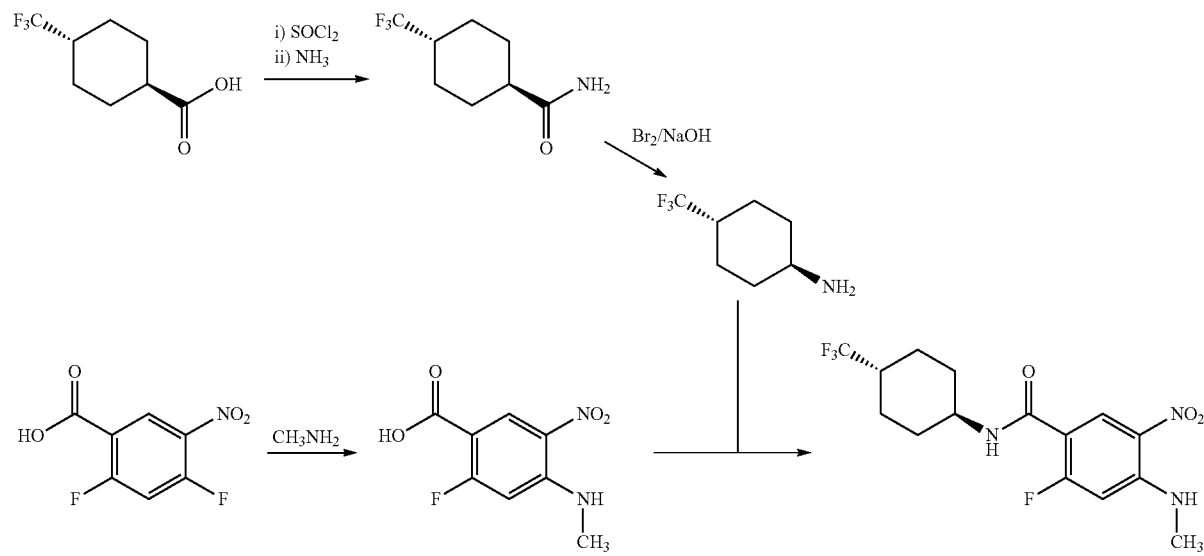

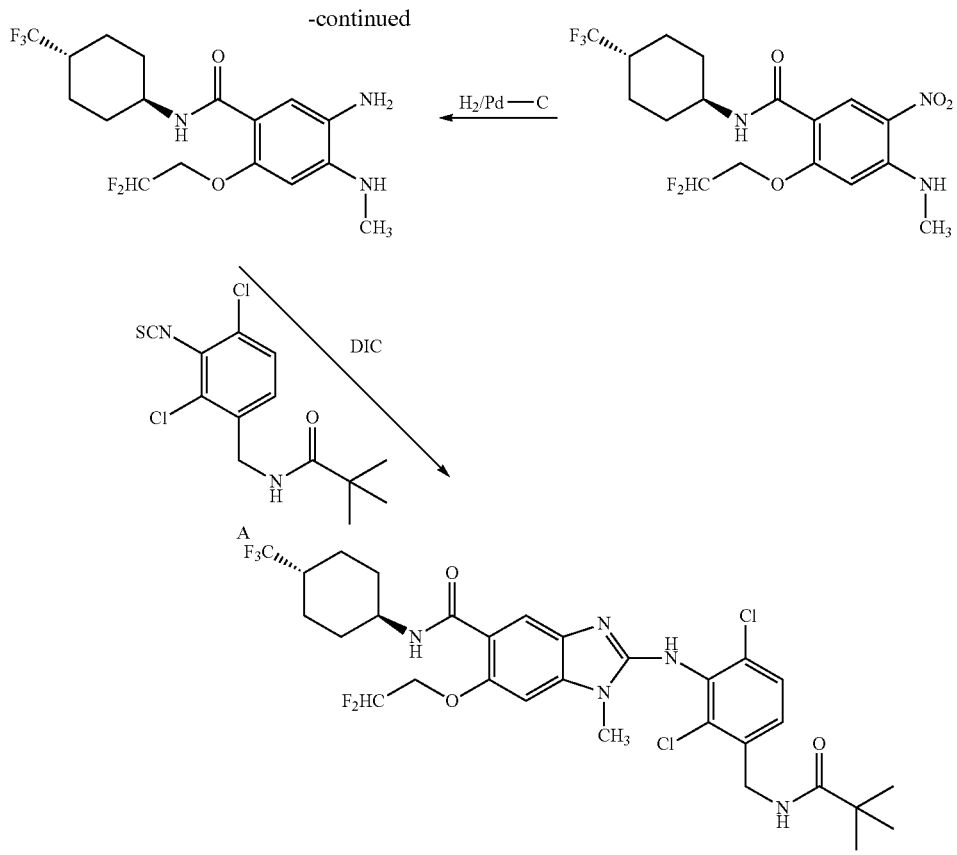

(a) trans-4-Trifluormethyl-cyclohexyl-carboxylic acid amide

A mixture of trans-4-trifluoromethyl-cyclohexane-carboxylic acid (10.4 g, 53.1 mmol), SOCl$_2$ (10 mL, 137 mmol), DCM (100 mL) and DMF (200 µl) is heated to reflux for 1.5 h and concentrated. The crude acid chloride is diluted with 100 mL THF and conc. NH$_3$ (350 mL) is slowly added. It is stirred for 5 min and the mixture is concentrated and dried at 40°.

Yield: 9.7 g.

(b) trans-4-Trifluormethyl-cyclohexyl-amine

Bromine (2.85 mL, 55 mmol) is stirred for 10 min in 1N aq. NaOH-solution (200 mL), then trans-4-trifluormethyl-cyclohexyl-carboxylic acid amide is added and it is stirred for 45 min at rt and for 3 h at reflux. After cooling to rt the mixture is extracted with Et$_2$O, the organic phase is dried with MgSO$_4$, filtered, treated with 2N HCl in Et$_2$O and concentrated to give the sub-title compound as HCl-salt.

Yield: 8.5 g MS m/z: 168 [M+H]$^+$.

(c) 2-Fluoro-4-methylamino-5-nitro-benzoic acid

Methylamine (13.5 mL, 40% in water) is added to an ice-cooled mixture of 2,4-difluoro-5-nitro-benzoic acid (10.0 g, 49 mmol) in water (100 mL) and it is stirred for 30 min at rt. The mixture is acidified with 6N aq. HCl-solution and the precipitate is filtered, washed with water and dried at 60° C. The crude material was recrystallized from MeOH. The final product was slightly contaminated by its regioisomer 4-fluoro-2-methylamino-5-nitro-benzoic acid.

(d) N-(trans-4-Trifluoromethyl-cyclohex-1-yl)-2-fluoro-4-methylamino-5-nitro-benzoic acid amide A mixture of crude 2-fluoro-4-methylamino-5-nitro-benzoic acid (4.88 g containing traces of regioisomer), DIPEA (11.7 mL, 68.3 mmol), TBTU (8.05 g, 25.1 mmol) and THF (100 mL) is stirred for 15 min, then trans-4-trifluormethyl-cyclohexyl-amine (4.64 g, HCl salt) is added and it is stirred overnight. The mixture is concentrated, aq NaHCO$_3$ is added and the resulting precipitate is filtered, washed and dried.

Yield: 8.14 g. R$_f$=0.3 (silica gel, DCM:EtOH 98:2). HPLC R$_t$=1.44 min (method B). MS m/z: 364 [M+H]$^+$.

(e) N-(trans-4-Trifluoromethyl-cyclohex-1-yl)-2-(2, 2-difluoro-ethoxy)-4-methylamino-5-nitro-benzoic acid amide A mixture of 2,2-difluoroethanol (2.12 mL, 33.6 mmol), KOtBu (3.84 g, 32.4 mmol) and THF (100 mL) is stirred for 15 min, then N-(trans-4-trifluoromethyl-cyclohex-1-yl)-2-fluoro-4-methylamino-5-nitro-benzoic acid amide (8.14 g, 22.4 mmol) is added and it is stirred for 1.5 h. Water is added to the mixture and THF is distilled off. The resulting precipitate is filtered, washed with water and dried.

Yield: 8.60 g. R$_f$=0.35 (silica gel, PE:Et$_2$O 1:1). HPLC R$_t$=1.47 min (method B). MS m/z: 426 [M+H]$^+$.

(f) N-(trans-4-Trifluoromethyl-cyclohex-1-yl)-2-(2,2-difluoro-ethoxy)-4-methylamino-5-amino-benzoic acid amide A mixture of N-(trans-4-trifluoromethyl-cyclohex-1-yl)-2-(2,2-difluoro-ethoxy)-4-methylamino-5-nitro-benzoic acid amide (6.38 g, 15.0 mmol), Pd/C (0.50 g) and MeOH (100 mL) is stirred under 50 psi $H_2$-atmosphere for 4 h. The mixture is filtered, the catalyst is washed with THF and the combined filtrate is concentrated. The crude mixture is purified by flash chromatography (silica gel; DCM/EtOH 97/3).

Yield: 5.38 g (91%). $R_f$=0.3 (DCM/EtOH 95:5). HPLC $R_t$=1.25 min (method B). MS m/z: 396 $[M+H]^+$.

(g) N-(trans-4-Trifluoromethyl-cyclohex-1-yl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide A mixture of N-(trans-4-trifluoromethyl-cyclohex-1-yl)-2-(2,2-difluoro-ethoxy)-4-methylamino-5-amino-benzoic acid amide (200 mg, 0.506 mmol), N-(2,4-dichloro-3-isothiocyanato-benzyl)-2,2-dimethyl-propionamide (160 mg, 0.505 mmol) and DMF (2.0 mL) is stirred for 3 h, then DIC (102 µl, 0.658 mmol) is added and it is stirred at 80° C. for 2 h. The crude mixture is concentrated and purified by flash chromatography (silica gel; DCM/EtOH 98:2→97:3).

Yield: 0.320 g (93%). Rf=0.35 (DCM/EtOH 95:5). HPLC $R_t$=1.42 min (method B). MS m/z: 678 $[M+H]^+$.

Example 2

N-(trans-4-Trifluoromethyl-cyclohex-1-yl)-2-{2,6-dichloro-3-[(2,2-dimethyl-propionylamino)-methyl]-phenylamino}-6-(2,2-difluoro-ethoxy)-1H-benzimidazole-5-carboxylic acid amide

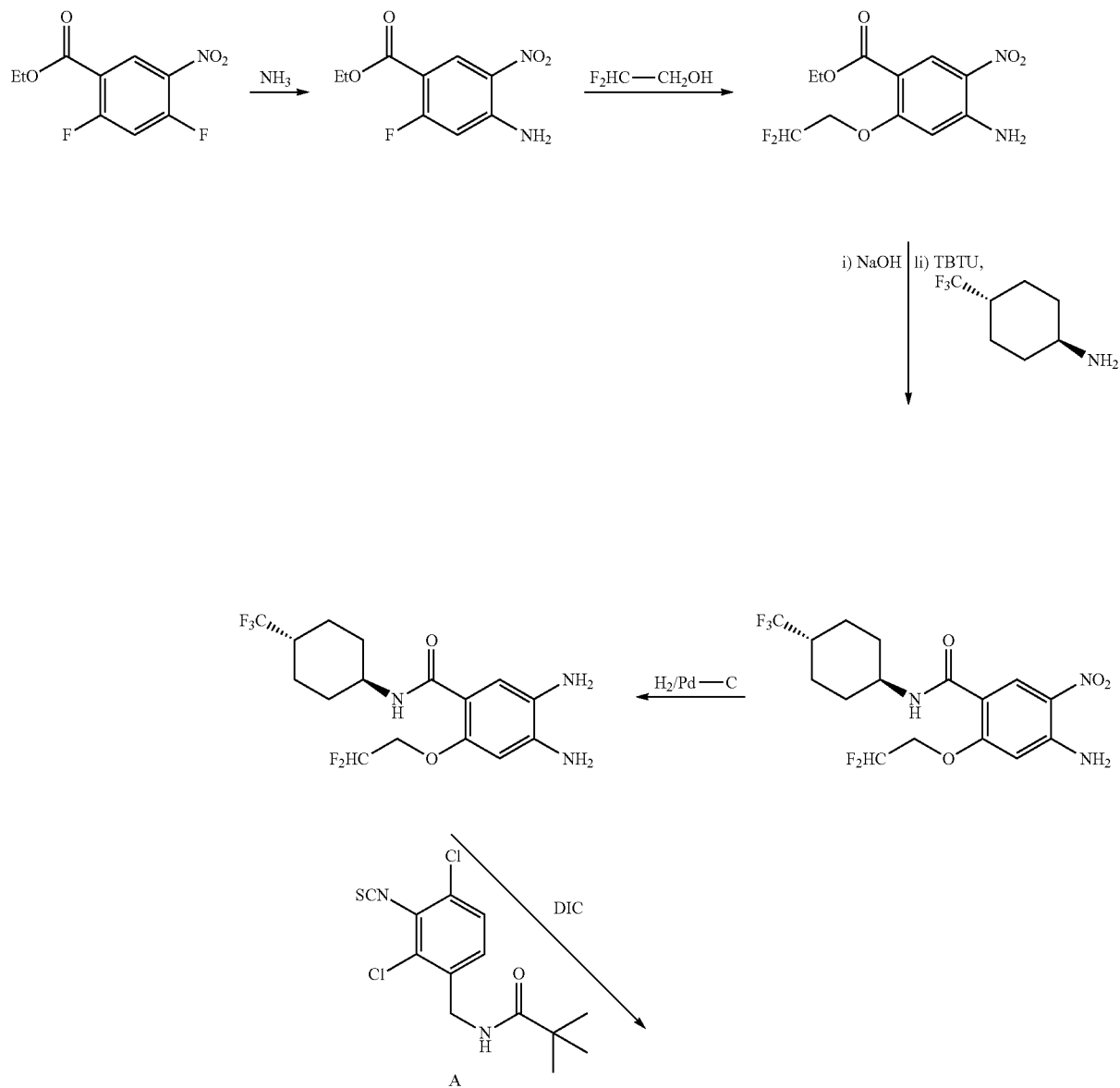

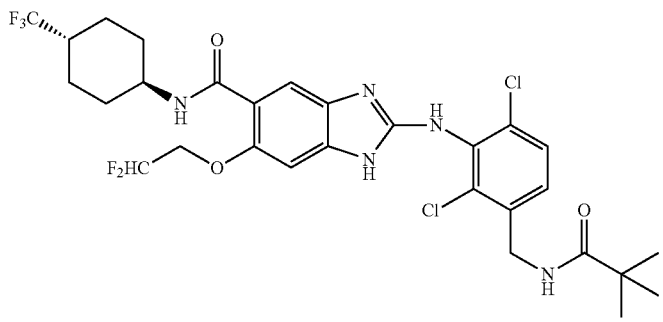

(a) Ethyl 2-fluoro-4-amino-5-nitro-benzoate

A mixture of ethyl 2,4-difluoro-5-nitro-benzoate (5.0 g, 21 mmol), 5.2 mL conc. $NH_3$ and THF (25 mL) is stirred for 30 min in an ice bath and overnight at rt. The mixture is concentrated and diluted with water. The precipitate is filtered, washed with water and dried at 55° C. to furnish the crude sub-title compound.

Yield: 4.58 g. $R_f$=0.57 (silica gel, PE/EtOAc 3:2). MS m/z: 227 [M−H]⁻.

(b) Ethyl 2-(2,2-difluoro-ethoxy)-4-amino-5-nitro-benzoate

A mixture of 2,2-difluoroethanol (0.062 mL, 0.97 mmol), KOtBu (0.108 g, 0.964 mmol) and THF (5 mL) is stirred for 15 min, then ethyl 2-fluoro-4-amino-5-nitro-benzoate (0.200 g) is added and it is stirred for 15 h. Water is added to the mixture and it is extracted with EtOAc. The organic phase is washed with water and brine, dried with $Na_2SO_4$ and concentrated.

Yield: 0.24 g. $R_f$=0.7 (silica gel, DCM/EtOH 95:5). HPLC $R_t$=1.34 min (method B). MS m/z: 291 [M+H]⁺.

(c) 2-(2,2-Difluoro-ethoxy)-4-amino-5-nitro-benzoic acid

A mixture of ethyl 2-(2,2-difluoro-ethoxy)-4-amino-5-nitro-benzoate (0.24 g, 0.827 mmol), 4 N aq. NaOH-solution (0.845 mL) and MeOH (10 mL) is stirred for 1.5 h at 70° C., The mixture is concentrated and the residue is diluted with water and acidified with 4N aq. HCl-solution. The precipitate is filtered off, washed with water and dried at 50° C.

Yield: 0.17 g (78%). $R_f$=0.4 (silica gel, DCM/EtOH 9:1). HPLC $R_t$=1.14 min (method B).

MS m/z: 263 [M+H]⁺.

(d) N-(trans-4-Trifluoromethyl-cyclohex-1-yl)-2-(2,2-difluoro-ethoxy)-4-amino-5-nitro-benzoic acid amide The subtitle compound is prepared from 2-(2,2-difluoro-ethoxy)-4-amino-5-nitro-benzoic acid and trans-4-trifluoromethyl-cyclohexyl-amine with TBTU and DIPEA in analogy to example 1d.

Yield: 100%. $R_f$=0.7 (silica gel, DCM:EtOH 9:1). HPLC $R_t$=1.43 min (method B). MS m/z: 412 [M+H]⁺.

(e) N-(trans-4-Trifluoromethyl-cyclohex-1-yl)-2-(2,2-difluoro-ethoxy)-4,5-diamino-benzoic acid amide The subtitle compound is prepared from N-(trans-4-trifluoromethyl-cyclohex-1-yl)-2-(2,2-difluoro-ethoxy)-4-amino-5-nitro-benzoic acid amide with Pd/C and $H_2$ in analogy to example 1f.

Yield: quantitative. $R_f$=0.4 (DCM/EtOH 9:1). HPLC $R_t$=1.19 min (method B). MS m/z: 382 [M+H]⁺.

(f) N-(trans-4-Trifluoromethyl-cyclohex-1-yl)-2-{2,6-dichloro-3-[(2,2-dimethyl-propionylamino)-methyl]-phenylamino}-6-(2,2-difluoro-ethoxy)-1H-benzimidazole-5-carboxylic acid amide The title compound is prepared from N-(trans-4-trifluoromethyl-cyclohex-1-yl)-2-(2,2-difluoro-ethoxy)-4,5-diamino-benzoic acid amide and N-(2,4-dichloro-3-isothiocyanato-benzyl)-2,2-dimethyl-propionamide with DIC in analogy to example 1 g.

Yield: 43%. $R_f$=0.2 (DCM/EtOH 95:5). HPLC $R_t$=1.34 min (method B). MS m/z: 664 [M+H]⁺

Example 3

N-(trans-4-Trifluoromethyl-cyclohex-1-yl)-2-{2,6-dichloro-3-[(2,2-dimethyl-propionylamino)-methyl]-phenylamino}-6-fluoro-1-methyl-1H-benzimidazole-5-carboxylic acid amide

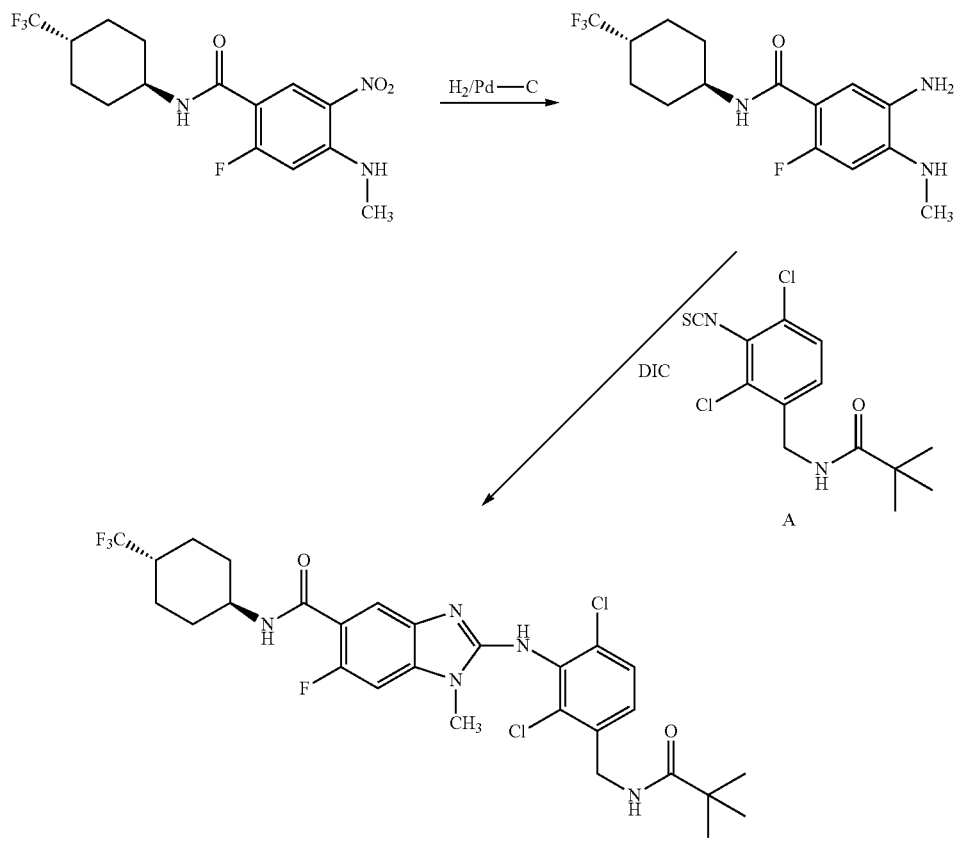

(a) N-(trans-4-Trifluoromethyl-cyclohex-1-yl)-2-fluoro-4-methylamino-5-amino-benzoic acid amide The subtitle compound is prepared from N-(trans-4-trifluoromethyl-cyclohex-1-yl)-2-fluoro-4-methylamino-5-nitro-benzoic acid amide with Pd/C and $H_2$ in analogy to example 1f.

Yield: 98%. $R_f$=0.25 (DCM/EtOH 95:5). HPLC $R_t$=1.32 min (method B). MS m/z: 334 $[M+H]^+$.

(b) N-(trans-4-Trifluoromethyl-cyclohex-1-yl)-2-{2,6-dichloro-3-[(2,2-dimethyl-propionylamino)-methyl]phenylamino}-6-fluoro-1-methyl-1H-benzimidazole-5-carboxylic acid amide The title compound is prepared from N-(trans-4-trifluoromethyl-cyclohex-1-yl)-2-fluoro-4-methylamino-5-amino-benzoic acid amide and N-(2,4-dichloro-3-isothiocyanato-benzyl)-2,2-dimethyl-propionamide with DIC in analogy to example 1g.

Yield: 60%. $R_f$=0.4 (DCM/EtOH 95:5). HPLC $R_t$=1.36 min (method B). MS m/z: 616 $[M+H]^+$

Example 4

N-(4-Bromo-phenyl)-2-{2,6-dichloro-3-[(2,2-dimethyl-propionylamino)-methyl]-phenylamino}-6-(2,2-difluoro-ethoxy)-1H-benzimidazole-5-carboxylic acid amide

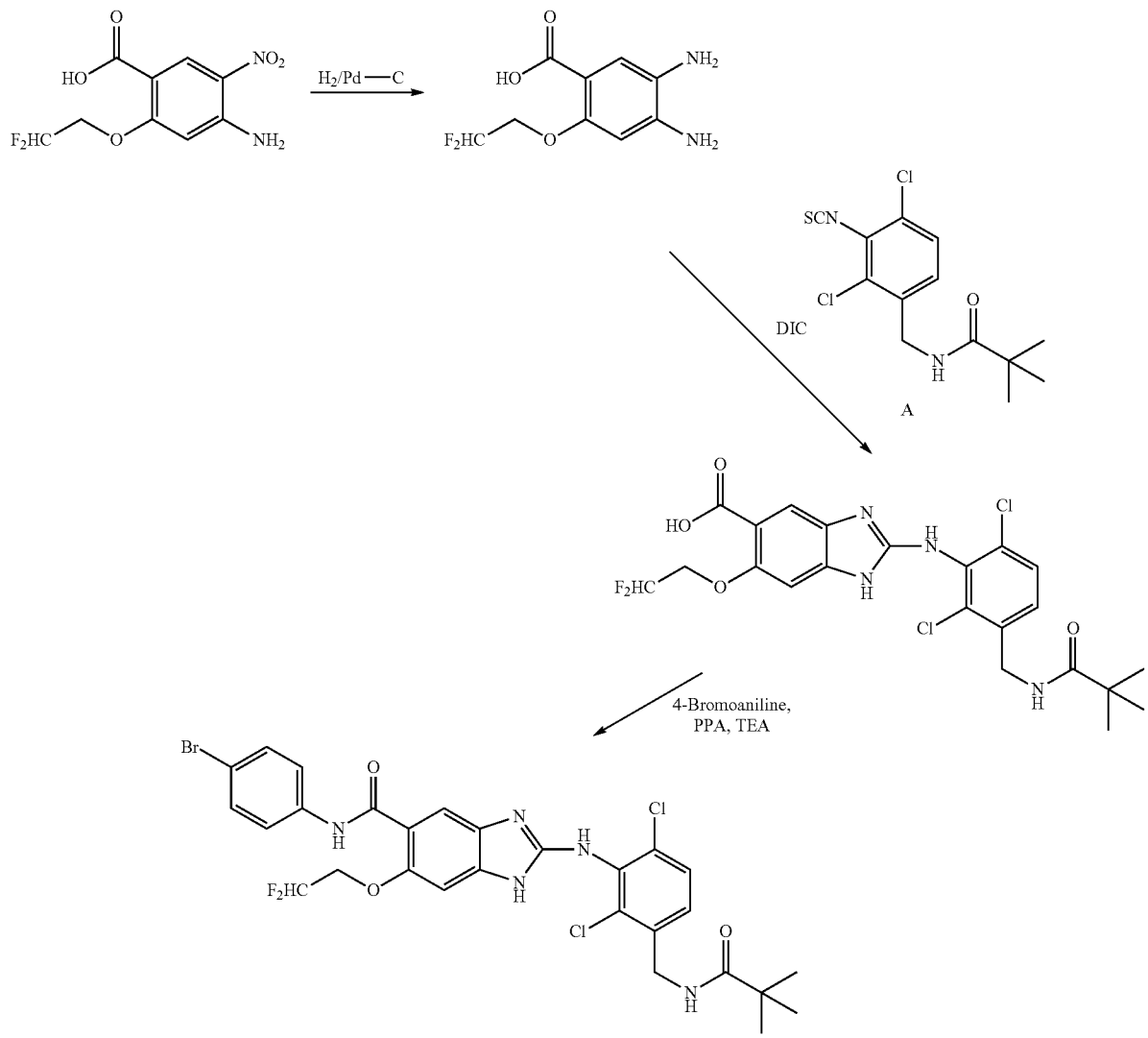

(a) 2-(2,2-Difluoro-ethoxy)-4,5-diamino-benzoic acid

The subtitle compound is prepared from 2-(2,2-difluoro-ethoxy)-4-amino-5-nitro-benzoic acid (example 2c) with Pd/C and $H_2$ in analogy to example 1f.

Yield: 99%. $R_f$=0.3 (DCM/EtOH 9:1).

(b) 2-{2,6-Dichloro-3-[(2,2-dimethyl-propionylamino)-methyl]-phenylamino}-6-(2,2-difluoro-ethoxy)-1H-benzimidazole-5-carboxylic acid A mixture of 2-(2,2-difluoro-ethoxy)-4,5-diamino-benzoic acid (732 mg, 3.15 mmol), N-(2,4-dichloro-3-isothiocyanato-benzyl)-2,2-dimethyl-propionamide (1.00 g, 3.15 mmol) and MeCN (15 mL) is stirred for 48 h, then BSTFA (1.03 mL, 3.15 mmol) is added and it is stirred at reflux for 10 min. Then DIC (0.494 mL, 3.15 mmol) is added and it is stirred for another 4 h. The mixture is cooled to rt, diluted with HOAc and concentrated. The residue is stirred with 1N NaOH, filtered and the filtrate is acidified with 4N HCl, extracted with EtOAc and purified via chromatography [DCM→DCM+10% EtOH/HOAc (95:5)] to give the subtitle compound.

Yield: 0.720 g (44%). $R_f$=0.13 (DCM/EtOH 95:5+few drops HOAc). MS m/z: 515 [M+H]⁺.

(c) N-(4-Bromo-phenyl)-2-{2,6-dichloro-3-[(2,2-dimethyl-propionylamino)-methyl]-phenylamino}-6-(2,2-difluoro-ethoxy)-1H-benzimidazole-5-carboxylic acid amide PPA (0.223 mL, 50% in EtOAc, ~0.38 mmol) is slowly added to a mixture of 2-{2,6-dichloro-3-[(2,2-dimethyl-propionylamino)-methyl]-phenylamino}-6-(2,2-difluoro-ethoxy)-1H-benzimidazole-5-carboxylic acid (0.150 g, 0.291 mmol), 4-bromoaniline (50 mg, 0.291 mmol), TEA (0.101 mL, 0.728 mmol) and THF (10 mL). The mixture is refluxed for 3 d, concentrated and purified via prep. HPLC (column: Zorbax stable bond C18, 5 μm, 30×100 mm, gradient: water+0.15% HCOOH/MeOH 95:5→10:90) to furnish the title compound.

Yield: 0.043 g (22%). HPLC $R_t$=1.67 min (method B). MS m/z: 668 [M+H]$^+$.

Example 5

N-(4-Bromo-phenyl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide mixture is left overnight at rt whereafter an additional portion of 2M MeNH$_2$ in THF (10.0 mL; 2 M; 21.6 mmol) is added at 0° C. After 3 h at rt, water is added and the mixture is concentrated. The resulting precipitate is filtered off and dried to give the sub-title compound. Yield: 5.0 g (96%).

(b) Ethyl 2-(2,2-difluoroethoxy)-4-(methylamino)-5-nitrobenzoate

A solution of 2,2-difluoroethanol (1.7 g; 20.6 mmol) in THF (50 mL) is added to a solution of ethyl 2-fluoro-4-(methylamino)-5-nitrobenzoate (5.0 g; 20.6 mmol) in DMF (100 mL). Sodium hydride (0.824 g; 60%; 20.6 mmol) is

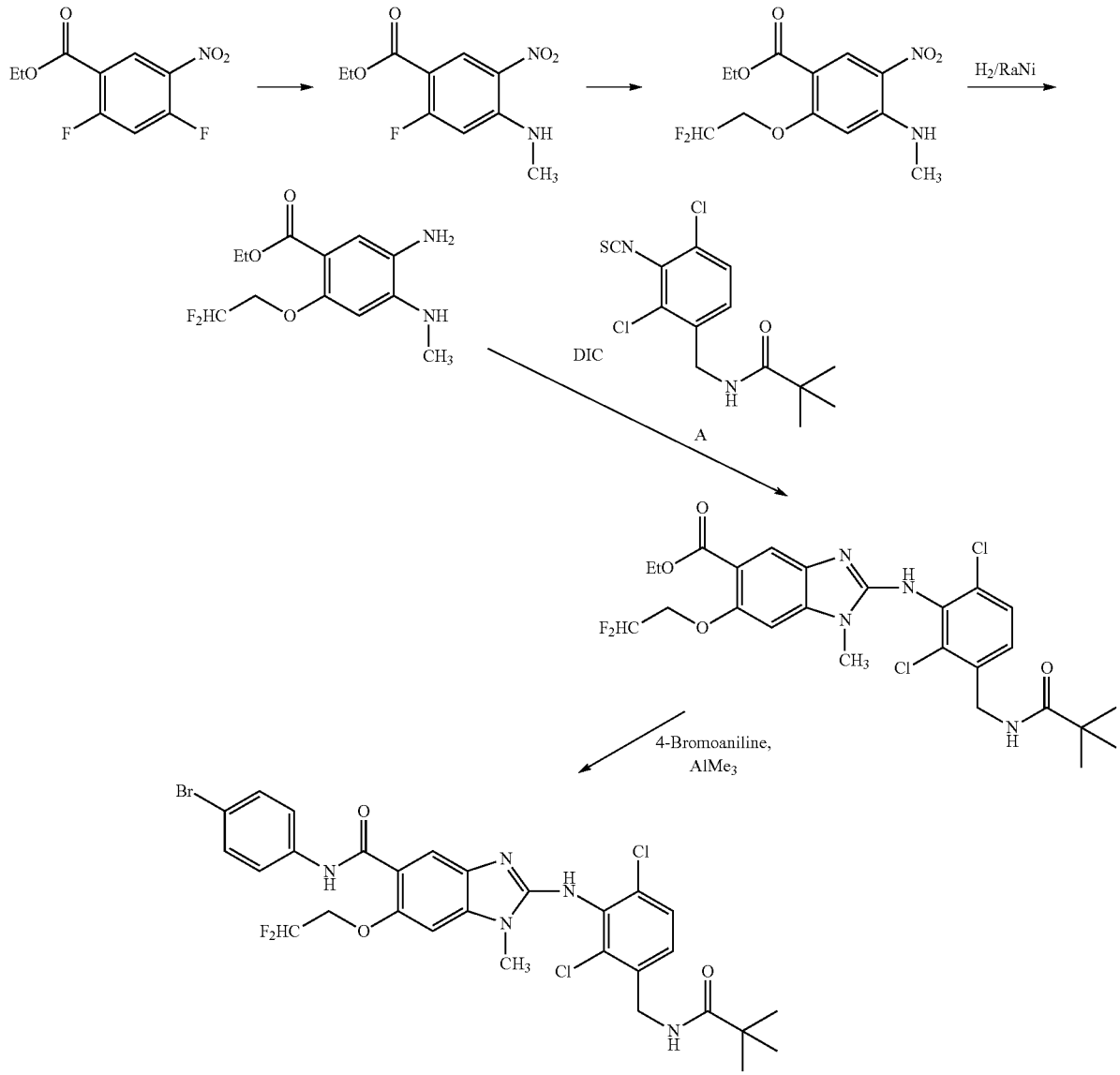

(a) Ethyl 2-fluoro-4-(methylamino)-5-nitrobenzoate

A 2M solution of MeNH$_2$ in THF (21.6 mL; 43.3 mmol) is added dropwise to a solution of ethyl 2,4-difluoro-5-nitrobenzoate (5.0 g; 21.6 mmol) in THF (70 mL) at −5° C. The added in portions and the mixture is stirred overnight at rt. A solution of TFA (30 mL; 0.45 M aq) is added and the mixture is concentrated. The resulting precipitate is filtered off, washed with water, dried and recrystallized from EtOH/water to give the sub-title compound. Yield: 4.8 g (76%).

(c) Ethyl 5-amino-2-(2,2-difluoroethoxy)-4-(methylamino)benzoate

A mixture of ethyl 2-(2,2-difluoroethoxy)-4-(methylamino)-5-nitrobenzoate (2.0 g; 6.57 mmol), RaNi (1.0 g) and THF (100 mL) is stirred under $H_2$-atmosphere (8 atm) overnight at rt. $Na_2SO_4$ is added and the mixture is stirred another 30 min under $H_2$-atmosphere. The mixture is filtered through celite and concentrated and the sub-title compound is used in the next step without further purification.

(d) Ethyl 2-{2,6-dichloro-3-[(2,2-dimethyl-propionylamino)-methyl]-phenylamino}-6-(2,2-difluoroethoxy)-1-methyl-1H-benzimidazole-5-carboxylic acid ester A mixture of ethyl 5-amino-2-(2,2-difluoroethoxy)-4-(methylamino)benzoate (0.942 g; 3.44 mmol), N-(2,4-dichloro-3-isothiocyanato-benzyl)-2,2-dimethyl-propionamide (1.09 g, 3.44 mmol) and DMF (5 mL) is stirred overnight at rt. Then DIC (0.695 mL, 4.44 mmol) is added and the mixture is heated for 6 h to 80° C. The mixture is concentrated, diluted with EtOAc, washed with water and the resulting organic phase is dried with $Na_2SO_4$. After concentration and purification via column chromatography (silica gel, DCM→DCM/EtOH 97:3) the sub-title compound is obtained Yield: 1.35 g (71%). $R_f$=0.42 (DCM/EtOH 95:5). MS m/z: 557 [M+H]$^+$.

(e) N-(4-Bromo-phenyl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide $Me_3Al$ in heptane (1.08 mL; 1 M; 1.08 mmol) is added to a solution of 4-bromoaniline (0.139 g; 0.807 mmol) in 1,4-dioxane (5 mL) and the mixture is stirred for 30 min at rt. Then ethyl 2{(2,6-dichloro-3-[(2,2-dimethyl-propionylamino)-methyl]-phenylamino}-6-(2,2-difluoro-ethoxy)-1-methyl-1H-benzimidazole-5-carboxylic acid ester in 5 mL 1,4-dioxane is added slowly and the mixture is stirred for 10 h at 60° C., cooled and MeOH is added carefully. The crude mixture is acidified with HOAc, concentrated and purified via chromatography (silica gel, DCM→DCM/EtOH 95:5).

Yield: 85 mg (46%). HPLC $R_t$=2.80 min (method G). MS m/z: 682 [M+H]$^+$.

Example 6

N-(4-Bromo-phenyl)-2-{(2,6-difluoro-3-[(2,2-dimethyl-propionylamino)-methyl]-phenylamino}-6-(2,2-difluoro-ethoxy)-1-methyl-1H-benzimidazole-5-carboxylic acid amide

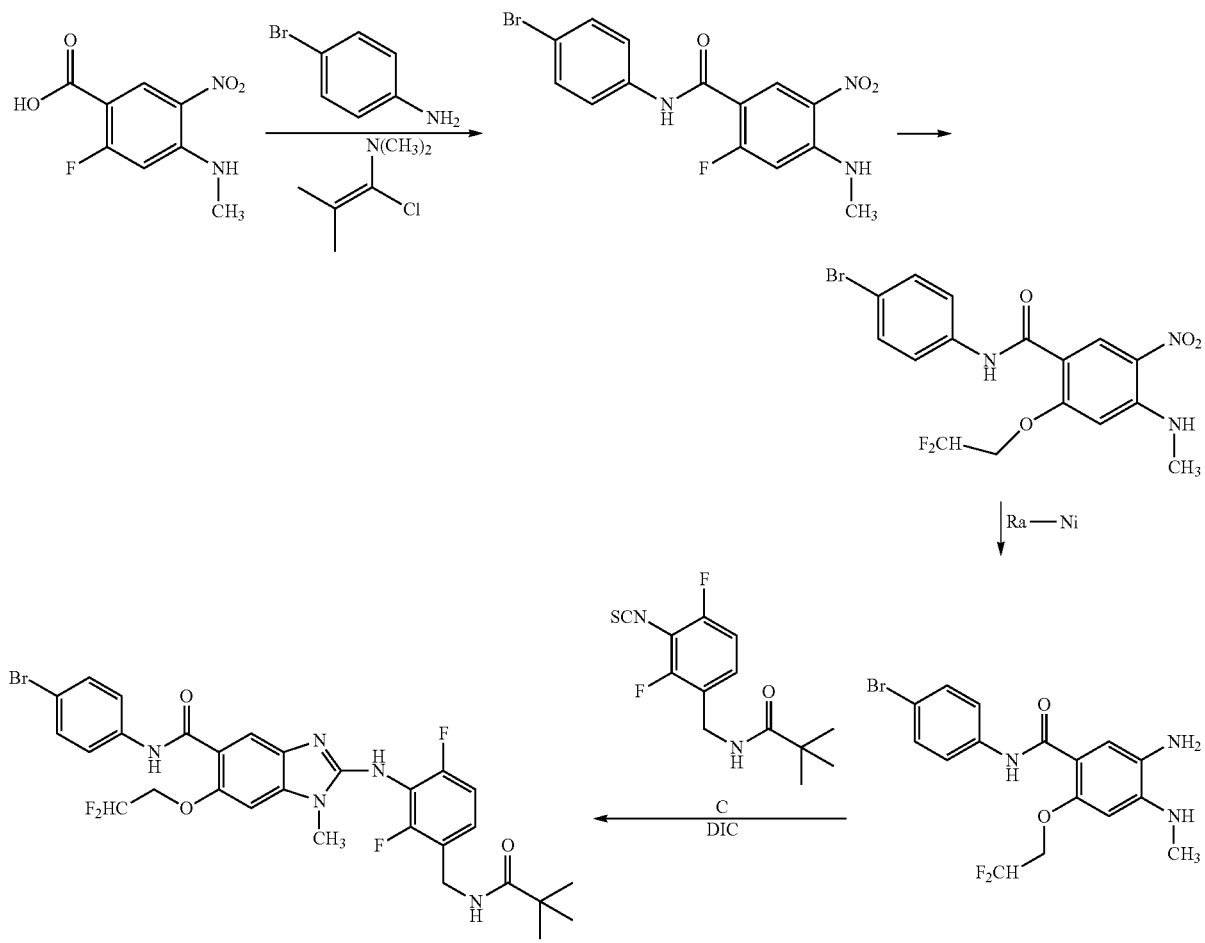

(a) N-(4-Bromophenyl)-2-fluoro-4-methylamino-5-nitro-benzamide

A mixture of 2-fluoro-4-methylamino-5-nitro-benzoic acid (0.500 g, 2.34 mmol), (1-chloro-2-methyl-propenyl)-dimethylamine (0.371 mL, 2.80 mmol) and DCM (50 mL) is stirred for 30 min, then 4-bromoaniline (0.402 mg, 2.34 mmol) and DIPEA (0.549 mL, 3.15 mmol) are added and it is stirred for 2 h. The mixture is concentrated, water is added and the precipitate is filtered, washed with water and dried to give the subtitle compound.

Yield: 0.820 g (95%). HPLC $R_t$=1.47 min (method B). MS m/z: 368 [M+H]$^+$.

(b) N-(4-Bromophenyl)-2-(2,2-difluoro-ethoxy)-4-methylamino-5-nitro-benzamide The subtitle compound is prepared from N-(4-bromophenyl)-2-fluoro-4-methylamino-5-nitro-benzamide, 2,2-difluoroethanol and KOtBu in analogy to example 1e.

Yield: 0.94 g (98%). HPLC $R_t$=1.54 min (method B). MS m/z: 430 [M+H]$^+$.

(c) N-(4-Bromophenyl)-2-(2,2-difluoro-ethoxy)-4-methylamino-5-amino-benzamide The subtitle compound is prepared from N-(4-bromophenyl)-2-(2,2-difluoro-ethoxy)-4-methylamino-5-nitro-benzamide, RaNi and H$_2$ in analogy to example 5c.

Yield: 0.86 g (98%). $R_f$=0.40 (DCM/EtOH 95:5). MS m/z: 400 [M+H]$^+$.

(d) N-(4-Bromo-phenyl)-2-{2,6-difluoro-3-[(2,2-dimethyl-propionylamino)-methyl]-phenylamino}-6-(2,2-difluoro-ethoxy)-1-methyl-1H-benzimidazole-5-carboxylic acid amide The title compound is prepared from N-(4-bromophenyl)-2-(2,2-difluoro-ethoxy)-4-methylamino-5-amino-benzamide and N-(2,4-difluoro-3-isothiocyanato-benzyl)-2,2-dimethyl-propionamide with DIC in analogy to example 1g.

Yield: 0.12 g (52%). $R_f$=0.35 (DCM/EtOH 95:5). HPLC $R_t$=1.52 min (method B). MS m/z: 650 [M+H]$^+$.

Example 7

N-(4-Bromo-phenyl)-2-{(2,6-dichloro-3-[(2,2-dimethyl-propionylamino)-methyl]-phenylamino}-6-fluoro-1-methyl-1H-benzimidazole-5-carboxylic acid amide

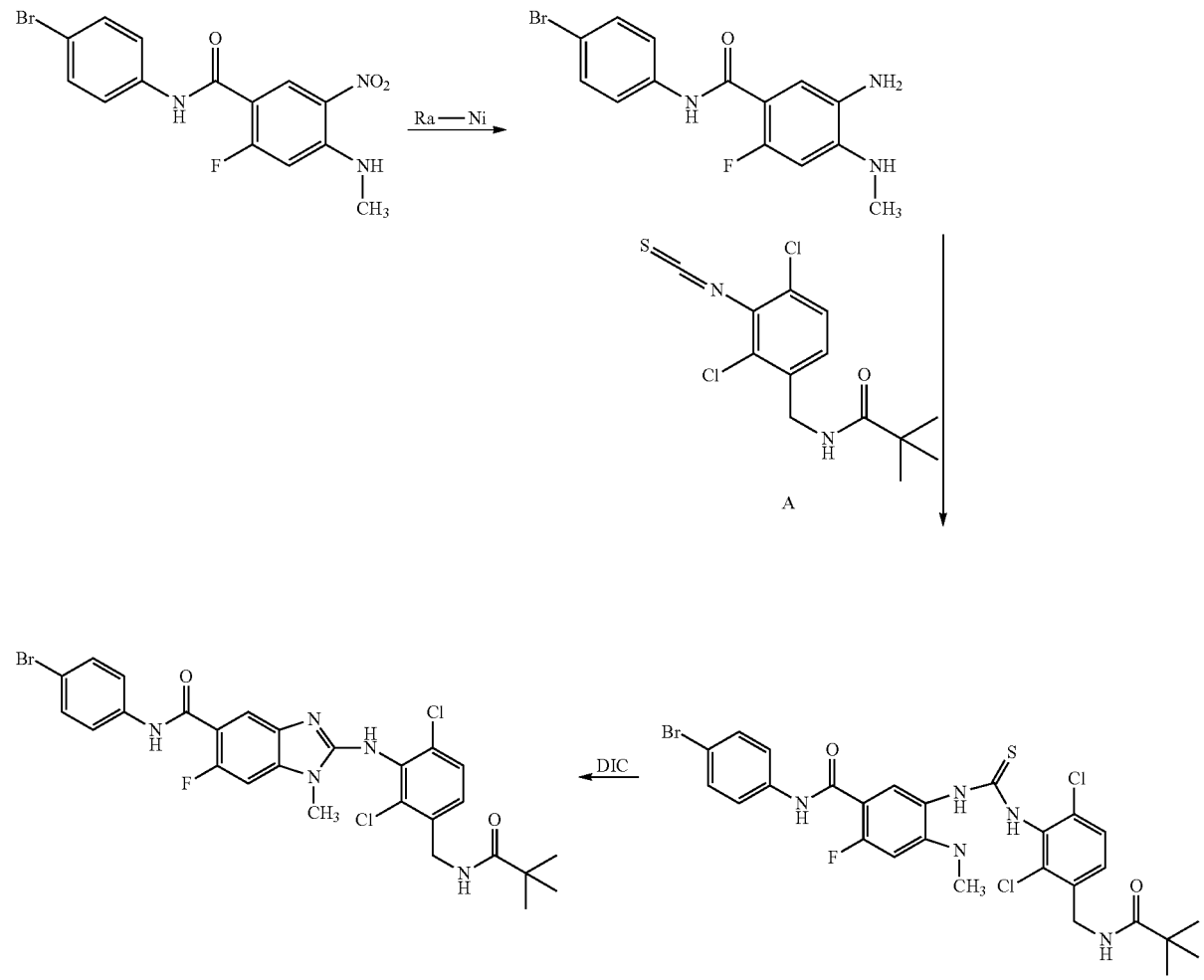

(a) N-(4-Bromophenyl)-2-fluoro-4-methylamino-5-amino-benzamide

The subtitle compound is prepared from N-(4-bromophenyl)-2-fluoro-4-methylamino-5-nitro-benzamide, RaNi and H₂ in analogy to example 5c.

Yield: quantitative. HPLC $R_t$=1.34 min (method B). MS m/z: 339 [M+H]⁺.

(b) N-(4-Bromophenyl)-5-(3-{2,6-dichloro-3-[(2,2-dimethyl-propionylamino)-methyl]-phenyl}-thioureido)-2-fluoro-4-methylamino-benzamide A mixture of N-(4-bromophenyl)-2-fluoro-4-methylamino-5-amino-benzamide (220 mg, 0.543 mmol), N-(2,4-Dichloro-3-isothiocyanato-benzyl)-2,2-dimethyl-propionamide (0.172 mg, 0.543 mmol) and DMF (5 mL) is stirred for 3 d, diluted with water, and extracted with EtOAc. The organic phase is washed with water, dried with Na₂SO₄ and concentrated to give the crude product.

HPLC $R_t$=1.48 min (method B). MS m/z: 656 [M+H]⁺.

(c) N-(4-Bromo-phenyl)-2-{2,6-dichloro-3-[(2,2-dimethyl-propionylamino)-methyl]-phenylamino}-6-fluoro-1-methyl-1H-benzimidazole-5-carboxylic acid amide A mixture of crude N-(4-Bromophenyl)-5-(3-{2,6-dichloro-3-[(2,2-dimethyl-propionylamino)-methyl]-phenyl}-thioureido)-2-fluoro-4-methylamino-benzamide (400 mg), DIC (111 µl, 0.700 mmol) and DMF (5 mL) is stirred at 80° C. for 8 h. The crude mixture is concentrated and purified by flash chromatography (silica gel; DCM→DCM/EtOH 97:3) to give the title compound.

Yield: 0.230 g (68%). $R_f$=0.34 (DCM/EtOH 95:5). MS m/z: 620 [M+H]⁺.

Example 11

N-(4-Bromo-phenyl)-2-{2,6-difluoro-3-[(2,2-dimethyl-propionylamino)-methyl]-phenylamino}-6-(2,2-difluoroethoxy-1-cyclopropyl-1H-benzimidazole-5-carboxylic acid amide

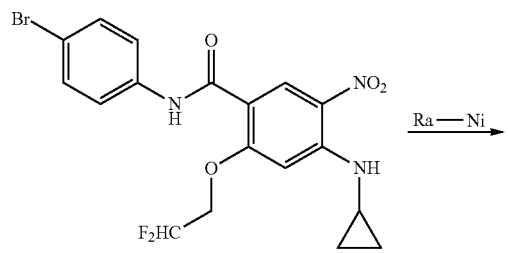

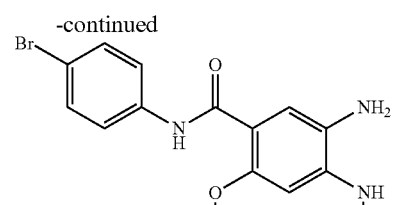

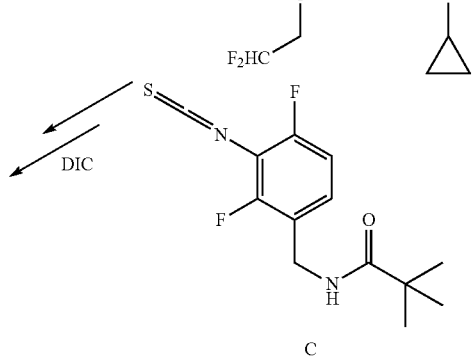

(a) N-(4-Bromophenyl)-2-(2,2-difluoroethoxy)-4-cyclopropylamino-5-amino-benzamide The subtitle compound is prepared from N-(4-bromophenyl)-2-(2,2-difluoroethoxy)-4-cyclopropylamino-5-nitro-benzamide (prepared from 2,4-difluoro-5-nitrobenzoic acid, cyclopropylamine, 4-bromoaniline and 2,2-difluoroethanol in analogy to the examples 1c, 6a, 1e) and RaNi/H₂ in analogy to example 5c.

HPLC $R_t$=1.4 min (method B). MS m/z: 427 [M+H]⁺.

(b) N-(4-Bromo-phenyl)-2-{2,6-difluoro-3-[(2,2-dimethyl-propionylamino)-methyl]-phenylamino}-6-(2,2-difluoroethoxy-1-cyclopropyl-1H-benzimidazole-5-carboxylic acid amide The title compound is prepared from N-(4-Bromophenyl)-2-(2,2-difluoroethoxy)-4-cyclopropylamino-5-amino-benzamide and N-(2,4-difluoro-3-isothiocyanato-benzyl)-2,2-dimethyl-propionamide with DIC in analogy to the examples 7b/7c.

$R_f$=0.36 (DCM/EtOH 95:5). MS m/z: 676 [M+H]⁺.

Example 12

N-(trans-4-Trifluoromethyl-cyclohex-1-yl)-2-{2,6-dichloro-3-[(2,2-dimethyl-propionylamino)-methyl]-phenylamino}-6-fluoro-1H-benzimidazole-5-carboxylic acid amide

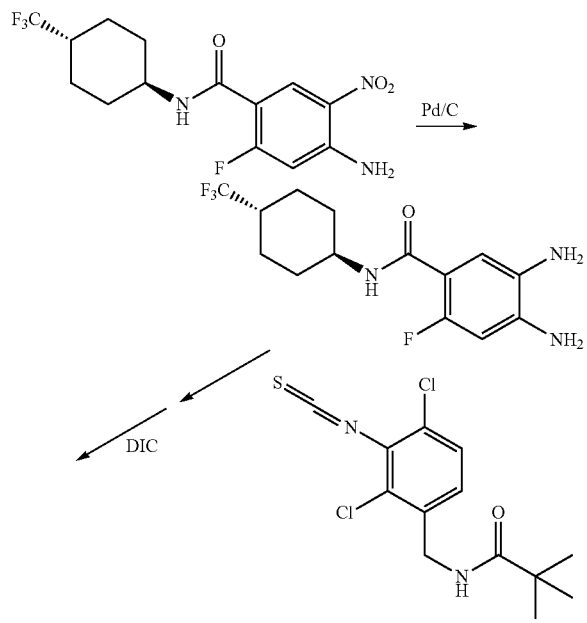

(a) N-(trans-4-Trifluoromethyl-cyclohex-1-yl)-2-fluoro-4,5-diamino-benzoic acid amide The subtitle compound is prepared from N-(trans-4-trifluoromethyl-cyclohex-1-yl)-2-fluoro-4-amino-5-nitro-benzoic acid amide (prepared from 2-fluoro-4-amino-5-nitro-benzoic acid, trans-4-trifluoromethyl-cyclohexylamine in analogy to the example 2d) with Pd/C and $H_2$ in analogy to example 1f.

HPLC $R_t$=1.58 min (method B). MS m/z: 320 [M+H]$^+$.

(b) N-(trans-4-Trifluoromethyl-cyclohex-1-yl)-2-{2,6-dichloro-3-[(2,2-dimethyl-propionylamino)-methyl]-phenylamino}-6-fluoro-1H-benzimidazole-5-carboxylic acid amide The title compound is prepared from N-(trans-4-trifluoromethyl-cyclohex-1-yl)-2-fluoro-4,5-diamino-benzoic acid amide and N-(2,4-dichloro-3-isothiocyanato-benzyl)-2,2-dimethyl-propionamide with DIC in analogy to examples 7b/7c.

HPLC $R_t$=2.52 min (method G). MS m/z: 602 [M+H]$^+$.

Example 13

N-(trans-4-Trifluoromethyl-cyclohex-1-yl)-2-{2,6-dichloro-3-[(tert-butoxy-carbonylamino)-methyl]-phenylamino}-6-(2,2-difluoroethoxy)-1-methyl-1H-benzimidazole-5-carboxylic acid amide

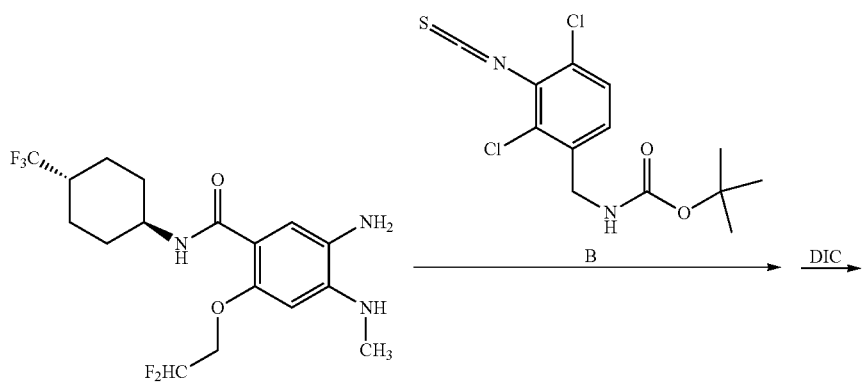

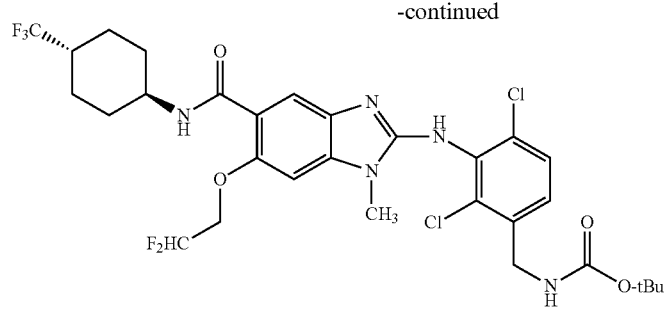

The title compound is prepared from N-(trans-4-trifluoromethyl-cyclohex-1-yl)-2-(2,2-difluoro-ethoxy)-4-methylamino-5-amino-benzoic acid amide and (2,4-dichloro-3-isothiocyanato-benzyl)-carbamic acid tert-butyl ester with DIC in analogy to examples 7b/7c.

$R_f$=0.25 (DCM/EtOH 95:5). MS m/z: 694 [M+H]$^+$.

Example 14

N-(trans-4-Trifluoromethyl-cyclohex-1-yl)-2-{2,6-dimethyl-3-[(2,2-dimethyl-propionylamino)-methyl]-phenylamino}-6-(2,2-difluoroethoxy)-1-methyl-1H-benzimidazole-5-carboxylic acid amide

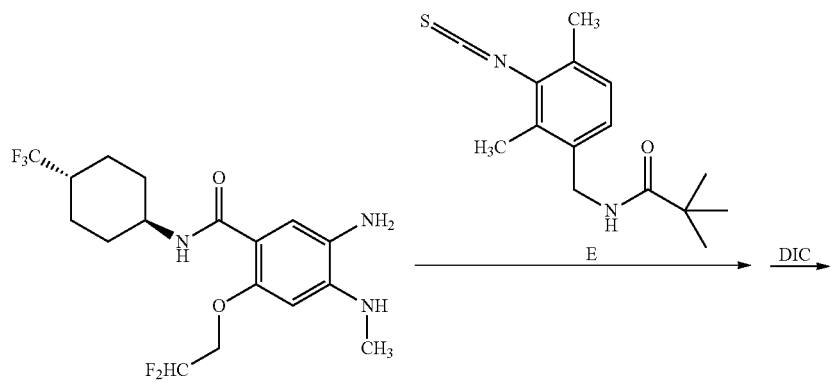

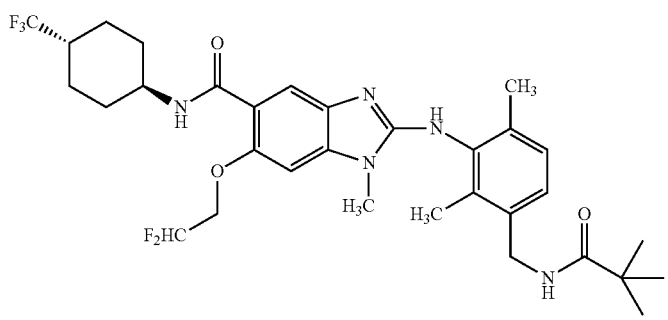

The title compound is prepared from N-(trans-4-trifluoromethyl-cyclohex-1-yl)-2-(2,2-difluoro-ethoxy)-4-methylamino-5-amino-benzoic acid amide and N-(2,4-dimethyl-3-isothiocyanato-benzyl)-2,2-dimethyl-propionamide with DIC in analogy to examples 7b/7c.

$R_f$=0.15 (DCM/EtOH 95:5). MS m/z: 638 [M+H]$^+$.

Example 17

N-(4-Fluoro-3-chloro-phenyl)-2-{2,6-dichloro-3-[(2,2-dimethyl-propionylamino)-methyl]-phenylamino}-6-fluoro-1-methyl-1H-benzimidazole-5-carboxylic acid amide

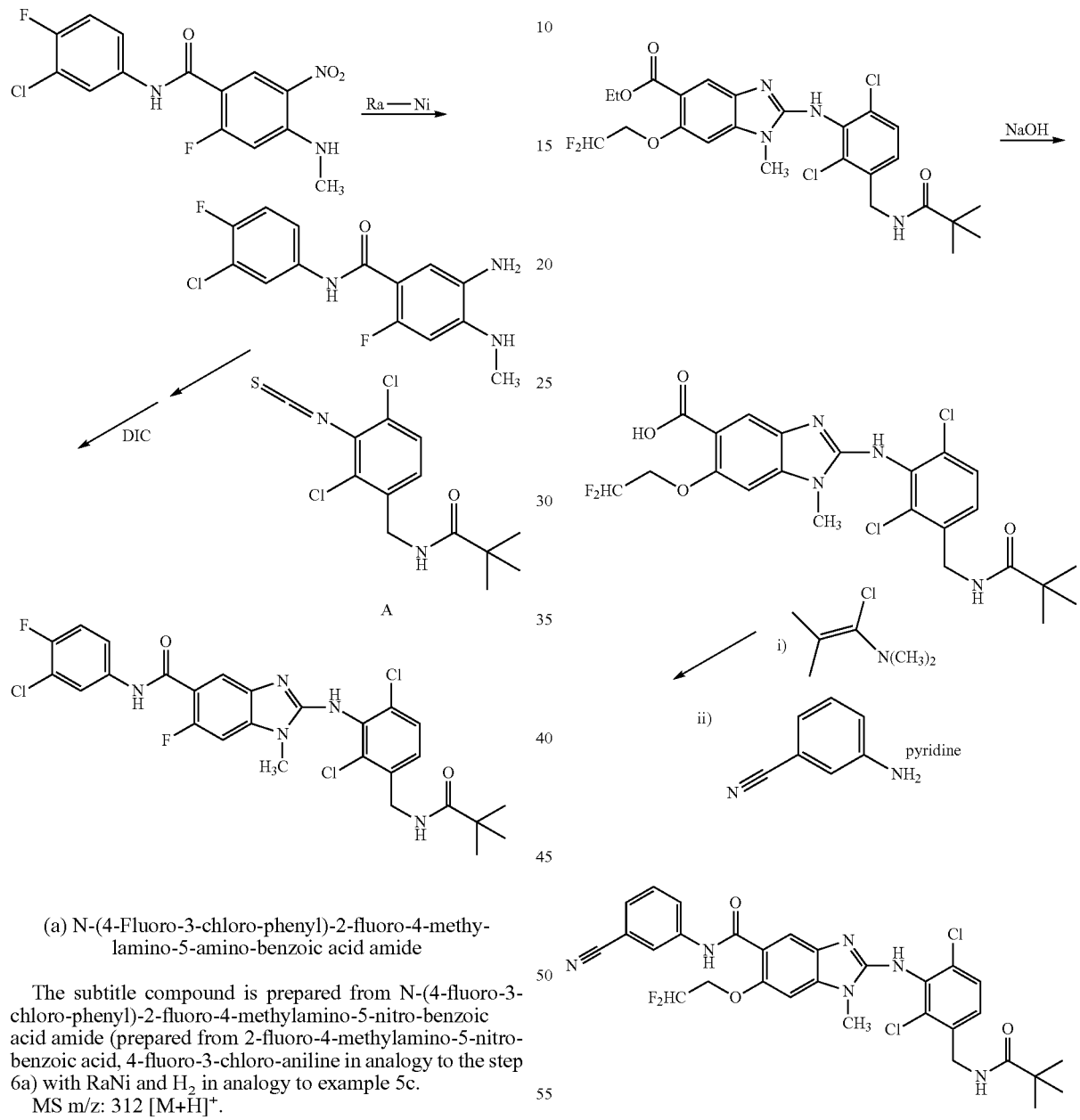

(a) N-(4-Fluoro-3-chloro-phenyl)-2-fluoro-4-methylamino-5-amino-benzoic acid amide The subtitle compound is prepared from N-(4-fluoro-3-chloro-phenyl)-2-fluoro-4-methylamino-5-nitro-benzoic acid amide (prepared from 2-fluoro-4-methylamino-5-nitro-benzoic acid, 4-fluoro-3-chloro-aniline in analogy to the step 6a) with RaNi and $H_2$ in analogy to example 5c.
MS m/z: 312 [M+H]$^+$.

(b) N-(4-Fluoro-3-chloro-phenyl)-2-{2,6-dichloro-3-[(2,2-dimethyl-propionylamino)-methyl]-phenylamino}-6-fluoro-1-methyl-1H-benzimidazole-5-carboxylic acid amide The title compound is prepared from N-(4-fluoro-3-chloro-phenyl)-2-fluoro-4-methylamino-5-amino-benzoic acid amide and N-(2,4-dichloro-3-isothiocyanato-benzyl)-2,2-dimethyl-propionamide with DIC in analogy to examples 7b/7c.
HPLC R$_t$=2.52 min (method G). MS m/z: 594 [M+H]$^+$.

Example 28

N-(3-Cyano-phenyl)-2-{(2,6-dichloro-3-[(2,2-dimethyl-propionylamino)-methyl]-phenylamino}-6-(2,2-difluoro-ethoxy)-1-methyl-1H-benzimidazole-5-carboxylic acid amide (a) 2-{2,6-Dichloro-3-[(2,2-dimethyl-propionylamino)-methyl]-phenylamino}-6-(2,2-difluoro-ethoxy)-1-methyl-1H-benzimidazole-5-carboxylic acid A mixture of ethyl 2-{2,6-dichloro-3-[(2,2-dimethyl-propionylamino)-methyl]-phenylamino}-6-(2,2-difluoro-ethoxy)-1-methyl-1H-benzimidazole-5-carboxylic acid ester (1.170 g; 2.10 mmol), 4 N aq. NaOH-solution (2.10 mL, 8.4 mmol) and EtOH (30 mL) is stirred for 4 d. Then, the mixture is concentrated, diluted with water and acidified with 4 N aq. HCl-solution. The precipitate is filtered, washed with water and dried to give 0.60 g of the product. The filtrate is extracted with EtOAc, the organic phase is dried with $Na_2SO_4$, and concentrated to give additional 0.23 g of the sub-title compound.

Yield: 0.83 g (75%). HPLC $R_t$=1.16 min (method C). MS m/z: 529 $[M+H]^+$.

(b) N-(3-Cyano-phenyl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide (1-Chloro-2-methyl-propenyl)-dimethylamine (20 µl) is added to a mixture of 2-{2,6-dichloro-3-[(2,2-dimethyl-propionylamino)-methyl]-phenylamino}-6-(2,2-difluoro-ethoxy)-1-methyl-1H-benzimidazole-5-carboxylic acid (53 mg, 0.10 mmol) in 2.0 mL acetonitrile and it is stirred 10 min at rt. Additional (1-chloro-2-methyl-propenyl)-dimethylamine (20 µl) is added and the mixture is stirred for additional 20 min at rt. The crude acid chloride solution is added to a mixture of 3-aminobenzonitrile (12 mg, 0.10 mmol), pyridine (24 µL, 0.30 mmol) and acetonitrile (1.0 mL) and it is stirred for 15 min at rt and additional 5 h at 55° C. The solvent is removed in vacuo and the residue is dissolved in 2 mL of a 19:1 DMF/water-solution and is purified via preparative HPLC to furnish the title compound.

Yield: 26 mg (42%). HPLC $R_t$=1.65 min (method A). MS m/z: 629 $[M+H]^+$.

Example 60

N-(2,4-dichloro-phenyl)-2-{2,6-dichloro-3-[(2,2-dimethyl-propionylamino)-methyl]-phenylamino}-6-(2,2-difluoro-ethoxy)-1-methyl-1H-benzimidazole-5-carboxylic acid amide

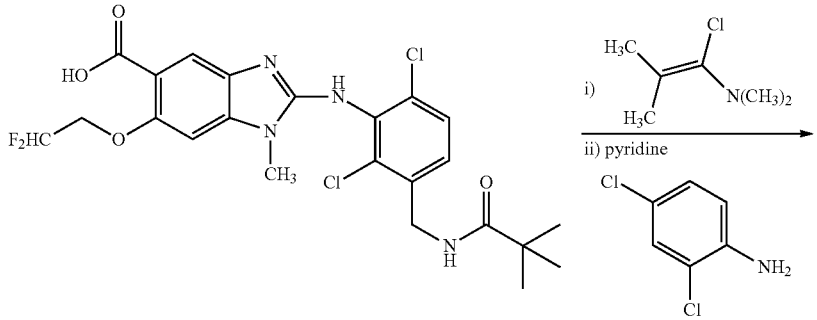

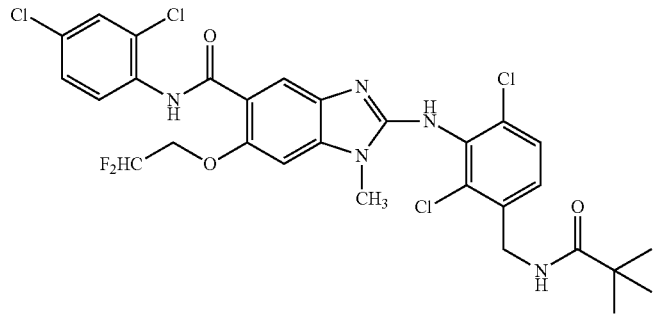

(1-Chloro-2-methyl-propenyl)-dimethylamine (20 µl) is added to a mixture of 2-{2,6-dichloro-3-[(2,2-dimethyl-propionylamino)-methyl]-phenylamino}-6-(2,2-difluoro-ethoxy)-1-methyl-1H-benzimidazole-5-carboxylic acid (53 mg, 0.10 mmol) in 1.0 mL acetonitrile and it is stirred 15 min at rt. The crude acid chloride solution is added to a mixture of 2,4-dichloroaniline (16 mg, 0.10 mmol), pyridine (24 µL, 0.30 mmol) and acetonitrile (1.0 mL) and it is stirred over the weekend at 60° C. The solvent is removed in vacuo and the residue is dissolved in 2 mL of a 9:1 DMF/water-solution and is purified via preparative HPLC.

Yield: 53 mg (79%). HPLC $R_t$=2.83 min (method D). MS m/z: 672 $[M+H]^+$.

Example 75

N-(3-Chloro-4-fluoro-phenyl)-2-{6-chloro-2-fluoro-3-[(2,2-dimethyl-propionylamino)-methyl]-phenylamino}-6-(2,2-difluoroethoxy)-1-methyl-1H-benzimidazole-5-carboxylic acid amide

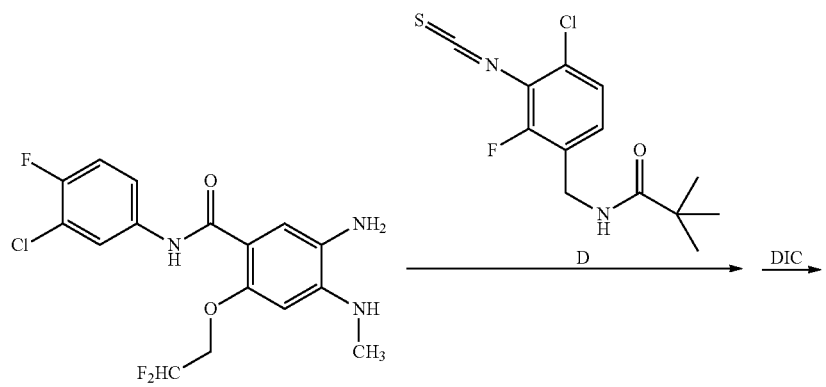

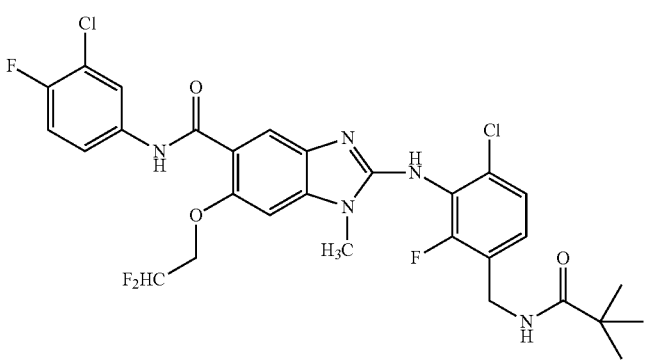

A mixture of N-(3-chloro-4-fluorophenyl)-2-(2,2-difluoroethoxy)-4-methylamino-5-amino-benzamide (60 mg, 0.161 mmol, prepared from 3-chloro-4-fluoro-aniline, 2,2-difluoroethanol and 2-fluoro-4-methylamino-5-nitro benzoic acid according to the sequence 1d-1f), N-(4-chloro-2-fluoro-3-isothiocyanato-benzyl)-2,2-dimethyl-propionamide (0.48 mg, 0.161 mmol) and DMF (2 mL) is stirred for 3 h. Then DIC (25 µl, 0.16 mmol) is added and it is stirred at 80° C. overnight. The crude mixture is concentrated and purified by flash chromatography (silica gel; DCM→DCM/EtOH 98:2).

Yield: 80 mg (78%). $R_f$=0.45 (DCM/EtOH 95:5). HPLC $R_t$=1.48 min (method B). MS m/z: 640 [M+H]$^+$.

Example 78

N-(trans-4-Trifluoromethyl-cyclohex-1-yl)-2-{(2,6-dichloro-3-[(2,2-dimethyl-propionylamino)-methyl]-phenylamino}-6-(difluoromethoxy)-1H-benzimidazole-5-carboxylic acid amide

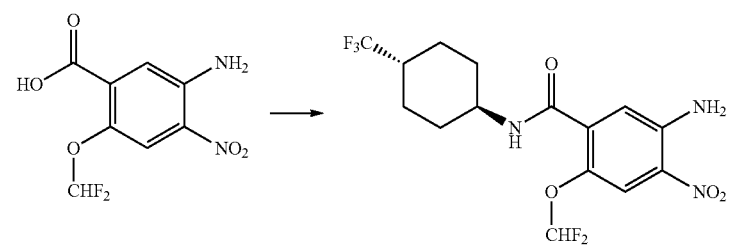
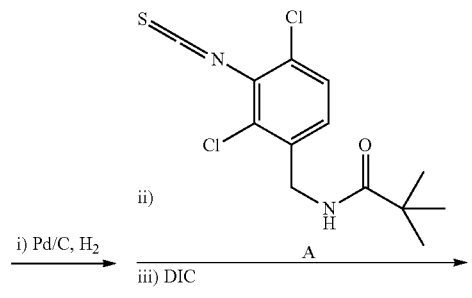

-continued

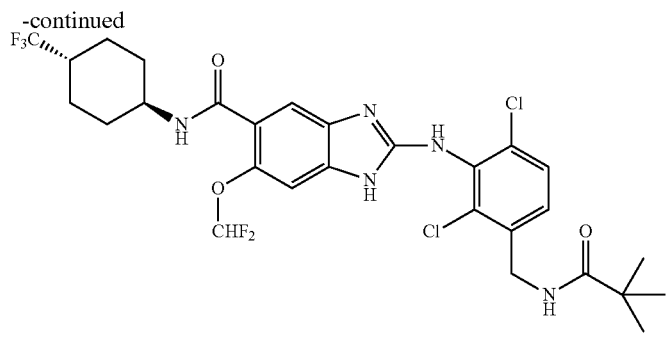

a) N-(trans-4-Trifluoromethyl-cyclohex-1-yl)-2-(difluoromethoxy)-5-amino-4-nitro-benzoic acid amide (1-Chloro-2-methyl-propenyl)-dimethylamine (102 μl) is added to a mixture of 2-(difluoro-methoxy)-5-amino-4-nitro-benzoic acid (175 mg, 0.705 mmol, prepared in analogy to WO2010/034797), 5 mL THF and 10 mL DCM and it is stirred for 5 h. Then trans-4-trifluoromethyl-cyclohexylamine (158 mg, 0.776 mmol) and pyridine (139 μL, 1.77 mmol) are added and it is stirred overnight. The solvent is removed i. vac., half-saturated aq. NaHCO$_3$— solution is added and it is extracted with DCM. The organic layers are dried with Na$_2$SO$_4$, filtered, concentrated and purified via preparative HPLC (Method F).

Yield: 70 mg (25%). HPLC R$_t$=2.06 min (method E). MS m/z: 398 [M+H]$^+$.

b) N-(trans-4-Trifluoromethyl-cyclohex-1-yl)-2-{2,6-dichloro-3-[(2,2-dimethyl-propionylamino)-methyl]-phenylamino}-6-(difluoromethoxy)-1H-benzimidazole-5-carboxylic acid amide A mixture of N-(trans-4-trifluoromethyl-cyclohex-1-yl)-2-(difluoromethoxy)-5-amino-4-nitro-benzoic acid amide (70 mg, 0.176 mmol), Pd/C (15 mg) and 10 mL THF is stirred under a H$_2$-atmosphere (3 bar) for 2 h. The crude mixture is filtered into a flask charged with N-(2,4-dichloro-3-isothiocyanato-benzyl)-2,2-dimethyl-propionamide (59 mg, 0.185 mmol) and the filter cake is washed with 40 mL THF. The mixture is stirred for 4 h at rt and overnight at 60° C. Then the reaction mixture is concentrated to ~10 mL and stirred for additional 8 h at 60° C. Then it is concentrated i. vac., diluted with MeCN (2.0 mL) and DIC (29 μl, 0.186 mmol) is added and it is stirred for 4 d. Then the mixture is concentrated, diluted with DMF and THF and purified via HPLC.

Yield: 34 mg (30%). HPLC R$_t$=2.00 min (method E). MS m/z: 650 [M+H]$^+$.

Example 79

N-(trans-4-Trifluoromethyl-cyclohex-1-yl)-2-{(2,6-dichloro-3-[(2,2-dimethyl-propionylamino)-methyl]-phenylamino}-6-(2,2,2-trifluoroethoxy)-7-fluoro-1H-benzimidazole-5-carboxylic acid amide

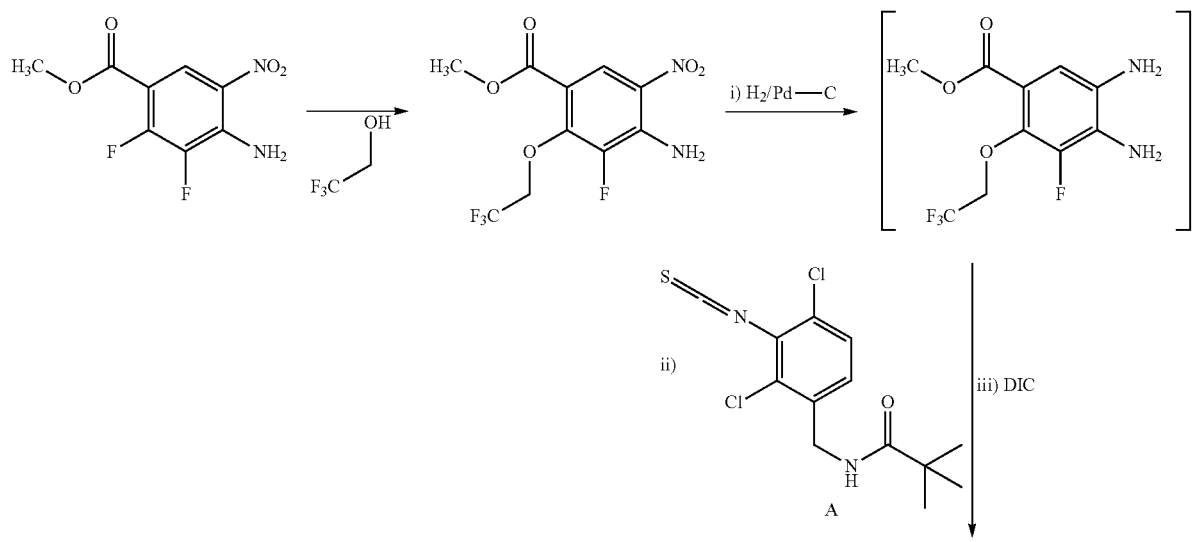

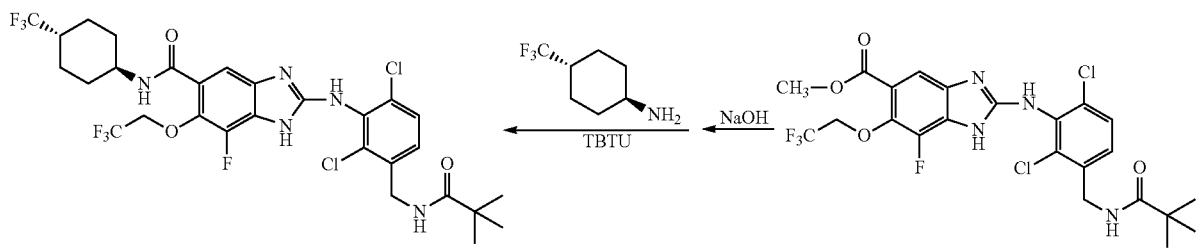

(a) 2-(2,2,3-Trifluoro-ethoxy)-3-fluoro-4-amino-5-nitro-benzoic acid methyl ester A mixture of 2,2,2-trifluoroethanol (0.377 mL, 5.2 mmol), KOtBu (0.580 g, 0.5.2 mmol) and THF (20 mL) is stirred for 15 min at 0° C., then methyl 2,3-difluoro-4-amino-5-nitrobenzoate (1.00 g) in THF (20 mL) is added and it is stirred for 15 h at rt. Water is added to the mixture and the mixture is concentrated. The resulting precipitate is filtered, washed with water and dried at 50° C.

Yield: 1.15 g (86%). HPLC $R_t$=1.95 min (method E). MS m/z: 313 [M+H]$^+$.

(b) 2-{2,6-Dichloro-3-[(2,2-dimethyl-propionylamino)-methyl]-phenylamino}-6-(2,2,2-trifluoroethoxy)-7-fluoro-1H-benzimidazole-5-carboxylic acid methyl ester The subtitle compound is prepared from 2-(2,2,3-trifluoro-ethoxy)-3-fluoro-4-amino-5-nitro-benzoic acid methyl ester in analogy to 78b using i) Pd/C and H$_2$, ii) N-(2,4-dichloro-3-isothiocyanato-benzyl)-2,2-dimethyl-propionamide and iii) DIC.

Yield: 90 mg (45%). HPLC $R_t$=2.01 min (method E). MS m/z: 565 [M+H]$^+$.

(c) 2-{2,6-Dichloro-3-[(2,2-dimethyl-propionylamino)-methyl]phenylamino}-6-(2,2,2-trifluoroethoxy)-7-fluoro-1H-benzimidazole-5-carboxylic acid The subtitle compound is prepared from 2-{2,6-dichloro-3-[(2,2-dimethyl-propionylamino)-methyl]-phenylamino}-6-(2,2,2-trifluoroethoxy)-7-fluoro-1H-benzimidazole-5-carboxylic acid methyl ester and NaOH in analogy to example 28a.

Yield: 60 mg (62%). HPLC $R_t$=1.81 min (method E). MS m/z: 551 [M+H]$^+$.

(d) N-(trans-4-Trifluoromethyl-cyclohex-1-yl)-2-{2,6-dichloro-3-[(2,2-dimethyl-propionylamino)-methyl]phenylamino}-6-(2,2,2-trifluoroethoxy)-7-fluoro-1H-benzimidazole-5-carboxylic acid amide A mixture of 2-{2,6-dichloro-3-[(2,2-dimethyl-propionylamino)-methyl]phenylamino}-6-(2,2,2-trifluoroethoxy)-7-fluoro-1H-benzimidazole-5-carboxylic acid (60 mg, 0.109 mmol), TBTU (36.7 mg, 0.114 mmol), DIPEA (66 µl, 0.38 mmol) and DMF (1 mL) is stirred for 30 min, then trans-4-trifluoromethyl-cyclohexylamine (24 mg, HCl salt) is added and it is stirred for 1 h.

The mixture is diluted with EtOAc, washed with satd. aq. NaHCO$_3$-solution, dried with Na$_2$SO$_4$ and concentrated to give the title compound.

Yield: 76 mg (100%). HPLC $R_t$=2.24 min (method E). MS m/z: 700 [M+H]$^+$.

Example 80

N-(trans-4-Trifluoromethyl-cyclohex-1-yl)-2-{2,6-dichloro-3-[(3,3-difluoro-azetidine-1-carbonylamino)-methyl]-phenylamino}-6-(2,2-difluoroethoxy)-1-methyl-1H-benzimidazole-5-carboxylic acid amide

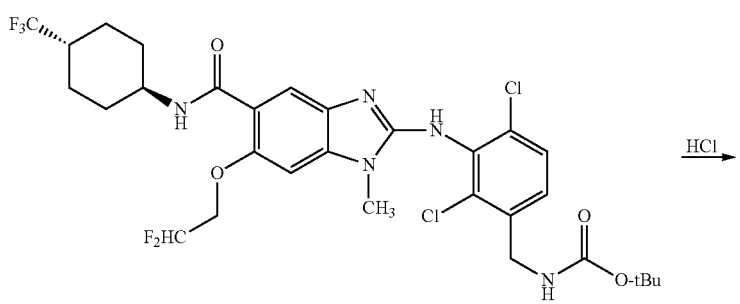

-continued

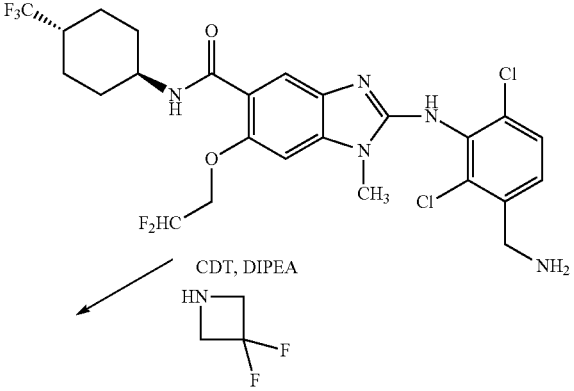

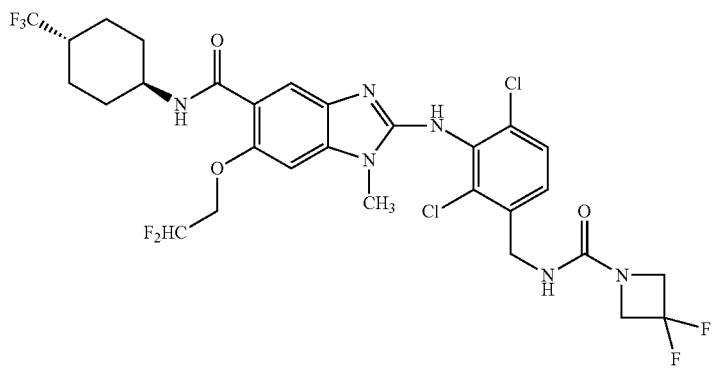

(a) N-(trans-4-Trifluoromethyl-cyclohex-1-yl)-2-(2,6-dichloro-3-aminomethyl-phenylamino)-6-(2,2-difluoroethoxy)-1-methyl-1H-benzimidazole-5-carboxylic acid amide A mixture of N-(trans-4-trifluoromethyl-cyclohex-1-yl)-2-{2,6-dichloro-3-[(tert-butoxy-carbonylamino)-methyl]-phenylamino}-6-(2,2-difluoroethoxy)-1-methyl-1H-benzimidazole-5-carboxylic acid amide (350 mg, 0.504 mmol), 6 M aq. HCl-solution (15 mL) and THF (15 mL) is stirred overnight, the mixture is concentrated and directly used in the next step.

Yield: 320 mg (quantitative). HPLC $R_t$=1.23 min (method B). MS m/z: 594 [M+H]$^+$.

(b) N-(trans-4-Trifluoromethyl-cyclohex-1-yl)-2-{2,6-dichloro-3-[(3,3-difluoro-azetidine-1-carbonylamino)-methyl]-phenylamino}-6-(2,2-difluoroethoxy)-1-methyl-1H-benzimidazole-5-carboxylic acid amide CDT (45 mg, 90%) is added to an ice-cooled mixture of crude N-(trans-4-trifluoromethyl-cyclohex-1-yl)-2-(2,6-dichloro-3-aminomethyl-phenylamino)-6-(2,2-difluoroethoxy)-1-methyl-1H-benzimidazole-5-carboxylic acid amide (140 mg), DIPEA (0.12 mL, 0.68 mmol) and THF (5.0 mL) and it is stirred for 30 min. Then 3,3-difluoroazetidine×HCl (30 mg, 0.22 mmol) is added and the mixture is heated to 60° C. for 4 d (every day another 30 mg of the azetidine is added). The reaction mixture is concentrated and purified via chromatography (silica gel, DCM→DCM/EtOH 95:5).

Yield: 60 mg (38%). $R_f$(TLC): 0.26 (DCM/EtOH 95:5). MS m/z: 713 [M+H]$^+$.

Example 84

N-(3-Chloro-4-fluoro-phenyl)-2-{2,6-dichloro-3-[(2-fluoro-2-methyl-propionylamino)-methyl]-phenylamino}-6-(2,2-difluoroethoxy)-1-methyl-1H-benzimidazole-5-carboxylic acid amide

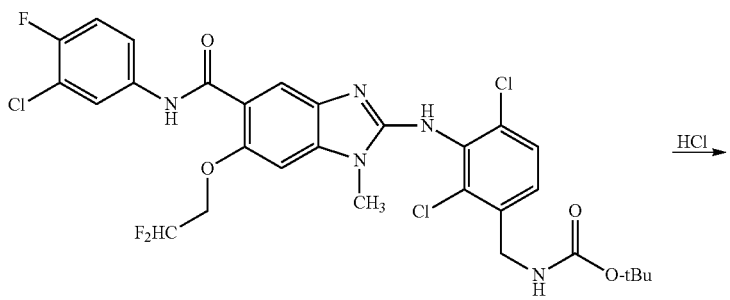

with building block B), 4 M HCl in dioxane (50 mL) and dioxane (200 mL) is stirred for 2 h. The precipitate is filtered off, washed with water and diluted with 10 mL conc. aq. $NH_3$. The mixture is extracted with EtOAc, the organic phase is dried with $Na_2SO_4$ and concentrated.

Yield: 2.62 g (77%). MS m/z: 572 [M+H]$^+$.

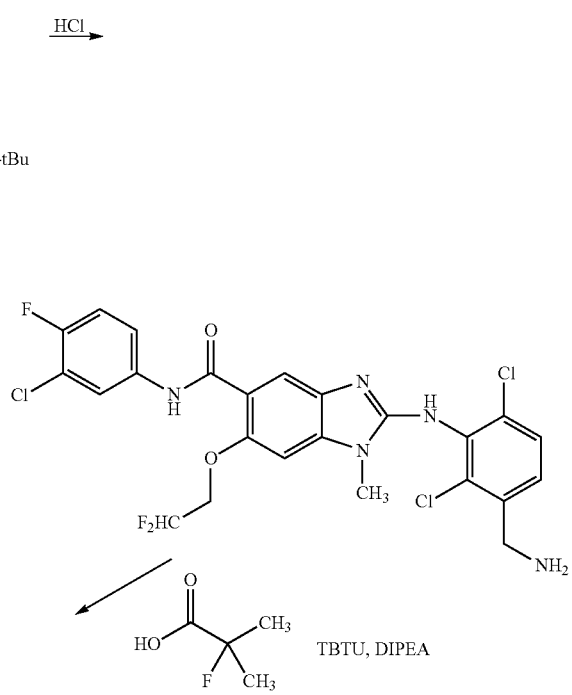

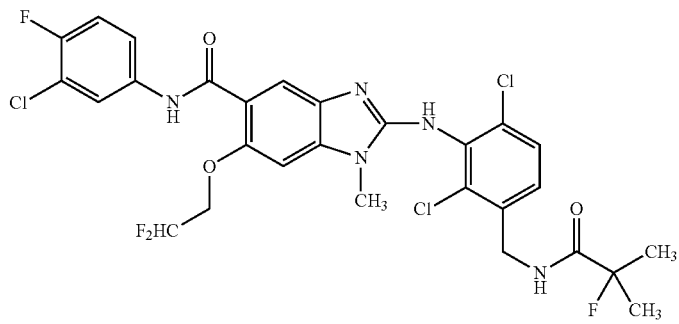

(a) N-(3-Chloro-4-fluoro-phenyl)-2-(2,6-dichloro-3-aminomethyl-phenylamino)-6-(2,2-difluoroethoxy)-1-methyl-1H-benzimidazole-5-carboxylic acid amide A mixture of N-(3-chloro-4-fluoro-phenyl)-2-{2,6-dichloro-3-[(tert-butoxy-carbonylamino)-methyl]phenylamino}-6-(2,2-difluoroethoxy)-1-methyl-1H-benzimidazole-5-carboxylic acid amide (4.0 g, 5.9 mmol, prepared in analogy to example 75 from N-(3-chloro-4-fluorophenyl)-2-(2,2-difluoroethoxy)-4-methylamino-5-amino-benzamide (b) N-(3-Chloro-4-fluoro-phenyl)-2-{2,6-dichloro-3-[(2-fluoro-2-methyl-propionylamino)-methyl]-phenylamino}-6-(2,2-difluoroethoxy)-1-methyl-1H-benzimidazole-5-carboxylic acid amide TBTU (1.0 mL of a 0.11 M solution in DMF) was added to a mixture of N-(3-chloro-4-fluoro-phenyl)-2-(2,6-dichloro-3-aminomethyl-phenylamino)-6-(2,2-difluoroethoxy)-1-methyl-1H-benzimidazole-5-carboxylic acid amide (1.0 mL of a 0.10 M solution in DMF), DIPEA (52 µl, 0.3 mmol) and 2-fluoro-2-methylpropionic acid (1.0 mL of a 0.13 M solution in DMF) and it was stirred for 3 d and the mixture was purified by prep. HPLC.

Yield: 38 mg (57%). HPLC $R_t$=1.69 min (method I). MS m/z: 661 [M+H]$^+$.

Example 177

N-(3-Chloro-4-fluoro-phenyl)-2-{2,6-dichloro-3-[(2,2-dimethyl-propionylamino)-methyl]-phenylamino}-6-(2-fluoroethoxy)-1-methyl-1H-benzimidazole-5-carboxylic acid amide

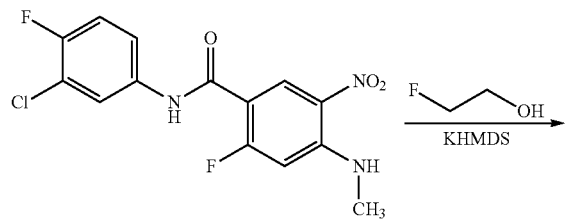

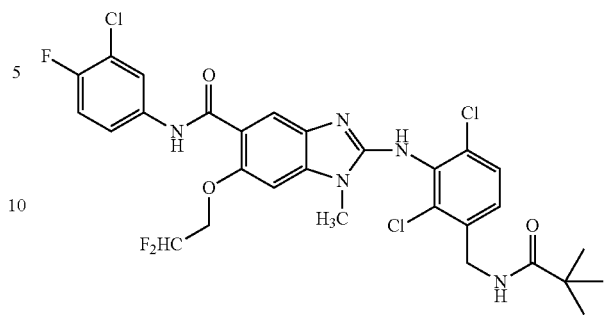

a) N-(3-chloro-4-fluorophenyl)-2-(2-fluoroethoxy)-4-methylamino-5-nitro-benzamide KHMDS (0.320 g, 1.60 mmol) is added to an ice-cooled mixture of N-(4-fluoro-3-chloro-phenyl)-2-fluoro-4-methylamino-5-nitro-benzoic acid amide (500 mg, 1.46 mmol), 2-fluoroethanol (0.129 ml, 2.19 mmol) and 30 ml THF. After 30 min the temperature is raised to 60° C. for 4.5 h, then it is stirred at rt overnight. Additional 2-fluoroethanol (0.129 ml, 2.19 mmol) and KHMDS (0.160 g, 0.80 mmol) are added and it is stirred for 4.5 h at 60° C. Then the mixture is diluted with satd. aq. NaHCO$_3$-solution and the precipitate is filtered off, washed with water and dried.

Yield: 360 mg (64%). HPLC $R_t$=2.28 min (method E). MS m/z: 386 [M+H]$^+$.

b) N-(3-Chloro-4-fluoro-phenyl)-2-{2,6-dichloro-3-[(2,2-dimethyl-propionylamino)-methyl]-phenylamino}-6-(2-fluoroethoxy)-1-methyl-1H-benzimidazole-5-carboxylic acid amide A mixture of N-(3-chloro-4-fluorophenyl)-2-(2-fluoroethoxy)-4-methylamino-5-nitro-benzamide (67.9 mg, 0.176 mmol), Pd/C (15 mg) and 10 mL THF is stirred under a H$_2$-atmosphere (3 bar) for 8 h. The crude mixture is filtered into a flask charged with N-(2,4-dichloro-3-isothiocyanato-benzyl)-2,2-dimethyl-propionamide (59 mg, 0.185 mmol) and concentrated to ~5 mL. The mixture is stirred for 2 h at rt and concentrated i. vac. The mixture is diluted with MeCN (2.0 mL), DIC (29 µl, 0.186 mmol) is added and it is stirred overnight at rt and 2 h at 60° C. The mixture is cooled to rt and the resulting precipitate is filtered off, washed with MeCN, redissolved in dioxane/MeCN and a few drops of HCOOH and lyophilized.

Yield: 29 mg (26%). HPLC $R_t$=2.09 min (method E). MS m/z: 638 [M+H]$^+$.

The following examples in Table 1 are prepared in analogy to the methods described above.

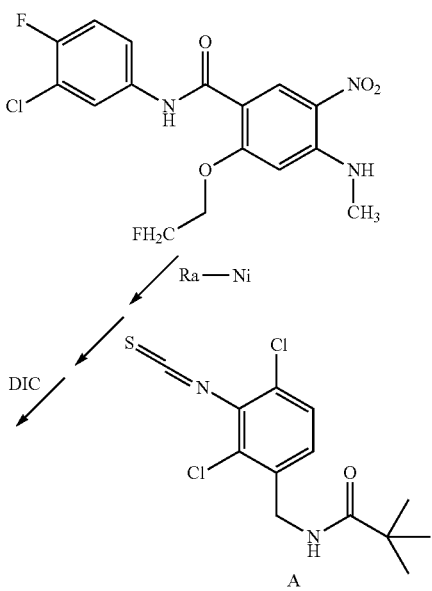

TABLE 1

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 8 | 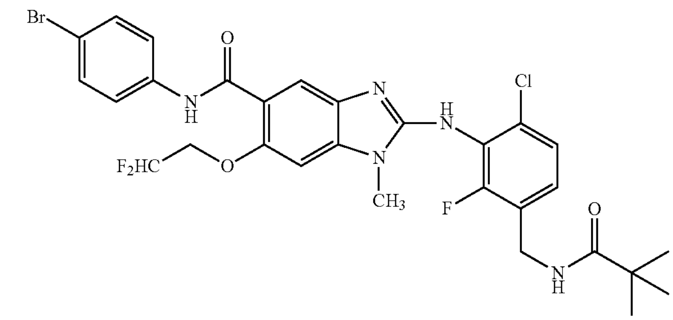 [SMILES: Cn1c(Nc2c(Cl)ccc(CNC(=O)C(C)(C)C)c2F)nc2cc(C(=O)Nc3ccc(Br)cc3)c(OCC(F)F)cc21] | $C_{29}H_{28}BrClF_3N_5O_3$ 666.916 | 666 | $R_t = 1.44$ (method B) | 6 |
| 9 | 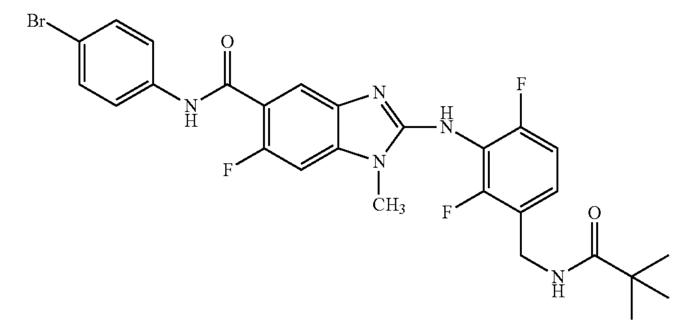 [SMILES: Cn1c(Nc2c(F)ccc(CNC(=O)C(C)(C)C)c2F)nc2cc(C(=O)Nc3ccc(Br)cc3)c(F)cc21] | $C_{27}H_{25}BrF_3N_5O_2$ 588.419 | 589 | $R_t = 1.39$ (method B) | 7 |
| 10 | 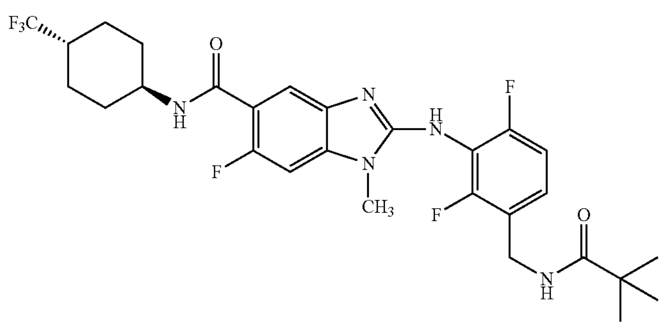 [SMILES: Cn1c(Nc2c(F)ccc(CNC(=O)C(C)(C)C)c2F)nc2cc(C(=O)N[C@H]3CC[C@H](C(F)(F)F)CC3)c(F)cc21] | $C_{28}H_{31}F_6N_5O_2$ 583.569 | 584 | $R_f = 0.25$ (DCM/EtOH 95:5) | 3 |
| 15 | 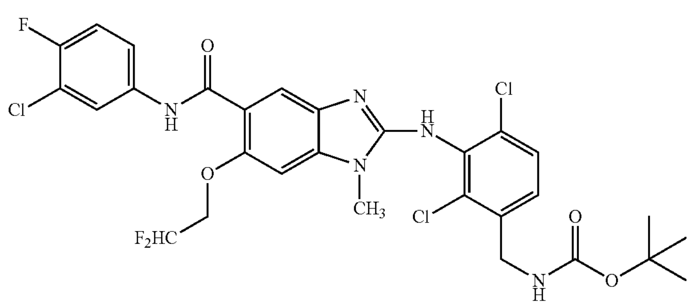 [SMILES: Cn1c(Nc2c(Cl)ccc(CNC(=O)OC(C)(C)C)c2Cl)nc2cc(C(=O)Nc3ccc(F)c(Cl)c3)c(OCC(F)F)cc21] | $C_{29}H_{37}Cl_3F_3N_5O_4$ 672.909 | 672 | $R_t = 2.21$ (method E) | 13 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 16 | 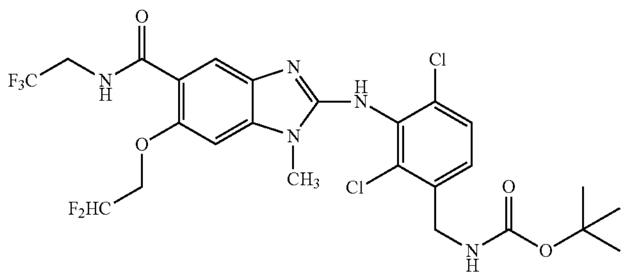 [SMILES: Cn1c(Nc2c(Cl)ccc(CNC(=O)OC(C)(C)C)c2Cl)nc2cc(C(=O)NCC(F)(F)F)c(OCC(F)F)cc21] | C{25}H{26}Cl{2}F{5}N{5}O{4} 626.403 | 626 | R_f = 0.36 (PE/EtOH 1:1) | 13 |
| 18 | 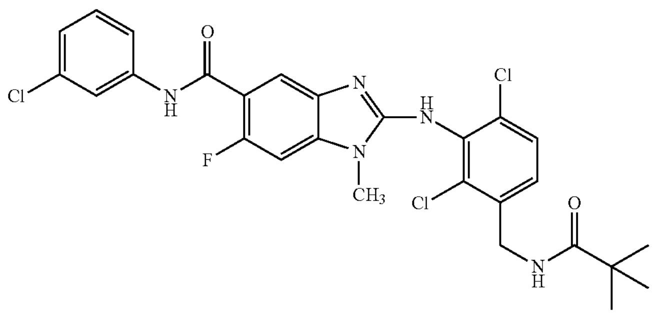 [SMILES: Cn1c(Nc2c(Cl)ccc(CNC(=O)C(C)(C)C)c2Cl)nc2cc(C(=O)Nc3cccc(Cl)c3)c(F)cc21] | C{27}H{25}Cl{3}FN{5}O{2} 576.876 | 576 | R_f = 0.35 (DCM/EtOH 95:5) | 17 |
| 19 | 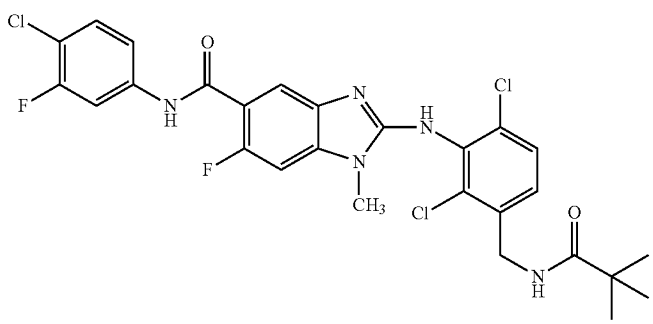 | C{27}H{24}Cl{3}F{2}N{5}O{2} 594.867 | 594 | R_f = 0.27 (DCM/EtOH 95:5) | 17 |
| 20 | 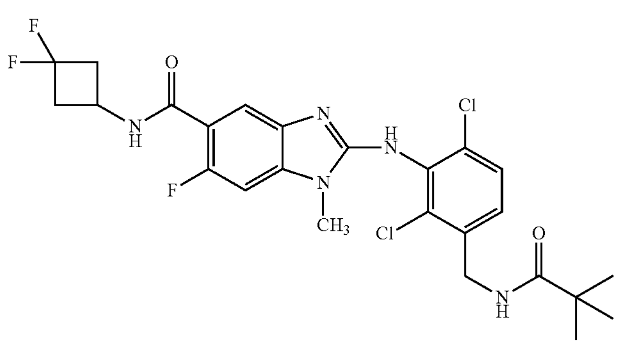 [SMILES: Cn1c(Nc2c(Cl)ccc(CNC(=O)C(C)(C)C)c2Cl)nc2cc(C(=O)NC3CC(F)(F)C3)c(F)cc21] | C{25}H{26}Cl{2}F{3}N{5}O{2} 556.407 | 556 | R_f = 0.22 (DCM/EtOH 95:5) | 17 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 21 | 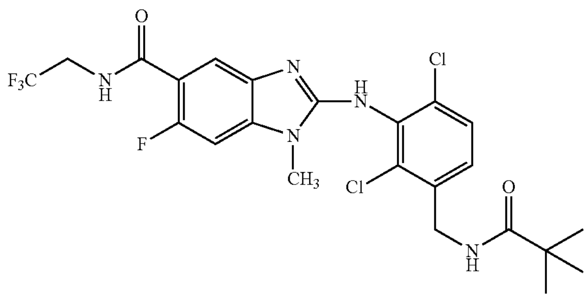 [SMILES: Cn1c(Nc2c(Cl)ccc(CNC(=O)C(C)(C)C)c2Cl)nc2cc(C(=O)NCC(F)(F)F)c(F)cc21] | $C_{23}H_{23}Cl_2F_4N_5O_2$ 548.360 | 548 | $R_f$ = 0.24 (DCM/EtOH 95:5) | 17 |
| 22 | 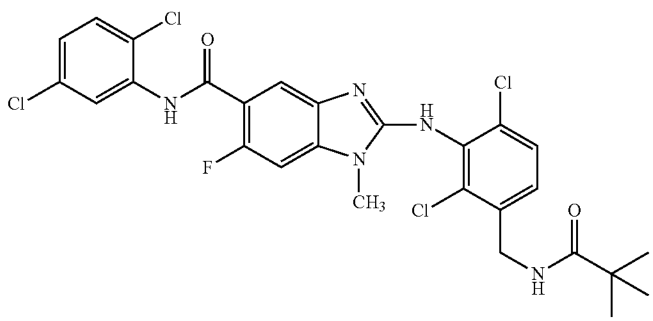 [SMILES: Cn1c(Nc2c(Cl)ccc(CNC(=O)C(C)(C)C)c2Cl)nc2cc(C(=O)Nc3cc(Cl)ccc3Cl)c(F)cc21] | $C_{27}H_{24}Cl_4FN_5O_2$ 611.321 | 610 | $R_f$ = 0.35 (DCM/EtOH 95:5) | 17 |
| 23 | 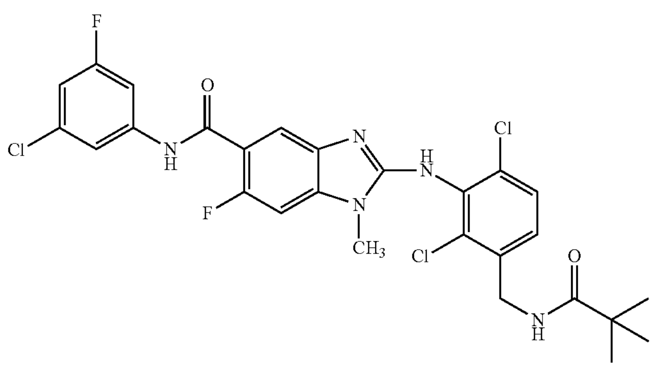 [SMILES: Cn1c(Nc2c(Cl)ccc(CNC(=O)C(C)(C)C)c2Cl)nc2cc(C(=O)Nc3cc(F)cc(Cl)c3)c(F)cc21] | $C_{27}H_{24}Cl_3F_2N_5O_2$ 594.867 | 594 | $R_f$ = 0.29 (DCM/EtOH 95:5) | 17 |
| 24 | 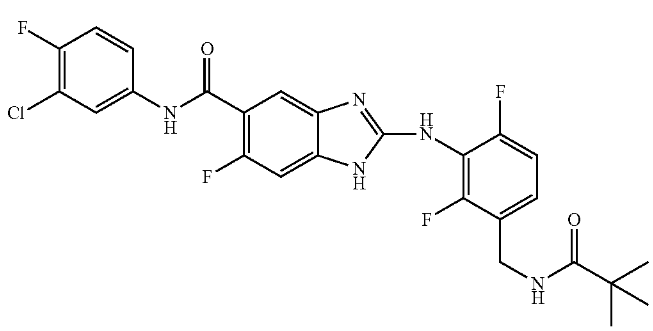 [SMILES: CC(C)(C)C(=O)NCc1ccc(F)c(Nc2nc3cc(C(=O)Nc4ccc(F)c(Cl)c4)c(F)cc3[nH]2)c1F] | $C_{26}H_{22}Cl_3F_2N_5O_2$ 547.932 | 548 | $R_f$ = 0.19 (DCM/EtOH 95:5) | 17 |

TABLE 1-continued

| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 25 | 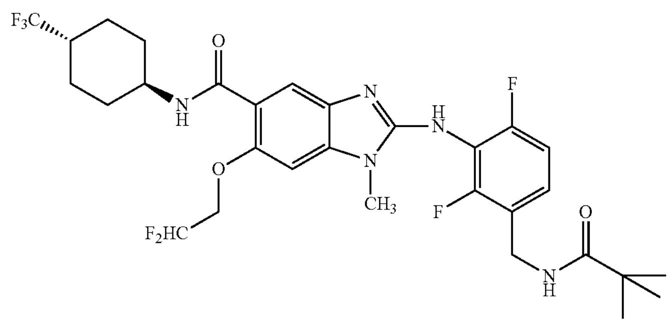 [SMILES: Cn1c(Nc2c(F)ccc(CNC(=O)C(C)(C)C)c2F)nc2cc(C(=O)N[C@H]3CC[C@H](C(F)(F)F)CC3)c(OCC(F)F)cc21] | $C_{30}H_{34}F_7N_5O_3$ 645.612 | 646 | $R_f$ = 0.22 (DCM/EtOH 95:5) | 1 |
| 26 | 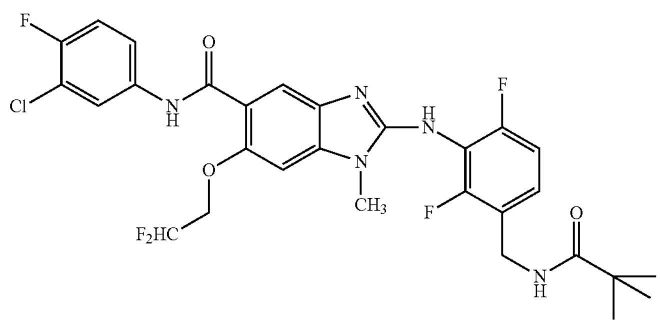 [SMILES: Cn1c(Nc2c(F)ccc(CNC(=O)C(C)(C)C)c2F)nc2cc(C(=O)Nc3ccc(F)c(Cl)c3)c(OCC(F)F)cc21] | $C_{29}H_{27}ClF_5N_5O_3$ 624.001 | 624 | $R_f$ = 0.27 (DCM/EtOH 95:5) | 11 |
| 27 | 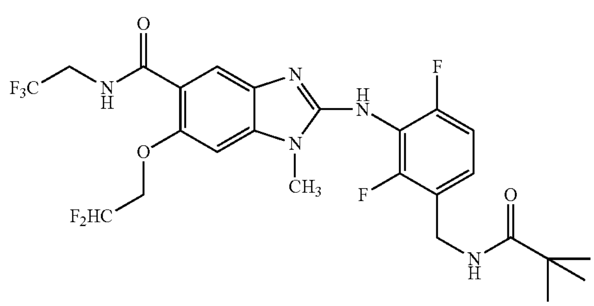 [SMILES: Cn1c(Nc2c(F)ccc(CNC(=O)C(C)(C)C)c2F)nc2cc(C(=O)NCC(F)(F)F)c(OCC(F)F)cc21] | $C_{25}H_{26}F_7N_5O_3$ 577.495 | 578 | $R_f$ = 0.19 (DCM/EtOH 95:5) | 11 |
| 29 | 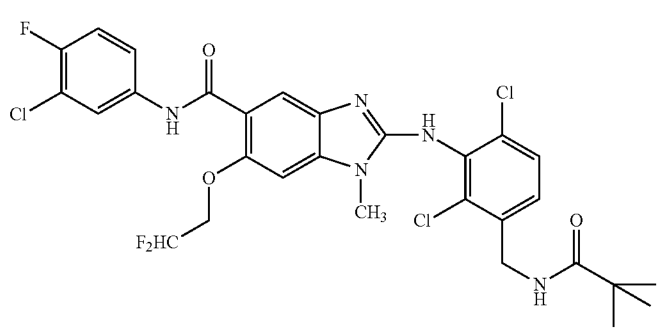 [SMILES: Cn1c(Nc2c(Cl)ccc(CNC(=O)C(C)(C)C)c2Cl)nc2cc(C(=O)Nc3ccc(F)c(Cl)c3)c(OCC(F)F)cc21] | $C_{29}H_{27}Cl_3F_3N_5O_3$ 656.917 | 656 | $R_t$ = 1.78 (method A) | 28 |

TABLE 1-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 30 | 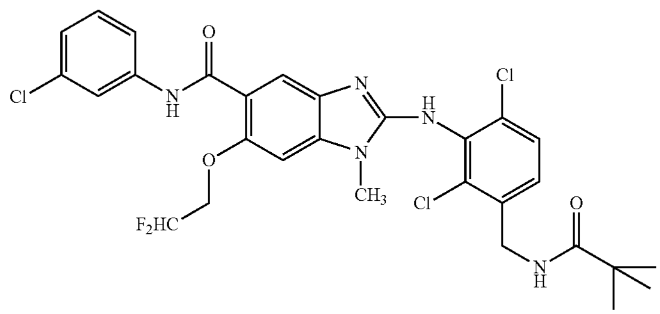 [SMILES: Cn1c(Nc2c(Cl)ccc(CNC(=O)C(C)(C)C)c2Cl)nc2cc(C(=O)Nc3cccc(Cl)c3)c(OCC(F)F)cc21] | C$_{29}$H$_{28}$Cl$_3$F$_2$N$_5$O$_3$ 638.927 | 638 | R$_t$ = 1.79 (method A) | 28 |
| 31 | 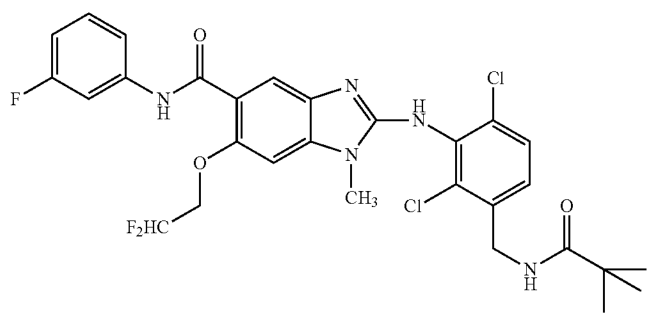 [SMILES: Cn1c(Nc2c(Cl)ccc(CNC(=O)C(C)(C)C)c2Cl)nc2cc(C(=O)Nc3cccc(F)c3)c(OCC(F)F)cc21] | C$_{29}$H$_{28}$Cl$_2$F$_3$N$_5$O$_3$ 622.472 | 622 | R$_t$ = 1.69 (method A) | 28 |
| 32 | 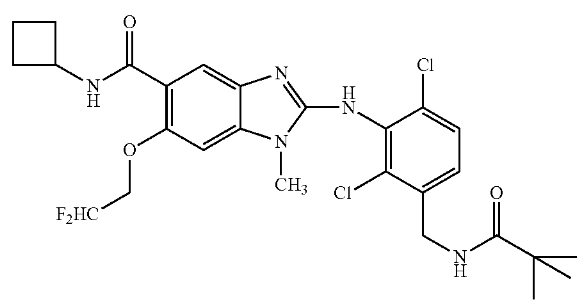 [SMILES: Cn1c(Nc2c(Cl)ccc(CNC(=O)C(C)(C)C)c2Cl)nc2cc(C(=O)NC3CCC3)c(OCC(F)F)cc21] | C$_{27}$H$_{31}$Cl$_2$F$_2$N$_5$O$_3$ 582.476 | 582 | R$_t$ = 1.51 (method A) | 28 |
| 33 | 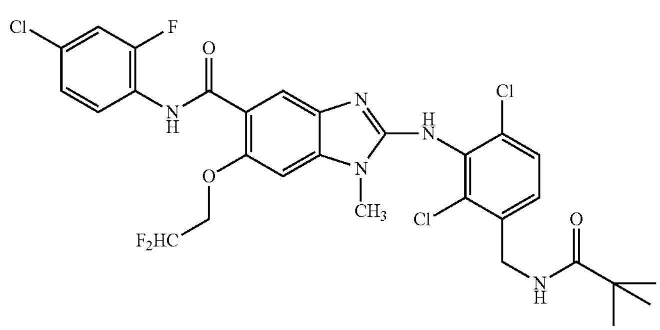 [SMILES: Cn1c(Nc2c(Cl)ccc(CNC(=O)C(C)(C)C)c2Cl)nc2cc(C(=O)Nc3ccc(Cl)cc3F)c(OCC(F)F)cc21] | C$_{29}$H$_{27}$Cl$_3$F$_3$N$_5$O$_3$ 656.917 | 656 | R$_t$ = 1.82 (method A) | 28 |

TABLE 1-continued

| Ex. | Structure | Formula/ Mw. | MS* m/z [M + H]+ | R$_f$ (TLC, silica gel) or R$_t$ [min] (HPLC-method) | Prepared in analogy to example |
|---|---|---|---|---|---|
| 34 | 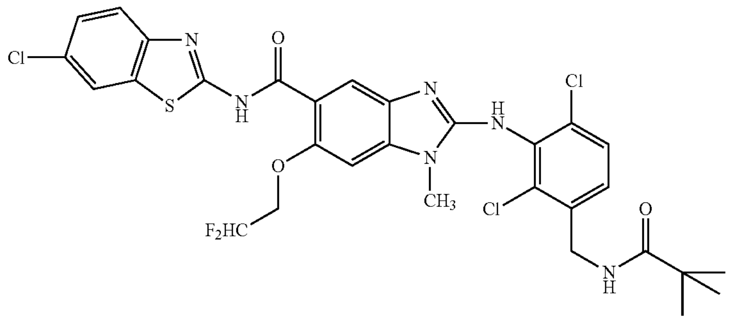 [SMILES: Cn1c(Nc2c(Cl)ccc(CNC(=O)C(C)(C)C)c2Cl)nc2cc(C(=O)Nc3nc4ccc(Cl)cc4s3)c(OCC(F)F)cc21] | C$_{30}$H$_{27}$Cl$_3$F$_3$N$_6$O$_3$S 696.003 | 695 | R$_t$ = 1.93 (method A) | 28 |
| 35 | 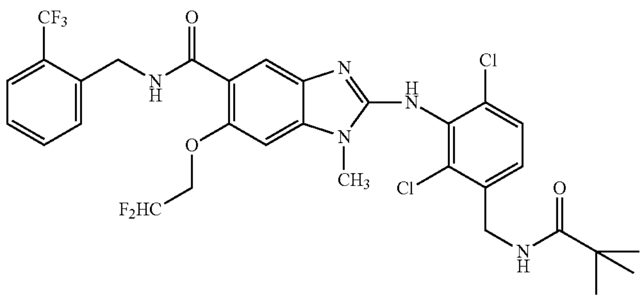 [SMILES: Cn1c(Nc2c(Cl)ccc(CNC(=O)C(C)(C)C)c2Cl)nc2cc(C(=O)NCc3ccccc3C(F)(F)F)c(OCC(F)F)cc21] | C$_{31}$H$_{30}$Cl$_2$F$_5$N$_5$O$_3$ 686.506 | 686 | R$_t$ = 1.70 (method A) | 28 |
| 36 | 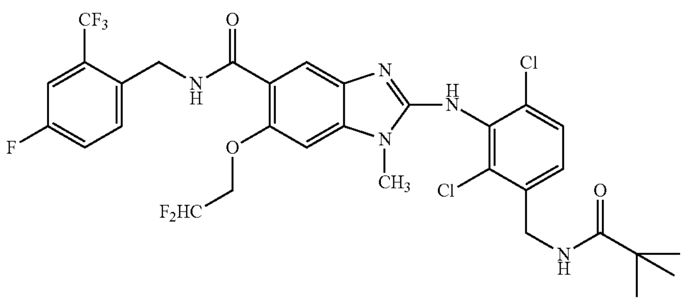 [SMILES: Cn1c(Nc2c(Cl)ccc(CNC(=O)C(C)(C)C)c2Cl)nc2cc(C(=O)NCc3ccc(F)cc3C(F)(F)F)c(OCC(F)F)cc21] | C$_{31}$H$_{29}$Cl$_2$F$_6$N$_5$O$_3$ 704.496 | 704 | R$_t$ = 1.72 (method A) | 28 |
| 37 | 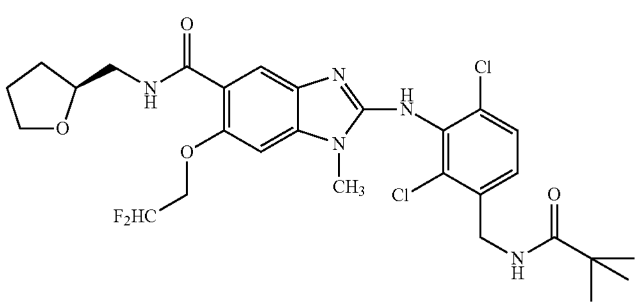 [SMILES: Cn1c(Nc2c(Cl)ccc(CNC(=O)C(C)(C)C)c2Cl)nc2cc(C(=O)NC[C@@H]3CCCO3)c(OCC(F)F)cc21] | C$_{28}$H$_{33}$Cl$_2$F$_2$N$_5$O$_4$ 612.502 | 612 | R$_t$ = 1.42 (method A) | 28 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 38 | 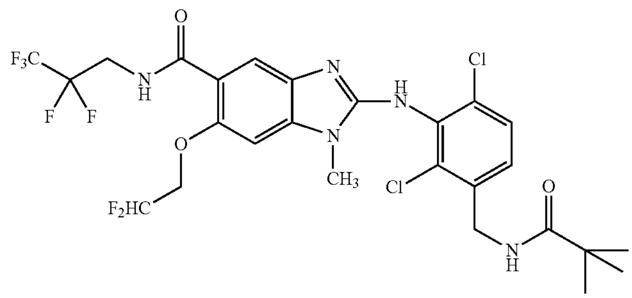 [SMILES: Cn1c(Nc2c(Cl)ccc(CNC(=O)C(C)(C)C)c2Cl)nc2cc(C(=O)NCC(F)(F)C(F)(F)F)c(OCC(F)F)cc21] | $C_{26}H_{26}Cl_2F_7N_5O_3$ 660.415 | 660 | $R_t$ = 1.65 (method A) | 28 |
| 39 | 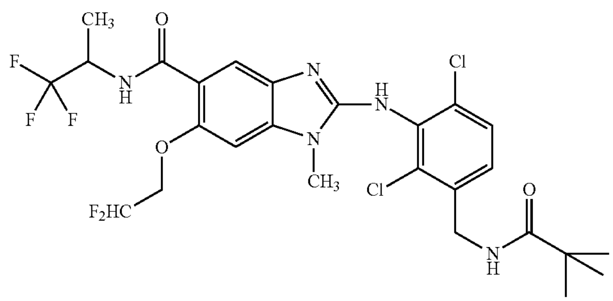 [SMILES: CC(NC(=O)c1cc2nc(Nc3c(Cl)ccc(CNC(=O)C(C)(C)C)c3Cl)n(C)c2cc1OCC(F)F)C(F)(F)F] | $C_{26}H_{28}Cl_2F_5N_5O_3$ 624.435 | 624 | $R_t$ = 1.60 (method A) | 28 |
| 40 | 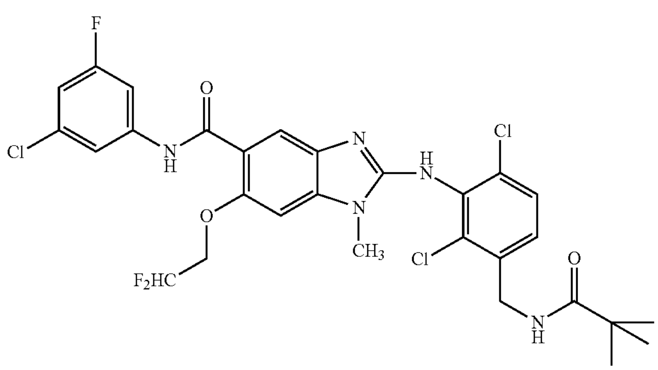 | $C_{29}H_{27}Cl_3F_3N_5O_3$ 656.917 | 656 | $R_t$ = 1.83 (method A) | 28 |
| 41 | 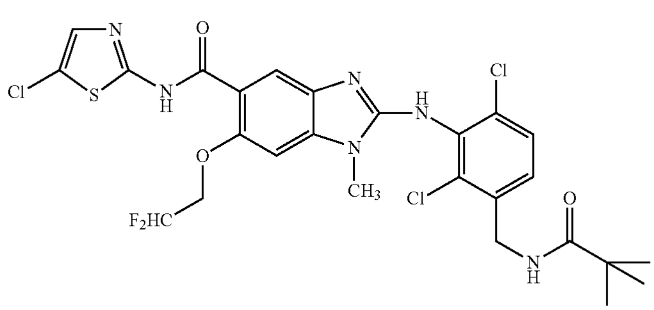 [SMILES: Cn1c(Nc2c(Cl)ccc(CNC(=O)C(C)(C)C)c2Cl)nc2cc(C(=O)Nc3ncc(Cl)s3)c(OCC(F)F)cc21] | $C_{26}H_{25}Cl_3F_2N_6O_3S$ 645.943 | 645 | $R_t$ = 1.79 (method A) | 28 |

TABLE 1-continued

| Ex. | Structure | Formula/ Mw. | MS* m/z [M + H]+ | $R_f$(TLC, silica gel) or $R_t$ [min] (HPLC-method) | Prepared in analogy to example |
|---|---|---|---|---|---|
| 42 | 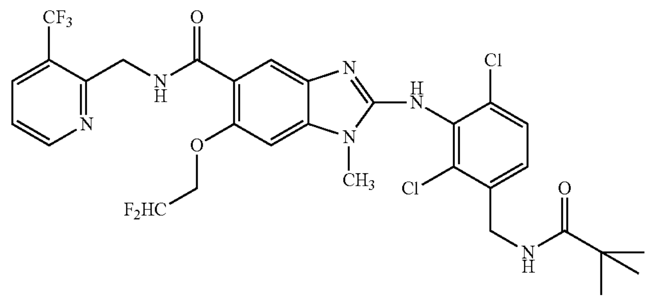 [SMILES: Cn1c(Nc2c(Cl)ccc(CNC(=O)C(C)(C)C)c2Cl)nc2cc(C(=O)NCc3ncccc3C(F)(F)F)c(OCC(F)F)cc21] | $C_{30}H_{29}Cl_2F_5N_6O_3$ 687.494 | 687 | $R_t$ = 1.62 (method A) | 28 |
| 43 | 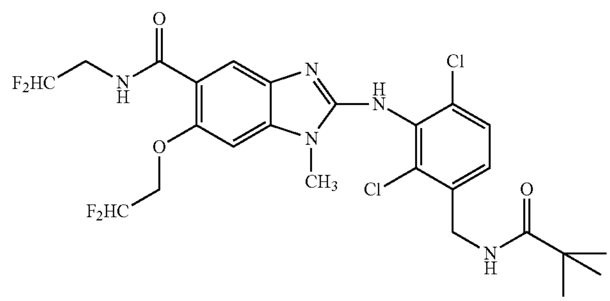 [SMILES: Cn1c(Nc2c(Cl)ccc(CNC(=O)C(C)(C)C)c2Cl)nc2cc(C(=O)NCC(F)F)c(OCC(F)F)cc21] | $C_{25}H_{27}Cl_2F_4N_5O_3$ 592.418 | 592 | $R_t$ = 1.44 (method A) | 28 |
| 44 | 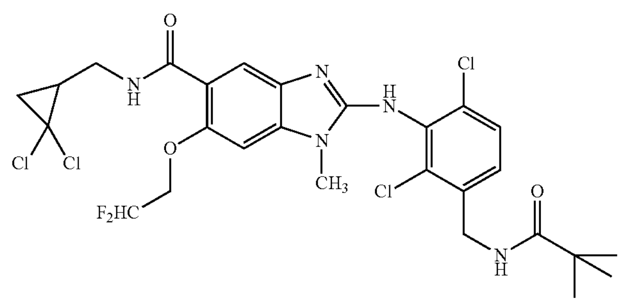 [SMILES: Cn1c(Nc2c(Cl)ccc(CNC(=O)C(C)(C)C)c2Cl)nc2cc(C(=O)NCC3CC3(Cl)Cl)c(OCC(F)F)cc21] | $C_{27}H_{29}Cl_4F_2N_5O_3$ 651.366 | 650 | $R_t$ = 1.62 (method A) | 28 |
| 45 | 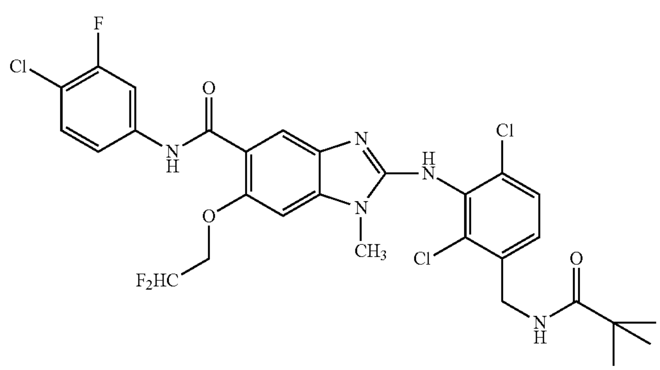 [SMILES: Cn1c(Nc2c(Cl)ccc(CNC(=O)C(C)(C)C)c2Cl)nc2cc(C(=O)Nc3ccc(Cl)c(F)c3)c(OCC(F)F)cc21] | $C_{29}H_{27}Cl_3F_3N_5O_3$ 656.917 | 656 | $R_t$ = 1.81 (method A) | 28 |

TABLE 1-continued

| Ex. | Structure | Formula/ Mw. | MS* m/z [M + H]+ | R$_f$(TLC, silica gel) or R$_t$ [min] (HPLC- method) | Prepared in analogy to example |
|---|---|---|---|---|---|
| 46 | 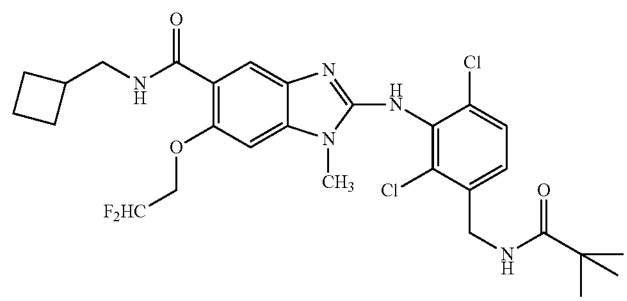 [SMILES: Cn1c(Nc2c(Cl)ccc(CNC(=O)C(C)(C)C)c2Cl)nc2cc(C(=O)NCC3CCC3)c(OCC(F)F)cc21] | C$_{28}$H$_{33}$Cl$_2$F$_2$N$_5$O$_3$ 596.503 | 596 | R$_t$ = 1.58 (method A) | 28 |
| 47 | 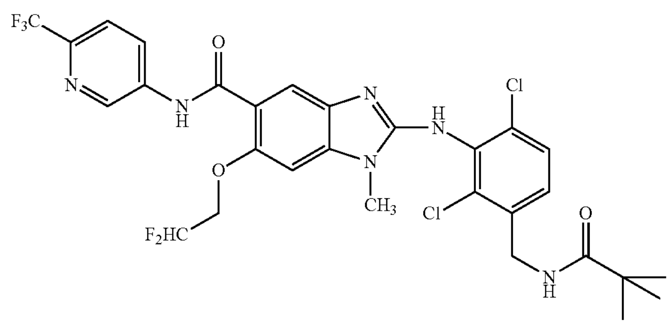 [SMILES: Cn1c(Nc2c(Cl)ccc(CNC(=O)C(C)(C)C)c2Cl)nc2cc(C(=O)Nc3ccc(C(F)(F)F)nc3)c(OCC(F)F)cc21] | C$_{29}$H$_{27}$Cl$_2$F$_5$N$_6$O$_3$ 673.467 | 673 | R$_t$ = 1.74 (method A) | 28 |
| 48 | 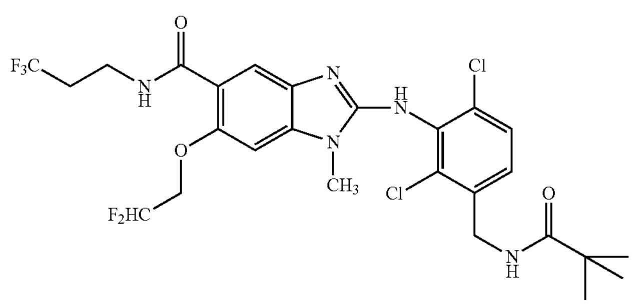 [SMILES: Cn1c(Nc2c(Cl)ccc(CNC(=O)C(C)(C)C)c2Cl)nc2cc(C(=O)NCCC(F)(F)F)c(OCC(F)F)cc21] | C$_{26}$H$_{28}$Cl$_2$F$_5$N$_5$O$_3$ 624.435 | 624 | R$_t$ = 1.54 (method A) | 28 |
| 49 | 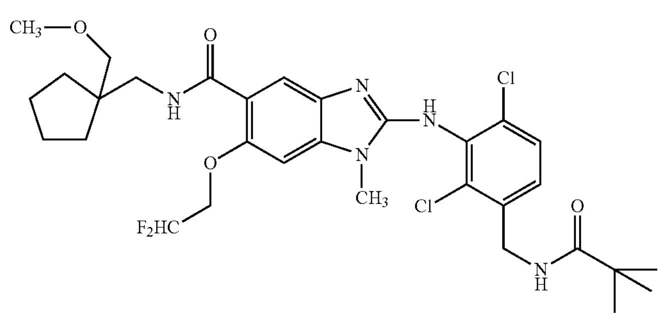 [SMILES: COCC1(CNC(=O)c2cc3nc(Nc4c(Cl)ccc(CNC(=O)C(C)(C)C)c4Cl)n(C)c3cc2OCC(F)F)CCCC1] | C$_{31}$H$_{39}$Cl$_2$F$_2$N$_5$O$_4$ 654.582 | 654 | R$_t$ = 1.66 (method A) | 28 |

TABLE 1-continued

| Ex. | Structure | Formula/ Mw. | MS* m/z [M + H]+ | R*f* (TLC, silica gel) or R*t* [min] (HPLC- method) | Prepared in analogy to example |
|---|---|---|---|---|---|
| 50 | 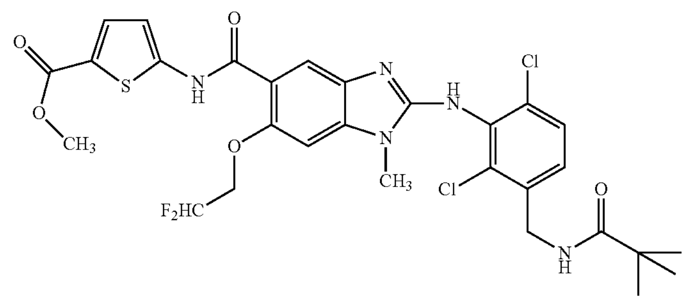 [SMILES: COC(=O)c1ccc(NC(=O)c2cc3nc(Nc4c(Cl)ccc(CNC(=O)C(C)(C)C)c4Cl)n(C)c3cc2OCC(F)F)s1] | $C_{29}H_{29}Cl_2F_2N_5O_5S$ 668.546 | 668 | R*t* = 1.70 (method A) | 28 |
| 51 | 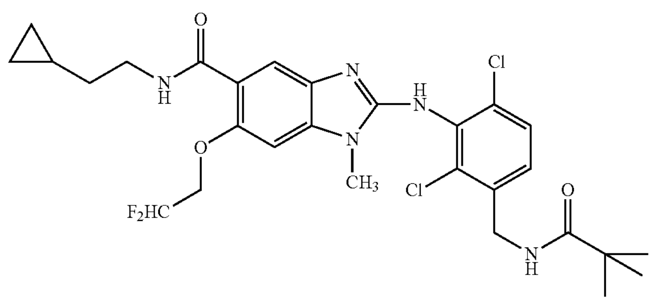 [SMILES: Cn1c(Nc2c(Cl)ccc(CNC(=O)C(C)(C)C)c2Cl)nc2cc(C(=O)NCCC3CC3)c(OCC(F)F)cc21] | $C_{28}H_{33}Cl_2F_2N_5O_3$ 596.503 | 596 | R*t* = 1.56 (method A) | 28 |
| 52 | 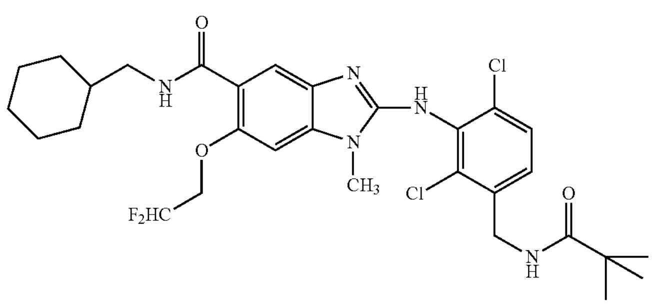 [SMILES: Cn1c(Nc2c(Cl)ccc(CNC(=O)C(C)(C)C)c2Cl)nc2cc(C(=O)NCC3CCCCC3)c(OCC(F)F)cc21] | $C_{30}H_{37}Cl_2F_2N_5O_3$ 624.556 | 624 | R*t* = 1.69 (method A) | 28 |
| 53 | 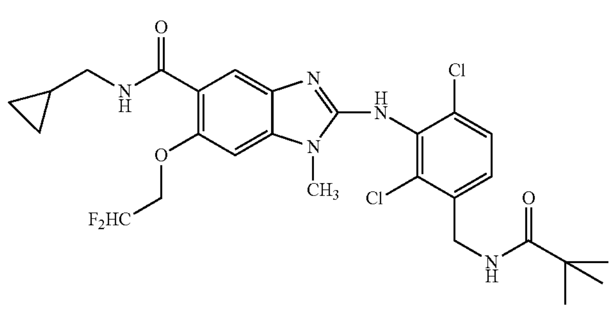 [SMILES: Cn1c(Nc2c(Cl)ccc(CNC(=O)C(C)(C)C)c2Cl)nc2cc(C(=O)NCC3CC3)c(OCC(F)F)cc21] | $C_{27}H_{31}Cl_2F_2N_5O_3$ 582.476 | 582 | R*t* = 1.50 (method A) | 28 |

TABLE 1-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 54 | 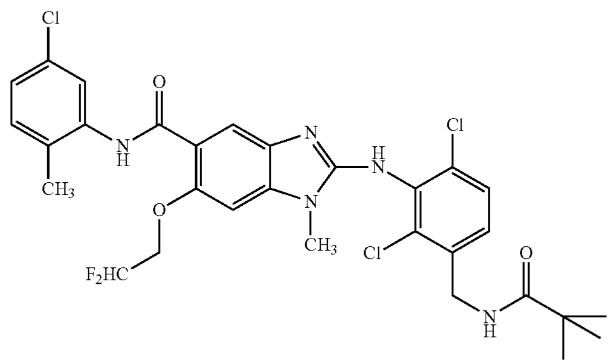 [SMILES: Cc1ccc(Cl)cc1NC(=O)c1cc2nc(Nc3c(Cl)ccc(CNC(=O)C(C)(C)C)c3Cl)n(C)c2cc1OCC(F)F] | C$_{30}$H$_{30}$Cl$_3$F$_2$N$_5$O$_3$ 652.954 | 652 | R$_t$ = 1.77 (method A) | 28 |
| 55 | 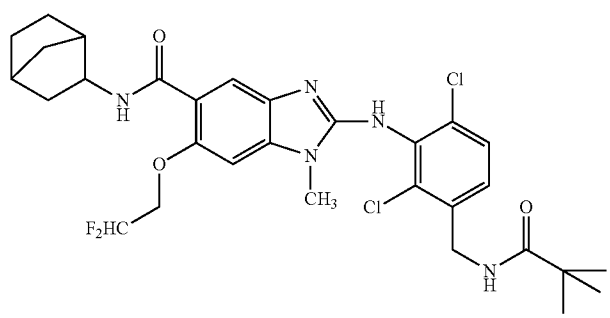 [SMILES: Cn1c(Nc2c(Cl)ccc(CNC(=O)C(C)(C)C)c2Cl)nc2cc(C(=O)NC3CC4CCC3C4)c(OCC(F)F)cc21] | C$_{30}$H$_{35}$Cl$_2$F$_2$N$_5$O$_3$ 622.541 | 622 | R$_t$ = 1.65 (method A) | 28 |
| 56 | 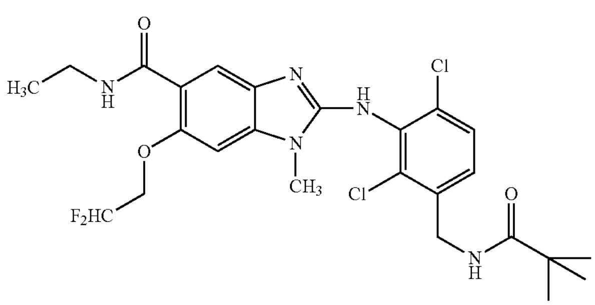 [SMILES: CCNC(=O)c1cc2nc(Nc3c(Cl)ccc(CNC(=O)C(C)(C)C)c3Cl)n(C)c2cc1OCC(F)F] | C$_{25}$H$_{29}$Cl$_2$F$_2$N$_5$O$_3$ 556.438 | 556 | R$_t$ = 1.36 (method A) | 28 |
| 57 | 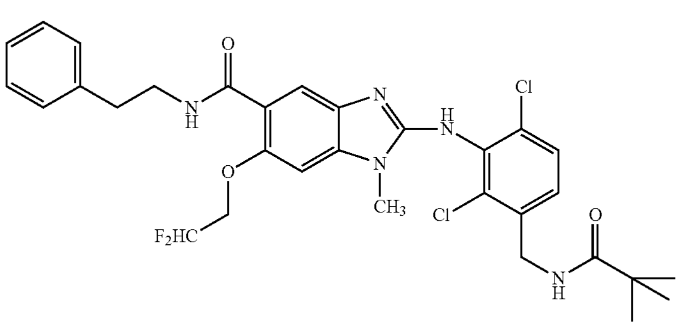 [SMILES: Cn1c(Nc2c(Cl)ccc(CNC(=O)C(C)(C)C)c2Cl)nc2cc(C(=O)NCCc3ccccc3)c(OCC(F)F)cc21] | C$_{31}$H$_{33}$Cl$_2$F$_2$N$_5$O$_3$ 632.536 | 632 | R$_t$ = 1.62 (method A) | 28 |

TABLE 1-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 58 | 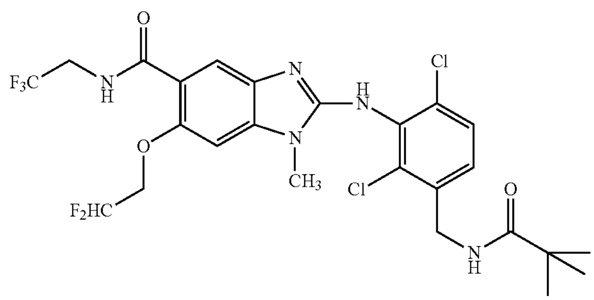 | C$_{25}$H$_{26}$Cl$_2$F$_5$N$_5$O$_3$ 610.408 | 610 | R$_t$ = 1.54 (method A) | 28 |
| 59 | 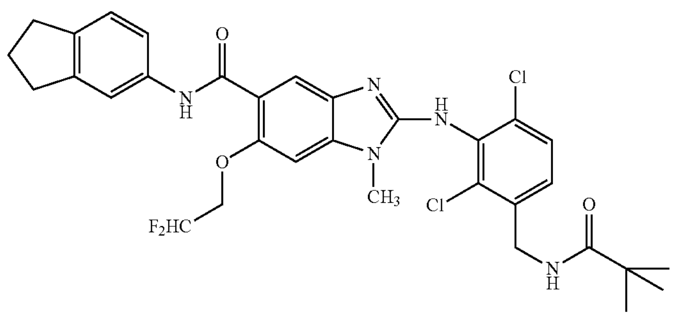 [SMILES: Cn1c(Nc2c(Cl)ccc(CNC(=O)C(C)(C)C)c2Cl)nc2cc(C(=O)Nc3ccc4c(c3)CCC4)c(OCC(F)F)cc21] | C$_{32}$H$_{33}$Cl$_2$F$_2$N$_5$O$_3$ 644.647 | 644 | R$_t$ = 1.77 (method A) | 28 |
| 61 | 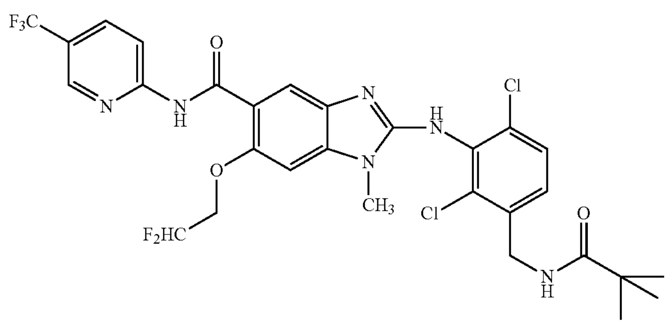 | C$_{29}$H$_{27}$Cl$_2$F$_5$N$_6$O$_3$ 673.461 | 673 | R$_t$ = 2.74 (method D) | 60 |
| 62 | 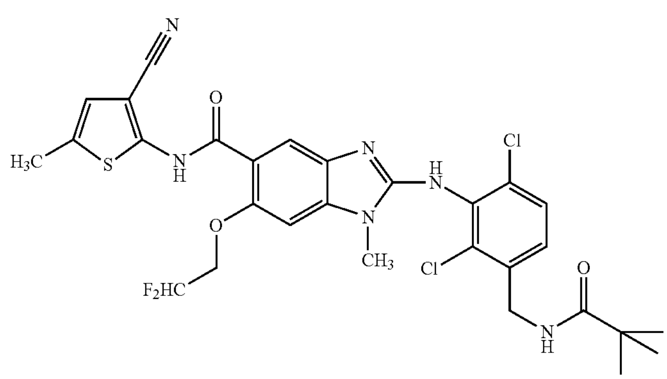 [SMILES: Cc1cc(C#N)c(NC(=O)c2cc3nc(Nc4c(Cl)ccc(CNC(=O)C(C)(C)C)c4Cl)n(C)c3cc2OCC(F)F)s1] | C$_{29}$H$_{28}$Cl$_2$F$_2$N$_6$O$_3$S 649.539 | 649 | R$_t$ = 2.73 (method D) | 60 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 63 | 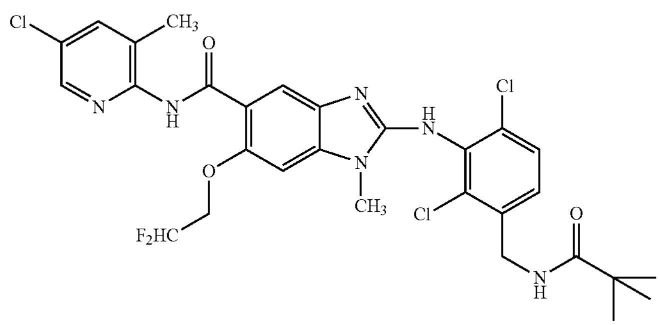 [SMILES: Cc1cc(Cl)cnc1NC(=O)c1cc2nc(Nc3c(Cl)ccc(CNC(=O)C(C)(C)C)c3Cl)n(C)c2cc1OCC(F)F] | $C_{29}H_{29}Cl_3F_5N_6O_3$ 653.934 | 653 | $R_t$ = 2.63 (method D) | 60 |
| 64 | 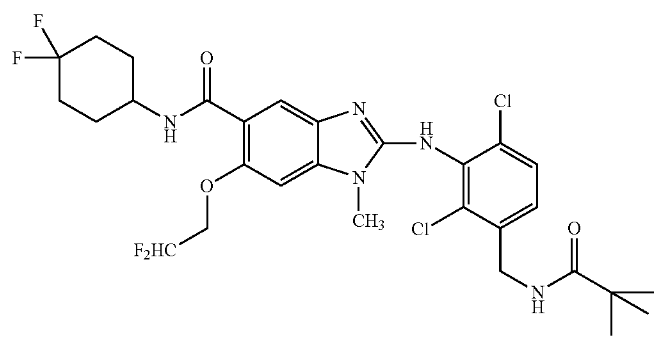 [SMILES: Cn1c(Nc2c(Cl)ccc(CNC(=O)C(C)(C)C)c2Cl)nc2cc(C(=O)NC3CCC(F)(F)CC3)c(OCC(F)F)cc21] | $C_{29}H_{33}Cl_2F_4N_5O_3$ 646.503 | 646 | $R_t$ = 2.61 (method D) | 60 |
| 65 | 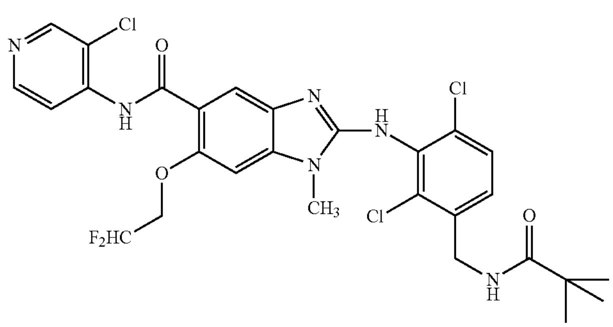 [SMILES: Cn1c(Nc2c(Cl)ccc(CNC(=O)C(C)(C)C)c2Cl)nc2cc(C(=O)Nc3ccncc3Cl)c(OCC(F)F)cc21] | $C_{29}H_{27}Cl_3F_2N_6O_3$ 639.908 | 639 | $R_t$ = 2.65 (method D) | 60 |
| 66 | 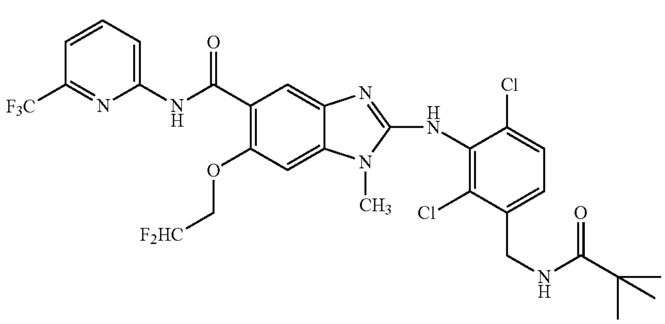 [SMILES: Cn1c(Nc2c(Cl)ccc(CNC(=O)C(C)(C)C)c2Cl)nc2cc(C(=O)Nc3cccc(C(F)(F)F)n3)c(OCC(F)F)cc21] | $C_{29}H_{27}Cl_2F_5N_6O_3$ 673.461 | 673 | $R_t$ = 2.70 (method D) | 60 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 67 | 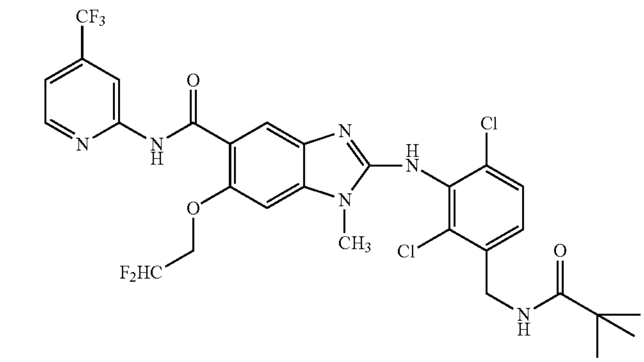 [SMILES: Cn1c(Nc2c(Cl)ccc(CNC(=O)C(C)(C)C)c2Cl)nc2cc(C(=O)Nc3cc(C(F)(F)F)ccn3)c(OCC(F)F)cc21] | C29H27Cl2F5N6O3 673.461 | 673 | R_t = 2.72 (method D) | 60 |
| 68 | 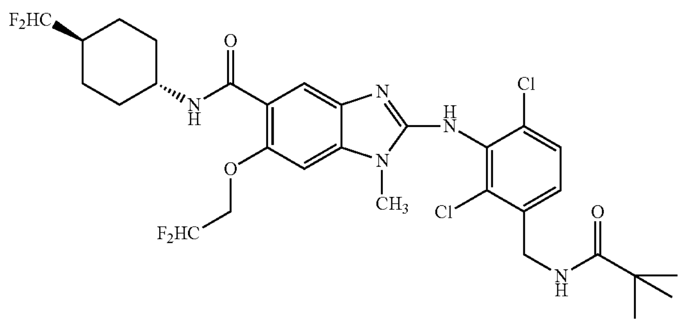 [SMILES: Cn1c(Nc2c(Cl)ccc(CNC(=O)C(C)(C)C)c2Cl)nc2cc(C(=O)N[C@H]3CC[C@H](C(F)F)CC3)c(OCC(F)F)cc21] | C30H35Cl2F4N5O3 660.530 | 660 | R_t = 2.64 (method D) | 60 |
| 69 | 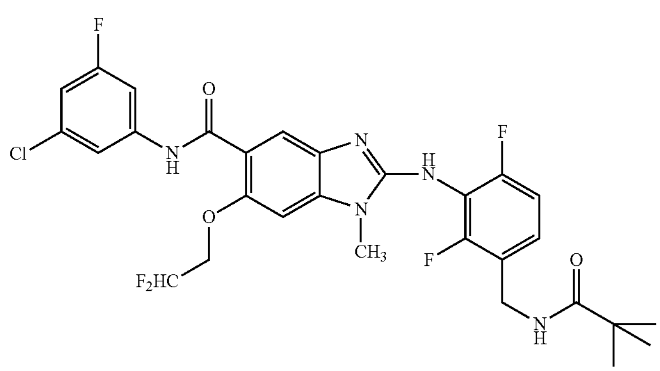 [SMILES: Cn1c(Nc2c(F)ccc(CNC(=O)C(C)(C)C)c2F)nc2cc(C(=O)Nc3cc(F)cc(Cl)c3)c(OCC(F)F)cc21] | C29H27ClF5N5O3 624.001 | 624 | R_f = 0.26 (DCM/EtOH 95:5) | 11 |
| 70 | 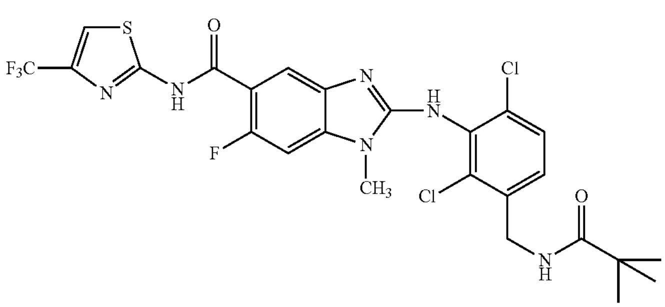 [SMILES: Cn1c(Nc2c(Cl)ccc(CNC(=O)C(C)(C)C)c2Cl)nc2cc(C(=O)Nc3nc(C(F)(F)F)cs3)c(F)cc21] | C25H22Cl2F4N6O2S 617.446 | 617 | R_f = 0.26 (DCM/EtOH 95:5) | 17 |

TABLE 1-continued

| Ex. | Structure | Formula/ Mw. | MS* m/z [M + H]+ | R_f (TLC, silica gel) or R_t [min] (HPLC-method) | Prepared in analogy to example |
|---|---|---|---|---|---|
| 71 | 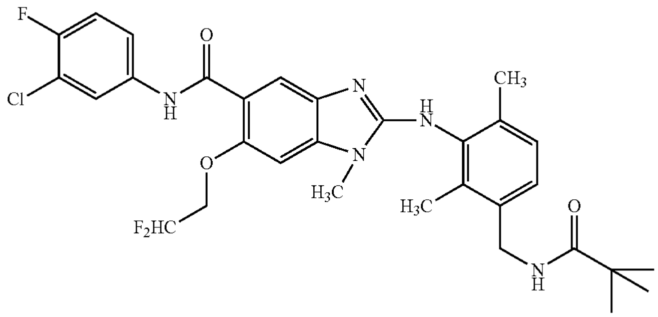 [SMILES: Cc1ccc(CNC(=O)C(C)(C)C)c(C)c1Nc1nc2cc(C(=O)Nc3ccc(F)c(Cl)c3)c(OCC(F)F)cc2n1C] | $C_{31}H_{33}ClF_3N_5O_3$ 616.074 | 616 | $R_f$ = 0.19 (DCM/EtOH 95:5) | 14 |
| 72 | 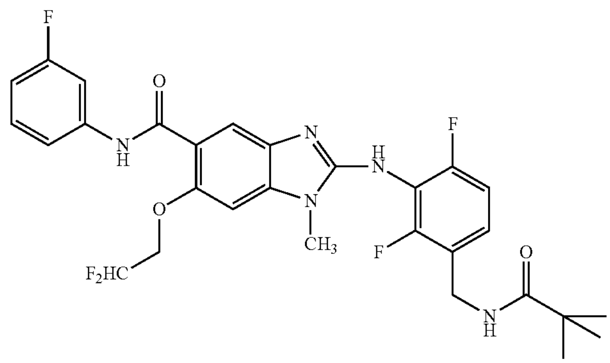 [SMILES: Cn1c(Nc2c(F)ccc(CNC(=O)C(C)(C)C)c2F)nc2cc(C(=O)Nc3cccc(F)c3)c(OCC(F)F)cc21] | $C_{29}H_{28}F_5N_5O_3$ 589.557 | 590 | $R_f$ = 0.27 (DCM/EtOH 95:5) | 6 |
| 73 | 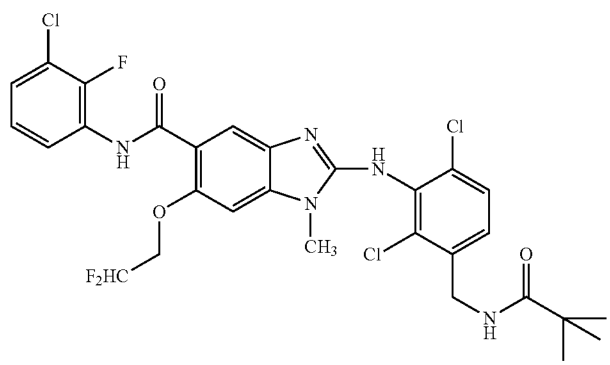 [SMILES: Cn1c(Nc2c(Cl)ccc(CNC(=O)C(C)(C)C)c2Cl)nc2cc(C(=O)Nc3cccc(Cl)c3F)c(OCC(F)F)cc21] | $C_{29}H_{27}Cl_3F_3N_5O_3$ 656.910 | 656 | $R_f$ = 0.28 (DCM/EtOH 95:5) | 7 |
| 74 | 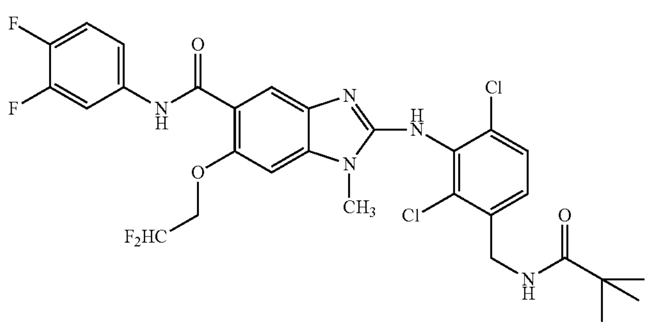 [SMILES: Cn1c(Nc2c(Cl)ccc(CNC(=O)C(C)(C)C)c2Cl)nc2cc(C(=O)Nc3ccc(F)c(F)c3)c(OCC(F)F)cc21] | $C_{29}H_{27}Cl_2F_4N_5O_3$ 640.456 | 640 | $R_t$ = 1.45 (method B) | 7 |

TABLE 1-continued

| Ex. | Structure | Formula/ Mw. | MS* m/z [M + H]+ | R$_f$ (TLC, silica gel) or R$_t$ [min] (HPLC-method) | Prepared in analogy to example |
|---|---|---|---|---|---|
| 76 | 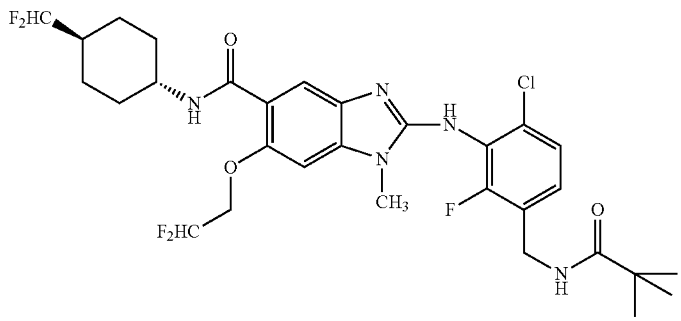 [SMILES: Cn1c(Nc2c(Cl)ccc(CNC(=O)C(C)(C)C)c2F)nc2cc(C(=O)N[C@H]3CC[C@H](C(F)F)CC3)c(OCC(F)F)cc21] | C$_{30}$H$_{34}$ClF$_6$N$_5$O$_3$ 662.066 | 662 | R$_t$ = 1.42 (method B) | 75 |
| 77 | 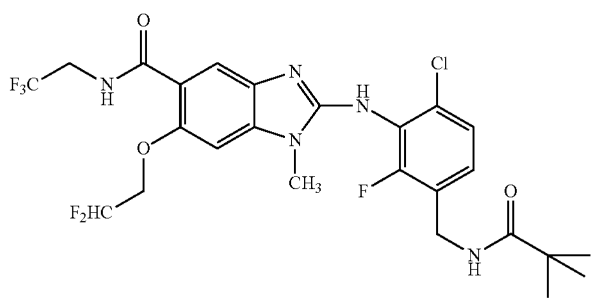 [SMILES: Cn1c(Nc2c(Cl)ccc(CNC(=O)C(C)(C)C)c2F)nc2cc(C(=O)NCC(F)(F)F)c(OCC(F)F)cc21] | C$_{25}$H$_{26}$ClF$_6$N$_5$O$_3$ 593.949 | 594 | R$_t$ = 1.31 (method B) | 75 |
| 81 | 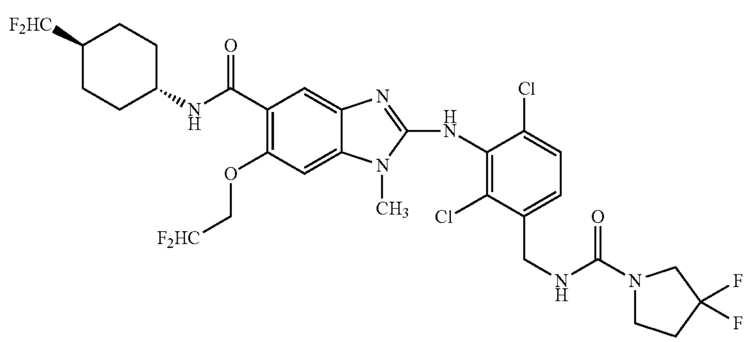 [SMILES: Cn1c(Nc2c(Cl)ccc(CNC(=O)N3CCC(F)(F)C3)c2Cl)nc2cc(C(=O)N[C@H]3CC[C@H](C(F)F)CC3)c(OCC(F)F)cc21] | C$_{30}$H$_{31}$Cl$_2$F$_7$N$_6$O$_3$ 727.500 | 727 | R$_f$ = 0.28 (DCM/EtOH 95:5) | 80 |
| 82 | 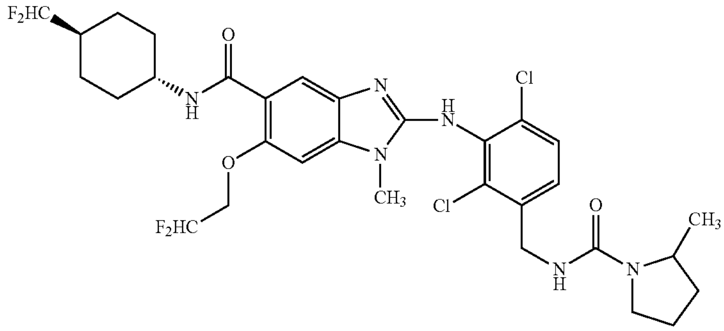 [SMILES: CC1CCCN1C(=O)NCc1ccc(Cl)c(Nc2nc3cc(C(=O)N[C@H]4CC[C@H](C(F)F)CC4)c(OCC(F)F)cc3n2C)c1Cl] | C$_{30}$H$_{31}$Cl$_2$F$_7$N$_6$O$_3$ 705.546 | 705 | R$_f$ = 0.23 (DCM/EtOH 95:5) | 80 |

TABLE 1-continued

| Ex. | Structure | Formula/ Mw. | MS* m/z [M + H]+ | $R_f$ (TLC, silica gel) or $R_t$ [min] (HPLC-method) | Prepared in analogy to example |
|---|---|---|---|---|---|
| 83 | 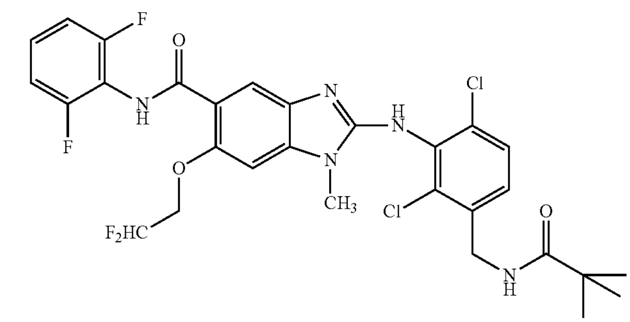 [SMILES: Cn1c(Nc2c(Cl)ccc(CNC(=O)C(C)(C)C)c2Cl)nc2cc(C(=O)Nc3c(F)cccc3F)c(OCC(F)F)cc21] | $C_{29}H_{27}Cl_2F_4N_5O_3$ 640.456 | 640 | $R_f$ = 0.28 (DCM/EtOH 95:5) | 7 |
| 85 | 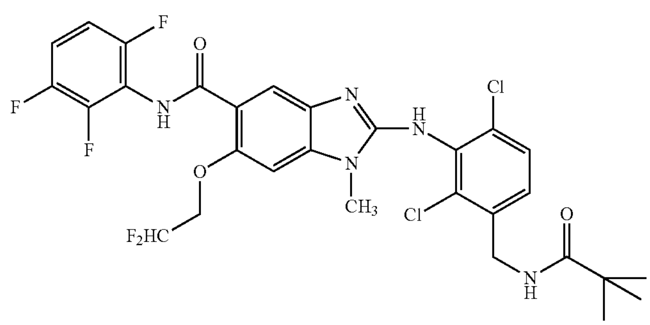 [SMILES: Cn1c(Nc2c(Cl)ccc(CNC(=O)C(C)(C)C)c2Cl)nc2cc(C(=O)Nc3c(F)ccc(F)c3F)c(OCC(F)F)cc21] | $C_{29}H_{26}Cl_2F_5N_5O_3$ 658.446 | 658 | $R_f$ = 0.25 (DCM/EtOH 95:5) | 7 |
| 178 | 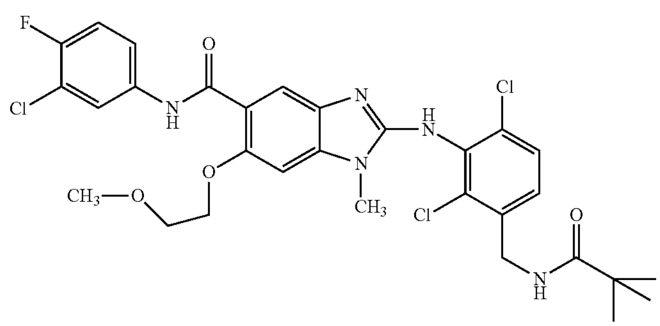 [SMILES: COCCOc1cc2c(cc1C(=O)Nc1ccc(F)c(Cl)c1)nc(Nc1c(Cl)ccc(CNC(=O)C(C)(C)C)c1Cl)n2C] | $C_{30}H_{31}Cl_3FN_5O_4$ 650.955 | 650 | $R_t$ = 2.08 (method E) | 177 |
| 179 | 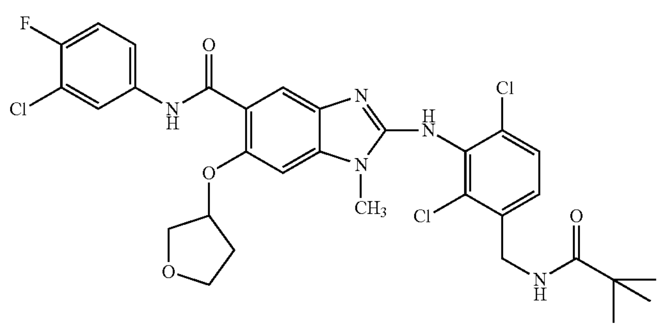 [SMILES: Cn1c(Nc2c(Cl)ccc(CNC(=O)C(C)(C)C)c2Cl)nc2cc(C(=O)Nc3ccc(F)c(Cl)c3)c(OC3CCOC3)cc21] | $C_{31}H_{31}Cl_3FN_5O_4$ 662.966 | 662 | $R_t$ = 2.01 (method E) | 177 |

TABLE 1-continued

| Ex. | Structure | Formula/ Mw. | MS* m/z [M + H]+ | R$_f$(TLC, silica gel) or R$_t$ [min] (HPLC-method) | Prepared in analogy to example |
|---|---|---|---|---|---|
| 180 | 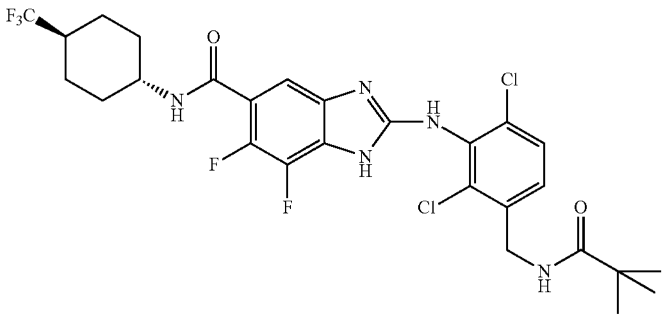 [SMILES: CC(C)(C)C(=O)NCc1ccc(Cl)c(Nc2nc3cc(C(=O)N[C@H]4CC[C@H](C(F)(F)F)CC4)c(F)c(F)c3[nH]2)c1Cl] | C$_{27}$H$_{28}$Cl$_2$F$_5$N$_5$O$_2$ 620.441 | 620 | R$_t$ = 2.10 (method E) | 79 |
| 181 | 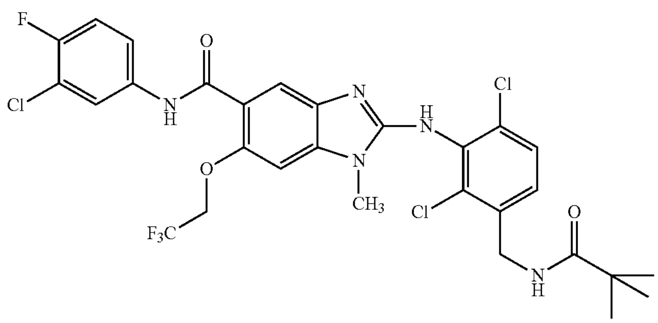 [SMILES: Cn1c(Nc2c(Cl)ccc(CNC(=O)C(C)(C)C)c2Cl)nc2cc(C(=O)Nc3ccc(F)c(Cl)c3)c(OCC(F)(F)F)cc21] | C$_{29}$H$_{26}$Cl$_3$F$_4$N$_5$O$_3$ 674.900 | 674 | R$_t$ = 2.18 (method E) | 177 |
| 182 | 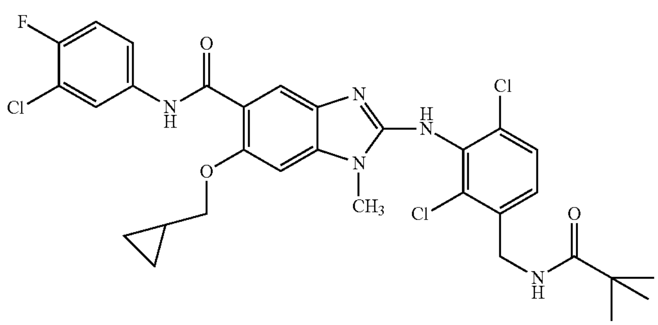 [SMILES: Cn1c(Nc2c(Cl)ccc(CNC(=O)C(C)(C)C)c2Cl)nc2cc(C(=O)Nc3ccc(F)c(Cl)c3)c(OCC3CC3)cc21] | C$_{31}$H$_{31}$Cl$_3$FN$_5$O$_3$ 646.966 | 646 | R$_t$ = 2.23 (method E) | 177 |

The following examples in Table 2 are prepared in analogy to example 84 (A and W are as defined in the table).

TABLE 2

| Ex. | A = F$_3$C$\diagup\!\!\diagup$* | Ex. | A = (4-F, 2-Cl-phenyl)* | W = |
|---|---|---|---|---|
| 128 | C$_{23}$H$_{19}$Cl$_2$F$_8$N$_5$O$_3$<br>MW: 636.325<br>MS* m/z [M + H]$^+$ = 636<br>R$_t$ = 1.5 (method I) | 131 | C$_{27}$H$_{20}$Cl$_3$F$_6$N$_5$O$_3$<br>MW: 682.834<br>MS* m/z [M + H]$^+$ = 682<br>R$_t$ = 1.70 (method I) | *—CH$_2$CF$_2$F |
| 101 | C$_{23}$H$_{22}$Cl$_2$F$_5$N$_5$O$_4$<br>MW: 598.354<br>MS* m/z [M + H]$^+$ = 598<br>Rt = 1.40 (method I) | 163 | C$_{27}$H$_{23}$Cl$_3$F$_3$N$_5$O$_4$<br>MW: 644.863<br>MS* m/z [M + H]$^+$ = 644<br>Rt = 1.61 (method I) | *—CH$_2$—O—CH$_3$ |
| 104 | C$_{22}$H$_{20}$Cl$_2$F$_5$N$_5$O$_4$<br>MW: 584.33<br>MS* m/z [M + H]$^+$ = 584<br>Rt = 1.34 (method I) | 139 | C$_{26}$H$_{21}$Cl$_3$F$_3$N$_5$O$_4$<br>MW: 630.836<br>MS* m/z [M + H]$^+$ = 630<br>Rt = 1.54 (method I) | *—CH$_2$OH |
| 106 | C$_{24}$H$_{24}$Cl$_2$F$_5$N$_5$O$_3$<br>MW: 596.382<br>MS* m/z [M + H]$^+$ = 596<br>Rt = 0.47 (method H) | 132 | C$_{28}$H$_{25}$Cl$_3$F$_3$N$_5$O$_3$<br>MW: 642.89<br>MS* m/z [M + H]$^+$ = 642<br>Rt = 1.67 (method I) | *—CH$_2$CH$_2$CH$_3$ |
| 111 | C$_{23}$H$_{22}$Cl$_2$F$_5$N$_5$O$_3$<br>MW: 582.355<br>MS* m/z [M + H]$^+$ = 582<br>Rt = 1.42 (method I) | 146 | C$_{27}$H$_{23}$Cl$_3$F$_3$N$_5$O$_3$<br>MW: 628.864<br>MS* m/z [M + H]$^+$ = 528<br>Rt = 1.63 (method I) | *—CH$_2$CH$_3$ |
| 112 | C$_{23}$H$_{19}$Cl$_2$F$_5$N$_6$O$_3$<br>MW: 593.338<br>MS* m/z [M + H]$^+$ = 593<br>Rt = 1.41 (method I) | 154 | C$_{27}$H$_{20}$Cl$_3$F$_3$N$_6$O$_3$<br>MW: 639.847<br>MS* m/z [M + H]$^+$ = 639<br>Rt = 0.52 (method H) | *—CH$_2$C≡N |
| 88 | C$_{25}$H$_{24}$Cl$_2$F$_5$N$_5$O$_3$<br>MW: 608.393<br>MS* m/z [M + H]$^+$ = 608<br>Rt = 1.48 (method I) | 144 | C$_{29}$H$_{25}$Cl$_3$F$_3$N$_5$O$_3$<br>MW: 654.902<br>MS* m/z [M + H]$^+$ = 654<br>Rt = 1.68 (method I) | *—CH$_2$-cyclopropyl |
| 87 | C$_{23}$H$_{20}$Cl$_2$F$_8$N$_6$O$_3$<br>MW: 651.34<br>MS* m/z [M + H]$^+$ = 651<br>Rt = 0.46 (method H) | 164 | C$_{27}$H$_{21}$Cl$_3$F$_6$N$_6$O$_3$<br>MW: 697.849<br>MS* m/z [M + H]$^+$ = 697<br>Rt = 0.54 (method H) | *—CH(NH$_2$)CF$_2$F |
| 89 | C$_{24}$H$_{21}$Cl$_2$F$_8$N$_5$O$_3$<br>MW: 650.352<br>MS* m/z [M + H]$^+$ = 650<br>Rt = 0.50 (method H) | 141 | C$_{28}$H$_{22}$Cl$_3$F$_6$N$_5$O$_3$<br>MW: 696.861<br>MS* m/z [M + H]$^+$ = 696<br>Rt = 0.58 (method H) | *—CH(CH$_3$)CF$_2$F |
| 96 | C$_{23}$H$_{19}$Cl$_2$F$_8$N$_5$O$_4$<br>MW: 652.324<br>MS* m/z [M + H]$^+$ = 652<br>Rt = 1.47 (method I) | 161 | C$_{27}$H$_{20}$Cl$_3$F$_6$N$_5$O$_4$<br>MW: 698.833<br>MS* m/z [M + H]$^+$ = 698<br>Rt = 1.66 (method I) | *—CH(OH)CF$_2$F |

TABLE 2-continued

[Structure: benzimidazole core with A-NH-C(=O)- at 5-position, -O-CH2-CHF2 at 6-position, N-CH3, 2-amino-linked to 2,6-dichlorophenyl bearing -CH2-NH-C(=O)-W]

| Ex. | A = F$_3$C-CH$_2$-* | Ex. | A = 3-Cl-4-F-phenyl-* | W = |
|---|---|---|---|---|
| 98 | C$_{24}$H$_{22}$Cl$_2$F$_8$N$_6$O$_3$<br>MW: 665.367<br>MS* m/z [M + H]$^+$ = 665<br>Rt = 0.48 (method H) | 152 | C$_{28}$H$_{23}$Cl$_3$F$_6$N$_6$O$_3$<br>MW: 711.876<br>MS* m/z [M + H]$^+$ = 711<br>Rt = 0.56 (method H) | *-C(NH$_2$)(CH$_3$)-CF$_3$ |
| 116 | C$_{25}$H$_{23}$Cl$_2$F$_8$N$_5$O$_3$<br>MW: 664.379<br>MS* m/z [M + H]$^+$ = 664<br>Rt = 0.52 (method H) | 176 | C$_{29}$H$_{24}$Cl$_3$F$_6$N$_5$O$_3$<br>MW: 710.88<br>MS* m/z [M + H]$^+$ = 710<br>Rt = 1.78 (method I) | *-C(CH$_3$)$_2$-CF$_3$ |
| 123 | C$_{24}$H$_{21}$Cl$_2$F$_8$N$_5$O$_4$<br>MW: 666.351<br>MS* m/z [M + H]$^+$ = 666<br>Rt = 1.49 (method I) | 149 | C$_{28}$H$_{22}$Cl$_3$F$_6$N$_5$O$_4$<br>MW: 712.86<br>MS* m/z [M + H]$^+$ = 712<br>Rt = 0.56 (method H) | *-C(OH)(CH$_3$)-CF$_3$ |
| 126 | C$_{25}$H$_{26}$Cl$_2$F$_5$N$_5$O$_4$<br>MW: 626.407<br>MS* m/z [M + H]$^+$ = 626<br>Rt = 1.41 (method I) | 155 | C$_{29}$H$_{27}$Cl$_3$F$_3$N$_5$O$_4$<br>MW: 672.916<br>MS* m/z [M + H]$^+$ = 672<br>Rt = 0.53 (method H) | *-C(CH$_3$)$_2$-CH$_2$OH |
| 130 | C$_{25}$H$_{26}$Cl$_2$F$_5$N$_5$O$_4$<br>MW: 626.407<br>MS* m/z [M + H]$^+$ = 626<br>Rt = 1.48 (method I) | 135 | C$_{29}$H$_{27}$Cl$_3$F$_3$N$_5$O$_4$<br>MW: 672.916<br>MS* m/z [M + H]$^+$ = 672<br>Rt = 1.68 (method I) | *-C(CH$_3$)$_2$-OCH$_3$ |
| 95 | C$_{23}$H$_{20}$Cl$_2$F$_7$N$_5$O$_3$<br>MW: 618.335<br>MS* m/z [M + H]$^+$ = 618<br>Rt = 0.48 (method H) | 162 | C$_{27}$H$_{21}$Cl$_3$F$_3$N$_5$O$_3$<br>MW: 664.844<br>MS* m/z [M + H]$^+$ = 664<br>Rt = 1.70 (method I) | *-C(CH$_3$)-CF$_2$(?) [*-CF$_2$-CH$_3$ group with CH$_3$] |
| 108 | C$_{24}$H$_{24}$Cl$_2$F$_5$N$_5$O$_4$<br>MW: 612.381<br>MS* m/z [M + H]$^+$ = 612<br>Rt = 0.44 (method H) | 175 | C$_{28}$H$_{25}$Cl$_3$F$_3$N$_5$O$_4$<br>MW: 658.89<br>MS* m/z [M + H]$^+$ = 658<br>Rt = 1.60 (method I) | *-C(CH$_3$)$_2$-OH |
| 109 | C$_{23}$H$_{22}$Cl$_2$F$_5$N$_5$O$_4$<br>MW: 598.354<br>MS* m/z [M + H]$^+$ = 598<br>Rt = 1.36 (method I) | 147 | C$_{27}$H$_{23}$Cl$_3$F$_3$N$_5$O$_4$<br>MW: 644.863<br>MS* m/z [M + H]$^+$ = 644<br>Rt = 0.51 (method H) | *-CH(OH)-CH$_3$ |
| 110 | C$_{24}$H$_{24}$Cl$_2$F$_5$N$_5$O$_3$<br>MW: 596.382<br>MS* m/z [M + H]$^+$ = 596<br>Rt = 1.47 (method I) | 151 | C$_{28}$H$_{25}$Cl$_3$F$_3$N$_5$O$_3$<br>MW: 642.89<br>MS* m/z [M + H]$^+$ = 642<br>Rt = 0.55 (method H) | *-CH(CH$_3$)$_2$ |
| 115 | C$_{22}$H$_{20}$Cl$_2$F$_5$N$_5$O$_3$<br>MW: 568.328<br>MS* m/z [M + H]$^+$ = 568<br>Rt = 1.37 (method I) | 173 | C$_{26}$H$_{21}$Cl$_3$F$_3$N$_5$O$_3$<br>MW: 614.837<br>MS* m/z [M + H]$^+$ = 614<br>Rt = 1.58 (method I) | *-CH$_3$ |

TABLE 2-continued

[Structure: benzimidazole core with A-NH-C(=O)- at 5-position, O-CH2-CHF2 at 6-position, N-CH3 at N1, and at 2-position NH linked to 2,6-dichloro-phenyl bearing CH2-NH-C(=O)-W]

| Ex. | A = F₃C-CH₂-* | Ex. | A = 3-Cl-4-F-phenyl-* | W = |
|---|---|---|---|---|
| 118 | C₂₄H₂₃Cl₂F₆N₅O₃<br>MW: 614.372<br>MS* m/z [M + H]⁺ = 614<br>Rt = 0.49 (method H) | | | *-C(CH₃)₂-F (H₃C, CH₃, F) |
| 124 | C₂₂H₁₈Cl₂F₇N₅O₃<br>MW: 604.308<br>MS* m/z [M + H]⁺ = 604<br>Rt = 1.45 (method I) | 159 | C₂₆H₁₉Cl₃F₅N₅O₃<br>MW: 650.817<br>MS* m/z [M + H]⁺ = 650<br>Rt = 0.55 (method H) | *-CHF₂ |
| 86 | C₂₆H₂₃Cl₂F₈N₅O₃<br>MW: 676.39<br>MS* m/z [M + H]⁺ = 676<br>Rt = 0.53 (method H) | 157 | C₃₀H₂₄Cl₃F₆N₅O₃<br>MW: 722.899<br>MS* m/z [M + H]⁺ = 722<br>Rt = 1.78 (method I) | *-cyclobutyl-CF₃ |
| 99 | C₂₅H₂₁Cl₂F₈N₅O₃<br>MW: 662.363<br>MS* m/z [M + H]⁺ = 662<br>Rt = 0.52 (method H) | 174 | C₂₉H₂₂Cl₃F₆N₅O₃<br>MW: 708.872<br>MS* m/z [M + H]⁺ = 708<br>Rt = 1.76 (method I) | *-cyclopropyl-CF₃ |
| 103 | C₂₅H₂₄Cl₂F₅N₅O₃<br>MW: 608.393<br>MS* m/z [M + H]⁺ = 608<br>Rt = 1.50 (method I) | 133 | C₂₉H₂₅Cl₃F₃N₅O₃<br>MW: 654.902<br>MS* m/z [M + H]⁺ = 654<br>Rt = 0.57 (method H) | *-cyclopropyl-CH₃ |
| 93 | C₂₄H₂₂Cl₂F₅N₅O₄<br>MW: 610.365<br>MS* m/z [M + H]⁺ = 610<br>Rt = 0.43 (method H) | 171 | C₂₈H₂₃Cl₃F₃N₅O₄<br>MW: 656.874<br>MS* m/z [M + H]⁺ = 656<br>Rt = 1.60 (method I) | *-cyclopropyl-OH |
| 97 | C₂₇H₂₅Cl₂F₈N₅O₃<br>MW: 690.417<br>MS* m/z [M + H]⁺ = 690<br>Rt = 0.55 (method H) | 165 | C₃₁H₂₆Cl₃F₆N₅O₃<br>MW: 736.925<br>MS* m/z [M + H]⁺ = 736<br>Rt = 1.84 (method I) | *-cyclopentyl-CF₃ |
| 113 | C₂₅H₂₁Cl₂F₅N₆O₃<br>MW: 619.378<br>MS* m/z [M + H]⁺ = 619<br>Rt = 0.47 (method H) | 145 | C₂₉H₂₂Cl₃F₃N₆O₃<br>MW: 665.885<br>MS* m/z [M + H]⁺ = 665<br>Rt = 0.56 (method H) | *-cyclopropyl-CN |
| 100 | C₂₄H₂₂Cl₂F₅N₅O₃<br>MW: 594.366<br>MS* m/z [M + H]⁺ = 594<br>Rt = 1.45 (method I) | 148 | C₂₈H₂₃Cl₃F₃N₅O₃<br>MW: 640.875<br>MS* m/z [M + H]⁺ = 640<br>Rt = 0.55 (method H) | *-cyclopropyl |
| 91 | C₂₅H₂₄Cl₂F₅N₅O₃<br>MW: 608.393<br>MS* m/z [M + H]⁺ = 608<br>Rt = 1.49 (method I) | 172 | C₂₉H₂₅Cl₃F₃N₅O₃<br>MW: 654.902<br>MS* m/z [M + H]⁺ = 654<br>Rt = 0.56 (method H) | *-cyclobutyl |

TABLE 2-continued

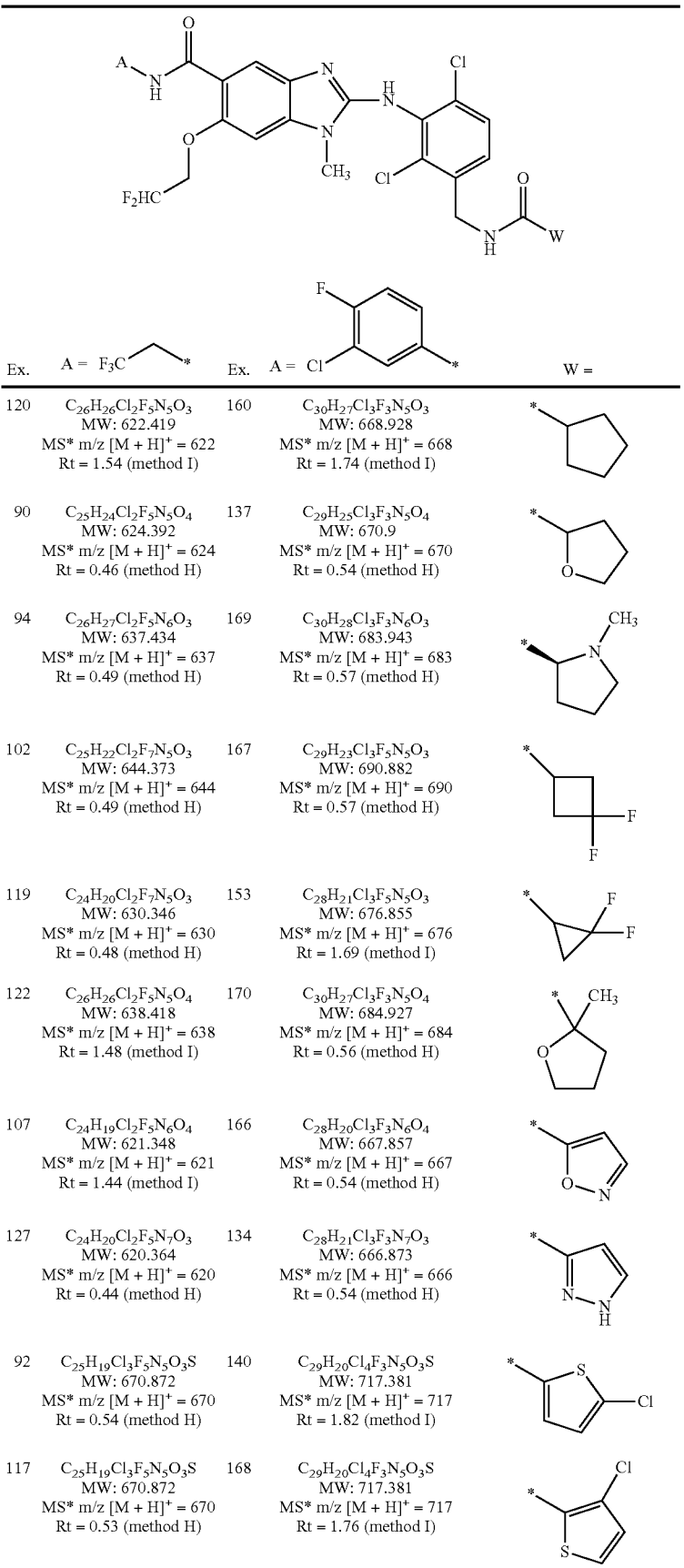

| Ex. | A = F₃C⌒* | Ex. | A = (4-F, 2-Cl-phenyl)CH₂* | W = |
|---|---|---|---|---|
| 120 | C₂₆H₂₆Cl₂F₅N₅O₃<br>MW: 622.419<br>MS* m/z [M + H]⁺ = 622<br>Rt = 1.54 (method I) | 160 | C₃₀H₂₇Cl₃F₃N₅O₃<br>MW: 668.928<br>MS* m/z [M + H]⁺ = 668<br>Rt = 1.74 (method I) | cyclopentyl |
| 90 | C₂₅H₂₄Cl₂F₅N₅O₄<br>MW: 624.392<br>MS* m/z [M + H]⁺ = 624<br>Rt = 0.46 (method H) | 137 | C₂₉H₂₅Cl₃F₃N₅O₄<br>MW: 670.9<br>MS* m/z [M + H]⁺ = 670<br>Rt = 0.54 (method H) | tetrahydrofuran-2-yl |
| 94 | C₂₆H₂₇Cl₂F₅N₆O₃<br>MW: 637.434<br>MS* m/z [M + H]⁺ = 637<br>Rt = 0.49 (method H) | 169 | C₃₀H₂₈Cl₃F₃N₆O₃<br>MW: 683.943<br>MS* m/z [M + H]⁺ = 683<br>Rt = 0.57 (method H) | 1-methylpyrrolidin-2-yl |
| 102 | C₂₅H₂₂Cl₂F₇N₅O₃<br>MW: 644.373<br>MS* m/z [M + H]⁺ = 644<br>Rt = 0.49 (method H) | 167 | C₂₉H₂₃Cl₃F₅N₅O₃<br>MW: 690.882<br>MS* m/z [M + H]⁺ = 690<br>Rt = 0.57 (method H) | 3,3-difluorocyclobutyl |
| 119 | C₂₄H₂₀Cl₂F₇N₅O₃<br>MW: 630.346<br>MS* m/z [M + H]⁺ = 630<br>Rt = 0.48 (method H) | 153 | C₂₈H₂₁Cl₃F₅N₅O₃<br>MW: 676.855<br>MS* m/z [M + H]⁺ = 676<br>Rt = 1.69 (method I) | 2,2-difluorocyclopropyl |
| 122 | C₂₆H₂₆Cl₂F₅N₅O₄<br>MW: 638.418<br>MS* m/z [M + H]⁺ = 638<br>Rt = 1.48 (method I) | 170 | C₃₀H₂₇Cl₃F₃N₅O₄<br>MW: 684.927<br>MS* m/z [M + H]⁺ = 684<br>Rt = 0.56 (method H) | 2-methyltetrahydrofuran-2-yl |
| 107 | C₂₄H₁₉Cl₂F₅N₆O₄<br>MW: 621.348<br>MS* m/z [M + H]⁺ = 621<br>Rt = 1.44 (method I) | 166 | C₂₈H₂₀Cl₃F₃N₆O₄<br>MW: 667.857<br>MS* m/z [M + H]⁺ = 667<br>Rt = 0.54 (method H) | isoxazol-5-yl |
| 127 | C₂₄H₂₀Cl₂F₅N₇O₃<br>MW: 620.364<br>MS* m/z [M + H]⁺ = 620<br>Rt = 0.44 (method H) | 134 | C₂₈H₂₁Cl₃F₃N₇O₃<br>MW: 666.873<br>MS* m/z [M + H]⁺ = 666<br>Rt = 0.54 (method H) | 1H-pyrazol-3-yl |
| 92 | C₂₅H₁₉Cl₃F₅N₅O₃S<br>MW: 670.872<br>MS* m/z [M + H]⁺ = 670<br>Rt = 0.54 (method H) | 140 | C₂₉H₂₀Cl₄F₃N₅O₃S<br>MW: 717.381<br>MS* m/z [M + H]⁺ = 717<br>Rt = 1.82 (method I) | 5-chlorothiophen-2-yl |
| 117 | C₂₅H₁₉Cl₃F₅N₅O₃S<br>MW: 670.872<br>MS* m/z [M + H]⁺ = 670<br>Rt = 0.53 (method H) | 168 | C₂₉H₂₀Cl₄F₃N₅O₃S<br>MW: 717.381<br>MS* m/z [M + H]⁺ = 717<br>Rt = 1.76 (method I) | 3-chlorothiophen-2-yl |

TABLE 2-continued

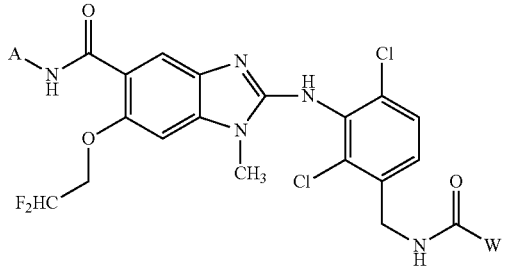

| Ex. | A = F₃C— | Ex. | A = (4-F, 3-Cl phenyl) | W = |
|---|---|---|---|---|
| 114 | C₂₆H₂₃Cl₂F₅N₆O₃<br>MW: 633.403<br>MS* m/z [M + H]⁺ = 633<br>Rt = 1.53 (method I) | 142 | C₃₀H₂₄Cl₃F₃N₆O₃<br>MW: 679.912<br>MS* m/z [M + H]⁺ = 679<br>Rt = 0.54 (method H) |  1-methylpyrrole |
| 121 | C₂₅H₂₂Cl₂F₅N₇O₃<br>MW: 634.391<br>MS* m/z [M + H]⁺ = 634<br>Rt = 1.35 (method I) | 156 | C₂₉H₂₃Cl₃F₃N₇O₃<br>MW: 680.9<br>MS* m/z [M + H]⁺ = 680<br>Rt = 0.55 (method H) |  1-methylimidazole |
| 125 | C₂₆H₂₁Cl₂F₈N₇O₃<br>MW: 702.388<br>MS* m/z [M + H]⁺ = 702<br>Rt = 0.54 (method H) | 143 | C₃₀H₂₂Cl₃F₆N₇O₃<br>MW: 748.897<br>MS* m/z [M + H]⁺ = 748<br>Rt = 1.81 (method I) | 1-methyl-3-(trifluoromethyl)pyrazole |
| 129 | C₂₆H₂₃Cl₂F₅N₆O₃S<br>MW: 665.469<br>MS* m/z [M + H]⁺ = 665<br>Rt = 0.47 (method H) | 138 | C₃₀H₂₄Cl₃F₃N₆O₃S<br>MW: 711.978<br>MS* m/z [M + H]⁺ = 711<br>Rt = 1.64 (method I) | 2,4-dimethylthiazole |
| 105 | C₂₇H₂₀Cl₃F₆N₅O₃<br>MW: 682.834<br>MS* m/z [M + H]⁺ = 682<br>Rt = 0.47 (method H) | 158 | C₃₁H₂₁Cl₄F₄N₅O₃<br>MW: 729.343<br>MS* m/z [M + H]⁺ = 729<br>Rt = 1.74 (method I) | 2-chloro-6-fluorophenyl |
|  |  | 136 | C₂₉H₂₀Cl₃F₆N₇O₃<br>MW: 734.87<br>MS* m/z [M + H]⁺ = 734<br>Rt = 1.74 (method I) | 3-(trifluoromethyl)-1H-pyrazole |
|  |  | 150 | C₂₉H₂₅Cl₃F₃N₅O₄<br>MW: 670.9<br>MS* m/z [M + H]⁺ = 670<br>Rt = 1.60 (method I) | 3-methyloxetane |

The invention claimed is:
1. A compound of formula I

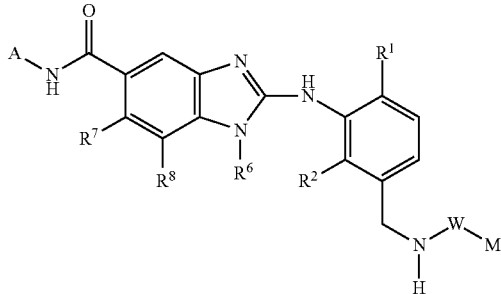

in which
R¹ and R² independently represent halo;
W represents —C(O)—, or —C(O)O—, which groups are bound to the nitrogen of the —NH— moiety via the carbon atom;
M represents
—C$_{1-6}$alkyl, or —C$_{3-7}$cycloalkyl, both of which groups are optionally substituted by one or more groups selected from —F, —OH, —CN, —NH$_2$, —NH(C$_{1-2}$ alkyl), —N(C$_{1-2}$alkyl)$_2$, —OC$_{1-3}$alkyl, —C$_{1-5}$alkyl, or —C$_{3-4}$cycloalkyl, in which latter three groups the alkyl or cycloalkyl groups are optionally substituted by one or more fluorine atoms;
or
oxetanyl-, tetrahydrofuranyl-, tetrahydropyranyl-, azetidinyl-, pyrrolidinyl-, or piperidinyl-, all of which groups are optionally substituted by one or more substituents selected from fluoro, —CN, or —C$_{1-3}$ alkyl, which latter alkyl group is optionally substituted by one or more fluorine atoms;
or
phenyl-, pyridyl-, thienyl-, pyrrolyl-, pyrazolyl-, imidazolyl-, thiazolyl-, oxazolyl-, or isoxazolyl-, all of which groups are optionally substituted by one or more substituents selected from halo, —CN or —C$_{1-3}$ alkyl, which latter alkyl group is optionally further substituted by one or more fluorine atoms;
R⁸ represents —H, halogen, or —C$_{1-3}$alkyl, which latter alkyl group is optionally substituted by one or more fluorine atoms;
R⁶ represents —H, —C$_{1-5}$alkyl, or —C$_{3-5}$cycloalkyl-C$_{0-2}$ alkyl, in which latter two groups the alkyl or cycloalkyl fragments are optionally substituted by one or more fluorine atoms;
R⁷ represents halo, C$_{1-5}$alkyl-O—, C$_{3-7}$cycloalkyl-C$_{0-2}$ alkyl-O—, or 4-7-membered heterocycloalkyl-C$_{0-2}$ alkyl-O—, in which latter three groups the alkyl, cycloalkyl or heterocycloalkyl fragments are optionally substituted by one or more substituents selected from —F and —OC$_{1-3}$alkyl which latter alkyl group is optionally further substituted by one or more fluorine atoms;
represents C$_{1-8}$ alkyl-, phenyl-, indanyl-, naphthyl-, 1,2,3,4-tetrahydronaphthyl-, pyridyl-, thienyl-, benzothienyl-, pyrrolyl-, indolyl-, pyrazolyl-, indazolyl-, thiazolyl-, benzothiazolyl-, oxazolyl-, benzooxazolyl-, isoxazolyl-, benzisoxazolyl-, phenyl-C$_{1-3}$alkyl-, thienyl-C$_{1-3}$alkyl-, pyridyl-C$_{1-3}$alkyl-, C$_{3-7}$cycloalkyl-C$_{0-3}$ alkyl-, oxetanyl-C$_{0-3}$alkyl-, tetrahydrofuranyl-C$_{0-3}$ alkyl, or tetrahydropyranyl-C$_{0-3}$alkyl, in which groups the alkyl-, cycloalkyl- and heterocycloalkyl fragments are optionally substituted by one or more substituents selected from R$^{9a}$ and the aryl and heteroaryl fragments are optionally substituted by one or more substituents selected from R$^{9b}$;
each R$^{9a}$ independently represents —F, —Cl, or —C$_{1-3}$ alkyl which is optionally substituted by one or more substituents selected from —F, or —OC$_{1-3}$ alkyl;
each R$^{9b}$ represents independently -halo, —CN; or —C$_{1-3}$ alkyl which is optionally substituted by one or more fluorine atoms;
or a salt thereof.

2. A compound according to claim 1, wherein
R⁸ represents —H or fluoro;
or a pharmaceutically acceptable salt thereof.

3. A compound according to claim 1, wherein
R⁶ represents —H, —CH$_3$, or cyclopropyl;
or a pharmaceutically acceptable salt thereof.

4. A compound according to claim 1, wherein
R¹ and R² independently represent chloro, or fluoro;
or a pharmaceutically acceptable salt thereof.

5. A compound according to claim 1, wherein
R⁷ represents fluoro, —OCHF$_2$, —OCF$_3$, —OCH$_2$CH$_2$F, —OCH$_2$CHF$_2$, —OCH$_2$CF$_3$, —O-tetrahydrofuran-3-yl, or —O—CH$_2$-cyclopropyl;
or a pharmaceutically acceptable salt thereof.

6. A compound according to claim 1, wherein
A represents C$_{1-4}$ alkyl-, C$_{3-7}$cycloalkyl-C$_{0-2}$alkyl-, tetrahydrofuranyl-methyl-, phenyl-C$_{1-2}$ alkyl-, pyridylmethyl-, phenyl-, indanyl-, pyridyl-, thienyl-, thiazolyl-, or benzothiazolyl-, in which groups the alkyl-, cycloalkyl- and heterocycloalkyl-fragments are optionally substituted by one or more substituents selected from —F, —CH$_3$, —CH$_2$F, —CHF$_2$, or —CF$_3$, and the aryl and heteroaryl fragments are optionally substituted by —F, —Cl, —Br, —CN, —CH$_3$, —CH$_2$F, —CHF$_2$, or —CF$_3$;
or a pharmaceutically acceptable salt thereof.

7. A compound according to claim 1, wherein
M represents
—C$_{1-4}$ alkyl, or —C$_{3-5}$ cycloalkyl, both of which groups are optionally substituted by one or more groups selected from —F, —OH, —CN, —NH$_2$, —OCH$_3$, —CH$_3$, —CH$_2$F, —CHF$_2$, —CF$_3$, or cyclopropyl;
or
oxetanyl-, tetrahydrofuranyl-, azetidinyl- or pyrrolidinyl-, all of which groups are optionally substituted by one or more substituents selected from —F, —CH$_3$, —CH$_2$F, —CHF$_2$, or —CF$_3$;
or
phenyl-, indanyl-, thienyl-, pyrrolyl-, pyrazolyl-, thiazolyl-, or isoxazolyl-, all of which groups are optionally substituted by one or more substituents selected from —F, —CH$_3$, —CH$_2$F, —CHF$_2$, or —CF$_3$;
or a pharmaceutically acceptable salt thereof.

8. A compound according to claim 1, which is a compound of formula Ia

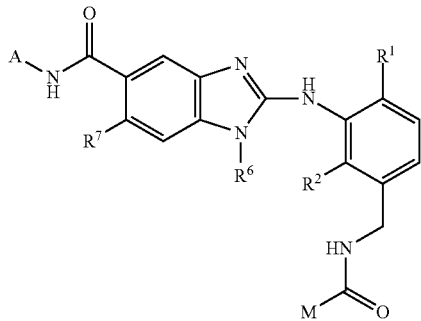

in which

M represents methyl, ethyl, propyl, i-propyl, n-butyl, s-butyl, t-butyl, cyclopropyl, —CH$_2$-cyclopropyl, cyclobutyl, or cyclopentyl, all of which groups are optionally substituted by one or more groups selected from —F, —OH, —CN, —NH$_2$, —OCH$_3$, —CH$_3$, or —CF$_3$;

or is selected from the following groups

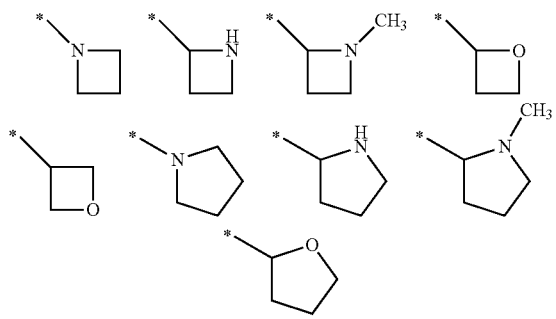

which latter nine groups are optionally substituted by one or more substituents selected from —F, —CH$_3$, or —CF$_3$;

or is selected from the following groups

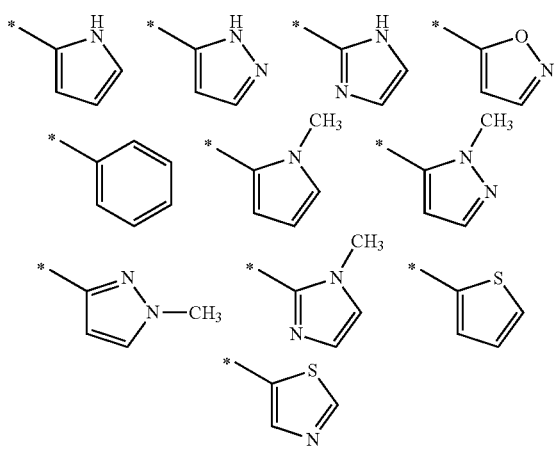

which latter eleven groups are optionally substituted by one or more substituents selected from —F, —Cl, —CH$_3$, or —CF$_3$;

and

A, R$^1$, R$^2$, R$^6$, R$^7$ have the same meaning as defined in claim 1;

or a pharmaceutically acceptable salt thereof.

9. A compound according to claim 8, wherein

A represents methyl, ethyl, propyl, i-propyl, n-butyl, s-butyl, or t-butyl, which latter seven groups are optionally substituted by one or more fluorine atoms, or cyclopropyl, cyclobutyl, cyclopentyl, or cyclohexyl, which latter four groups are optionally substituted by one or more substituents selected from —F, —CH$_3$, —CHF$_2$, or —CF$_3$;

or is selected from the following groups:

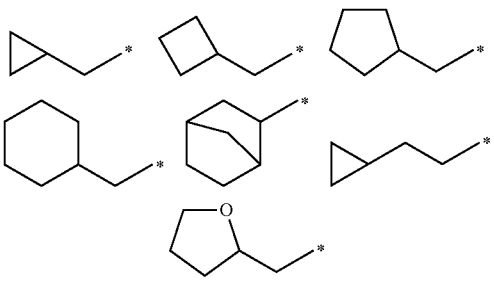

which latter seven groups are optionally substituted by one or more substituents selected from —F, —CH$_3$, —CHF$_2$, or —CF$_3$;

or is selected from the following groups:

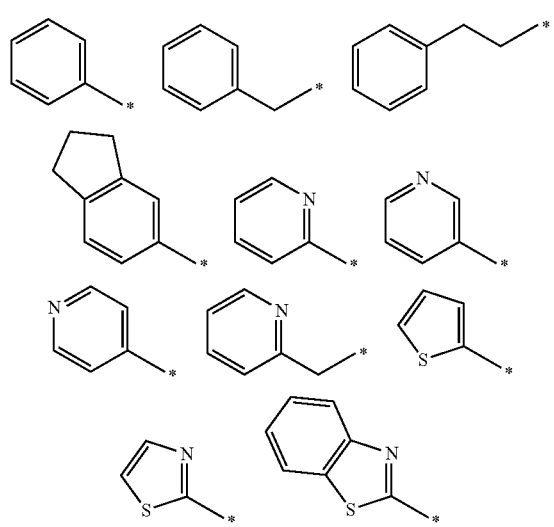

in which latter eleven groups the aryl and heteroaryl fragments are optionally substituted by one or more substituents selected from —F, —Cl, —Br, —CN, —CH$_3$, or —CF$_3$;

or a pharmaceutically acceptable salt thereof.

10. A compound according to claim 1, which is a compound of formula Ia or Ib

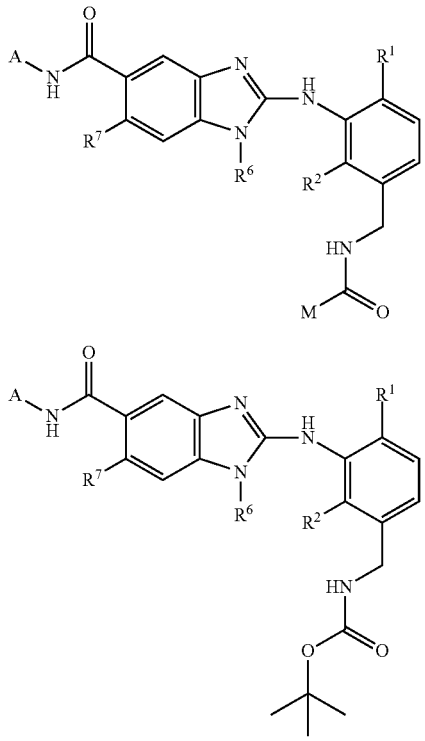

in which
- R¹ and R² independently represent -chloro or fluoro;
- R⁶ represents —H, —CH₃, or cyclopropyl;
- R⁷ represents fluoro, —OCHF₂, —OCF₃, —OCH₂CH₂F, —OCH₂CHF₂, —OCH₂CF₃, tetrahydrofuran-3-yl-O—, or —O—CH₂-cyclopropyl;
- A represents methyl, ethyl, propyl, i-propyl, n-butyl, s-butyl, or t-butyl, which latter seven groups are optionally substituted by one or more fluorine atoms,
  - or cyclopropyl, cyclobutyl, cyclopentyl, or cyclohexyl, which latter four groups are optionally substituted by one or more substituents selected from —F, —CH₃, —CHF₂, or —CF₃;
  - or is selected from the following groups:

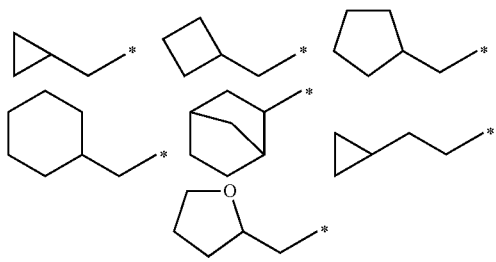

which latter seven groups are optionally substituted by one or more substituents selected from —F, —CH₃, —CHF₂, or —CF₃;
or is selected from the following groups:

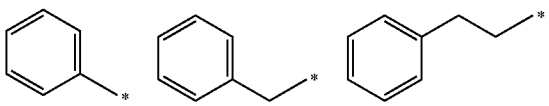

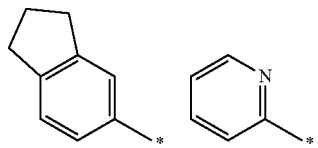

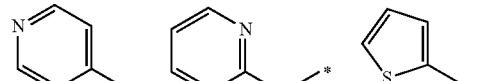

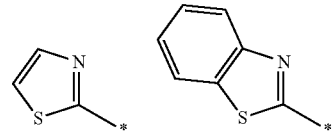

in which latter eleven groups the aryl and heteroaryl fragments are optionally substituted by one or more substituents selected from —F, —Cl, —Br, —CN, —CH₃, or —CF₃;

M represents
methyl, ethyl, propyl, i-propyl, n-butyl, s-butyl, t-butyl, cyclopropyl, —CH₂-cyclopropyl, cyclobutyl, or cyclopentyl, all of which groups are optionally substituted by one or more groups selected from —F, —OH, —CN, —NH₂, —OCH₃, —CH₃, or —CF₃;
or is selected from the following groups

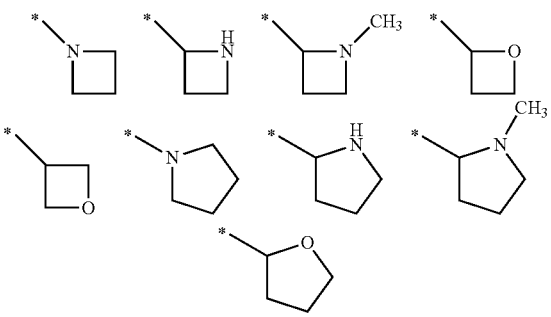

which latter nine groups are optionally substituted by one or more substituents selected from —F, —CH₃, or —CF₃;
or is selected from the following groups

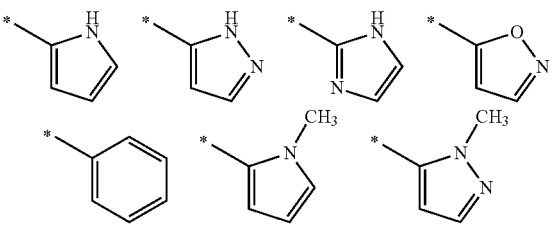

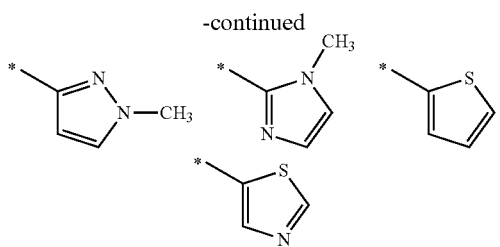
which latter eleven groups are optionally substituted by one or more substituents selected from —F, —Cl, —CH₃, or —CF₃;
or a salt thereof.
11. A compound according to claim 1 selected from the compounds in the following table, or the pharmaceutically acceptable salts thereof:
| | Structure |
|---|---|
| 1 | 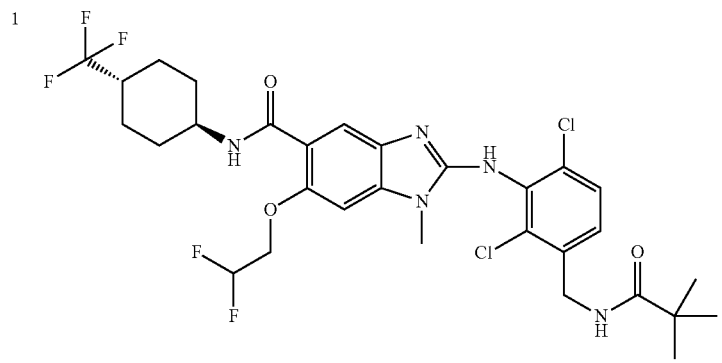 |
| 2 | 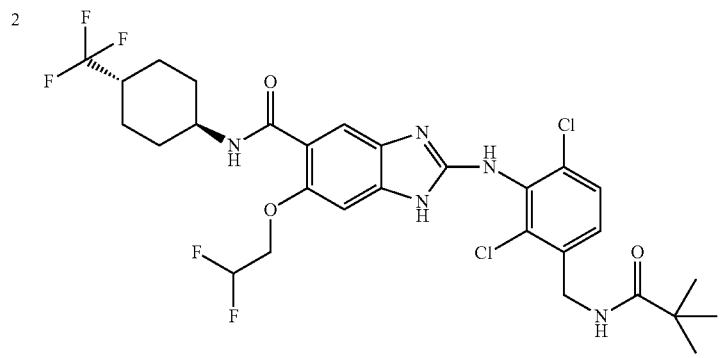 |
| 3 | 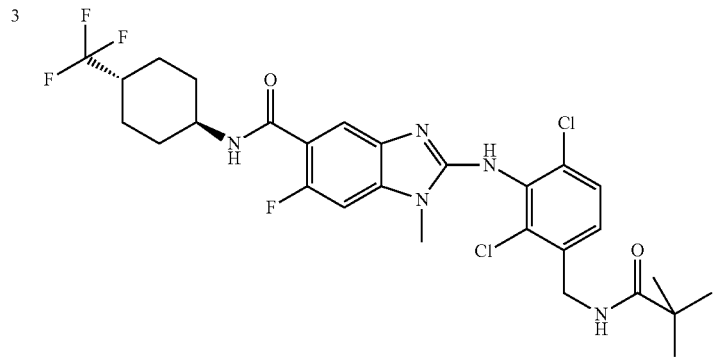 |

| Structure |
|---|
| 4 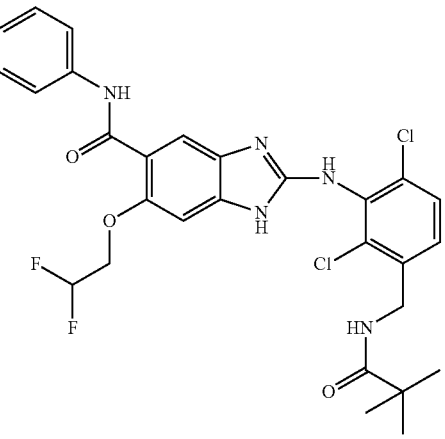 |
| 5 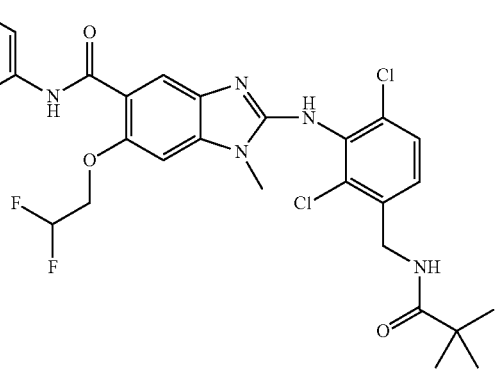 |
| 6 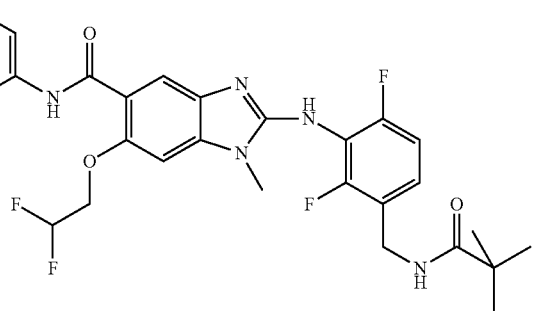 |
| 7 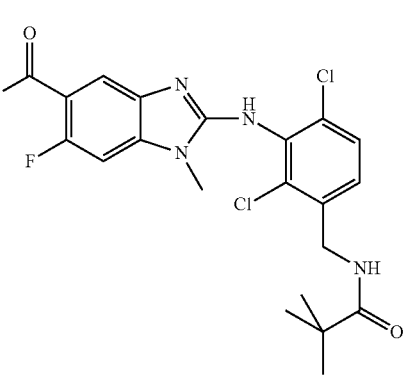 |

-continued
| | Structure |
|---|---|
| 8 | 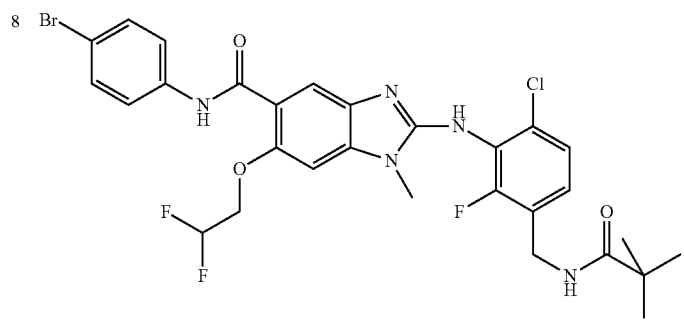 |
| 9 | 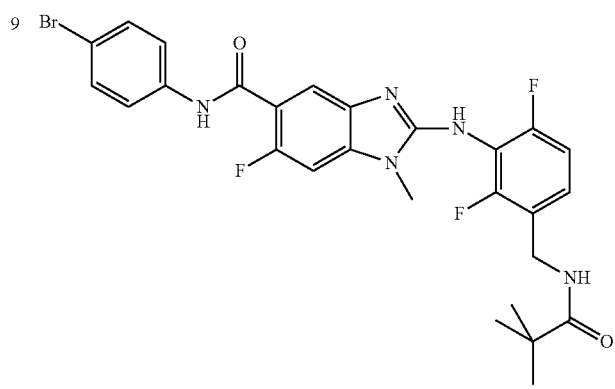 |
| 10 | 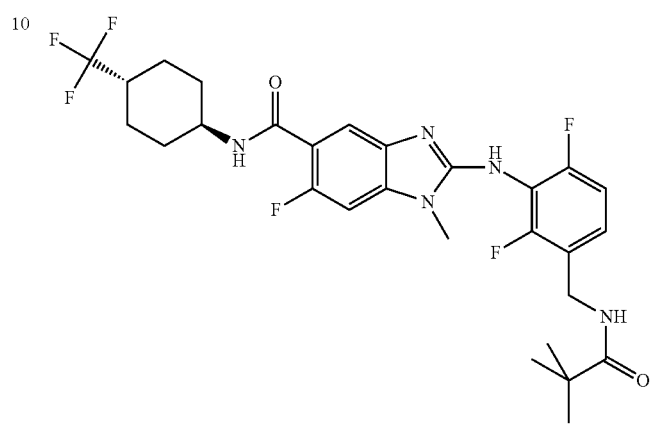 |
| 11 | 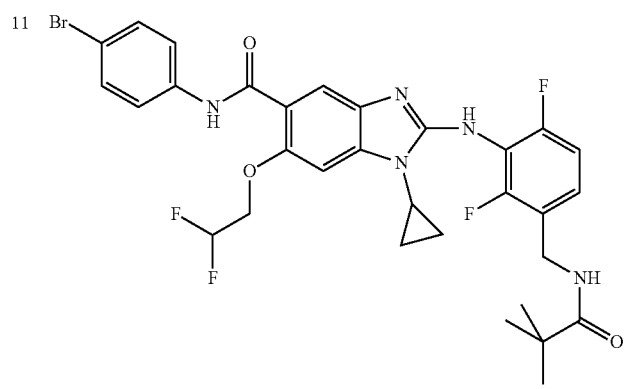 |

| Structure |
|---|
| 12 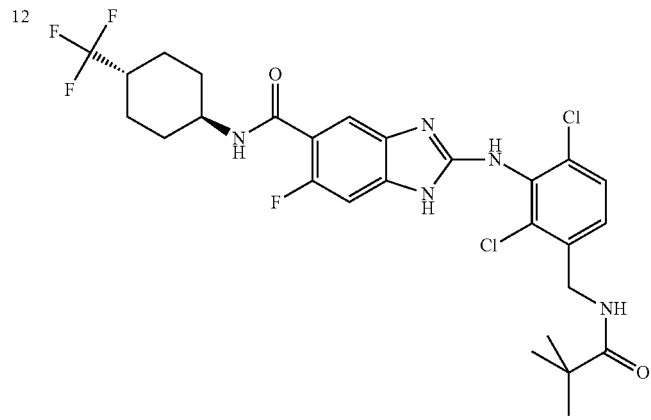 |
| 13 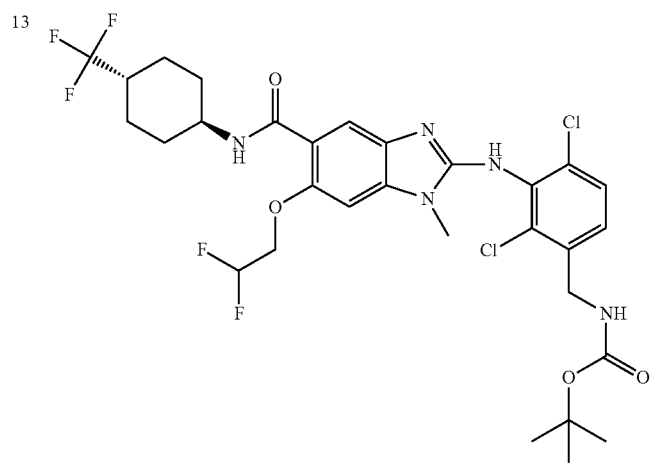 |
| 15 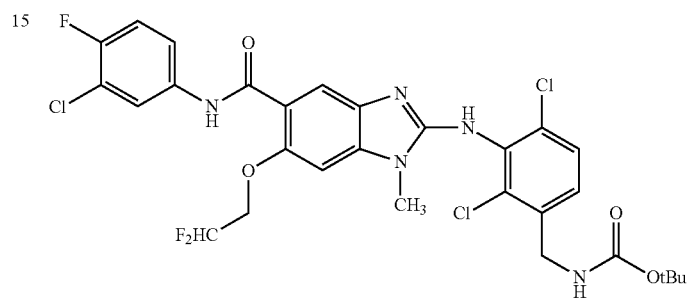 |
| 16 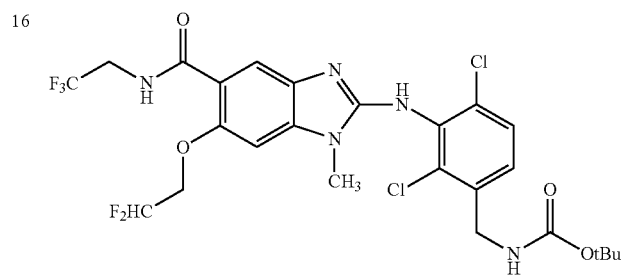 |

-continued
| | Structure |
|---|---|
| 17 | 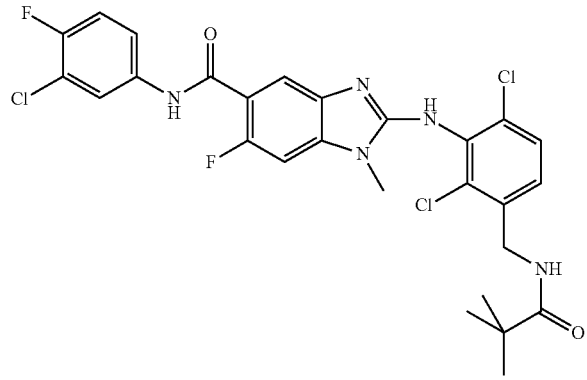 [SMILES: Cn1c(Nc2c(Cl)ccc(CNC(=O)C(C)(C)C)c2Cl)nc2cc(C(=O)Nc3ccc(F)c(Cl)c3)c(F)cc21] |
| 18 | 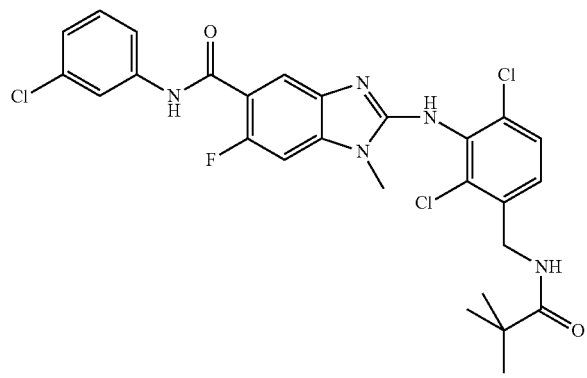 [SMILES: Cn1c(Nc2c(Cl)ccc(CNC(=O)C(C)(C)C)c2Cl)nc2cc(C(=O)Nc3cccc(Cl)c3)c(F)cc21] |
| 19 | 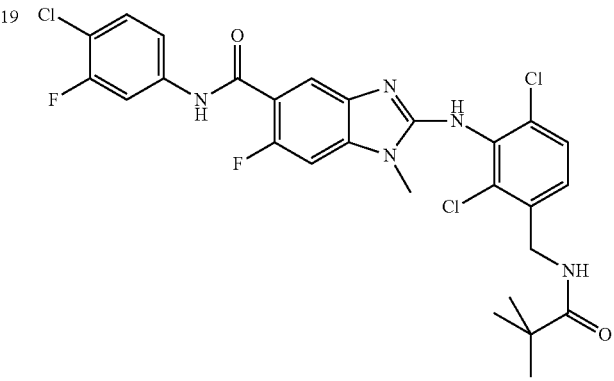 |
| 20 | 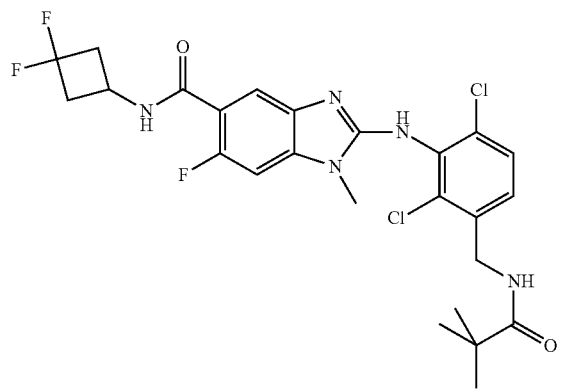 [SMILES: Cn1c(Nc2c(Cl)ccc(CNC(=O)C(C)(C)C)c2Cl)nc2cc(C(=O)NC3CC(F)(F)C3)c(F)cc21] |

-continued
| Structure |
|---|
| 21 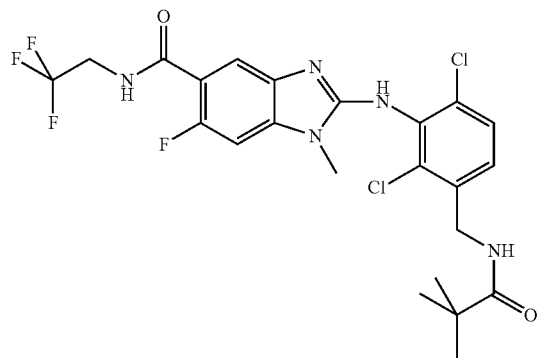 [SMILES: Cn1c(Nc2c(Cl)ccc(CNC(=O)C(C)(C)C)c2Cl)nc2cc(C(=O)NCC(F)(F)F)c(F)cc21] |
| 22 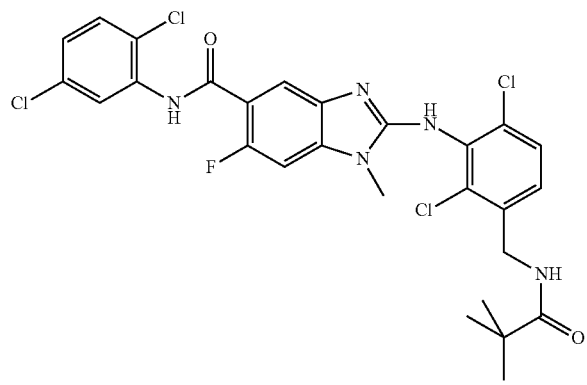 [SMILES: Cn1c(Nc2c(Cl)ccc(CNC(=O)C(C)(C)C)c2Cl)nc2cc(C(=O)Nc3cc(Cl)ccc3Cl)c(F)cc21] |
| 23 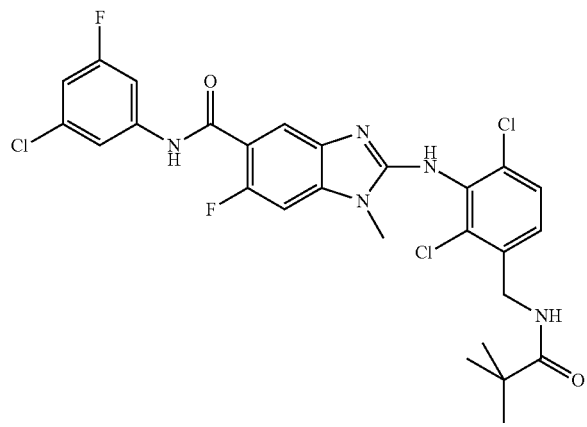 [SMILES: Cn1c(Nc2c(Cl)ccc(CNC(=O)C(C)(C)C)c2Cl)nc2cc(C(=O)Nc3cc(F)cc(Cl)c3)c(F)cc21] |
| 24 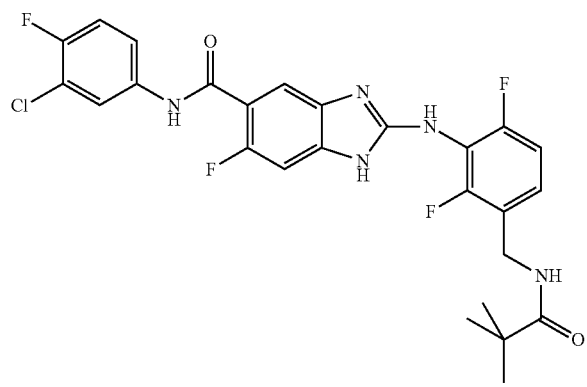 [SMILES: CC(C)(C)C(=O)NCc1ccc(F)c(Nc2nc3cc(C(=O)Nc4ccc(F)c(Cl)c4)c(F)cc3[nH]2)c1F] |

|     | Structure |
| --- | --- |
| 25  | 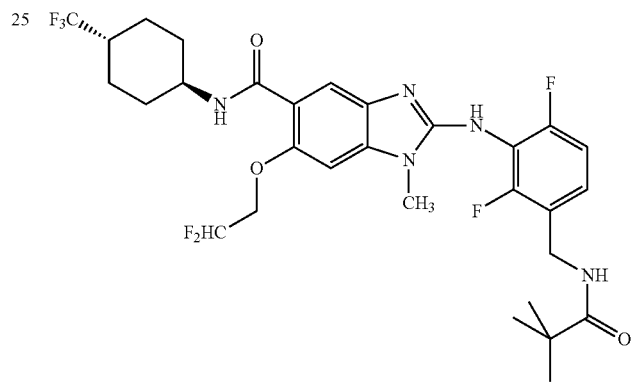 |
| 26  | 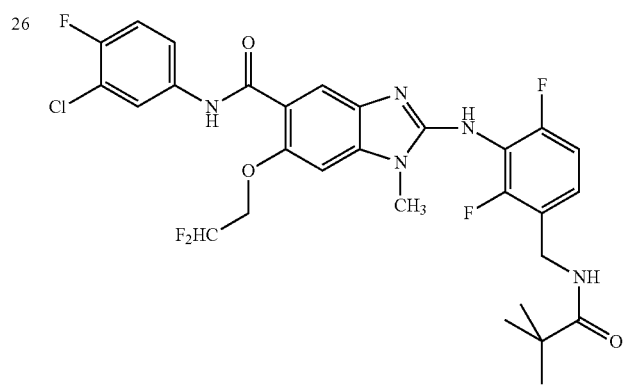 |
| 27  | 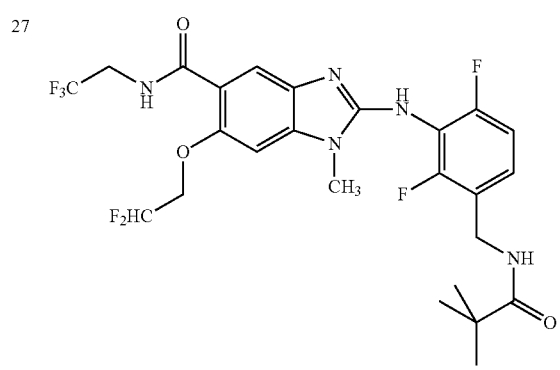 |
| 28  | 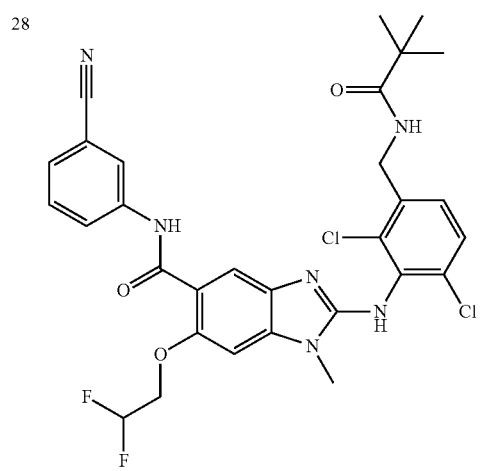 |

-continued
| | Structure |
|---|---|
| 29 | 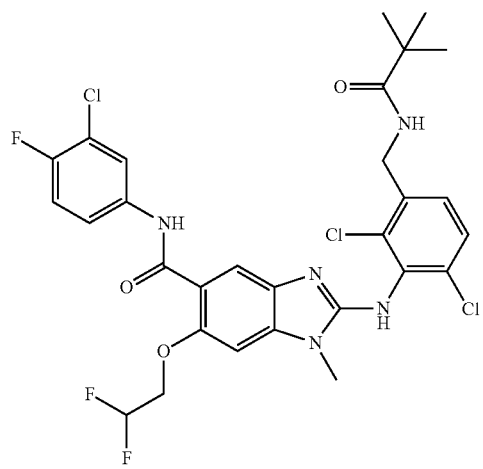 [SMILES: Cn1c(Nc2c(Cl)ccc(CNC(=O)C(C)(C)C)c2Cl)nc2cc(C(=O)Nc3ccc(F)c(Cl)c3)c(OCC(F)F)cc21] |
| 30 | 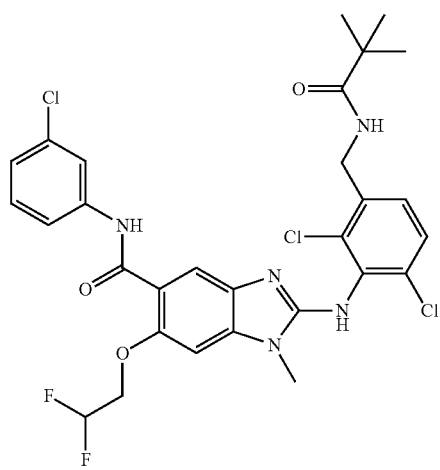 [SMILES: Cn1c(Nc2c(Cl)ccc(CNC(=O)C(C)(C)C)c2Cl)nc2cc(C(=O)Nc3cccc(Cl)c3)c(OCC(F)F)cc21] |
| 31 | 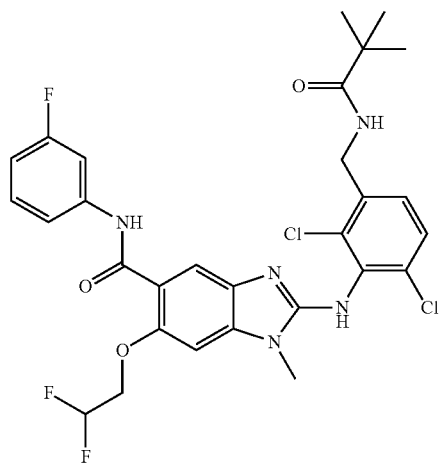 [SMILES: Cn1c(Nc2c(Cl)ccc(CNC(=O)C(C)(C)C)c2Cl)nc2cc(C(=O)Nc3cccc(F)c3)c(OCC(F)F)cc21] |

-continued
| Structure |
|---|
| 32 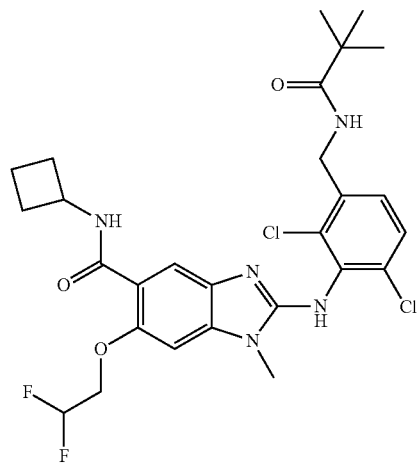 [SMILES: Cn1c(Nc2c(Cl)ccc(CNC(=O)C(C)(C)C)c2Cl)nc2cc(C(=O)NC3CCC3)c(OCC(F)F)cc21] |
| 33 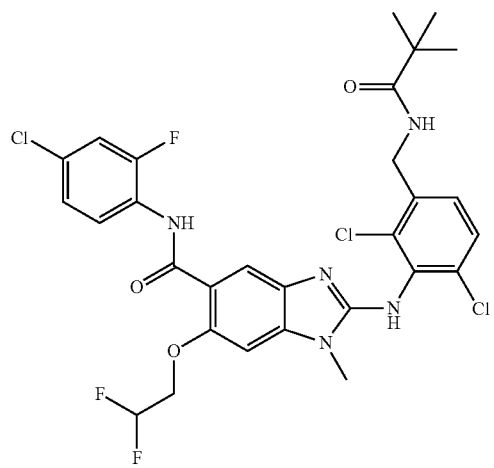 [SMILES: Cn1c(Nc2c(Cl)ccc(CNC(=O)C(C)(C)C)c2Cl)nc2cc(C(=O)Nc3ccc(Cl)cc3F)c(OCC(F)F)cc21] |
| 34 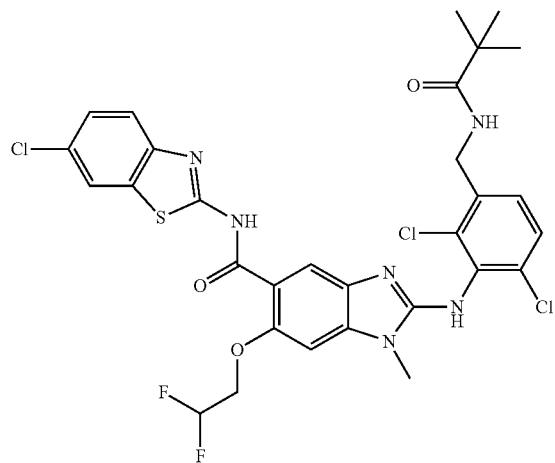 [SMILES: Cn1c(Nc2c(Cl)ccc(CNC(=O)C(C)(C)C)c2Cl)nc2cc(C(=O)Nc3nc4ccc(Cl)cc4s3)c(OCC(F)F)cc21] |

-continued
| Structure |
|---|
| 35 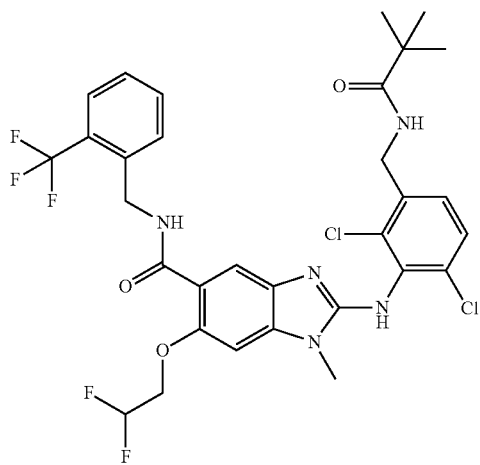 [SMILES: Cn1c(Nc2c(Cl)ccc(CNC(=O)C(C)(C)C)c2Cl)nc2cc(C(=O)NCc3ccccc3C(F)(F)F)c(OCC(F)F)cc21] |
| 36 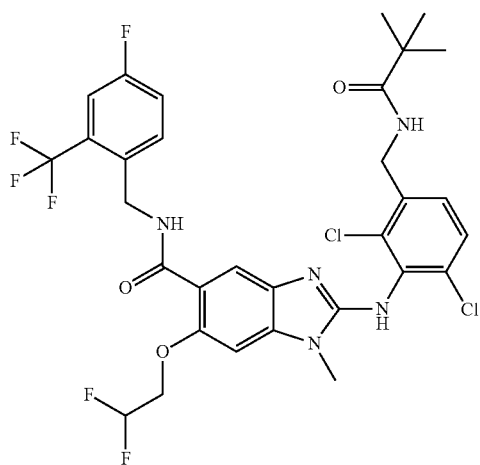 [SMILES: Cn1c(Nc2c(Cl)ccc(CNC(=O)C(C)(C)C)c2Cl)nc2cc(C(=O)NCc3ccc(F)cc3C(F)(F)F)c(OCC(F)F)cc21] |
| 37 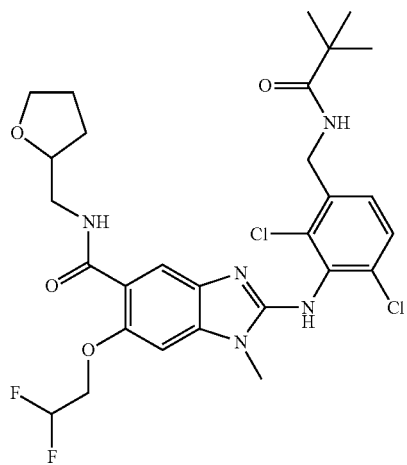 [SMILES: Cn1c(Nc2c(Cl)ccc(CNC(=O)C(C)(C)C)c2Cl)nc2cc(C(=O)NCC3CCCO3)c(OCC(F)F)cc21] |

-continued
| Structure |
|---|
| 38 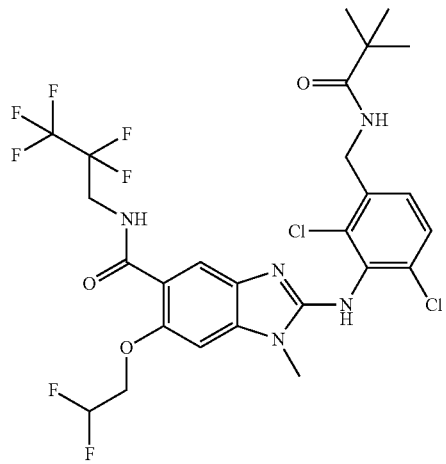 [SMILES: Cn1c(Nc2c(Cl)ccc(CNC(=O)C(C)(C)C)c2Cl)nc2cc(C(=O)NCC(F)(F)C(F)(F)F)c(OCC(F)F)cc21] |
| 39 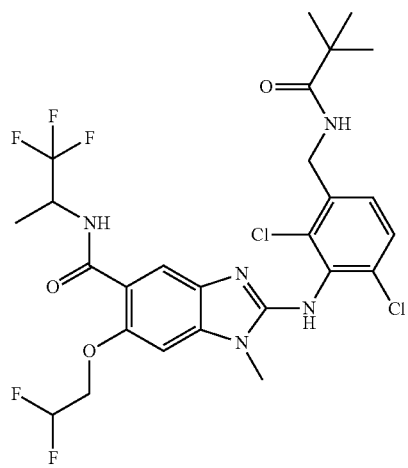 [SMILES: CC(NC(=O)c1cc2nc(Nc3c(Cl)ccc(CNC(=O)C(C)(C)C)c3Cl)n(C)c2cc1OCC(F)F)C(F)(F)F] |
| 40 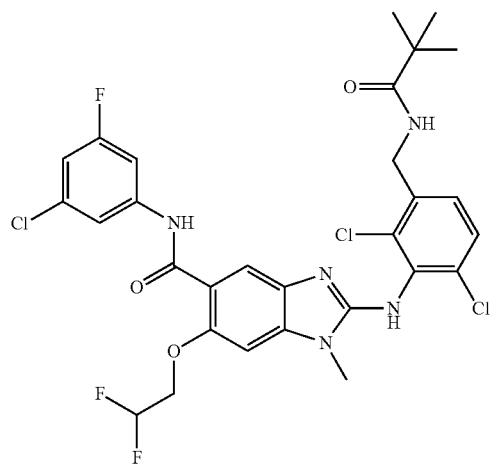 [SMILES: Cn1c(Nc2c(Cl)ccc(CNC(=O)C(C)(C)C)c2Cl)nc2cc(C(=O)Nc3cc(F)cc(Cl)c3)c(OCC(F)F)cc21] |

-continued
| | Structure |
|---|---|
| 41 | 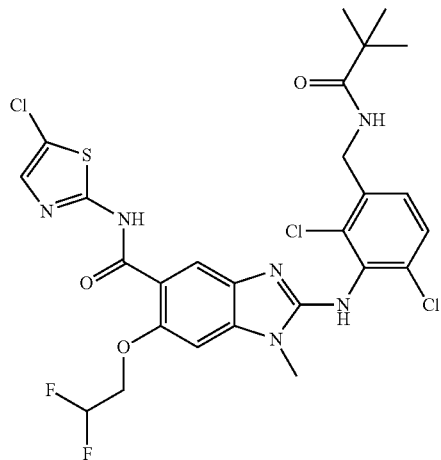 [SMILES: Cn1c(Nc2c(Cl)ccc(CNC(=O)C(C)(C)C)c2Cl)nc2cc(C(=O)Nc3ncc(Cl)s3)c(OCC(F)F)cc21] |
| 42 | 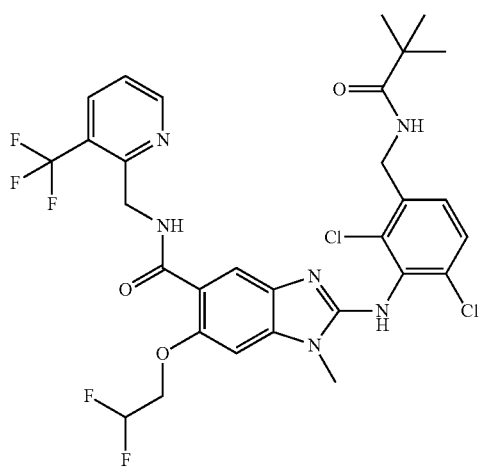 [SMILES: Cn1c(Nc2c(Cl)ccc(CNC(=O)C(C)(C)C)c2Cl)nc2cc(C(=O)NCc3ncccc3C(F)(F)F)c(OCC(F)F)cc21] |
| 43 | 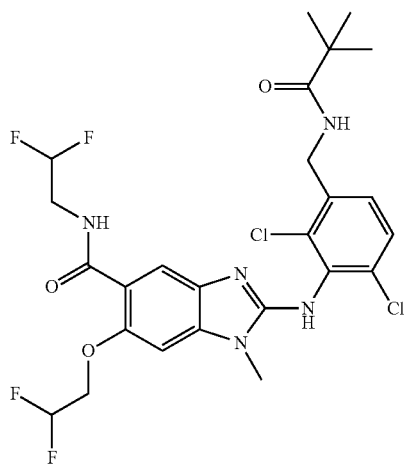 [SMILES: Cn1c(Nc2c(Cl)ccc(CNC(=O)C(C)(C)C)c2Cl)nc2cc(C(=O)NCC(F)F)c(OCC(F)F)cc21] |

| Structure |
|---|
| 44 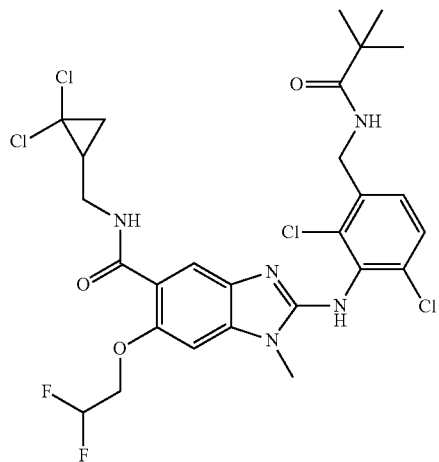 [SMILES: Cn1c(Nc2c(Cl)ccc(CNC(=O)C(C)(C)C)c2Cl)nc2cc(C(=O)NCC3CC3(Cl)Cl)c(OCC(F)F)cc21] |
| 45 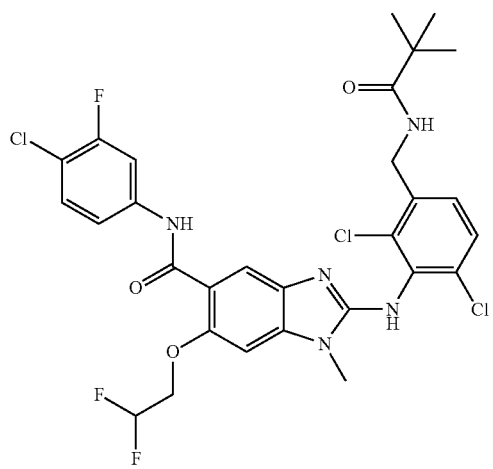 [SMILES: Cn1c(Nc2c(Cl)ccc(CNC(=O)C(C)(C)C)c2Cl)nc2cc(C(=O)Nc3ccc(Cl)c(F)c3)c(OCC(F)F)cc21] |
| 46 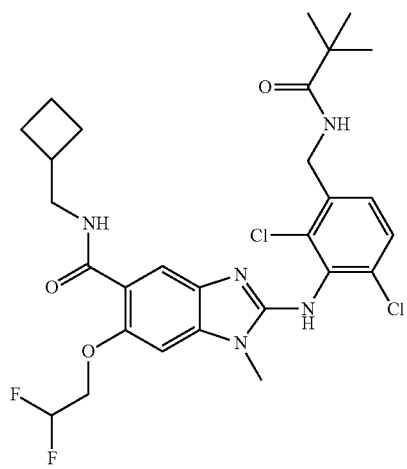 [SMILES: Cn1c(Nc2c(Cl)ccc(CNC(=O)C(C)(C)C)c2Cl)nc2cc(C(=O)NCC3CCC3)c(OCC(F)F)cc21] |

-continued
| | Structure |
|---|---|
| 47 | 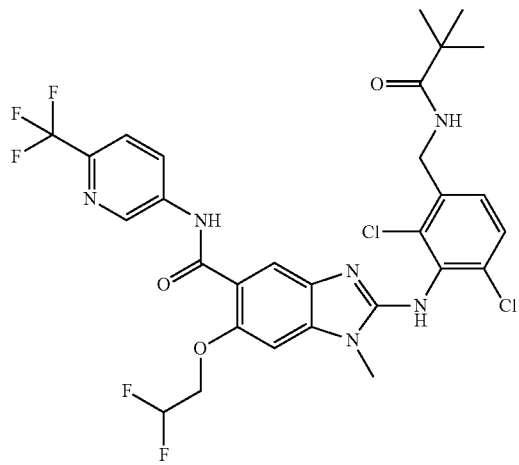 [SMILES: Cn1c(Nc2c(Cl)ccc(CNC(=O)C(C)(C)C)c2Cl)nc2cc(C(=O)Nc3ccc(C(F)(F)F)nc3)c(OCC(F)F)cc21] |
| 48 | 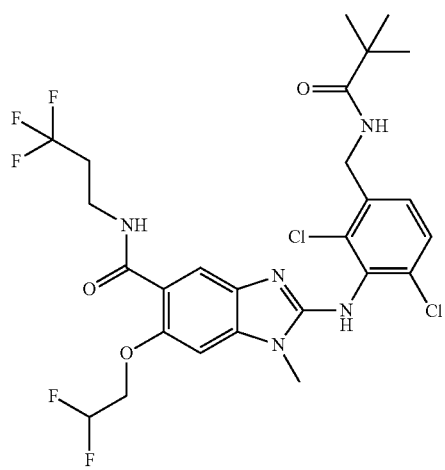 [SMILES: Cn1c(Nc2c(Cl)ccc(CNC(=O)C(C)(C)C)c2Cl)nc2cc(C(=O)NCCC(F)(F)F)c(OCC(F)F)cc21] |
| 49 | 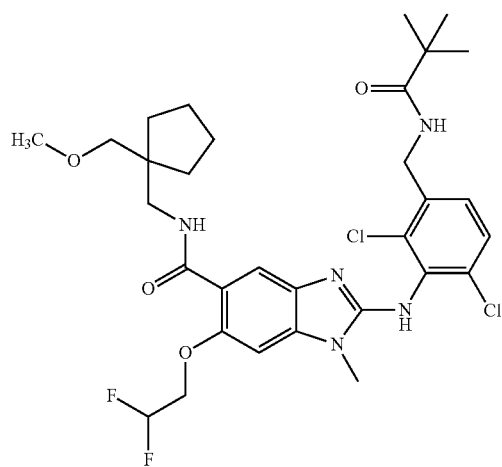 [SMILES: COCC1(CNC(=O)c2cc3nc(Nc4c(Cl)ccc(CNC(=O)C(C)(C)C)c4Cl)n(C)c3cc2OCC(F)F)CCCC1] |

| Structure |
|---|
| 50 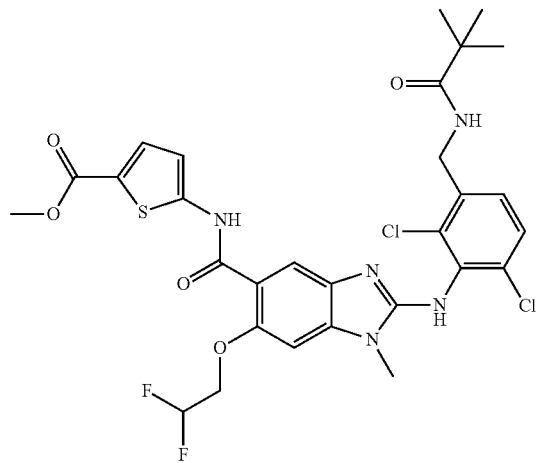 [SMILES: COC(=O)c1ccc(NC(=O)c2cc3nc(Nc4c(Cl)ccc(CNC(=O)C(C)(C)C)c4Cl)n(C)c3cc2OCC(F)F)s1] |
| 51 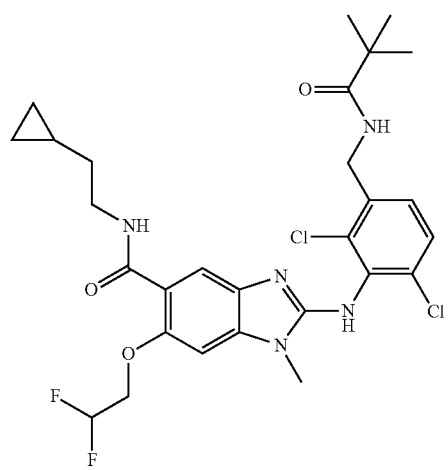 [SMILES: Cn1c(Nc2c(Cl)ccc(CNC(=O)C(C)(C)C)c2Cl)nc2cc(C(=O)NCCC3CC3)c(OCC(F)F)cc21] |
| 52 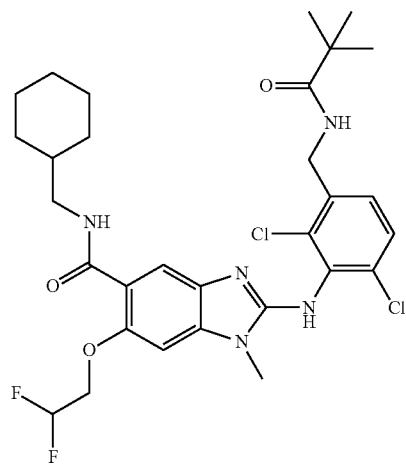 [SMILES: Cn1c(Nc2c(Cl)ccc(CNC(=O)C(C)(C)C)c2Cl)nc2cc(C(=O)NCC3CCCCC3)c(OCC(F)F)cc21] |

-continued
| | Structure |
|---|---|
| 53 | 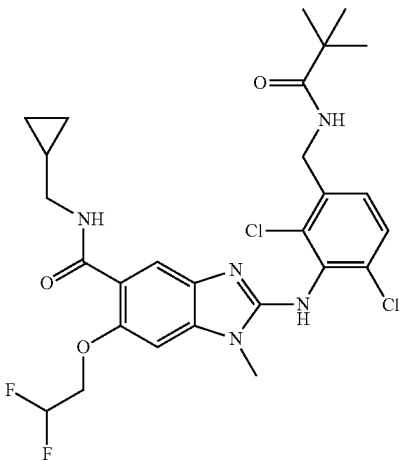 [SMILES: Cn1c(Nc2c(Cl)ccc(CNC(=O)C(C)(C)C)c2Cl)nc2cc(C(=O)NCC3CC3)c(OCC(F)F)cc21] |
| 54 | 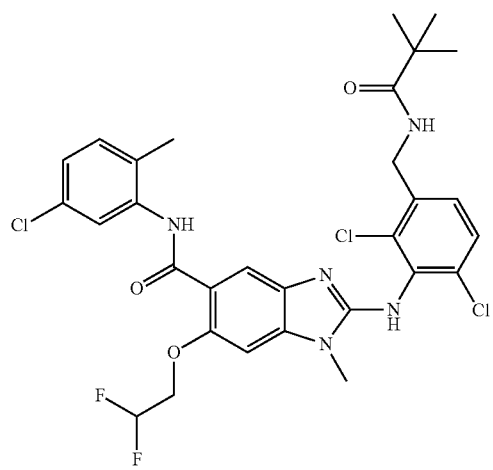 [SMILES: Cc1ccc(Cl)cc1NC(=O)c1cc2nc(Nc3c(Cl)ccc(CNC(=O)C(C)(C)C)c3Cl)n(C)c2cc1OCC(F)F] |
| 55 | 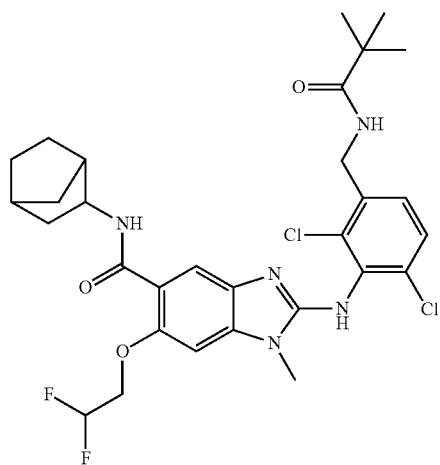 [SMILES: Cn1c(Nc2c(Cl)ccc(CNC(=O)C(C)(C)C)c2Cl)nc2cc(C(=O)NC3CC4CCC3C4)c(OCC(F)F)cc21] |

| Structure |
|---|
| 56 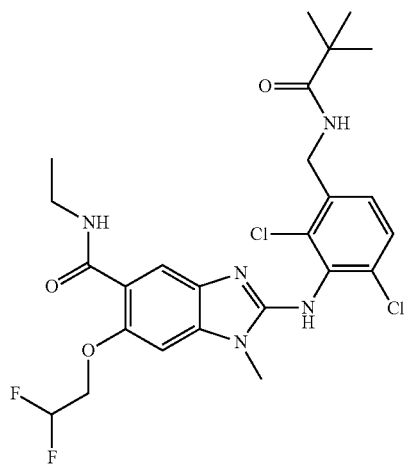 [SMILES: CCNC(=O)c1cc2nc(Nc3c(Cl)ccc(CNC(=O)C(C)(C)C)c3Cl)n(C)c2cc1OCC(F)F] |
| 57 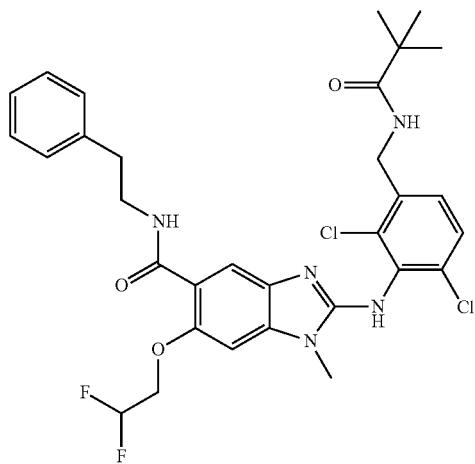 [SMILES: Cn1c(Nc2c(Cl)ccc(CNC(=O)C(C)(C)C)c2Cl)nc2cc(C(=O)NCCc3ccccc3)c(OCC(F)F)cc21] |
| 58 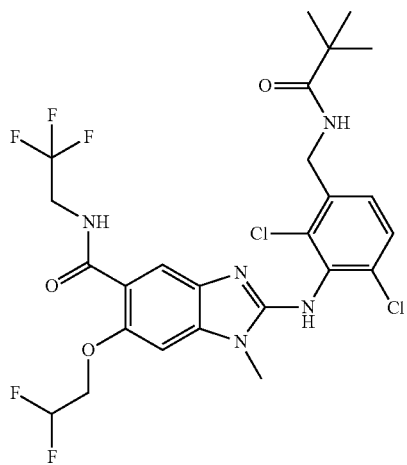 [SMILES: Cn1c(Nc2c(Cl)ccc(CNC(=O)C(C)(C)C)c2Cl)nc2cc(C(=O)NCC(F)(F)F)c(OCC(F)F)cc21] |

-continued
| | Structure |
|---|---|
| 59 | 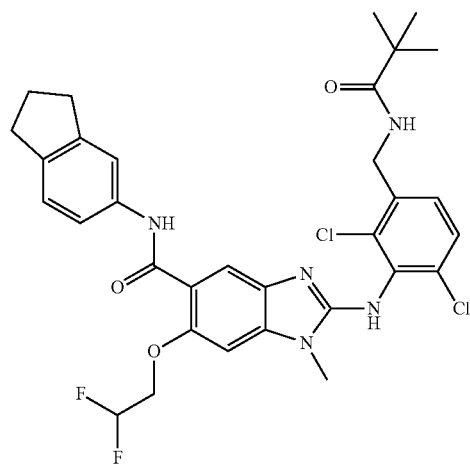 [SMILES: Cn1c(Nc2c(Cl)ccc(CNC(=O)C(C)(C)C)c2Cl)nc2cc(C(=O)Nc3ccc4c(c3)CCC4)c(OCC(F)F)cc21] |
| 60 | 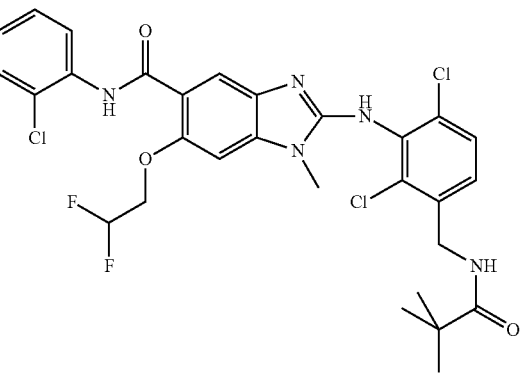 |
| 61 | 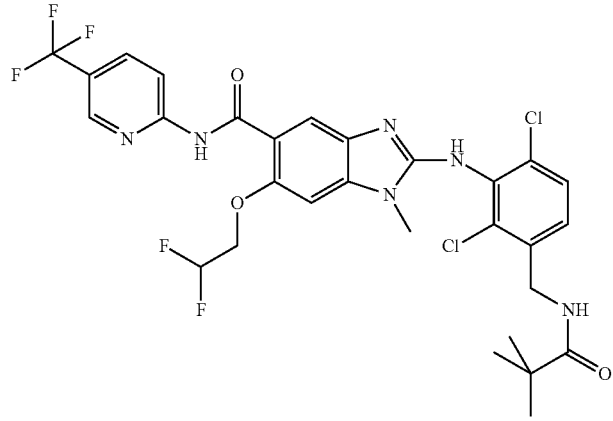 [SMILES: Cn1c(Nc2c(Cl)ccc(CNC(=O)C(C)(C)C)c2Cl)nc2cc(C(=O)Nc3ccc(C(F)(F)F)cn3)c(OCC(F)F)cc21] |

| Structure |
|---|
| 62 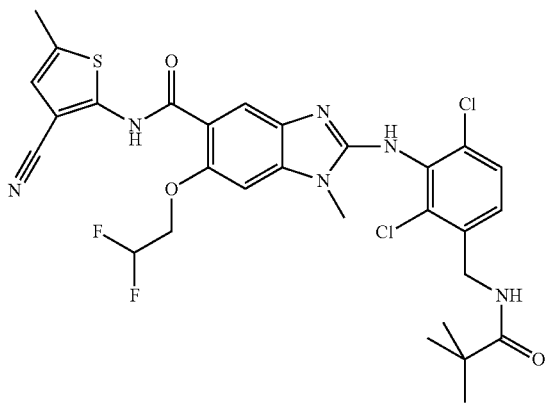 [SMILES: Cc1cc(C#N)c(NC(=O)c2cc3nc(Nc4c(Cl)ccc(CNC(=O)C(C)(C)C)c4Cl)n(C)c3cc2OCC(F)F)s1] |
| 63 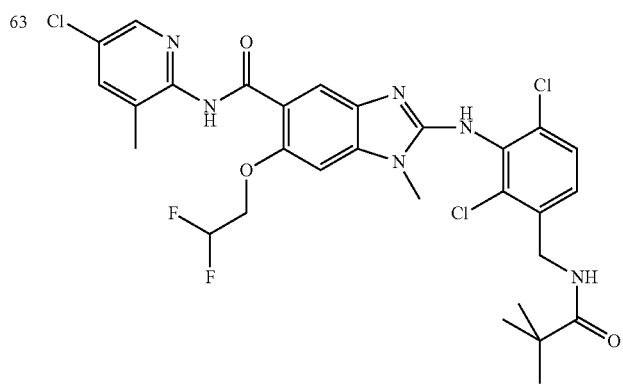 |
| 64 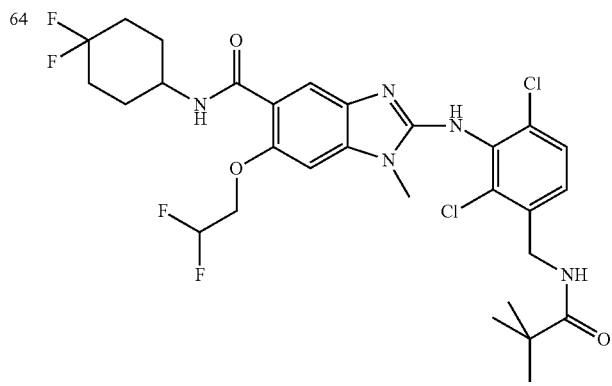 |
| 65 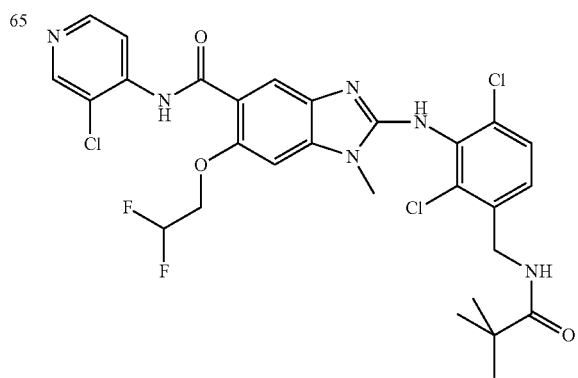 |

-continued
| | Structure |
|---|---|
| 66 | 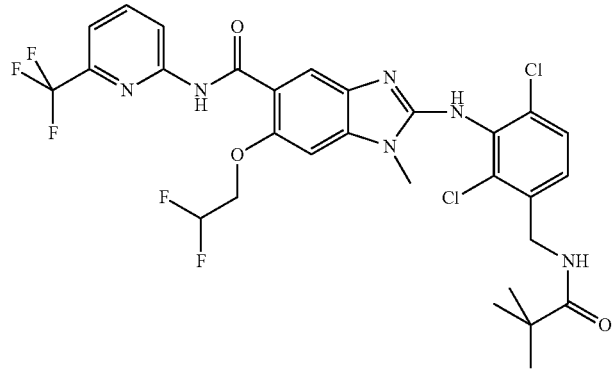 [SMILES: Cn1c(Nc2c(Cl)ccc(CNC(=O)C(C)(C)C)c2Cl)nc2cc(C(=O)Nc3cccc(C(F)(F)F)n3)c(OCC(F)F)cc21] |
| 67 | 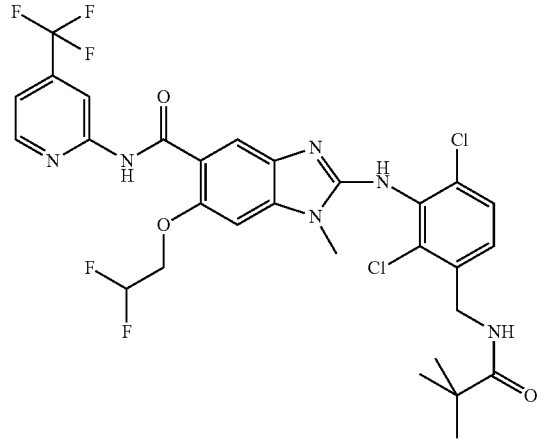 [SMILES: Cn1c(Nc2c(Cl)ccc(CNC(=O)C(C)(C)C)c2Cl)nc2cc(C(=O)Nc3cc(C(F)(F)F)ccn3)c(OCC(F)F)cc21] |
| 68 | 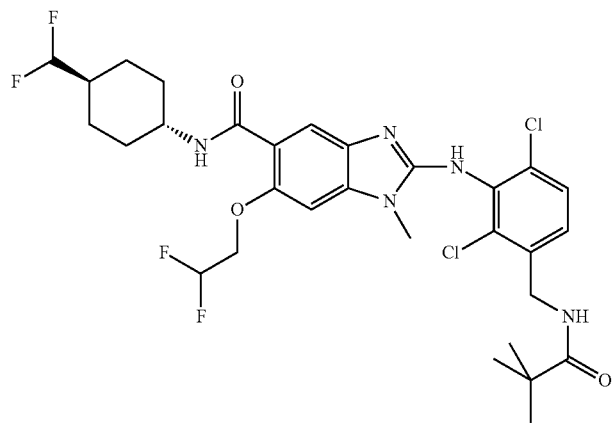 [SMILES: Cn1c(Nc2c(Cl)ccc(CNC(=O)C(C)(C)C)c2Cl)nc2cc(C(=O)N[C@H]3CC[C@H](C(F)F)CC3)c(OCC(F)F)cc21] |
| 69 | 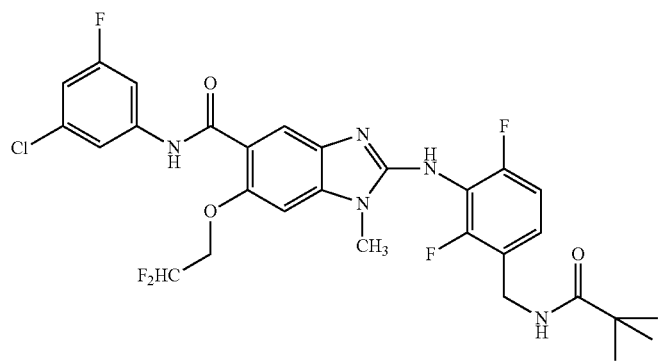 [SMILES: Cn1c(Nc2c(F)ccc(CNC(=O)C(C)(C)C)c2F)nc2cc(C(=O)Nc3cc(F)cc(Cl)c3)c(OCC(F)F)cc21] |

-continued
| | Structure |
|---|---|
| 70 | 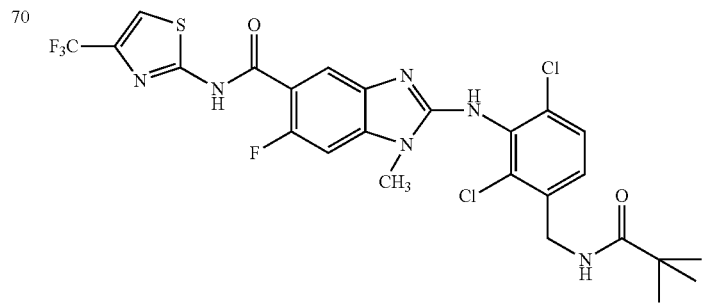 |
| 72 | 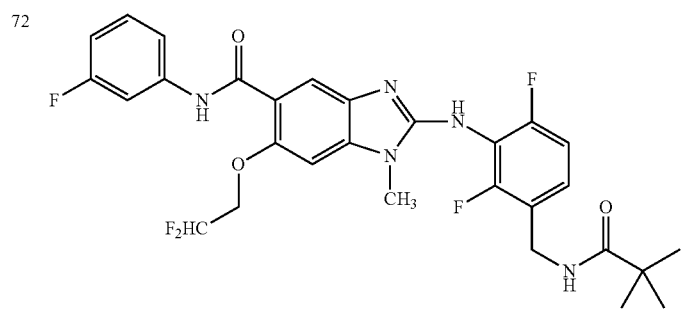 |
| 73 | 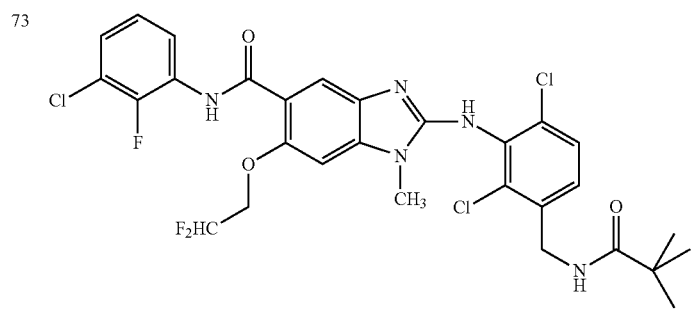 |
| 74 | 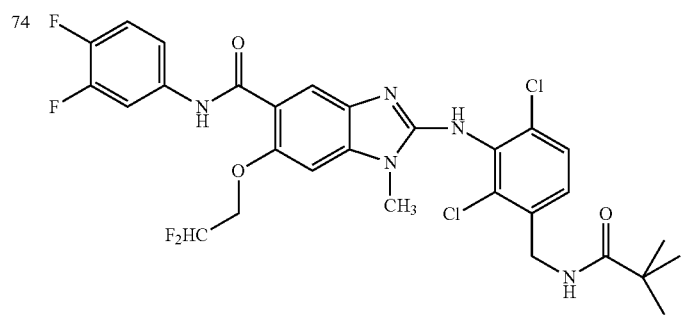 |
| 75 | 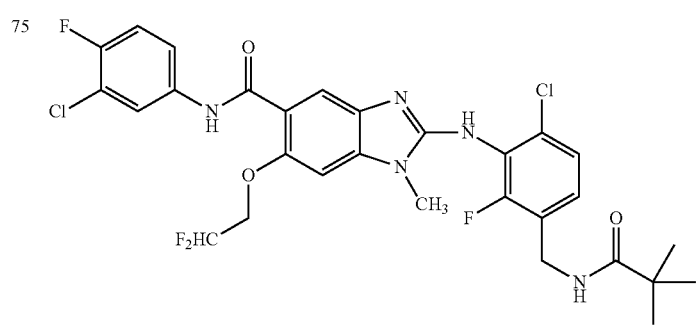 |

| | Structure |
|---|---|
| 76 | 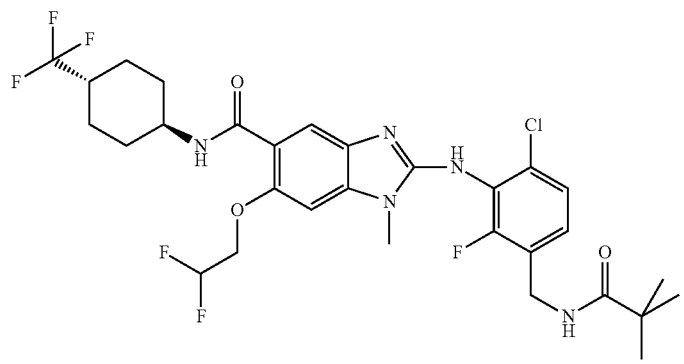 [SMILES: Cn1c(Nc2c(Cl)ccc(CNC(=O)C(C)(C)C)c2F)nc2cc(C(=O)N[C@H]3CC[C@H](C(F)(F)F)CC3)c(OCC(F)F)cc21] |
| 77 | 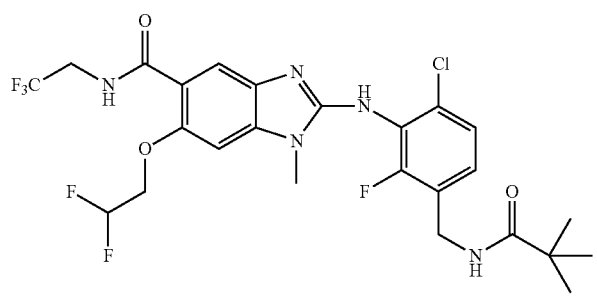 [SMILES: Cn1c(Nc2c(Cl)ccc(CNC(=O)C(C)(C)C)c2F)nc2cc(C(=O)NCC(F)(F)F)c(OCC(F)F)cc21] |
| 78 | 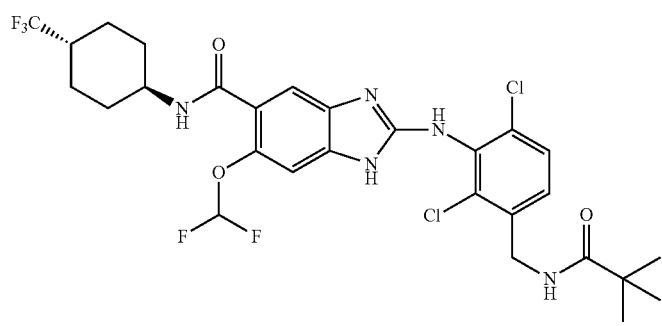 [SMILES: CC(C)(C)C(=O)NCc1ccc(Cl)c(Nc2nc3cc(C(=O)N[C@H]4CC[C@H](C(F)(F)F)CC4)c(OC(F)F)cc3[nH]2)c1Cl] |
| 79 | 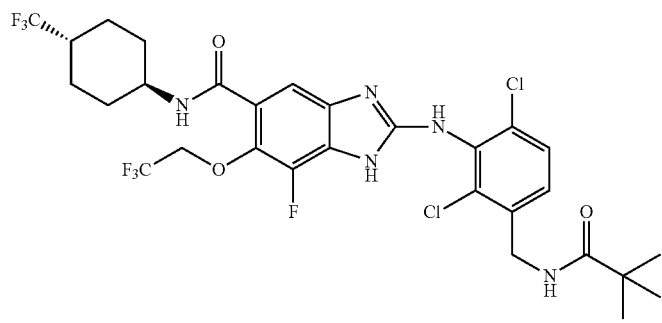 [SMILES: CC(C)(C)C(=O)NCc1ccc(Cl)c(Nc2nc3cc(C(=O)N[C@H]4CC[C@H](C(F)(F)F)CC4)c(OCC(F)(F)F)c(F)c3[nH]2)c1Cl] |

| Structure |
|---|
| 80 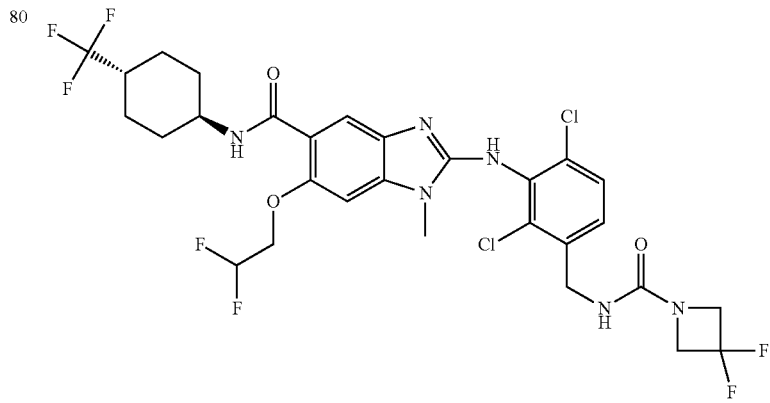 |
| 81 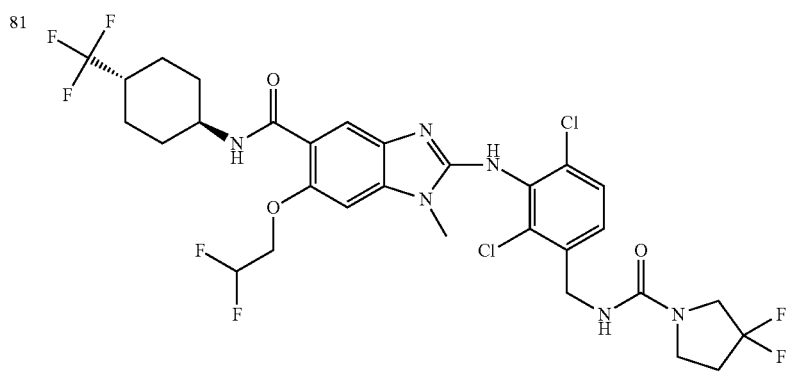 |
| 82 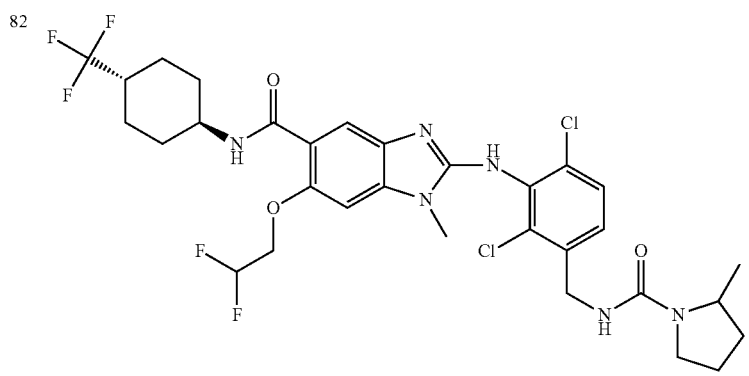 |
| 83 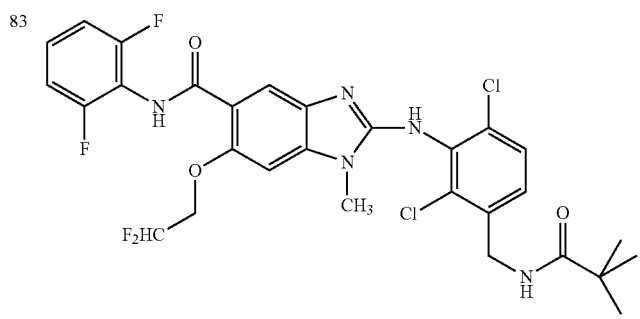 |

| Structure |
|---|
| 84 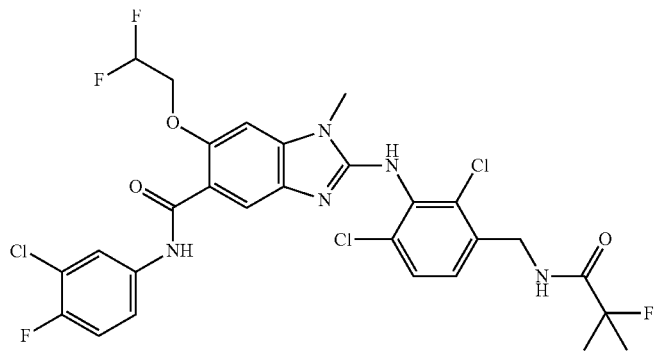 [SMILES: Cn1c(Nc2c(Cl)ccc(CNC(=O)C(C)(C)F)c2Cl)nc2cc(C(=O)Nc3ccc(F)c(Cl)c3)c(OCC(F)F)cc21] |
| 85 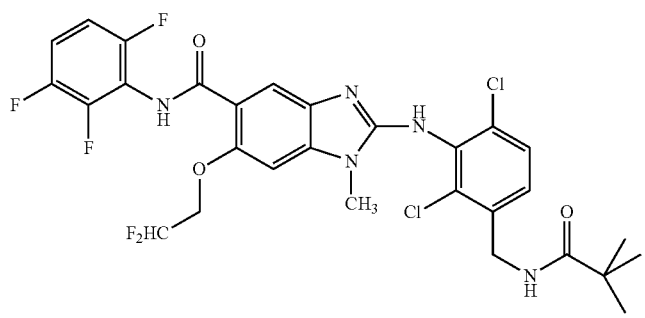 [SMILES: Cn1c(Nc2c(Cl)ccc(CNC(=O)C(C)(C)C)c2Cl)nc2cc(C(=O)Nc3c(F)ccc(F)c3F)c(OCC(F)F)cc21] |
| 86 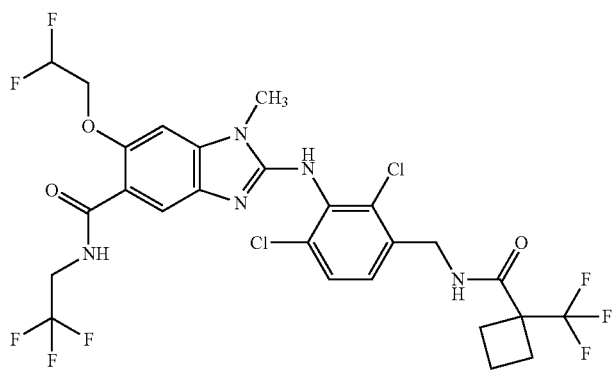 [SMILES: Cn1c(Nc2c(Cl)ccc(CNC(=O)C3(C(F)(F)F)CCC3)c2Cl)nc2cc(C(=O)NCC(F)(F)F)c(OCC(F)F)cc21] |
| 87 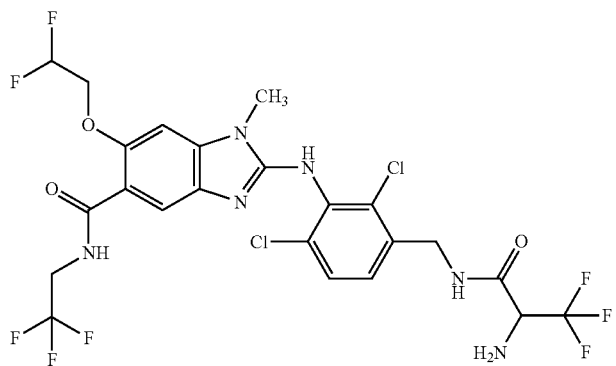 [SMILES: Cn1c(Nc2c(Cl)ccc(CNC(=O)C(N)C(F)(F)F)c2Cl)nc2cc(C(=O)NCC(F)(F)F)c(OCC(F)F)cc21] |

| Structure |
|---|
| 88 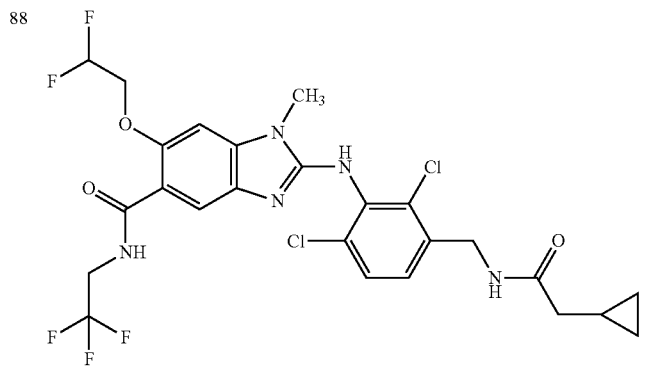 |
| 89 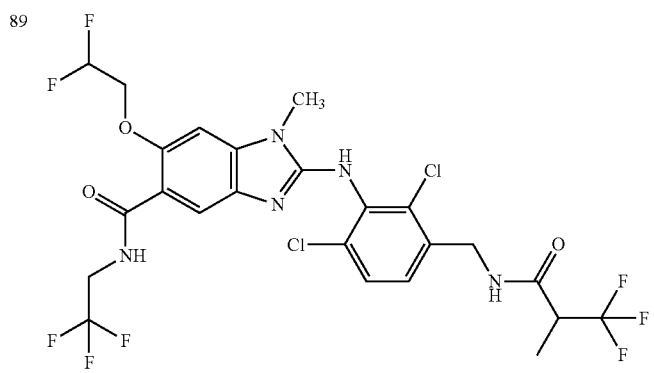 |
| 90 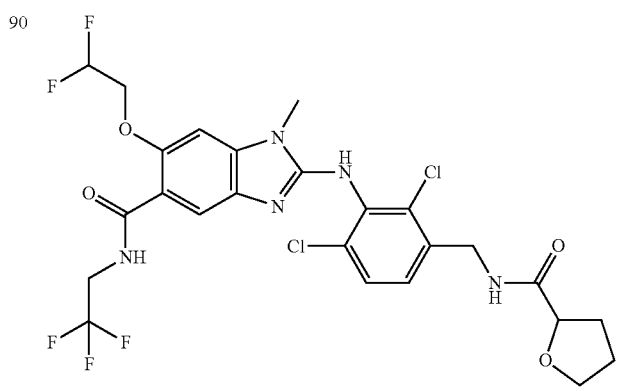 |
| 91 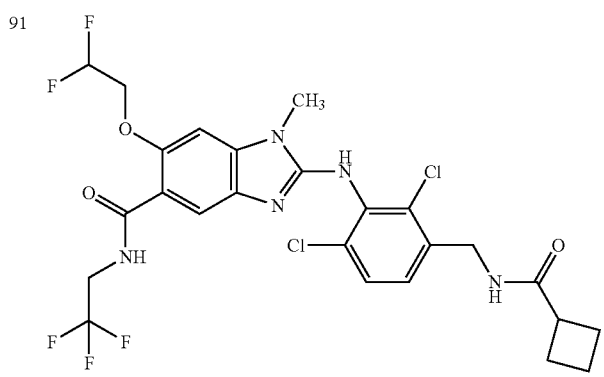 |

-continued
| | Structure |
|---|---|
| 92 | 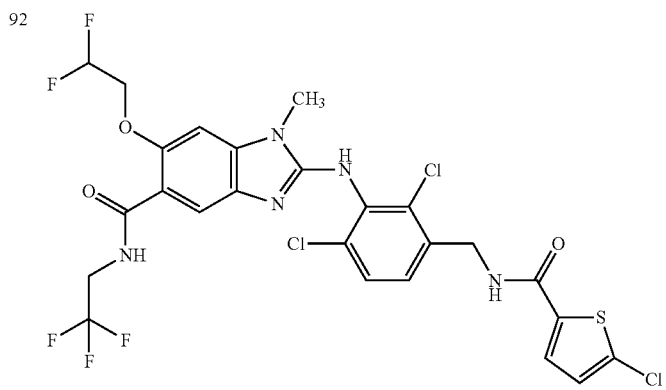 |
| 93 | 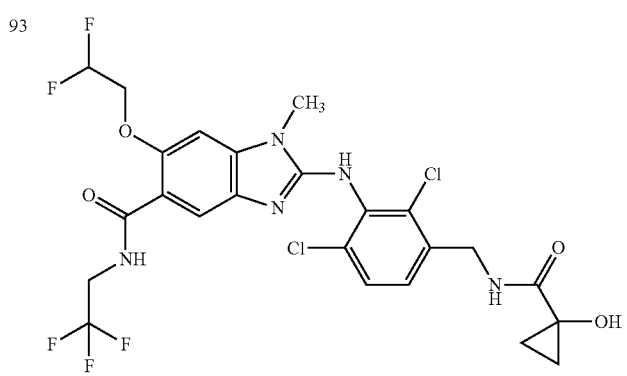 |
| 94 | 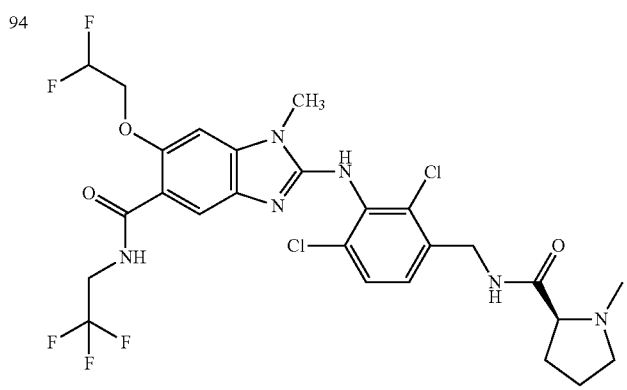 |
| 95 | 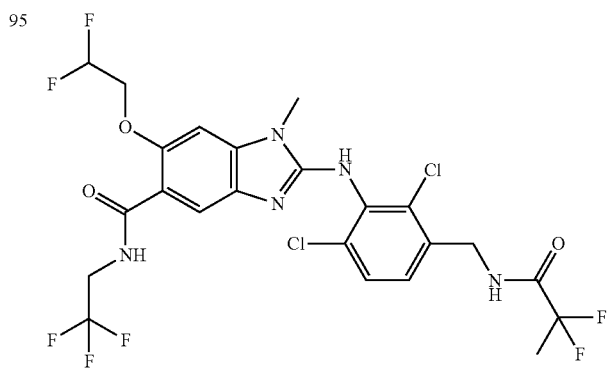 |

-continued
| | Structure |
|---|---|
| 96 | 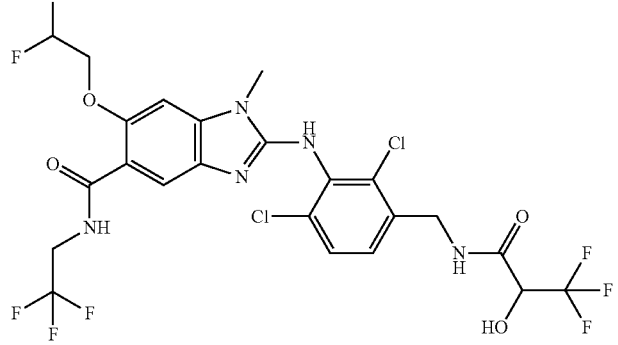 |
| 97 | 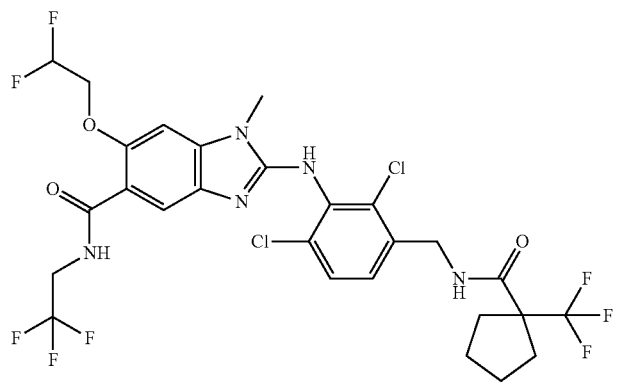 [SMILES: Cn1c(Nc2c(Cl)ccc(CNC(=O)C3(C(F)(F)F)CCCC3)c2Cl)nc2cc(C(=O)NCC(F)(F)F)c(OCC(F)F)cc21] |
| 98 | 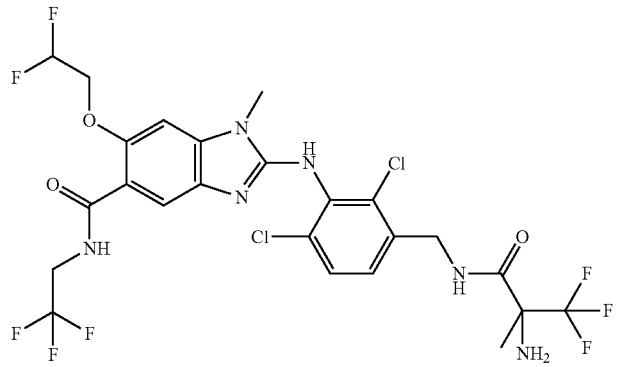 [SMILES: Cn1c(Nc2c(Cl)ccc(CNC(=O)C(C)(N)C(F)(F)F)c2Cl)nc2cc(C(=O)NCC(F)(F)F)c(OCC(F)F)cc21] |
| 99 | 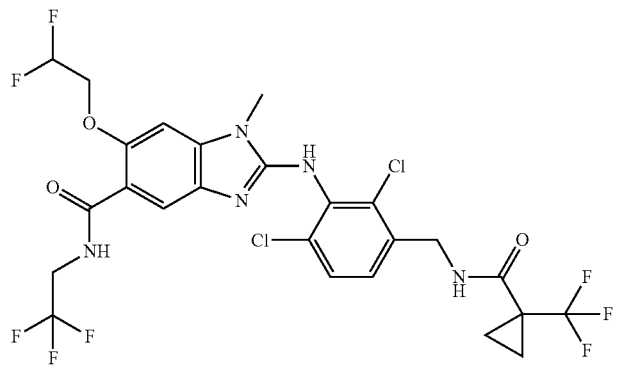 [SMILES: Cn1c(Nc2c(Cl)ccc(CNC(=O)C3(C(F)(F)F)CC3)c2Cl)nc2cc(C(=O)NCC(F)(F)F)c(OCC(F)F)cc21] |

-continued
| Structure |
|---|
| 100 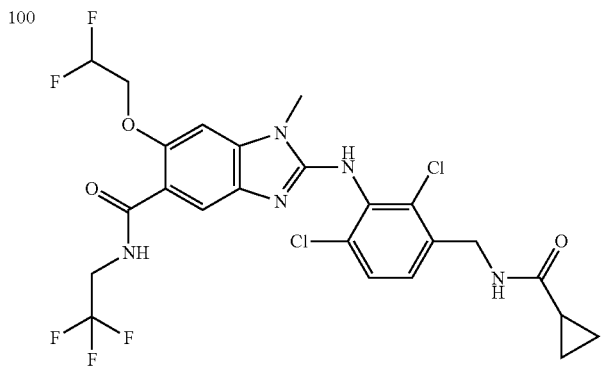 |
| 101 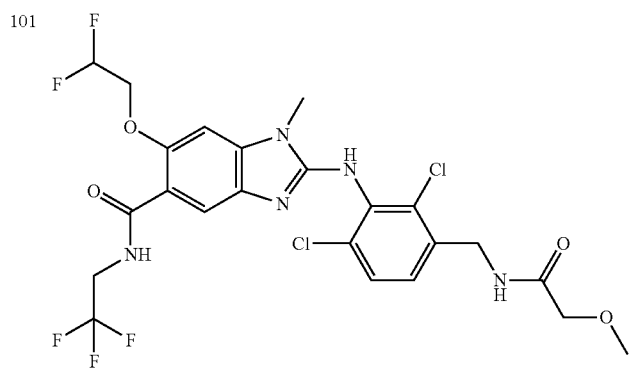 |
| 102 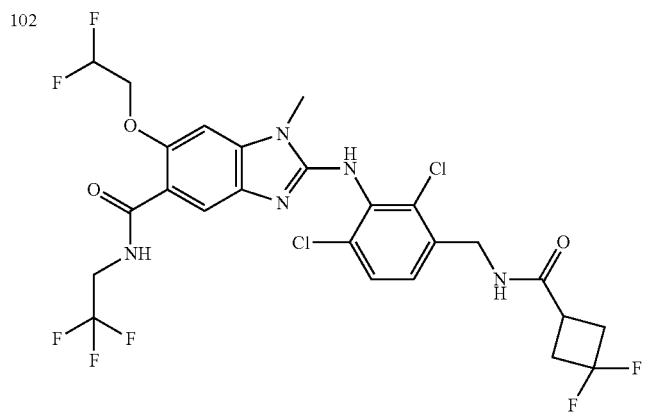 |
| 103 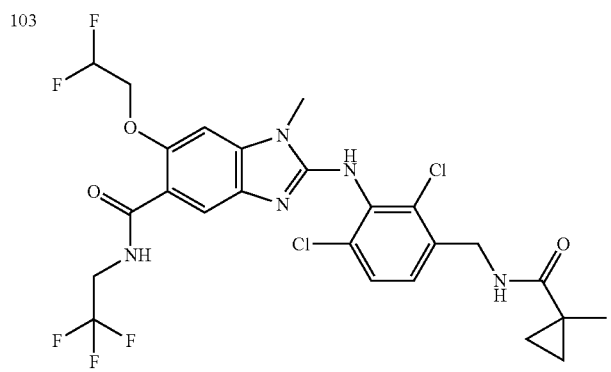 |

| Structure |
|---|
| 104 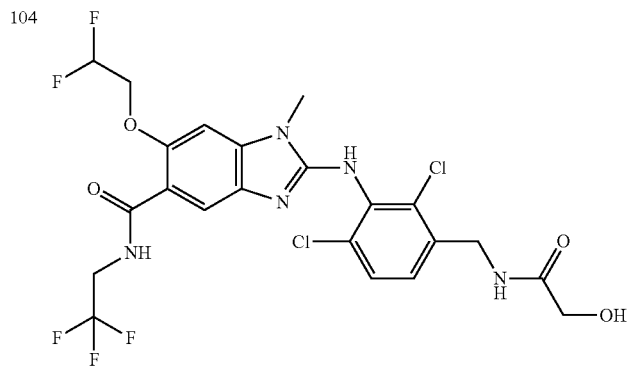 |
| 105 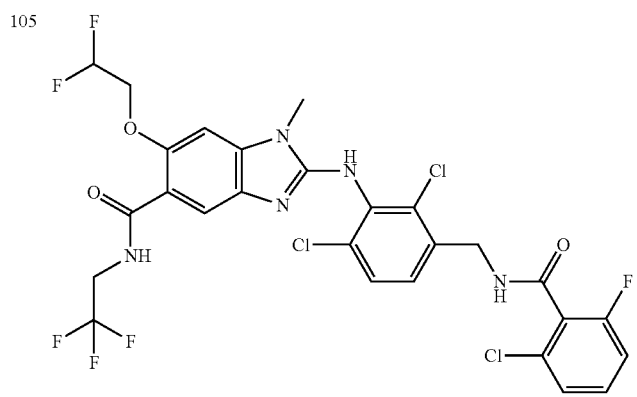 |
| 106 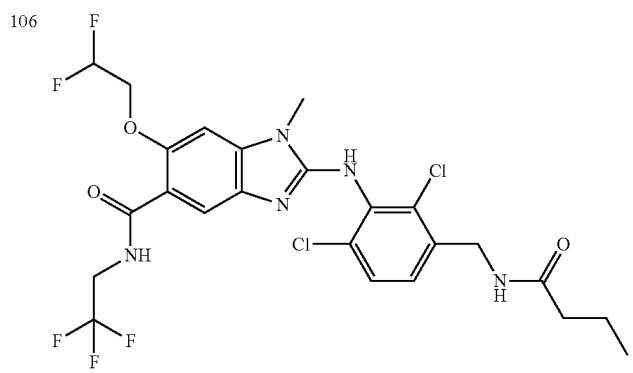 |
| 107 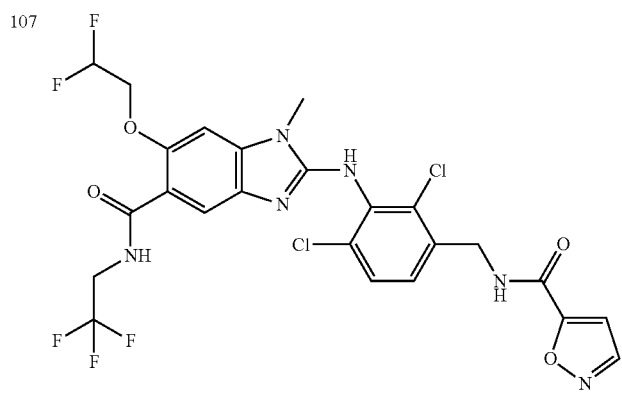 |

-continued
| | Structure |
|---|---|
| 108 | 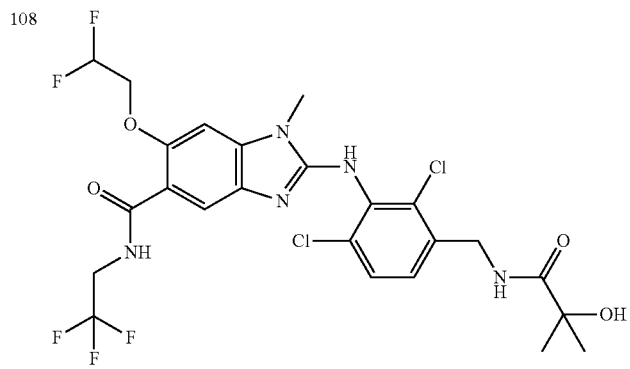 |
| 109 | 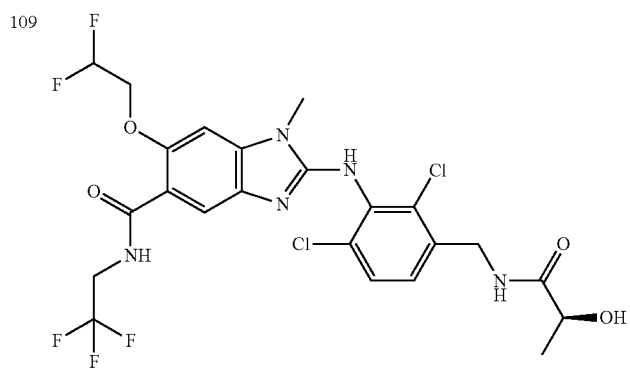 |
| 110 | 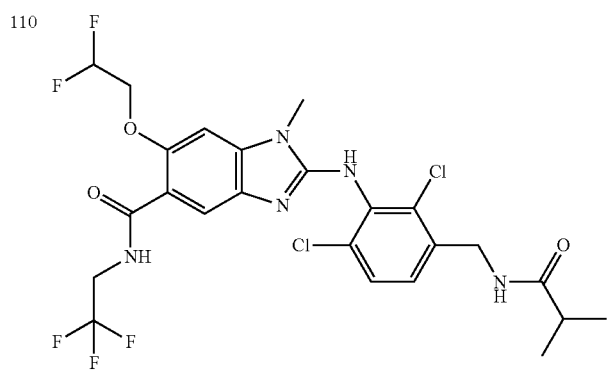 |
| 111 | 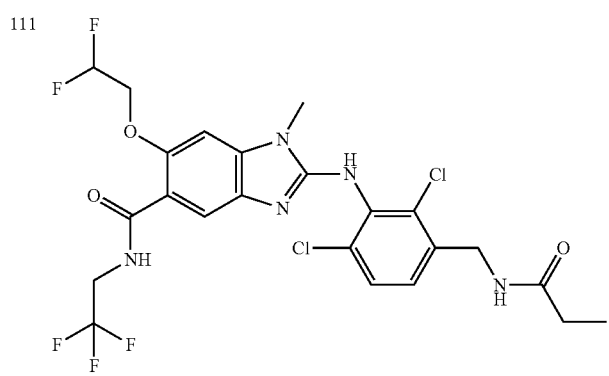 |

| Structure |
|---|
| 112 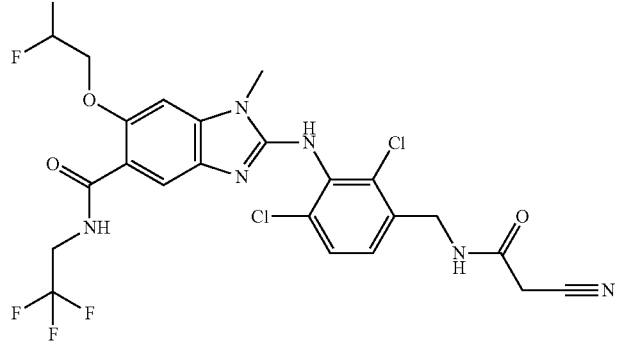 |
| 113 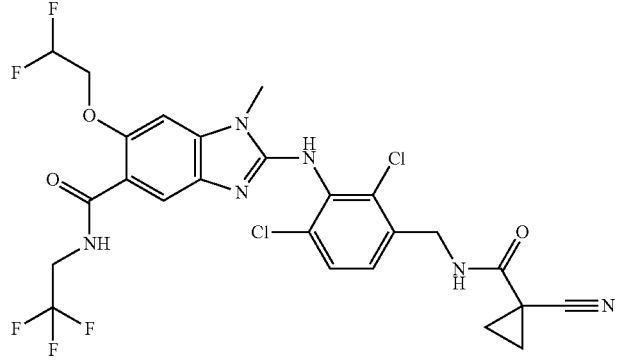 [SMILES: Cn1c(Nc2c(Cl)ccc(CNC(=O)C3(C#N)CC3)c2Cl)nc2cc(C(=O)NCC(F)(F)F)c(OCC(F)F)cc21] |
| 114 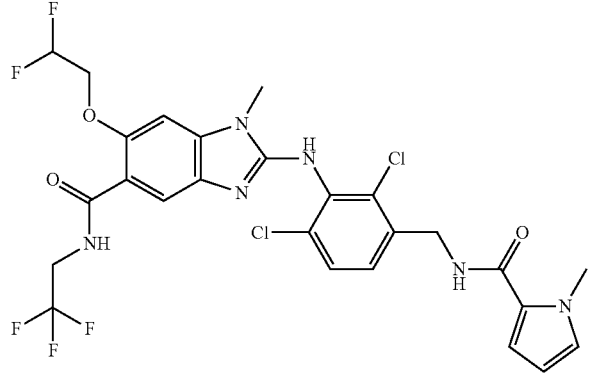 |
| 115 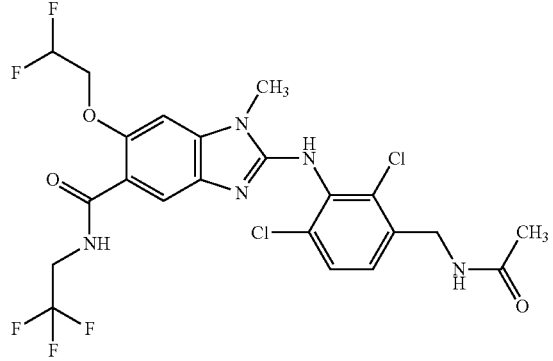 [SMILES: CC(=O)NCc1ccc(Cl)c(Nc2nc3cc(C(=O)NCC(F)(F)F)c(OCC(F)F)cc3n2C)c1Cl] |

| Structure |
|---|
| 116 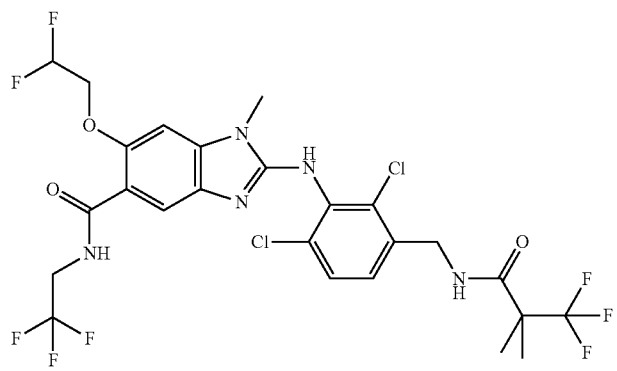 [SMILES: Cn1c(Nc2c(Cl)ccc(CNC(=O)C(C)(C)C(F)(F)F)c2Cl)nc2cc(C(=O)NCC(F)(F)F)c(OCC(F)F)cc21] |
| 117 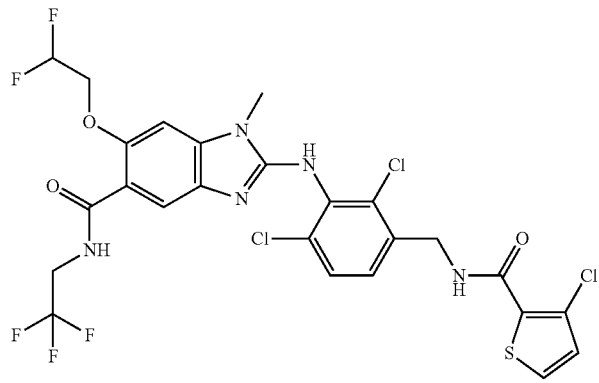 [SMILES: Cn1c(Nc2c(Cl)ccc(CNC(=O)c3sccc3Cl)c2Cl)nc2cc(C(=O)NCC(F)(F)F)c(OCC(F)F)cc21] |
| 118 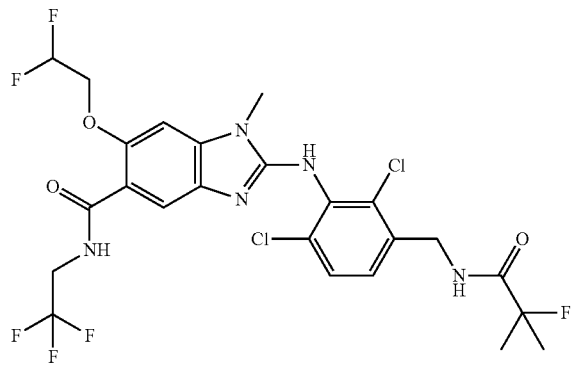 [SMILES: Cn1c(Nc2c(Cl)ccc(CNC(=O)C(C)(C)F)c2Cl)nc2cc(C(=O)NCC(F)(F)F)c(OCC(F)F)cc21] |
| 119 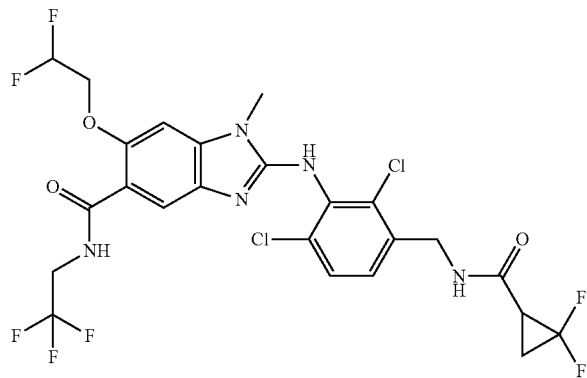 [SMILES: Cn1c(Nc2c(Cl)ccc(CNC(=O)C3CC3(F)F)c2Cl)nc2cc(C(=O)NCC(F)(F)F)c(OCC(F)F)cc21] |

-continued
| | Structure |
|---|---|
| 120 | 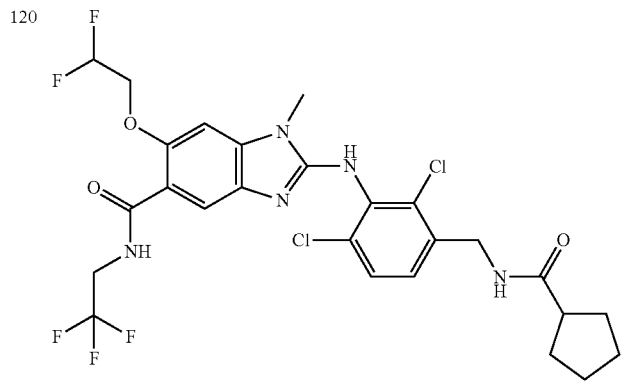 |
| 121 | 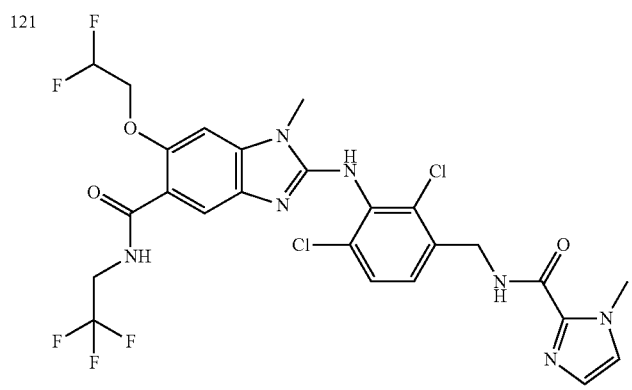 |
| 122 | 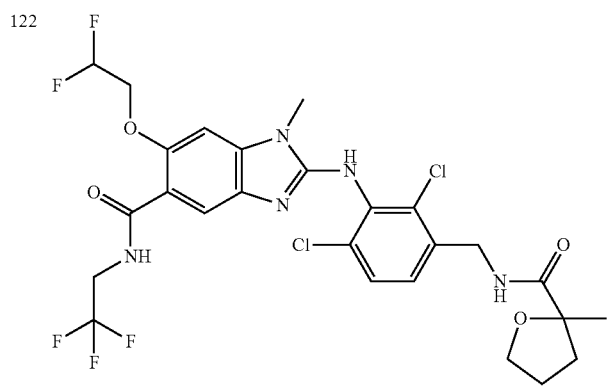 |
| 123 | 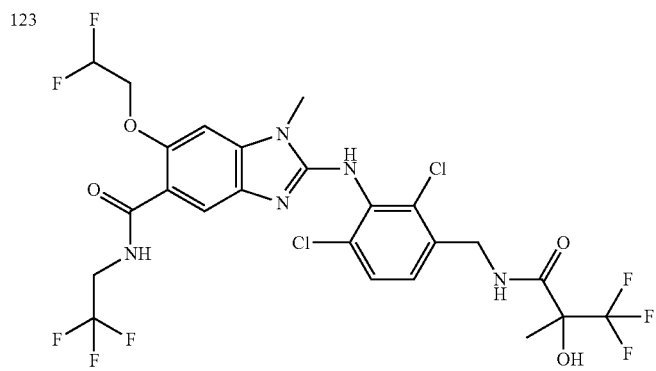 |

-continued
| Structure |
|---|
| 124 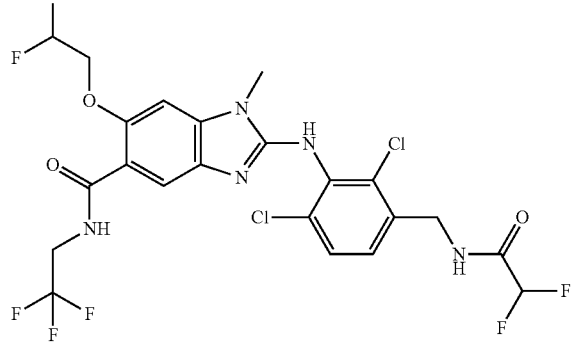 |
| 125 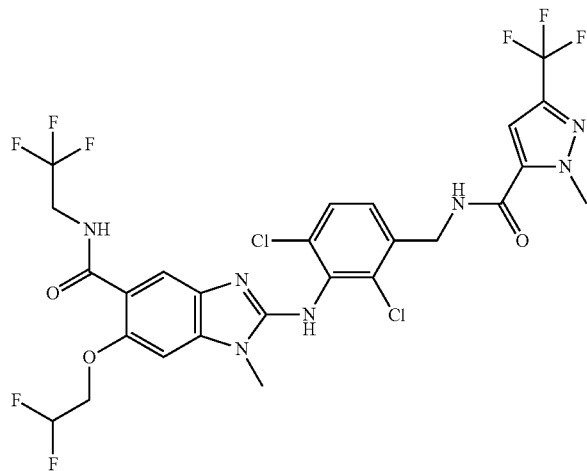 [SMILES: Cn1nc(C(F)(F)F)cc1C(=O)NCc1ccc(Cl)c(Nc2nc3cc(C(=O)NCC(F)(F)F)c(OCC(F)F)cc3n2C)c1Cl] |
| 126 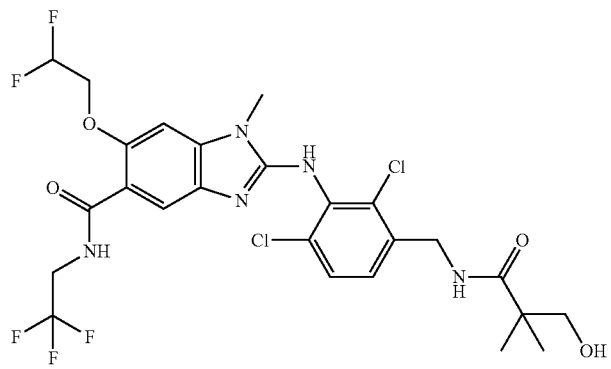 [SMILES: Cn1c(Nc2c(Cl)ccc(CNC(=O)C(C)(C)CO)c2Cl)nc2cc(C(=O)NCC(F)(F)F)c(OCC(F)F)cc21] |
| 127 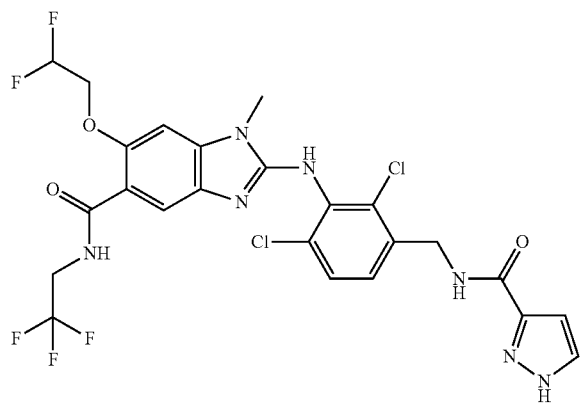 [SMILES: Cn1c(Nc2c(Cl)ccc(CNC(=O)c3cc[nH]n3)c2Cl)nc2cc(C(=O)NCC(F)(F)F)c(OCC(F)F)cc21] |

| Structure |
|---|
| 128 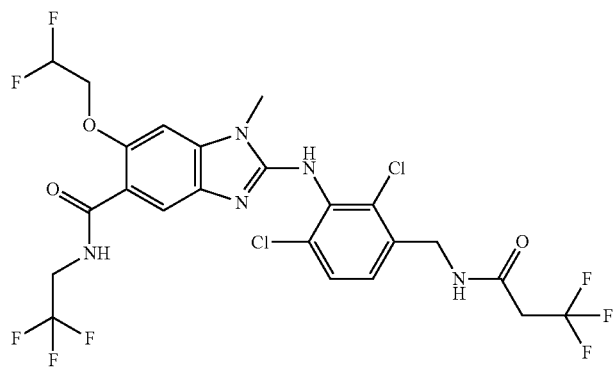 [SMILES: Cn1c(Nc2c(Cl)ccc(CNC(=O)CC(F)(F)F)c2Cl)nc2cc(C(=O)NCC(F)(F)F)c(OCC(F)F)cc21] |
| 129 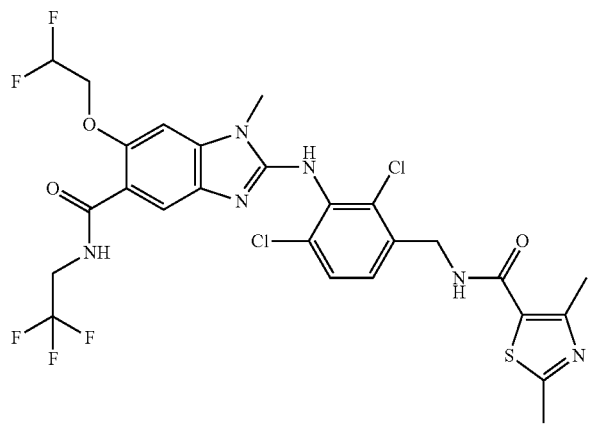 [SMILES: Cc1nc(C)c(C(=O)NCc2ccc(Cl)c(Nc3nc4cc(C(=O)NCC(F)(F)F)c(OCC(F)F)cc4n3C)c2Cl)s1] |
| 130 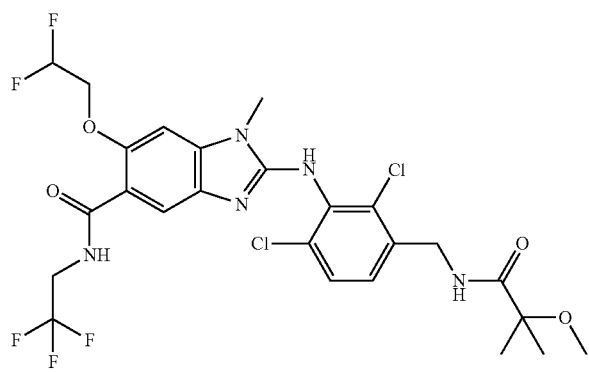 [SMILES: COC(C)(C)C(=O)NCc1ccc(Cl)c(Nc2nc3cc(C(=O)NCC(F)(F)F)c(OCC(F)F)cc3n2C)c1Cl] |
| 131 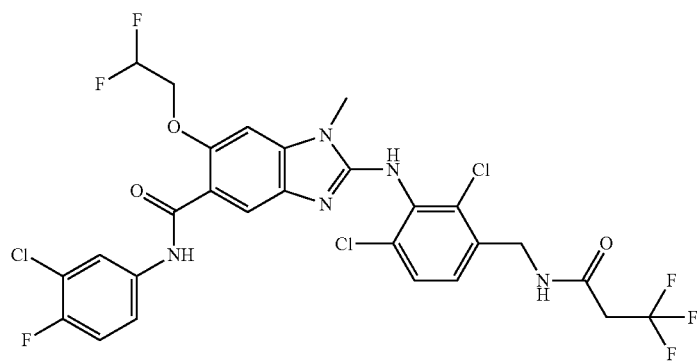 [SMILES: Cn1c(Nc2c(Cl)ccc(CNC(=O)CC(F)(F)F)c2Cl)nc2cc(C(=O)Nc3ccc(F)c(Cl)c3)c(OCC(F)F)cc21] |

| Structure |
|---|
| 132 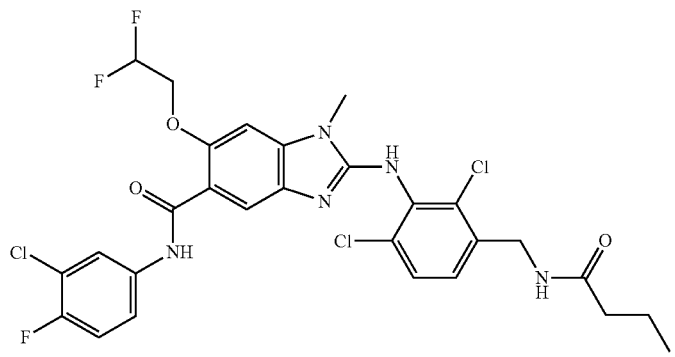 |
| 133 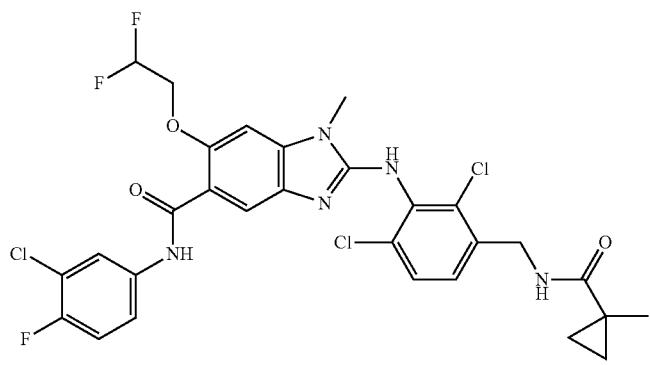 [SMILES: Cn1c(Nc2c(Cl)ccc(CNC(=O)C3(C)CC3)c2Cl)nc2cc(C(=O)Nc3ccc(F)c(Cl)c3)c(OCC(F)F)cc21] |
| 134 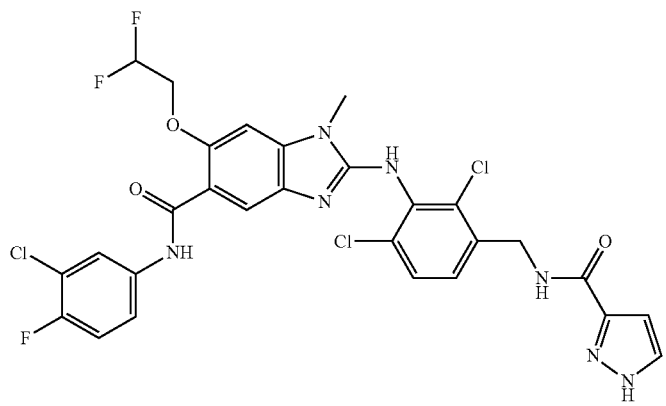 [SMILES: Cn1c(Nc2c(Cl)ccc(CNC(=O)c3cc[nH]n3)c2Cl)nc2cc(C(=O)Nc3ccc(F)c(Cl)c3)c(OCC(F)F)cc21] |
| 135 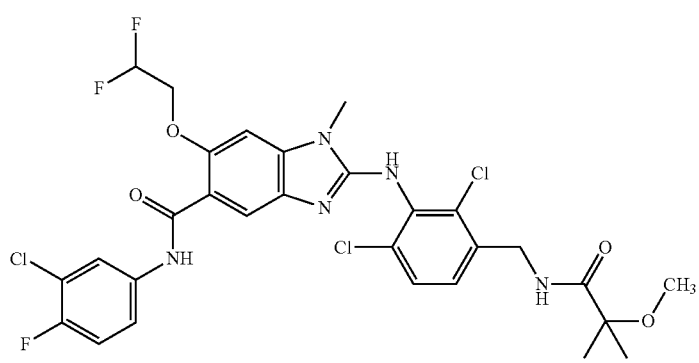 [SMILES: COC(C)(C)C(=O)NCc1ccc(Cl)c(Nc2nc3cc(C(=O)Nc4ccc(F)c(Cl)c4)c(OCC(F)F)cc3n2C)c1Cl] |

| Structure |
| --- |
| 136 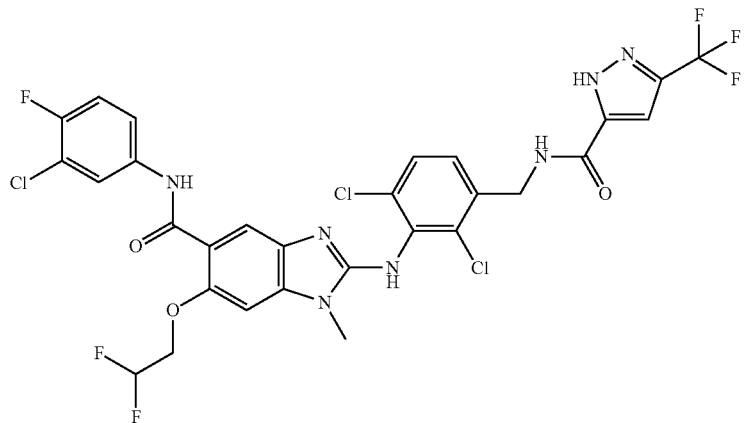 [SMILES: Cn1c(Nc2c(Cl)ccc(CNC(=O)c3cc(C(F)(F)F)n[nH]3)c2Cl)nc2cc(C(=O)Nc3ccc(F)c(Cl)c3)c(OCC(F)F)cc21] |
| 137 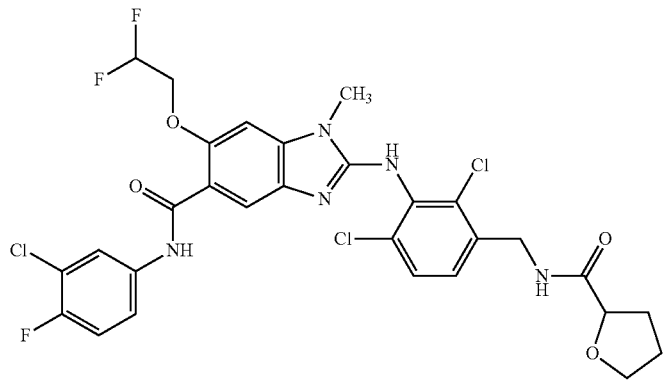 [SMILES: Cn1c(Nc2c(Cl)ccc(CNC(=O)C3CCCO3)c2Cl)nc2cc(C(=O)Nc3ccc(F)c(Cl)c3)c(OCC(F)F)cc21] |
| 138 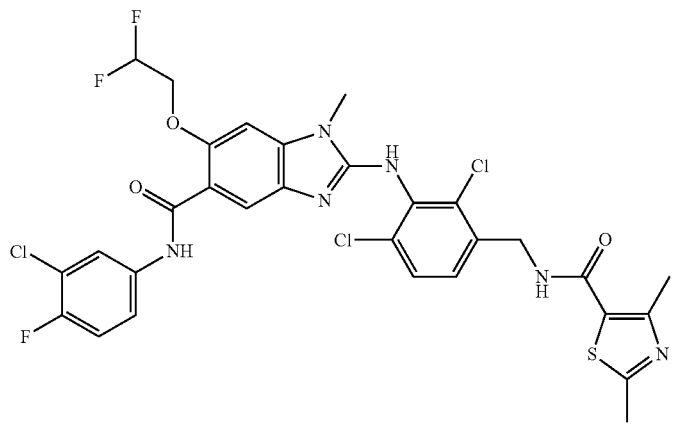 [SMILES: Cc1nc(C)c(C(=O)NCc2ccc(Cl)c(Nc3nc4cc(C(=O)Nc5ccc(F)c(Cl)c5)c(OCC(F)F)cc4n3C)c2Cl)s1] |
| 139 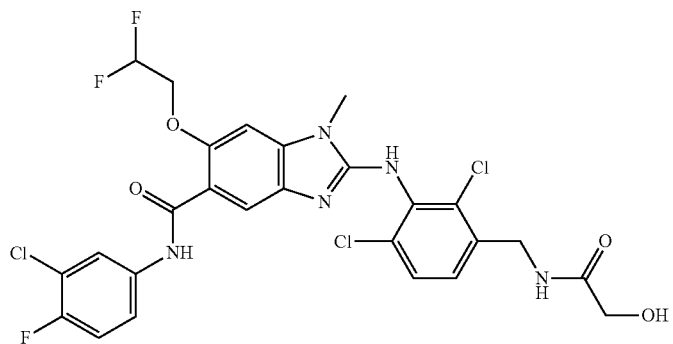 [SMILES: Cn1c(Nc2c(Cl)ccc(CNC(=O)CO)c2Cl)nc2cc(C(=O)Nc3ccc(F)c(Cl)c3)c(OCC(F)F)cc21] |

| | Structure |
|---|---|
| 140 | 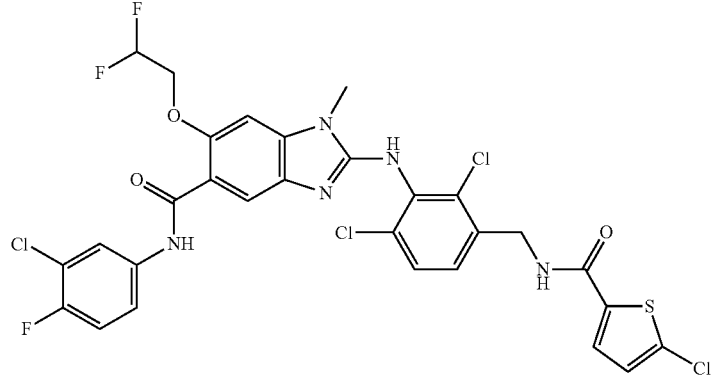 [SMILES: Cn1c(Nc2c(Cl)ccc(CNC(=O)c3ccc(Cl)s3)c2Cl)nc2cc(C(=O)Nc3ccc(F)c(Cl)c3)c(OCC(F)F)cc21] |
| 141 | 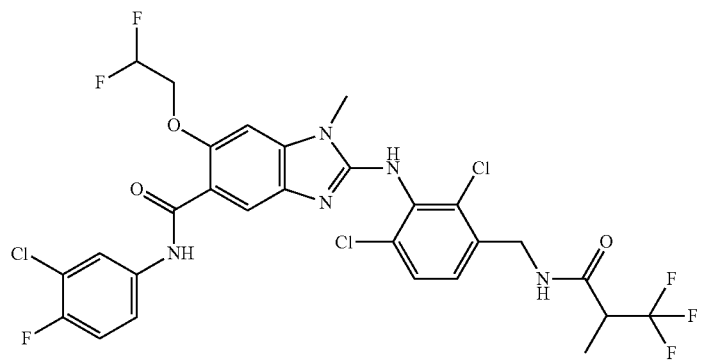 [SMILES: CC(C(=O)NCc1ccc(Cl)c(Nc2nc3cc(C(=O)Nc4ccc(F)c(Cl)c4)c(OCC(F)F)cc3n2C)c1Cl)C(F)(F)F] |
| 142 | 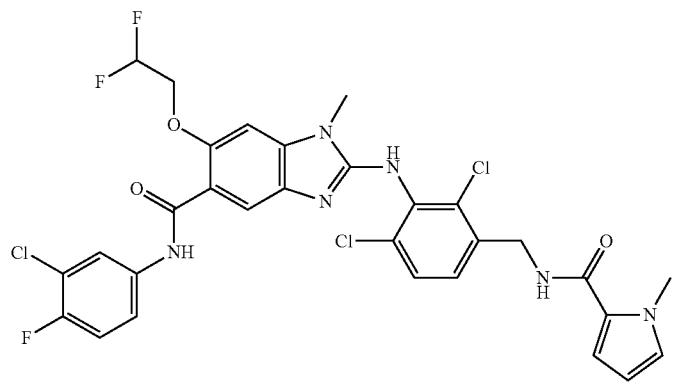 [SMILES: Cn1cccc1C(=O)NCc1ccc(Cl)c(Nc2nc3cc(C(=O)Nc4ccc(F)c(Cl)c4)c(OCC(F)F)cc3n2C)c1Cl] |
| 143 | 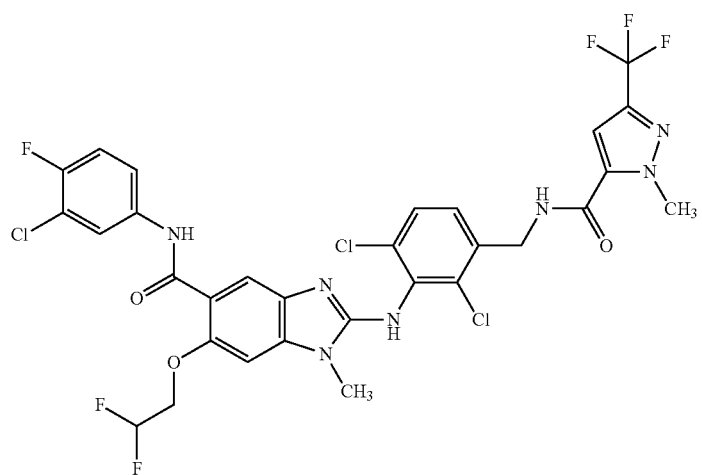 [SMILES: Cn1nc(C(F)(F)F)cc1C(=O)NCc1ccc(Cl)c(Nc2nc3cc(C(=O)Nc4ccc(F)c(Cl)c4)c(OCC(F)F)cc3n2C)c1Cl] |

| Structure |
|---|
| 144 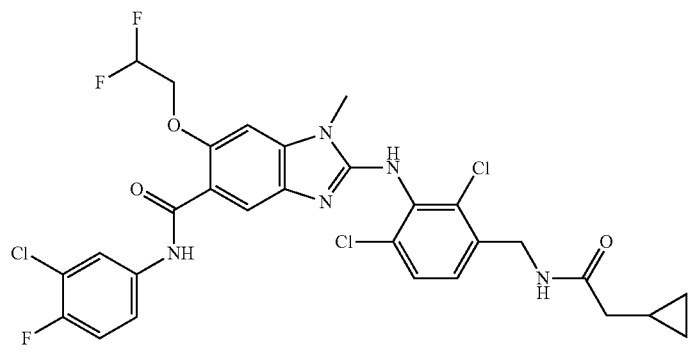 [SMILES: Cn1c(Nc2c(Cl)ccc(CNC(=O)CC3CC3)c2Cl)nc2cc(C(=O)Nc3ccc(F)c(Cl)c3)c(OCC(F)F)cc21] |
| 145 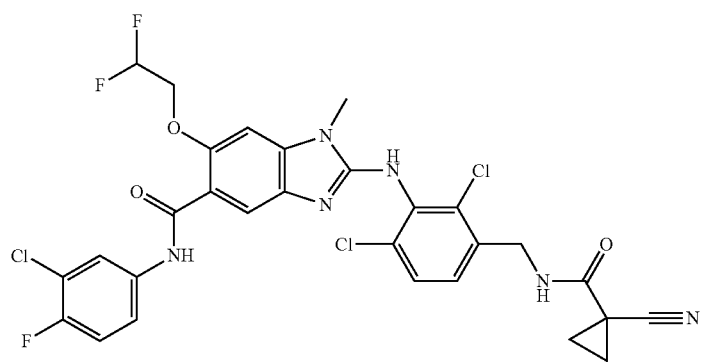 [SMILES: Cn1c(Nc2c(Cl)ccc(CNC(=O)C3(C#N)CC3)c2Cl)nc2cc(C(=O)Nc3ccc(F)c(Cl)c3)c(OCC(F)F)cc21] |
| 146 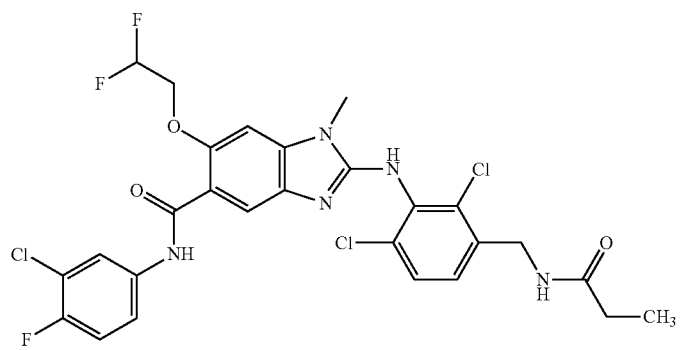 [SMILES: CCC(=O)NCc1ccc(Cl)c(Nc2nc3cc(C(=O)Nc4ccc(F)c(Cl)c4)c(OCC(F)F)cc3n2C)c1Cl] |
| 147 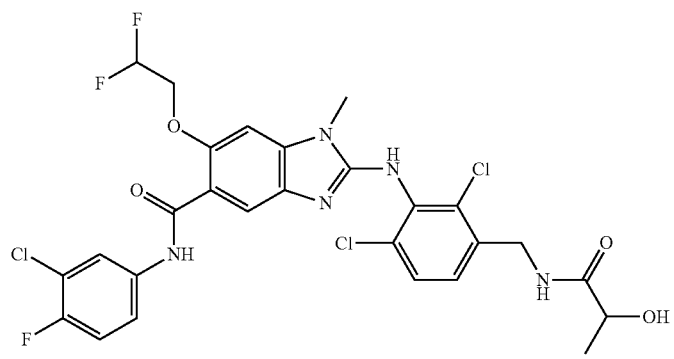 [SMILES: CC(O)C(=O)NCc1ccc(Cl)c(Nc2nc3cc(C(=O)Nc4ccc(F)c(Cl)c4)c(OCC(F)F)cc3n2C)c1Cl] |

| Structure |
|---|
| 148 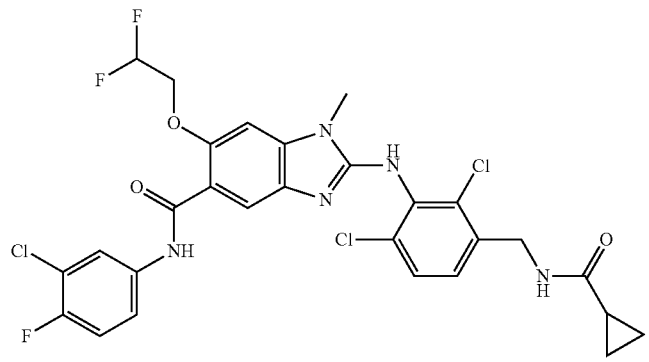 [SMILES: Cn1c(Nc2c(Cl)ccc(CNC(=O)C3CC3)c2Cl)nc2cc(C(=O)Nc3ccc(F)c(Cl)c3)c(OCC(F)F)cc21] |
| 149 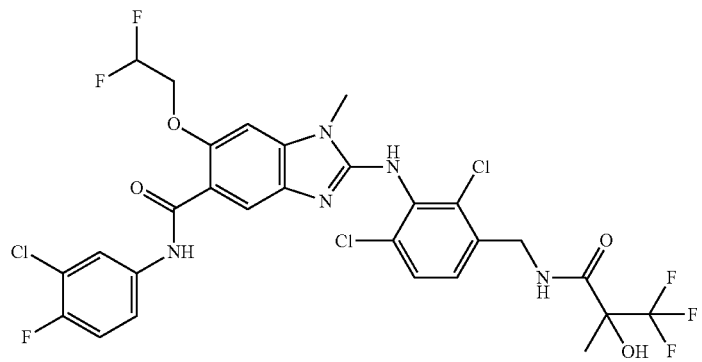 [SMILES: Cn1c(Nc2c(Cl)ccc(CNC(=O)C(C)(O)C(F)(F)F)c2Cl)nc2cc(C(=O)Nc3ccc(F)c(Cl)c3)c(OCC(F)F)cc21] |
| 150 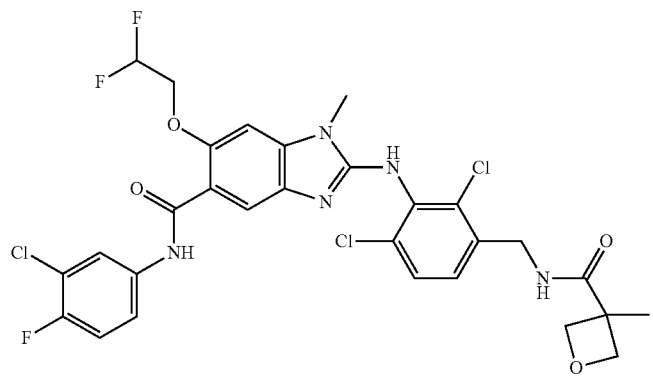 [SMILES: Cn1c(Nc2c(Cl)ccc(CNC(=O)C3(C)COC3)c2Cl)nc2cc(C(=O)Nc3ccc(F)c(Cl)c3)c(OCC(F)F)cc21] |
| 151 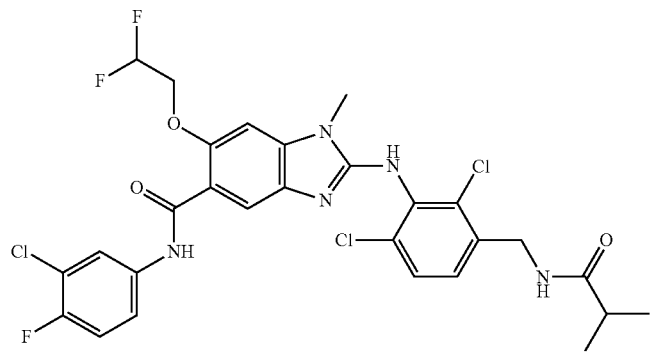 [SMILES: CC(C)C(=O)NCc1ccc(Cl)c(Nc2nc3cc(C(=O)Nc4ccc(F)c(Cl)c4)c(OCC(F)F)cc3n2C)c1Cl] |

-continued
| Structure |
|---|
| 152 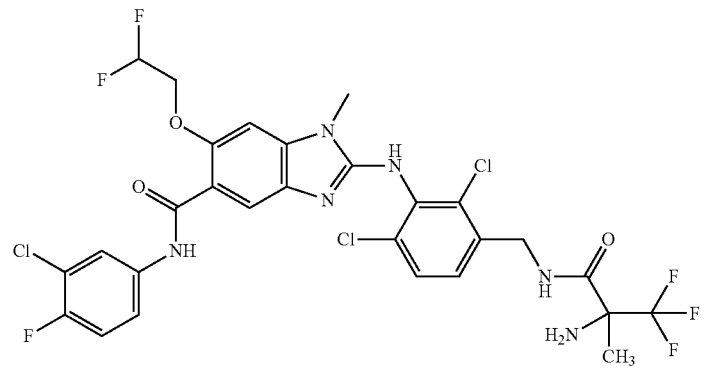 [SMILES: Cn1c(Nc2c(Cl)ccc(CNC(=O)C(C)(N)C(F)(F)F)c2Cl)nc2cc(C(=O)Nc3ccc(F)c(Cl)c3)c(OCC(F)F)cc21] |
| 153 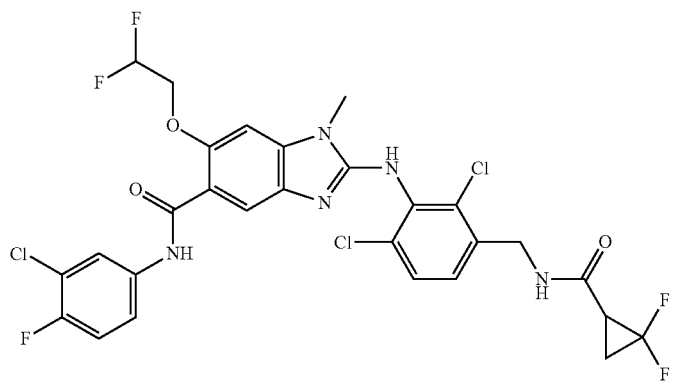 [SMILES: Cn1c(Nc2c(Cl)ccc(CNC(=O)C3CC3(F)F)c2Cl)nc2cc(C(=O)Nc3ccc(F)c(Cl)c3)c(OCC(F)F)cc21] |
| 154 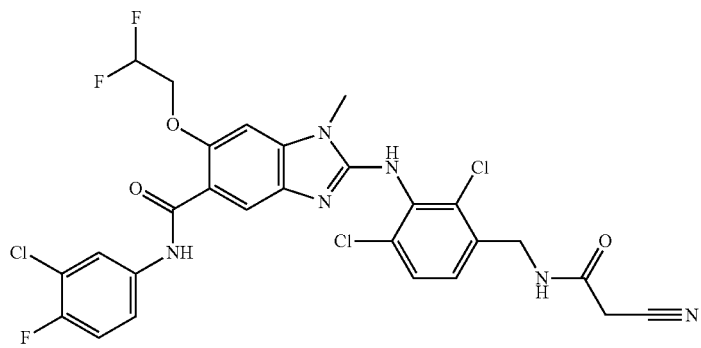 [SMILES: Cn1c(Nc2c(Cl)ccc(CNC(=O)CC#N)c2Cl)nc2cc(C(=O)Nc3ccc(F)c(Cl)c3)c(OCC(F)F)cc21] |
| 155 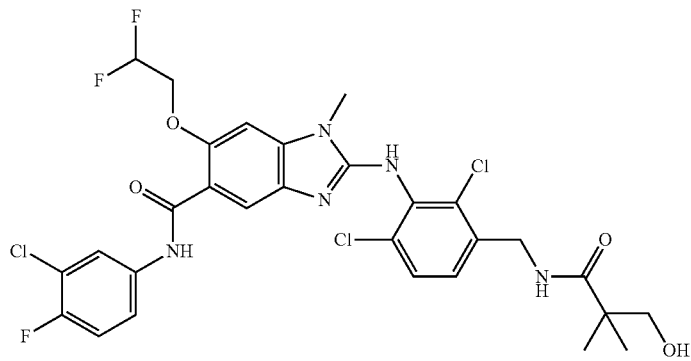 [SMILES: Cn1c(Nc2c(Cl)ccc(CNC(=O)C(C)(C)CO)c2Cl)nc2cc(C(=O)Nc3ccc(F)c(Cl)c3)c(OCC(F)F)cc21] |

| Structure |
|---|
| 156 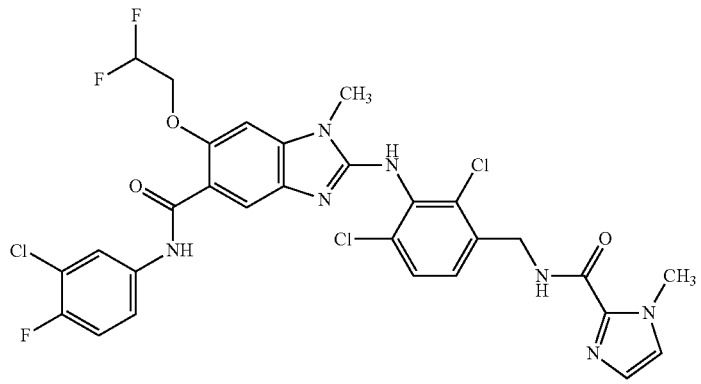 [SMILES: Cn1ccnc1C(=O)NCc1ccc(Cl)c(Nc2nc3cc(C(=O)Nc4ccc(F)c(Cl)c4)c(OCC(F)F)cc3n2C)c1Cl] |
| 157 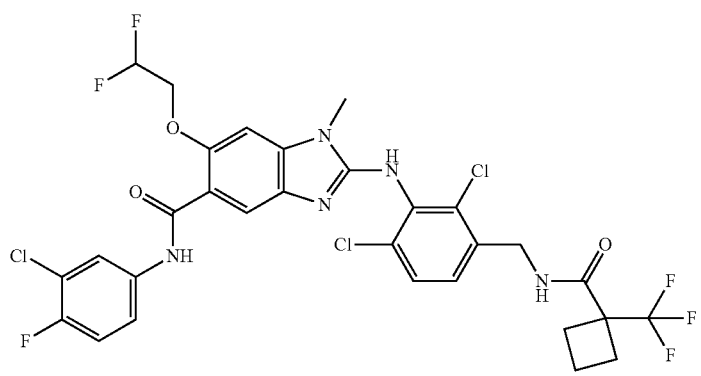 [SMILES: Cn1c(Nc2c(Cl)ccc(CNC(=O)C3(C(F)(F)F)CCC3)c2Cl)nc2cc(C(=O)Nc3ccc(F)c(Cl)c3)c(OCC(F)F)cc21] |
| 158 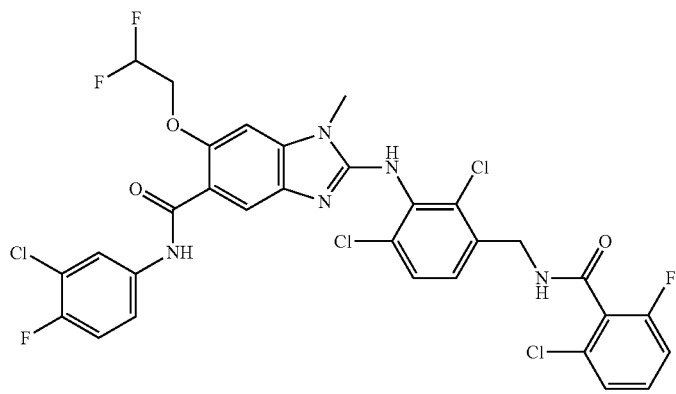 [SMILES: Cn1c(Nc2c(Cl)ccc(CNC(=O)c3c(F)cccc3Cl)c2Cl)nc2cc(C(=O)Nc3ccc(F)c(Cl)c3)c(OCC(F)F)cc21] |
| 159 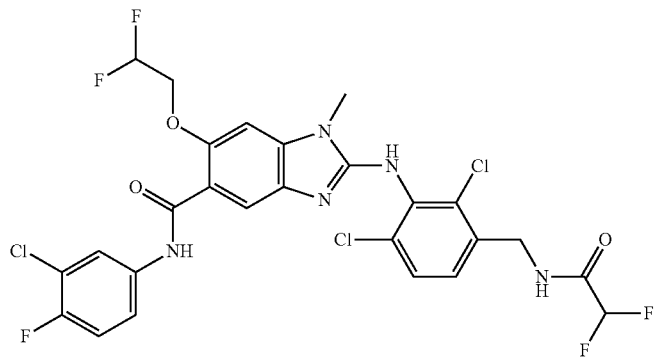 [SMILES: Cn1c(Nc2c(Cl)ccc(CNC(=O)C(F)F)c2Cl)nc2cc(C(=O)Nc3ccc(F)c(Cl)c3)c(OCC(F)F)cc21] |

| Structure |
|---|
| 160 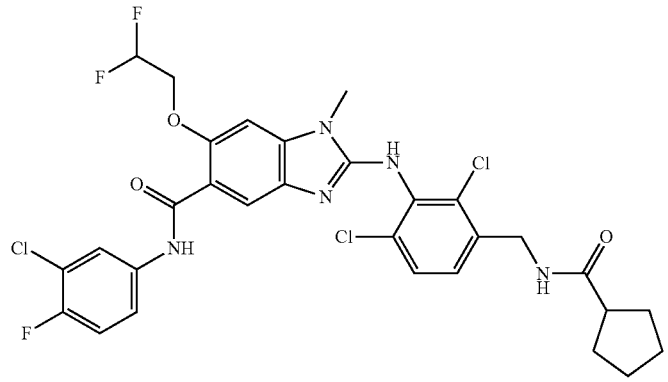 [SMILES: Cn1c(Nc2c(Cl)ccc(CNC(=O)C3CCCC3)c2Cl)nc2cc(C(=O)Nc3ccc(F)c(Cl)c3)c(OCC(F)F)cc21] |
| 161 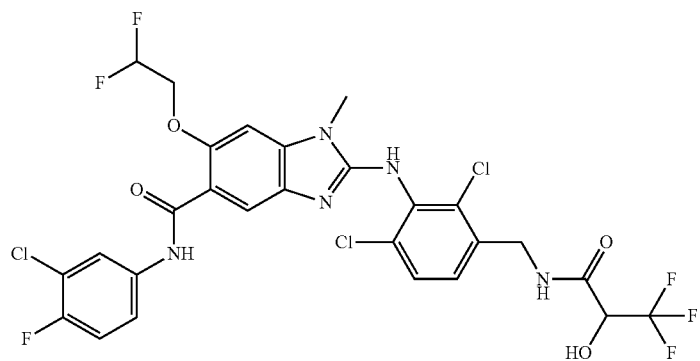 [SMILES: Cn1c(Nc2c(Cl)ccc(CNC(=O)C(O)C(F)(F)F)c2Cl)nc2cc(C(=O)Nc3ccc(F)c(Cl)c3)c(OCC(F)F)cc21] |
| 162 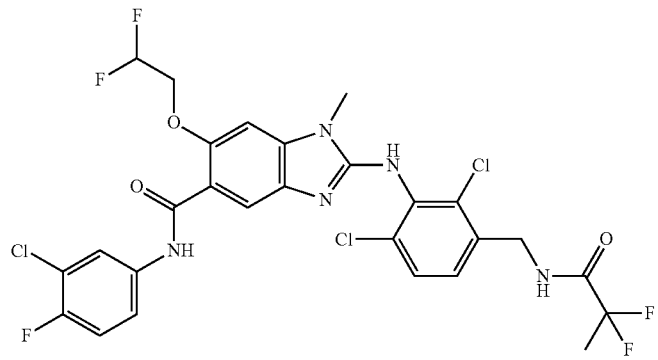 [SMILES: Cn1c(Nc2c(Cl)ccc(CNC(=O)C(C)(F)F)c2Cl)nc2cc(C(=O)Nc3ccc(F)c(Cl)c3)c(OCC(F)F)cc21] |
| 163 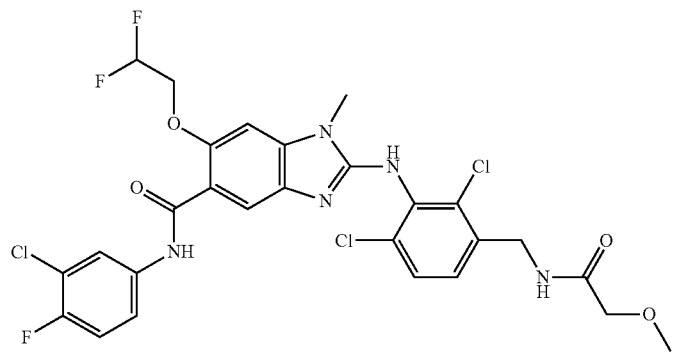 [SMILES: COCC(=O)NCc1ccc(Cl)c(Nc2nc3cc(C(=O)Nc4ccc(F)c(Cl)c4)c(OCC(F)F)cc3n2C)c1Cl] |

| Structure |
|---|
| 164 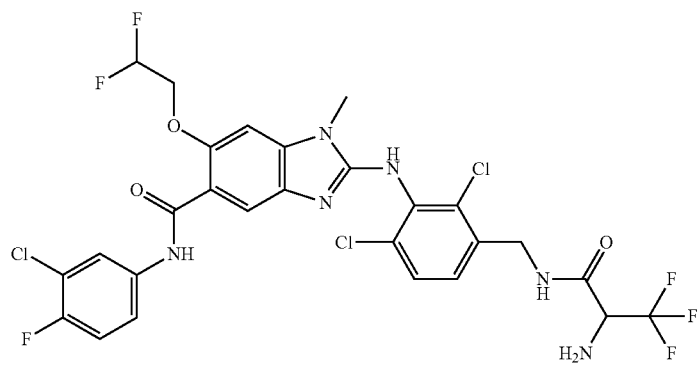 [SMILES: Cn1c(Nc2c(Cl)ccc(CNC(=O)C(N)C(F)(F)F)c2Cl)nc2cc(C(=O)Nc3ccc(F)c(Cl)c3)c(OCC(F)F)cc21] |
| 165 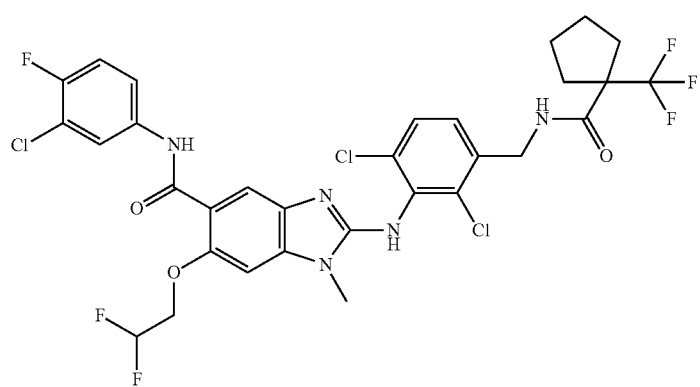 [SMILES: Cn1c(Nc2c(Cl)ccc(CNC(=O)C3(C(F)(F)F)CCCC3)c2Cl)nc2cc(C(=O)Nc3ccc(F)c(Cl)c3)c(OCC(F)F)cc21] |
| 166 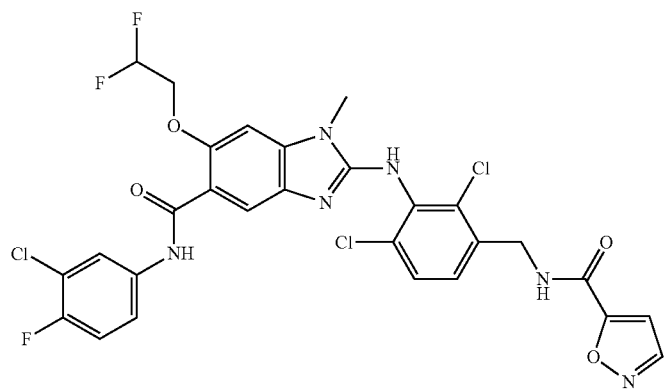 [SMILES: Cn1c(Nc2c(Cl)ccc(CNC(=O)c3ccno3)c2Cl)nc2cc(C(=O)Nc3ccc(F)c(Cl)c3)c(OCC(F)F)cc21] |
| 167 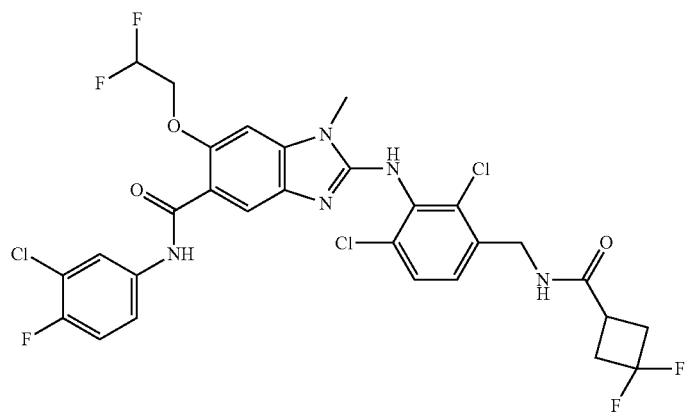 [SMILES: Cn1c(Nc2c(Cl)ccc(CNC(=O)C3CC(F)(F)C3)c2Cl)nc2cc(C(=O)Nc3ccc(F)c(Cl)c3)c(OCC(F)F)cc21] |

-continued
| | Structure |
|---|---|
| 168 | 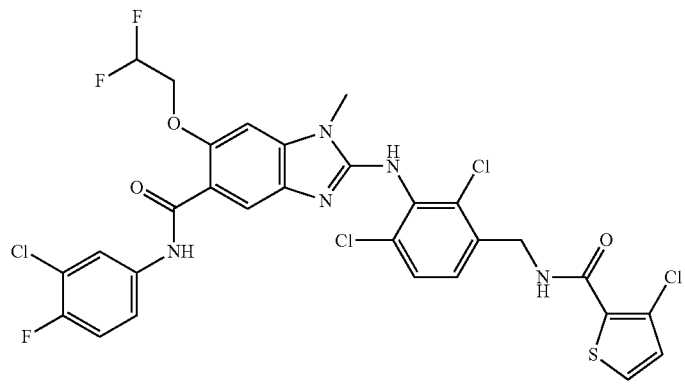 [SMILES: Cn1c(Nc2c(Cl)ccc(CNC(=O)c3sccc3Cl)c2Cl)nc2cc(C(=O)Nc3ccc(F)c(Cl)c3)c(OCC(F)F)cc21] |
| 169 | 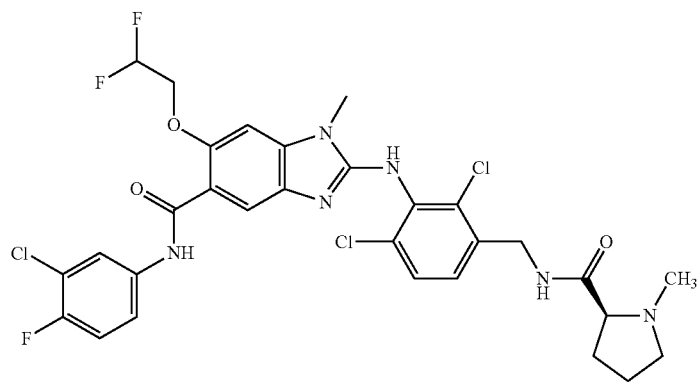 [SMILES: CN1CCC[C@H]1C(=O)NCc1ccc(Cl)c(Nc2nc3cc(C(=O)Nc4ccc(F)c(Cl)c4)c(OCC(F)F)cc3n2C)c1Cl] |
| 170 | 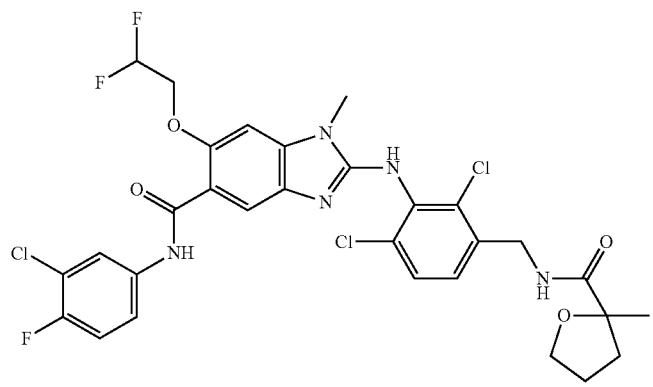 [SMILES: Cn1c(Nc2c(Cl)ccc(CNC(=O)C3(C)CCCO3)c2Cl)nc2cc(C(=O)Nc3ccc(F)c(Cl)c3)c(OCC(F)F)cc21] |
| 171 | 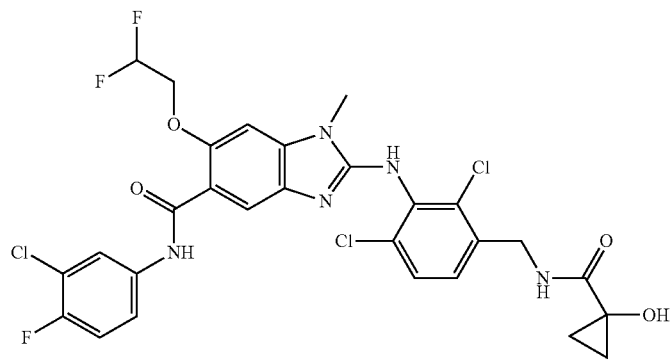 [SMILES: Cn1c(Nc2c(Cl)ccc(CNC(=O)C3(O)CC3)c2Cl)nc2cc(C(=O)Nc3ccc(F)c(Cl)c3)c(OCC(F)F)cc21] |

-continued
| Structure |
|---|
| 172 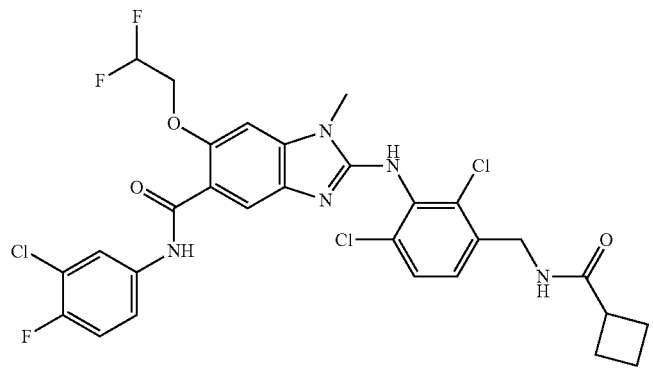 [SMILES: Cn1c(Nc2c(Cl)ccc(CNC(=O)C3CCC3)c2Cl)nc2cc(C(=O)Nc3ccc(F)c(Cl)c3)c(OCC(F)F)cc21] |
| 173 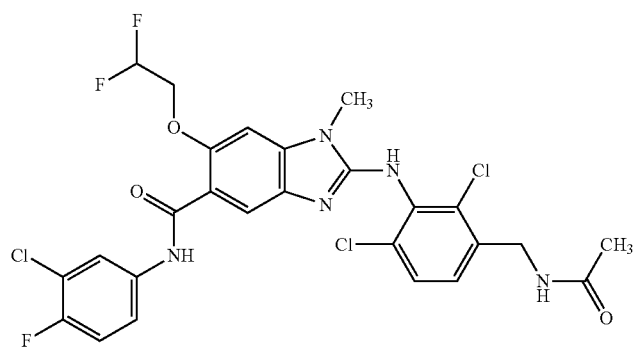 [SMILES: CC(=O)NCc1ccc(Cl)c(Nc2nc3cc(C(=O)Nc4ccc(F)c(Cl)c4)c(OCC(F)F)cc3n2C)c1Cl] |
| 174 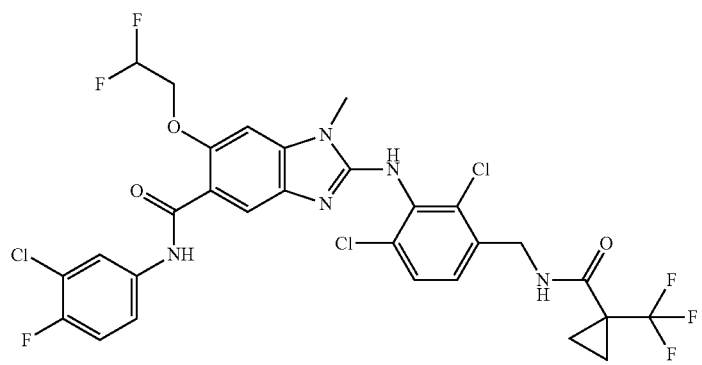 [SMILES: Cn1c(Nc2c(Cl)ccc(CNC(=O)C3(C(F)(F)F)CC3)c2Cl)nc2cc(C(=O)Nc3ccc(F)c(Cl)c3)c(OCC(F)F)cc21] |
| 175 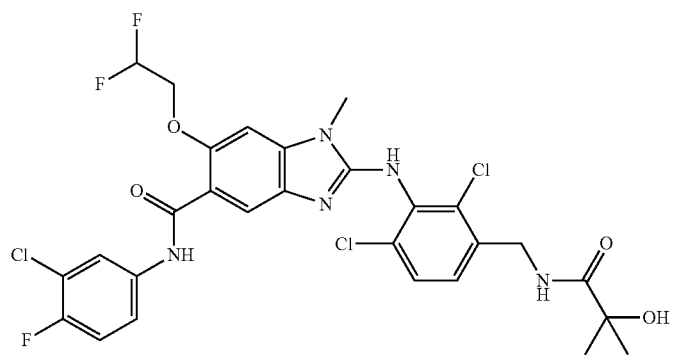 [SMILES: Cn1c(Nc2c(Cl)ccc(CNC(=O)C(C)(C)O)c2Cl)nc2cc(C(=O)Nc3ccc(F)c(Cl)c3)c(OCC(F)F)cc21] |

| Structure |
|---|
| 176 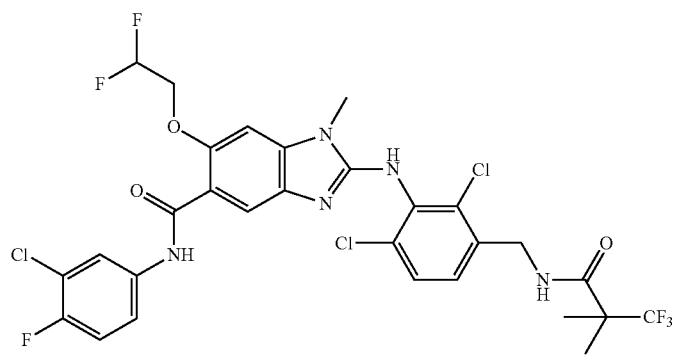 [SMILES: Cn1c(Nc2c(Cl)ccc(CNC(=O)C(C)(C)C(F)(F)F)c2Cl)nc2cc(C(=O)Nc3ccc(F)c(Cl)c3)c(OCC(F)F)cc21] |
| 177 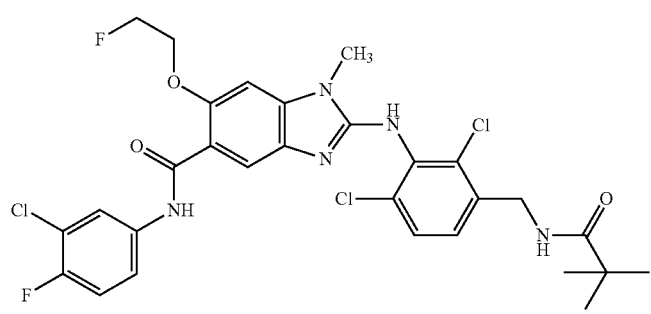 [SMILES: Cn1c(Nc2c(Cl)ccc(CNC(=O)C(C)(C)C)c2Cl)nc2cc(C(=O)Nc3ccc(F)c(Cl)c3)c(OCCF)cc21] |
| 178 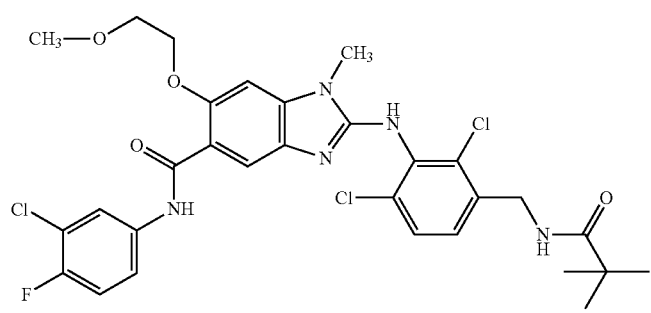 [SMILES: COCCOc1cc2c(cc1C(=O)Nc1ccc(F)c(Cl)c1)nc(Nc1c(Cl)ccc(CNC(=O)C(C)(C)C)c1Cl)n2C] |
| 179 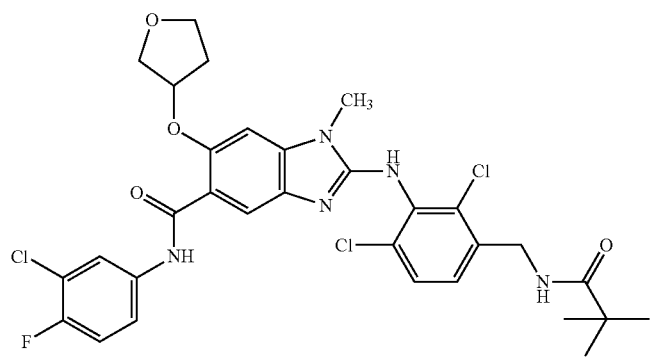 [SMILES: Cn1c(Nc2c(Cl)ccc(CNC(=O)C(C)(C)C)c2Cl)nc2cc(C(=O)Nc3ccc(F)c(Cl)c3)c(OC3CCOC3)cc21] |

|   | Structure |
|---|---|
| 180 | 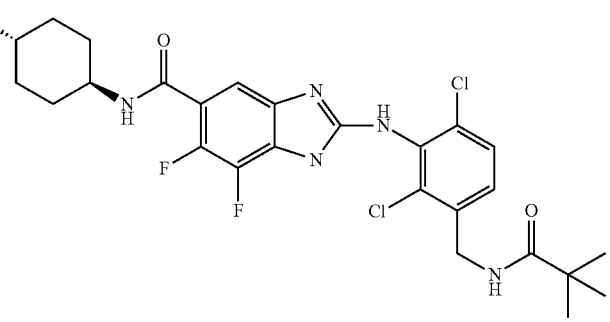 |
| 181 | 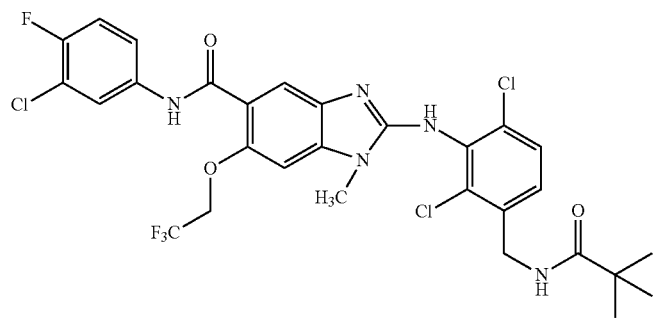 [SMILES: Cn1c(Nc2c(Cl)ccc(CNC(=O)C(C)(C)C)c2Cl)nc2cc(C(=O)Nc3ccc(F)c(Cl)c3)c(OCC(F)(F)F)cc21] |
| and | |
| 182 | 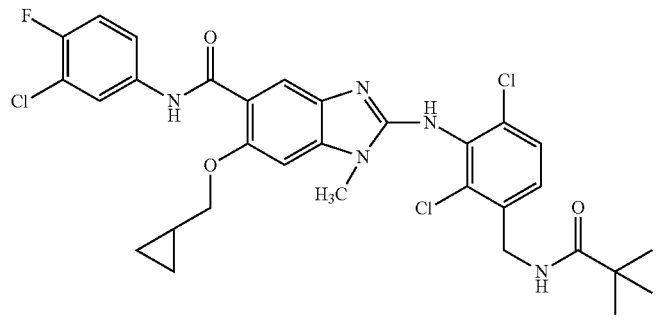 [SMILES: Cn1c(Nc2c(Cl)ccc(CNC(=O)C(C)(C)C)c2Cl)nc2cc(C(=O)Nc3ccc(F)c(Cl)c3)c(OCC3CC3)cc21] |

.

12. A pharmaceutical composition comprising at least one compound according to claim 1, or a pharmaceutically acceptable salt thereof, in admixture with a pharmaceutically acceptable adjuvant, diluent and/or carrier.

13. Compound 1 according to claim 11:

1

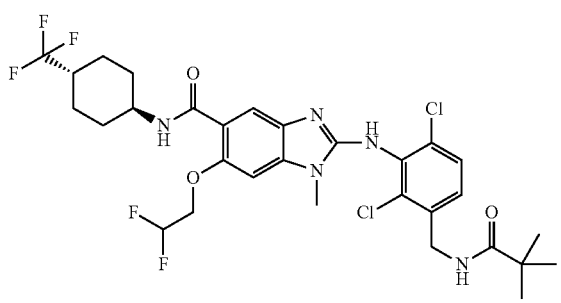

or a pharmaceutically acceptable salt thereof.

14. Compound 3 according to claim 11:

3

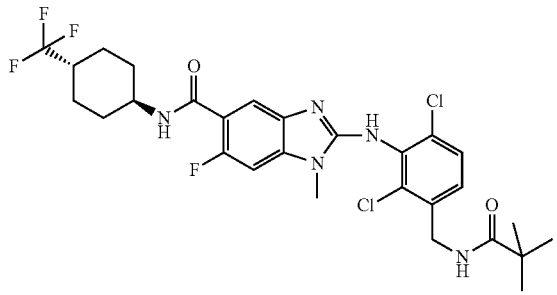

or a pharmaceutically acceptable salt thereof.

15. Compound 5 according to claim 11:

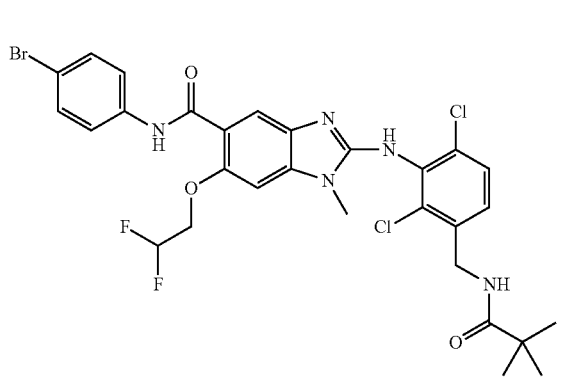

5 or a pharmaceutically acceptable salt thereof.

16. Compound 6 according to claim 11:

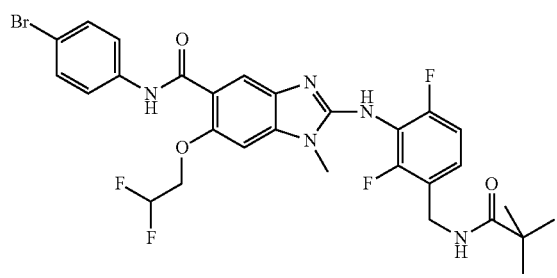

6 or a pharmaceutically acceptable salt thereof.

17. Compound 7 according to claim 11:

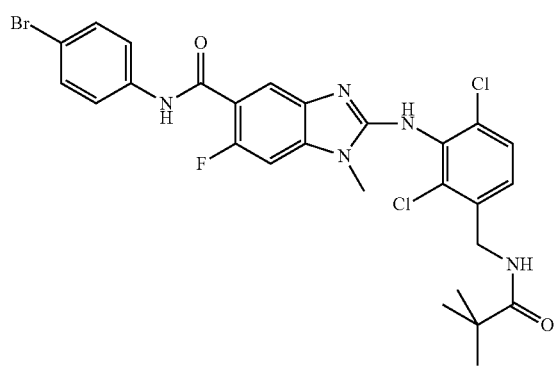

7 or a pharmaceutically acceptable salt thereof.

18. Compound 29 according to claim 11:

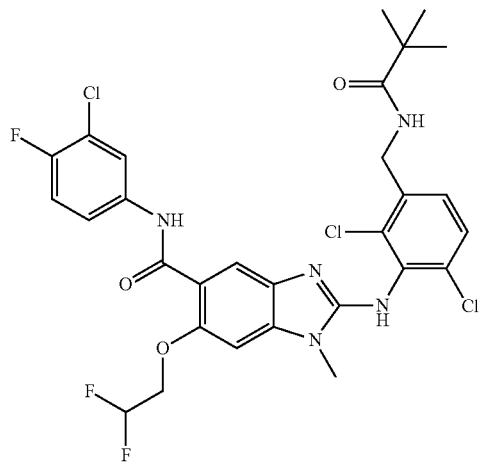

29 or a pharmaceutically acceptable salt thereof.

19. Compound 33 according to claim 11:

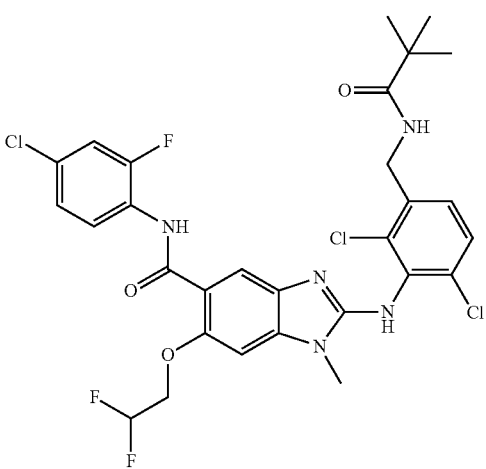

33 or a pharmaceutically acceptable salt thereof.

20. Compound 39 according to claim 11:
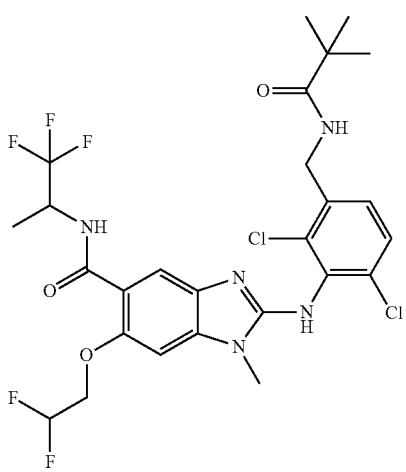
or a pharmaceutically acceptable salt thereof.
21. Compound 40 according to claim 11:
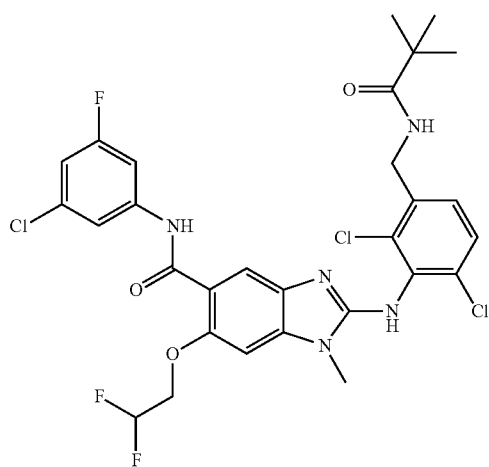
or a pharmaceutically acceptable salt thereof.
22. Compound 45 according to claim 11:
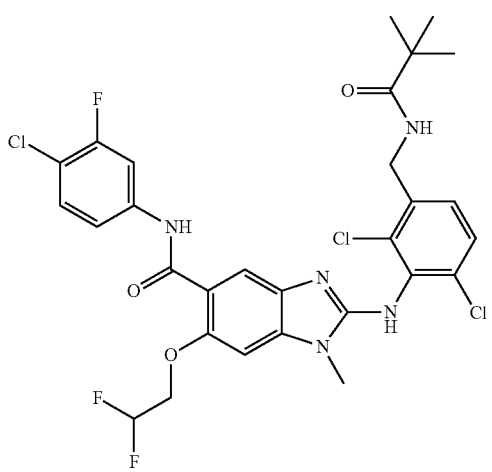
or a pharmaceutically acceptable salt thereof.
23. Compound 58 according to claim 11:
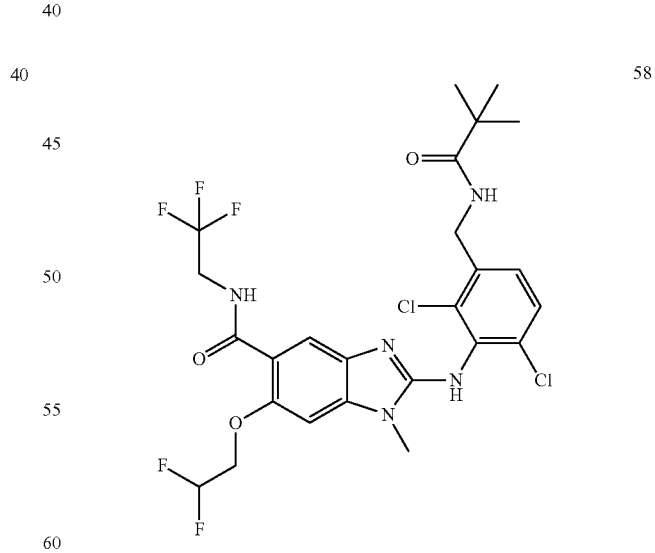
or a pharmaceutically acceptable salt thereof.

24. Compound 66 according to claim 11:
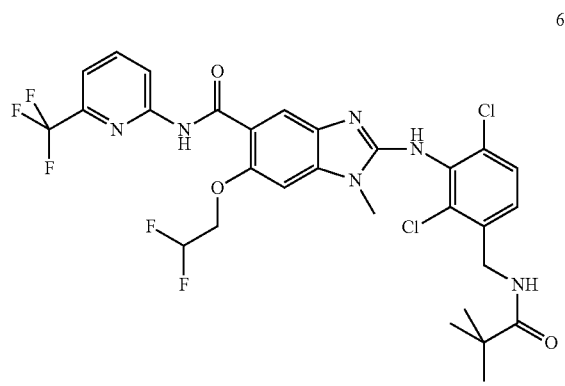
or a pharmaceutically acceptable salt thereof.
25. Compound 67 according to claim 11:
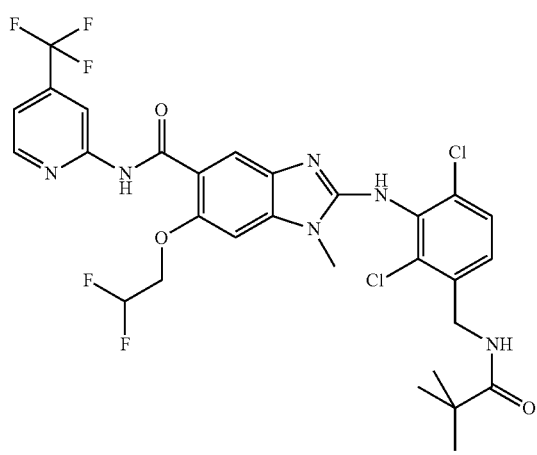
or a pharmaceutically acceptable salt thereof.
26. Compound 73 according to claim 11:
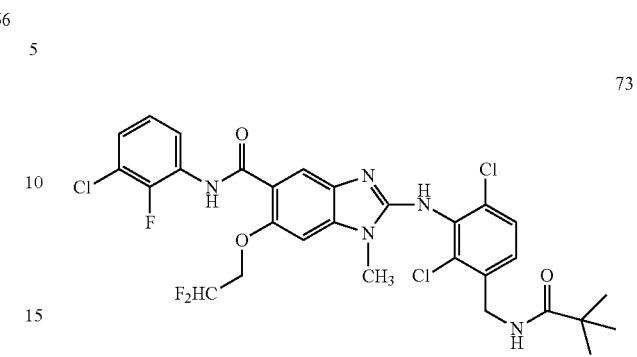
or a pharmaceutically acceptable salt thereof.
27. Compound 75 according to claim 11:
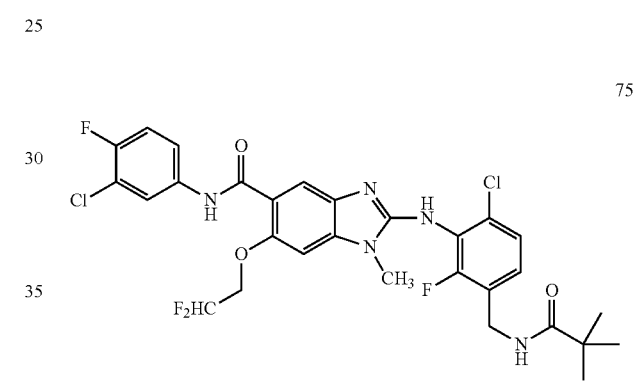
or a pharmaceutically acceptable salt thereof.
* * * * *